US012612413B2

(12) United States Patent
Zhang et al.

(10) Patent No.: US 12,612,413 B2
(45) Date of Patent: Apr. 28, 2026

(54) HETEROARYL COMPOUNDS AS INHIBITORS OF PROGRAMMED NECROSIS PATHWAY, COMPOSITION AND METHOD USING THE SAME

(71) Applicant: ACCRO BIOSCIENCE INC., Grand Cayman (KY)

(72) Inventors: Xiaohu Zhang, Suzhou (CN); Haikuo Ma, Suzhou (CN); Sudan He, Suzhou (CN)

(73) Assignee: Accro Bioscience (HK) Limited, Hong Kong (CN)

( * ) Notice: Subject to any disclaimer, the term of this patent is extended or adjusted under 35 U.S.C. 154(b) by 925 days.

(21) Appl. No.: 17/790,728

(22) PCT Filed: Jan. 4, 2021

(86) PCT No.: PCT/US2021/012124

§ 371 (c)(1),
(2) Date: Jul. 2, 2022

(87) PCT Pub. No.: WO2021/138694

PCT Pub. Date: Jul. 8, 2021

(65) Prior Publication Data

US 2023/0121233 A1 Apr. 20, 2023

(30) Foreign Application Priority Data

Jan. 2, 2020 (CN) ......................... 202010002951.8
Jan. 7, 2020 (CN) ......................... 202010013699.0

(51) Int. Cl.
*C07D 495/04* (2006.01)
*C07D 495/20* (2006.01)
*C07D 519/00* (2006.01)

(52) U.S. Cl.
CPC ......... *C07D 495/04* (2013.01); *C07D 495/20* (2013.01); *C07D 519/00* (2013.01)

(58) Field of Classification Search
CPC .................................................... C07D 495/04
See application file for complete search history.

(56) References Cited

U.S. PATENT DOCUMENTS

2006/0167035 A1 7/2006 Schwede et al.
2017/0290790 A1 10/2017 Zhang et al.
2019/0119297 A1 4/2019 Park et al.
2019/0241583 A1 8/2019 Ban et al.

OTHER PUBLICATIONS

Wolff, Manfred E. "Burger's Medicinal Chemistry, 5ed, Part I", John Wiley & Sons, 1995, pp. 975-977.*
Banker, G.S et al, "Modern Pharmaceutics, 3ed.", Marcel Dekker, New York, 1996, pp. 451 and 596.*
Rautio et al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Malmborg "Predicting human exposure of active drug after oral prodrug administration, using a joined in vitro/in silico-in vivo extrapolation and physiologically-based pharmacokinetic modeling approach" Journal of Pharmacological and Toxicological Methods 67 (2013) 203-213.*
Sedger "TNF and TNF-receptors: From mediators of cell death and inflammation to therapeutic giants—past, present and future" Cytokine & Growth Factor Reviews 25 (2014) 453-472.*
Yang "Ferroptosis: Death by Lipid Peroxidation" Trends in Cell Biology, Mar. 2016, vol. 26, No. 3 165-175.*
Bae, Cancer Targeted Drug Delivery, Springer: New York, 2013, p. v.*
Hayat, M.A. Autophagy Cancer, Other Pathologies, Inflammation, Immunity, Infection, and Aging vol. 5 Academic Press: San Diego, 2015, p. xxi.*
Carlo C. Maley and Mel Greaves Frontiers in Cancer Research Springer: 2016, pp. 18-19.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Gong et al. Molecular Cancer (2019) 18:100, 1-117.*

(Continued)

*Primary Examiner* — David K O'Dell

(57) ABSTRACT

The present disclosure provides heteroaryl compounds of Formula I, processes for their preparation, pharmaceutical compositions containing them, and their use in the treatment of diseases and disorders, arising from or related to the programmed necrosis pathway. Formula I is:

I

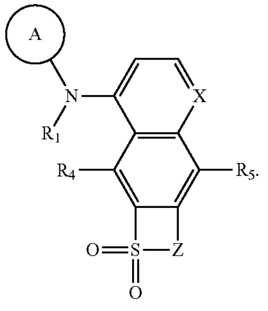

16 Claims, 3 Drawing Sheets

(56) References Cited

OTHER PUBLICATIONS

Pasparakis "Necroptosis and its role in inflammation" Nature, 2015, 517, 311-320.*
A.M. Bendele "Animal models of rheumatoid arthritis" J Musculoskel Neuron Interact 2001; 1(4):377-385.*
Poli-de-Figueiredo "Experimental Models of Sepsis and Their Clinical Relevance" Shock, vol. 30, Supplement 1, pp. 53-59, 2008.*
Gentile "HMGB1 as a therapeutic target for sepsis: it's all in the timing!" Expert Opinion on Therapeutic Targets, 2014, 18:3, 243-245.*
Garrido "Experimental models of sepsis and septic shock: an overview" Acta Cirúrgica Brasileira—vol. 19 (2) 2004 82-88.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

* cited by examiner

HETEROARYL COMPOUNDS AS INHIBITORS OF PROGRAMMED NECROSIS PATHWAY, COMPOSITION AND METHOD USING THE SAME

CROSS REFERENCE TO RELATED APPLICATIONS

This application claims the benefit of Chinese Patent Applications 202010002951.8, filed on Jan. 2, 2020; and 202010013699.0, filed on Jan. 7, 2020; all of which are hereby incorporated by reference.

FIELD OF INVENTION

The present invention generally relates to heteroaryl compounds and, more particularly, relates to novel heteroaryl compounds that are inhibitors of programmed necrosis pathway. The present invention also relates to compositions comprising the heteroaryl compounds, their method of making, and their applications the therapies targeting necrosis mediated diseases including receptor-interacting protein kinase-3 (RIP3) related diseases, including tumors, autoimmune diseases, neurodegenerative diseases, metabolic diseases, and aging.

BACKGROUND OF THE INVENTION

Receptor-interacting protein kinase 3 (RIP3) is a multi-functional protein involved in cell death pathways and a member of the receptor-interacting protein family. The human rip3 gene is located on chromosome 14 (FEBS Lett. 2000; 473:285-291). RIP3 is a polypeptide of 518 amino acids, having an active Ser/Thr kinase domain in its N terminus. Its substrates include Receptor-interacting protein kinase 1 (RIP1) from the same kinase family and metabolic enzymes (Nat Rev Mol Cell Biol. 2010; 11: 700-714). RIP3 can impact cell survival, ontogeny, immunity, and other physiological and pathological response processes (see, e.g., Nature 2011; 471: 368-472; Proc Natl Acad Sci USA 2011; 108: 15312-15317; Immunol. 2011; 12: 1143-1149). Recent papers reported that RIP3 plays pivotal role in extrinsic mechanism of cell apoptosis and programmed necrosis (Science 2009; 325: 332-336; Cell 2009; 137: 1100-1111; Nature 2011; 471: 363-367; Cell. 2009; 137: 1112-1123), hence, facilitating research of RIPS. Research shows that RIP3, via its RIP homotypic interaction motif (RHIM) motif, interacts with RIP to recruit Fas-associated death domain (FADD) and cysteine-aspartic acid protease 8 (caspase-8) to form a signaling complex known as Complex II, thereby initiating cell death. The inhibition or deletion of casepase-8 in complex II converts complex II into complex IIc, also known as the necrosome, composing mainly of RIP1 and RIP3, combined via the RHIM. Necrosome is critical to programmed necrosis or necroptosis. RIP3 can be auto-phosphorylated in the necrosome. Hyperphosphorylated RIP3 also activates the kinase activity of RIP1. Serine/threonine residues are the favored phosphorylation sites on RIP3. One phosphorylation site on RIP3, Ser227, is particularly important for recruitment and activation of mixed-lineage kinase domain-like (MLKL), a crucial downstream substrate of RIP3 in the necrosis pathway. Interaction of RIPS with MLKL leads to MLKL phosphorylation and transduction of necroptosis signaling RIP3-dependent plasma membrane localization of MLKL is necessary for programmed necrotic cell death to occur (see, e.g., Nature 2011; 471: 363-367; Cell 2012; 150: 339-350; Nat Immun. 2018; 19; 912-922).

Studies have shown that the imbalance of RIP3 can be associated with a variety of pathological states and diseases. RIP3 signaling is involved in controlling multiple viral infections including: influenza A virus (IAV) (FEBS J. 2016; 283: 2616-2625), vaccinia virus (Cell 2014; 137: 1112-1123), herpes simplex virus-1 (HSV-1) (Cell Host Microbe 2015; 17: 229-242), Murine cytomegalovirus (MCMV) (Cell Host Microbe 2010; 7: 302-313), and West Nile virus (WNV) (Cell 2017; 169: 1-13). Because RIP3 mediates hepatocyte necrosis caused by acetaminophen overdose (Hepatology. 2013; 58: 2099-2108) and ethanol-induced liver injury (Hepatology. 2013; 57: 1773-1783), absence of RIP3 may reduce or prevent such liver damages. Tumor necrosis factor (TNF) is a prime mediator of inflammation in septic shock, implying that RIP3 may also participate in the occurrence of bacteria-induced sepsis. Indeed, RIP3−/− mice were protected from TNF or cecal ligation and puncture (CLP)-induced systemic inflammation, two experimental models for clinical sepsis (Immunity. 2011; 35: 908-918; Mol Med. 2012; 18: 577-586). RIP3 can also mediate epithelial cell necrosis and chronic intestinal inflammation (Nature 2011; 477: 330-334). Deletion of RIP3 can improve the condition of acute pancreatitis induced by cerulean (Science 2009; 325: 332-336; Cell 2009; 137: 1100-1111). In an animal model for atherosclerosis, deletion of RIP3 can lead to a significant reduction of macrophage primary necrosis (Cell Rep. 2013; 3: 200-210). Deletion of RIP3 can inhibit photoreceptor cell loss in an animal model of retinal detachment and deter necrotic cone cell death in retinitis pigementosa (Proc Natl Acad Sci 2010; 107: 21695-21700; Proc Natl Acad Sci 2012; 109: 14598-14603). Male reproductive organs of both Ripk3- and Mlkl-knockout mice retain "youthful" morphology and function into advanced age, while those of age-matched wild-type mice deteriorate (Elife. 2017 Aug. 15; 6: e27692). Because RIP3 is an essential part of the cellular machinery that executes "programmed" or "regulated" necrosis, reduced or silenced RIP3 expression and the associated repressed programmed necrosis have been observed in cancer cells including acute myeloid leukemia, breast cancer and colorectal cancer (Cell Res 2015; 25: 707-725; Cell Death Dis 2017; 8: e3084; Cell Death Dis 2014; 5: e1384; Neoplasma 2015; 62: 592-601). Deficiency of RIP3 may promote hepatocarcinogenesis in TAK1-deficient liver (Cell Rep 2013; 4 (4): 776-790).

RIP3 is associated with various diseases including tumors, autoimmune diseases, neurodegenerative diseases, metabolic diseases, and aging. RIP3 can be a potential therapeutic target for some diseases. Therefore, the development of small molecule inhibitors that inhibit the RIP3 kinase may block the RIP3-dependent programmed necrosis, slow down the progression of the diseases or pathological states caused by the programmed necrosis, and afford preventive or therapeutic effects. Accordingly, in order to treat the afore-mentioned diseases caused by programmed necrosis, there is a need for effective inhibitors of RIP3.

SUMMARY OF THE INVENTION

The present disclosure provides heteroaryl compounds as inhibitors of RIP3, and compositions and applications thereof. These disclosed heteroaryl compounds, and compositions and applications thereof, may effectively inhibit programmed necrosis, thereby finding application in treatments of necrotic pathway-related diseases and disorders mediated by RIP3, including, for example, inflammation, tumors, metabolic diseases and neurodegenerative diseases.

An aspect of the present disclosure provides a compound of Formula I:

I

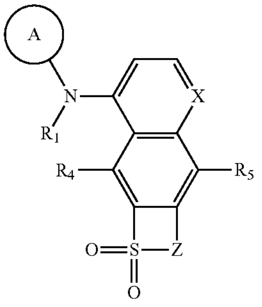

or a pharmaceutically acceptable salt, ester, solvate, prodrug, isotope-labeled derivative, stereoisomer or tautomer thereof, wherein X is N or $CR_6$;

Z is

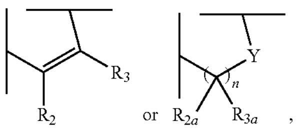

wherein the sulfonyl group in Formula I is connected to the carbon bearing $R_2$ or $R_{2a}$;

wherein when Z is

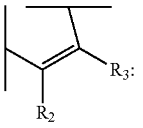

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_7$ groups;

$R_1$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium;

$R_2$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and deuterium;

$R_3$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, 3-6 membered heterocycle, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, $C_{1-3}$ alkoxy, —NH($C_{1-3}$ alkyl), —N($C_{1-3}$ alkyl)$_2$, cyclopropyl, halide and deuterium;

or $R_3$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_8$ groups;

or $R_3$ is L-BB, wherein L is —O—, —S—, —NH— or —$CH_2$—, BB is $C_{3-8}$ cycloalkyl or 3-8 membered heterocycle, wherein 3-8 membered heteroaryl comprises 1 to 3 heteroatoms independently selected from N, O and S, wherein $C_{3-8}$ cycloalkyl and 3-8 membered heterocycle are unsubstituted or substituted with 1 to 3 $R_9$ groups;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_7$ is independently H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl, —C(=O)$NH_2$ or —$CO_2$($C_{1-6}$ alkyl), wherein amino, $C_{1-6}$ alkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium, or two adjacent $R_7$ groups being connected to form a ring together with the atoms they are attached to; and each of $R_8$ and $R_9$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium;

wherein when Z is

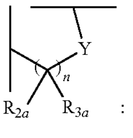

n is 1 or 2;

Y is O, $NR_{7a}$ or $CR_{7a}R_{8a}$;

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_{9a}$ groups;

$R_1$ is independently H, deuterium, $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium;

each of $R_{2a}$ and $R_{3a}$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl, or $R_{2a}$ and $R_{3a}$ forming ring B together with atoms connected to $R_{2a}$ or $R_{3a}$;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_{7a}$ is H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl;

$R_{8a}$ is H, deuterium, halide, amino, —OH, —$CO_2$H, —$CO_2$($C_{1-6}$ alkyl), —CN, —$SOR_{20}$, —$SO_2R_{20}$, $C_{1-6}$ alkyl, $C_{3-6}$ cycloalkyl, 3-6 membered heterocycle comprising 1-3 heteroatoms independently selected from N, O and S, $C_{1-6}$ alkoxy, —NH($C_{1-6}$ alkyl), —N($C_{1-6}$ alkyl)$_2$, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-6}$ alkoxy, $C_{3-6}$ cycloalkyl, $C_{2-6}$ alkenyl and $C_{2-6}$ alkynyl are unsubstituted or substituted with 1 to 3 groups independently selected from —OH, $C_{1-3}$ alkoxy, cyclopropyl, halide and deuterium, or $R_{8a}$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_{10a}$ groups;

or $R_{7a}$ and $R_{8a}$ together with the carbon they attached to are C═O or C═$CH_2$;

or $R_{7a}$ and $R_{8a}$ form ring C together with atoms attached to $R_{7a}$ and $R_{8a}$;

each of ring B and ring C is independently selected from the group consisting of $C_{3-8}$ cycloalkyl, 3-8 membered heterocycle, $C_{4-8}$ cycloalkenyl and $C_{4-8}$ heterocycloalkenyl, wherein $C_{3-8}$ cycloalkyl, 3-8 membered heterocycle, $C_{4-8}$ cycloalkenyl and $C_{4-8}$ heterocycloalkenyl are unsubstituted or substituted with 1 to 3 $R_{11a}$ groups, wherein 3-8 membered heterocycle and $C_{4-8}$ heterocycloalkenyl comprises 1 to 3 groups independently selected from the group consisting of heteroatom(s) of N, O and S, and hetero group(s) of —C(═O) N($R_{11a}$)—, —C(═O)O—, —C(═O)—, —C(═S)—, —S(═O)—, —S(═O)$_2$— and —NHC(═O)NH—;

each of $R_{9a}$ and $R_{10a}$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium;

$R_{11a}$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium; and $R_{20}$ is $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium.

In some embodiments of aspects provided herein, the compound has Formula II:

II

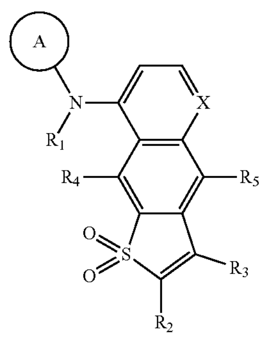

or a pharmaceutically acceptable salt, ester, solvate, prodrug, isotope-labeled derivative, stereoisomer or tautomer thereof, wherein X is N or $CR_6$;

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_7$ groups;

$R_1$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium;

$R_2$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and deuterium;

$R_3$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, 3-6 membered heterocycle, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, $C_{1-3}$ alkoxy, —NH($C_{1-3}$ alkyl), —N($C_{1-3}$ alkyl)$_2$, cyclopropyl, halide and deuterium;

or $R_3$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_8$ groups;

or $R_3$ is L-BB, wherein L is —O—, —S—, —NH— or —$CH_2$—, BB is $C_{3-8}$ cycloalkyl or 3-8 membered heterocycle, wherein 3-8 membered heteroaryl comprises 1 to 3 heteroatoms independently selected from N, O and S, wherein $C_{3-8}$ cycloalkyl and 3-8 membered heterocycle are unsubstituted or substituted with 1 to 3 $R_9$ groups;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_7$ is independently H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium, or two adjacent $R_7$ groups being connected to form a ring together with the atoms they are attached to; and each of $R_8$ and $R_9$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium.

In some embodiments, the compound has Formula III:

III

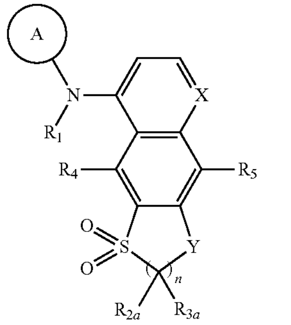

or a pharmaceutically acceptable salt, ester, solvate, prodrug, isotope-labeled derivative, stereoisomer or tautomer thereof, wherein n is 1 or 2;

X is N or $CR_6$;

Y is O, $NR_{7a}$ or $CR_{7a}R_{8a}$;

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_{9a}$ groups;

$R_1$ is independently H, deuterium, $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium;

each of $R_{2a}$ and $R_{3a}$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH ($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl, or $R_{2a}$ and $R_{3a}$ forming ring B together with atoms connected to $R_{2a}$ or $R_{3a}$;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_{7a}$ is H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl;

$R_{8a}$ is H, deuterium, halide, amino, —OH, —$CO_2$H, —$CO_2$($C_{1-6}$ alkyl), —CN, —$SOR_{20}$, —$SO_2R_{20}$, $C_{1-6}$ alkyl, $C_{3-6}$ cycloalkyl, 3-6 membered heterocycle comprising 1-3 heteroatoms independently selected from N, O and S, $C_{1-6}$ alkoxy, —NH($C_{1-6}$ alkyl), —N($C_{1-6}$ alkyl)$_2$, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-6}$ alkoxy, $C_{3-6}$ cycloalkyl, $C_{2-6}$ alkenyl and $C_{2-6}$ alkynyl are unsubstituted or substituted with 1 to 3 groups independently selected from —OH, $C_{1-3}$ alkoxy, cyclopropyl, halide and deuterium, or $R_{8a}$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_{10a}$ groups;

or $R_{7a}$ and $R_{8a}$ together with the carbon they attached to are C═O or C═$CH_2$;

or $R_{7a}$ and $R_{8a}$ form ring C together with atoms attached to $R_{7a}$ and $R_{8a}$;

each of Ring B and Ring C is independently selected from the group consisting of $C_{3-8}$ cycloalkyl, 3-8 membered heterocycle, $C_{4-8}$ cycloalkenyl and $C_{4-8}$ heterocycloalkenyl, wherein $C_{3-8}$ cycloalkyl, 3-8 membered heterocycle, $C_{4-8}$ cycloalkenyl and $C_{4-8}$ heterocycloalkenyl are unsubstituted or substituted with 1 to 3 $R_{11a}$ groups, wherein 3-8 membered heterocycle and $C_{4-8}$ heterocycloalkenyl comprises 1 to 3 groups independently selected from the group consisting of heteroatom(s) of N, O and S, and hetero group(s) of —C(═O)N($R_{11a}$)—, —(C═O)O—, —C(═O)—, —C(═S)—, —S(═O)—, —S(═O)$_2$— and —NHC(═O)NH—;

each of $R_{9a}$ and $R_{10a}$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium;

$R_{11a}$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium; and $R_{20}$ is $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium.

In some embodiments, the compound of Formula II:

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_7$ groups; and $R_7$ is independently H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl, —C(=O)$NH_2$ or —$CO_2$($C_{1-6}$ alkyl), wherein amino, $C_{1-6}$ alkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium, or two adjacent $R_7$ groups being connected to form a 4-8 membered ring together with the atoms they are attached to.

In some embodiments, the compound of Formula II:

$R_3$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, 3-6 membered heterocycle, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, $C_{1-3}$ alkoxy, —NH($C_{1-3}$ alkyl), —N($C_{1-3}$ alkyl)$_2$, cyclopropyl, halide and deuterium;

or $R_3$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_8$ groups;

or $R_3$ is L-BB, wherein L is —O—, —S—, —NH— or —$CH_2$—, BB is $C_{3-8}$ cycloalkyl or 4-7 membered heterocycle, wherein 4-7 membered heteroaryl comprises 1 to 3 heteroatoms independently selected from N, O and S, wherein $C_{3-8}$ cycloalkyl and 3-8 membered heterocycle are unsubstituted or substituted with 1 to 3 $R_9$ groups; and each of $R_8$ and $R_9$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl or $C_{1-8}$ alkoxy, wherein amino, $C_{1-6}$ alkyl, $C_{3-6}$ cycloalkyl and $C_{1-8}$ alkoxy are unsubstituted or substituted with 1 to 3 groups independently selected from halide, —OH, amino, acetyl and deuterium.

In some embodiments, the compound of Formula II has: ring A is selected from the group consisting of:

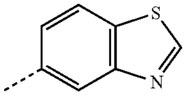
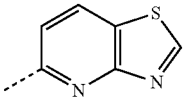
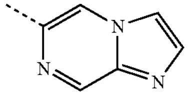
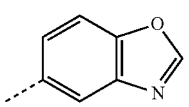
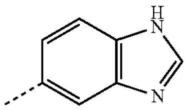
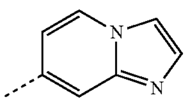

-continued

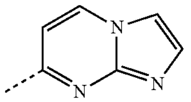
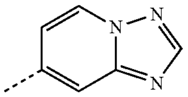
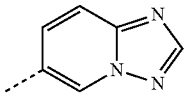
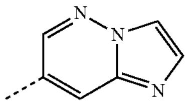
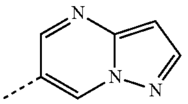
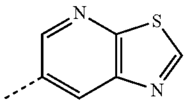
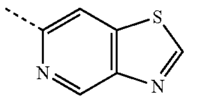
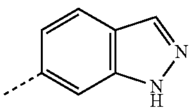
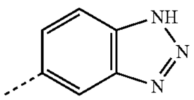
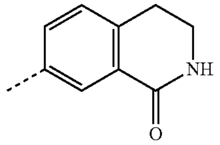
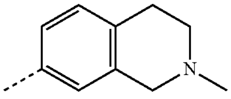
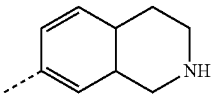
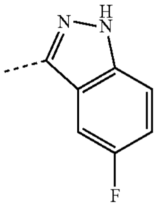
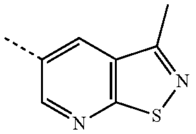
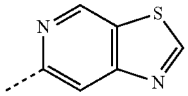
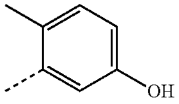
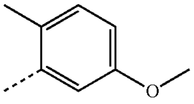
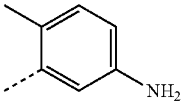
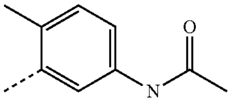
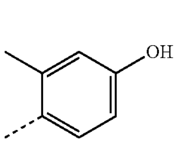
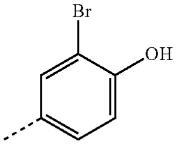
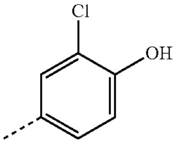
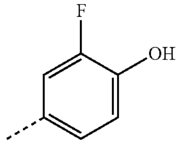
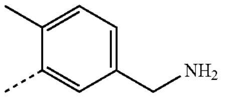
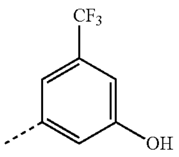
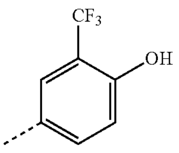
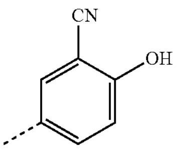
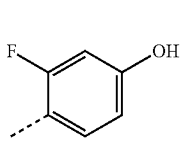
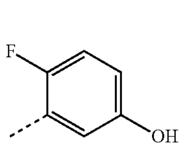
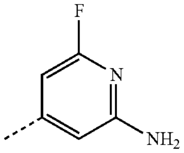
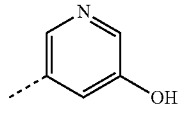
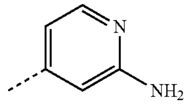
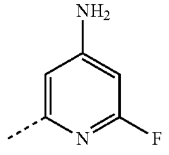

-continued

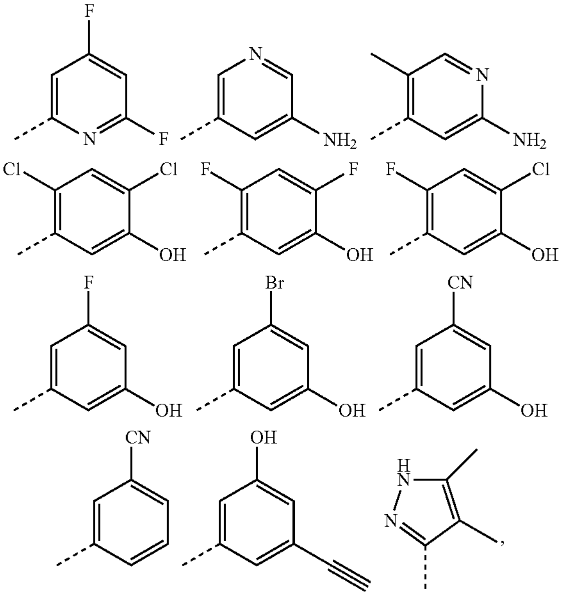

ring A is unsubstituted or substituted with 1 to 3 groups independently selected from deuterium, halide, —OH, $C_{1-3}$ alkyl and $C_{1-3}$ alkoxy.

In some embodiments, the compound of Formula II comprises $R_3$ selected from the group consisting of:

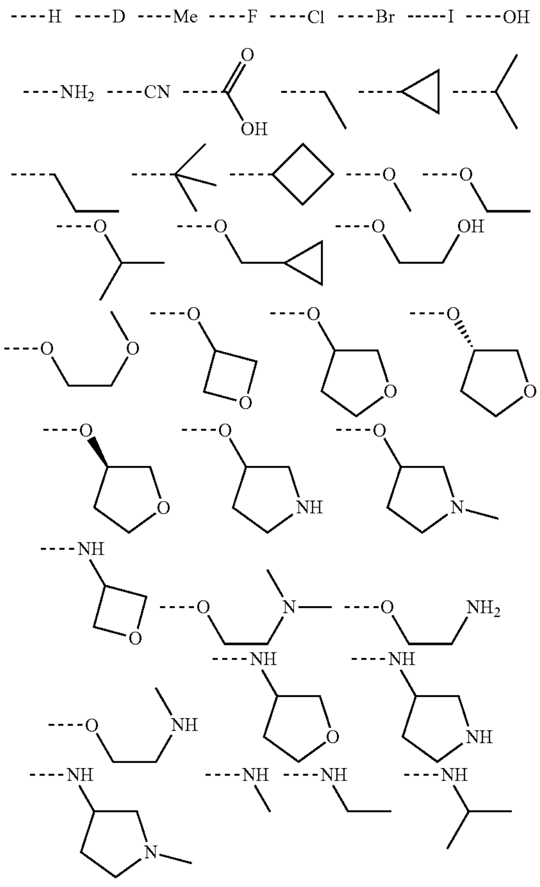

-continued

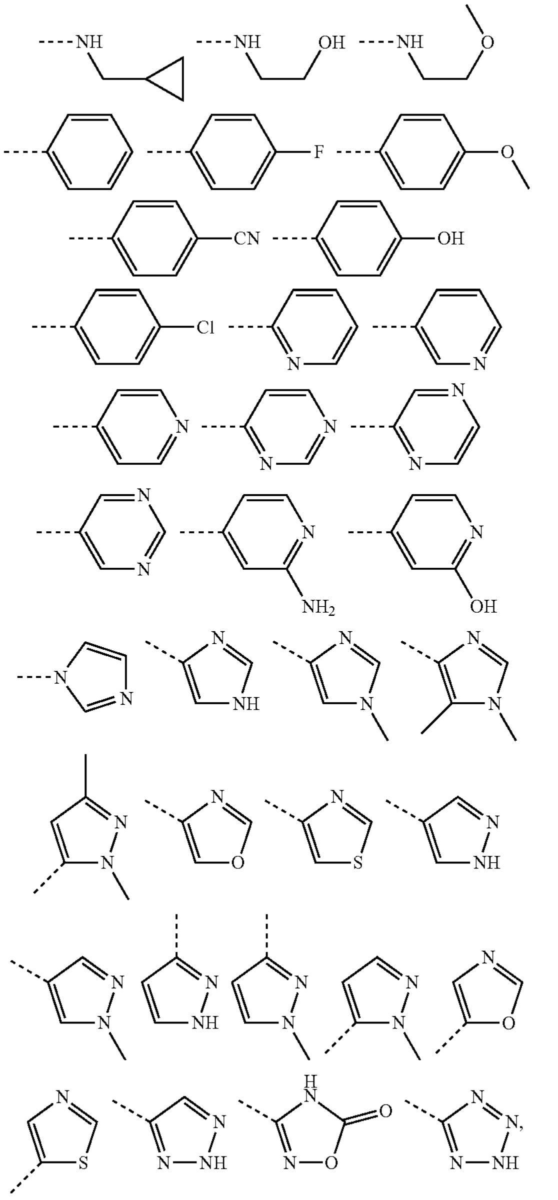

unsubstituted or substituted with 1 to 3 groups of —OH, $C_{1-3}$ alkoxy, —NH($C_{1-3}$ alkyl), —N($C_{1-3}$ alkyl)$_2$, cyclopropyl, halide, deuterium, $R_8$ or $R_9$.

In some embodiments, the compound of Formula II is selected from the group consisting of:

A1

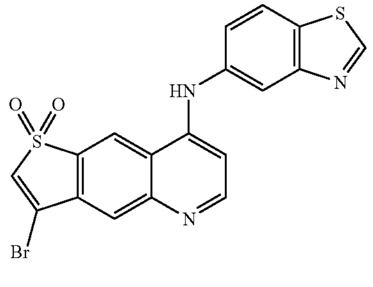

-continued
A2
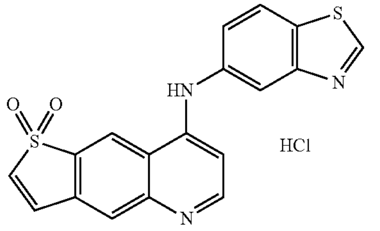
A3
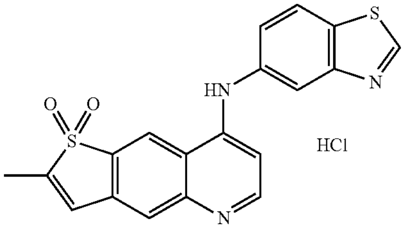
A4
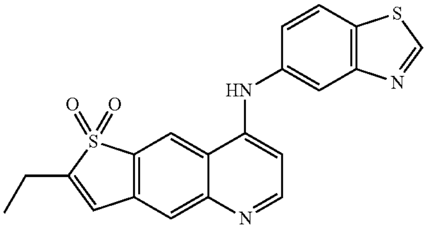
A5
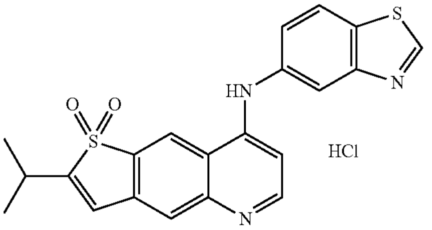
A6
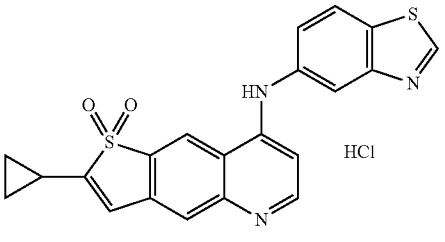
A7
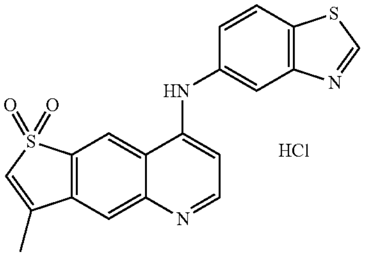
-continued
A8
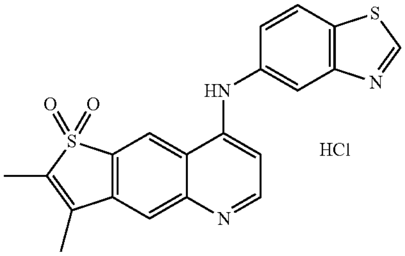
A9
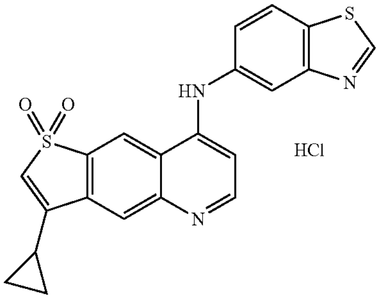
A10
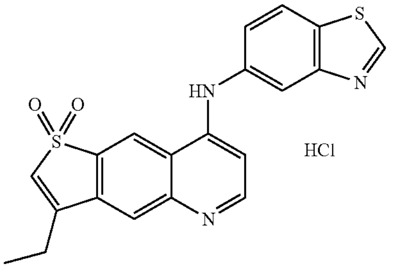
A11
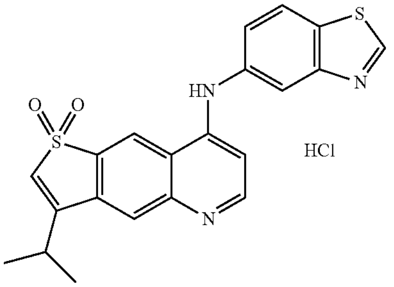
A12
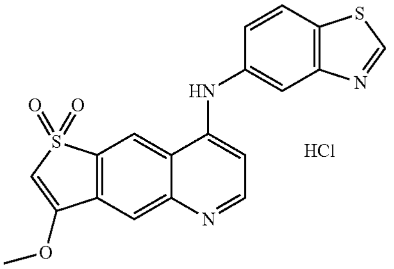

-continued
A13
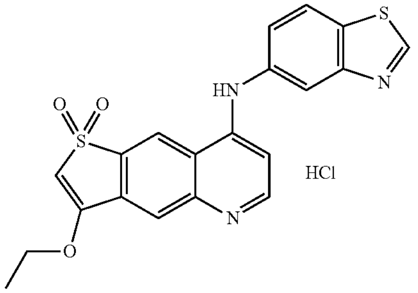
A14
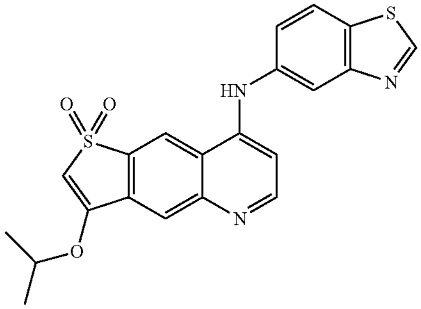
A15
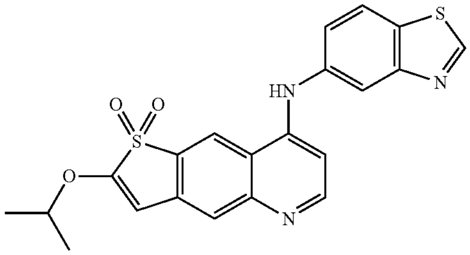
A16
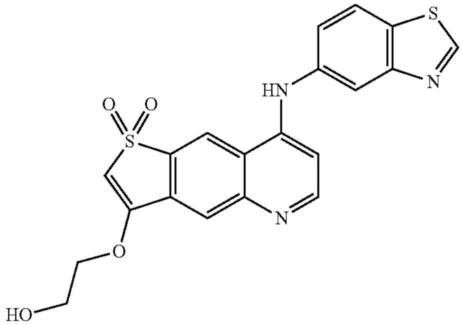
A17
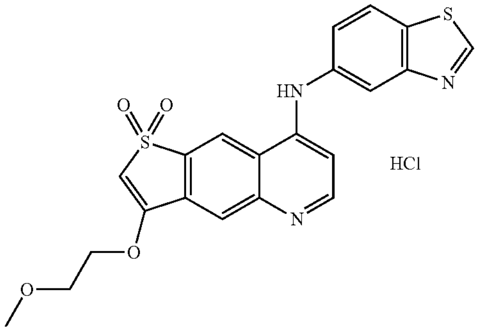
-continued
A18
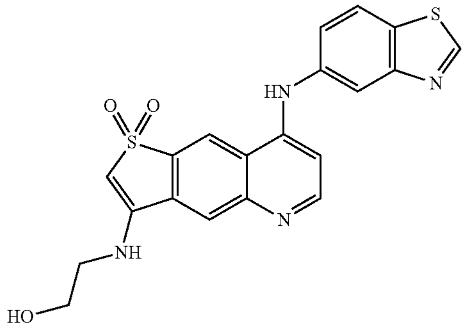
A19
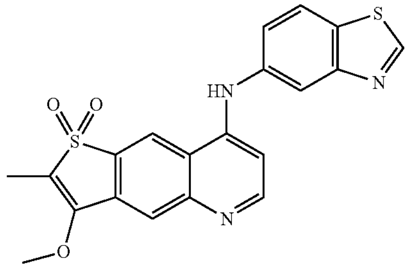
A20
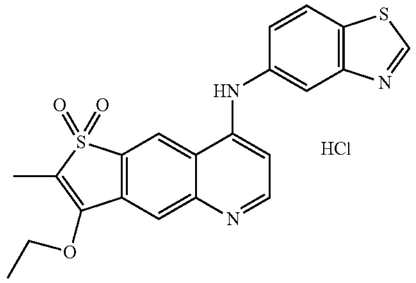
A21
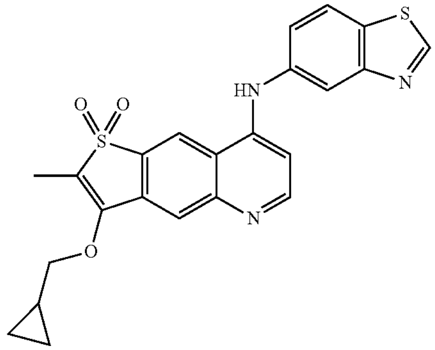
A22
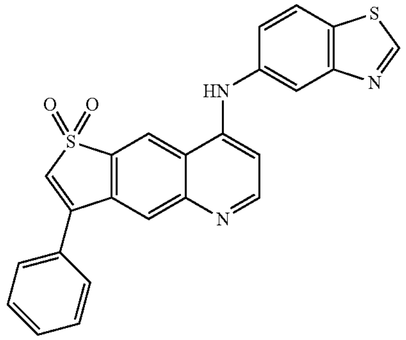

-continued
A24
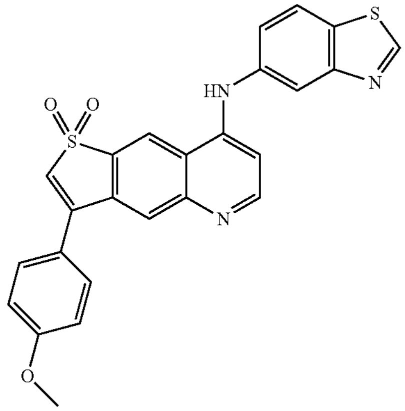
A25
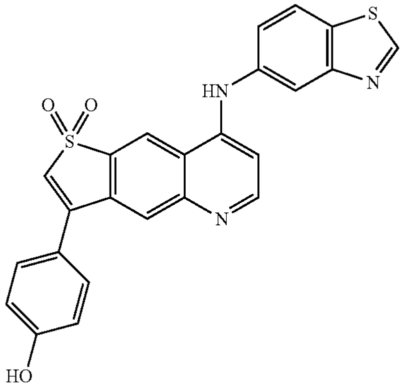
A26
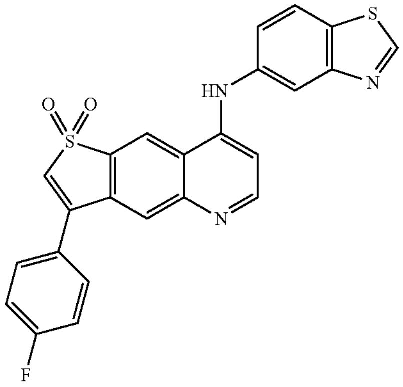
A27
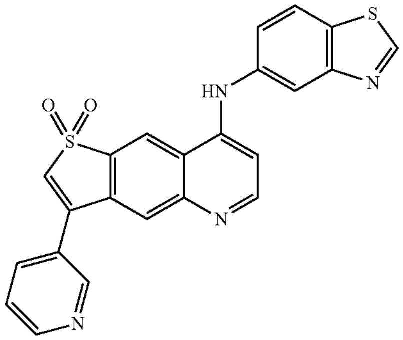
-continued
A28
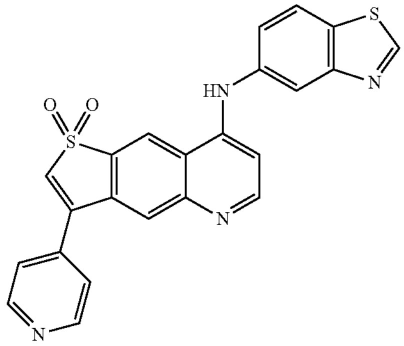
A29
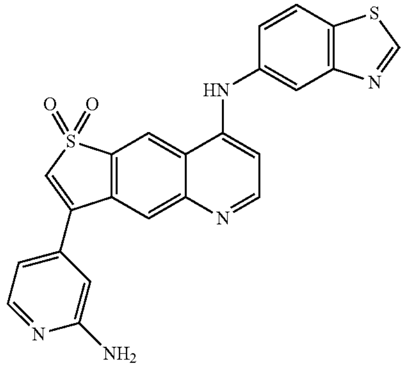
A30
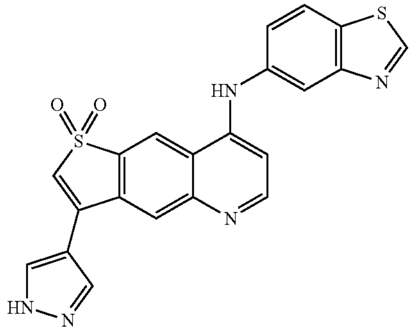
A31
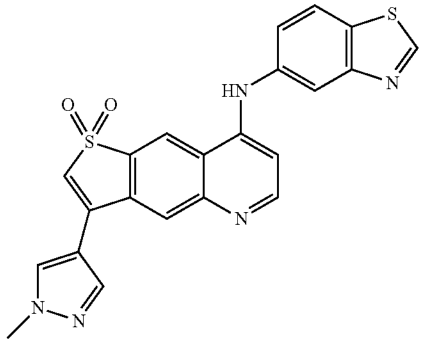

-continued
A32
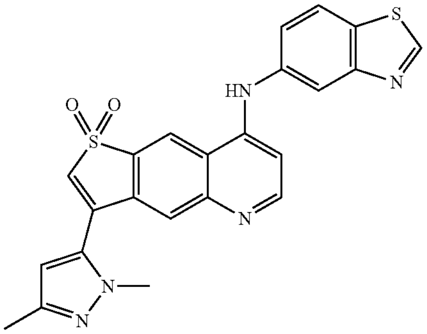
A33
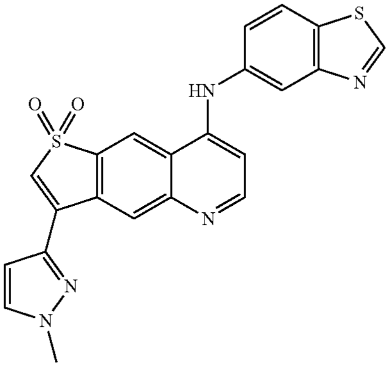
A34
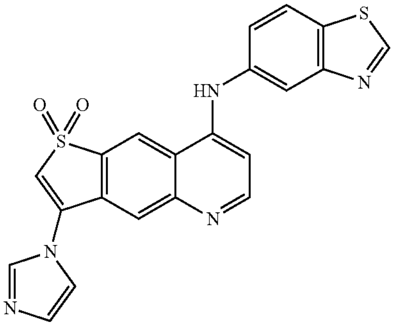
A35
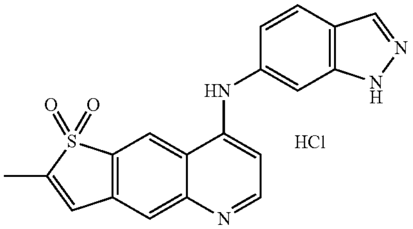
HCl
A36
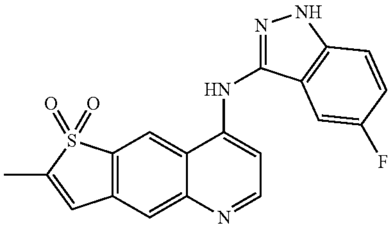
-continued
A38
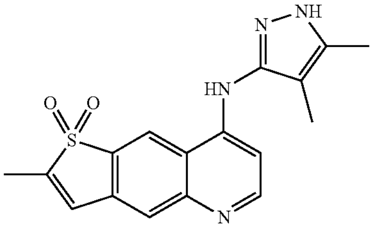
A39
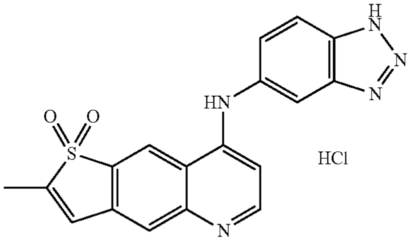
HCl
A40
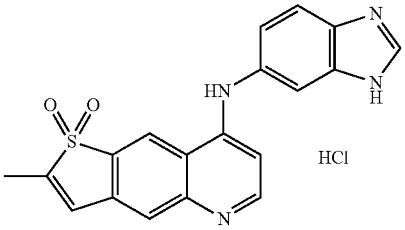
HCl
A41
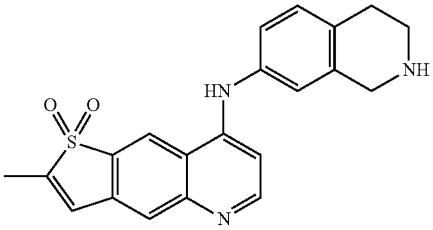
A42
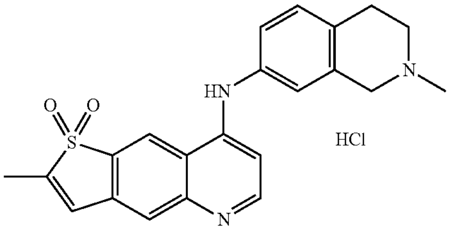
HCl
A43
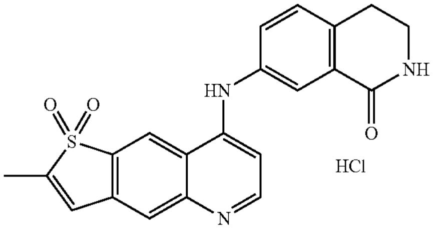
HCl -continued
A44
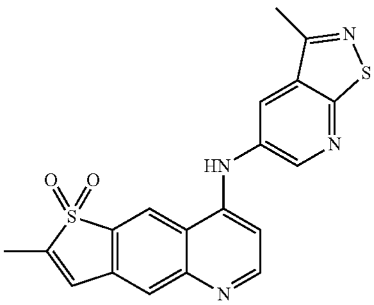
A45
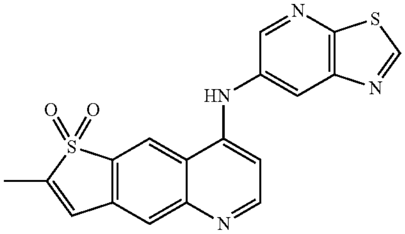
A46
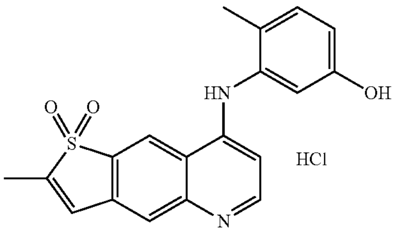
HCl
A47
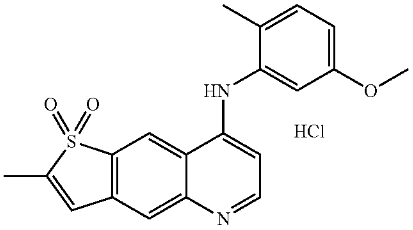
HCl
A48
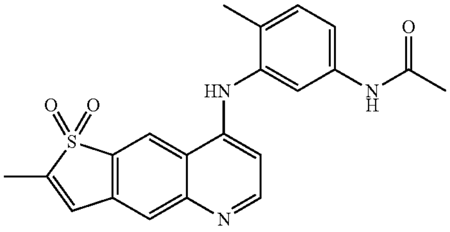
A49
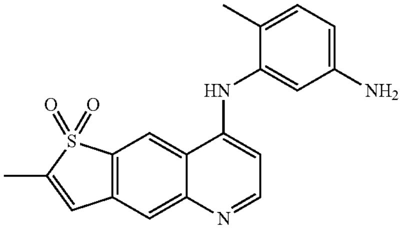
-continued
A50
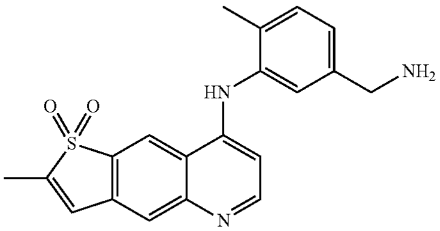
A51
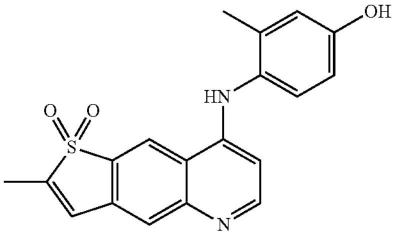
A52
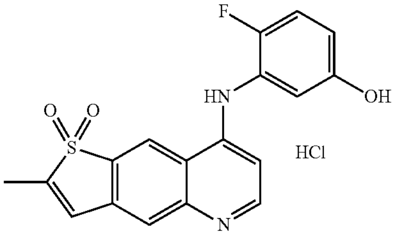
HCl
A53
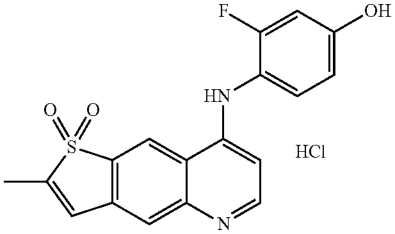
HCl
A54
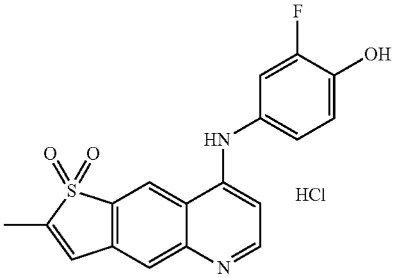
HCl
A55
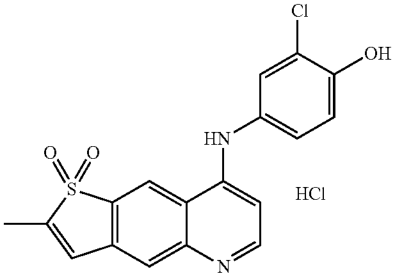
HCl

23
-continued
A56
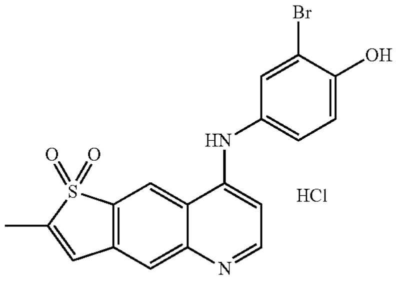
A57
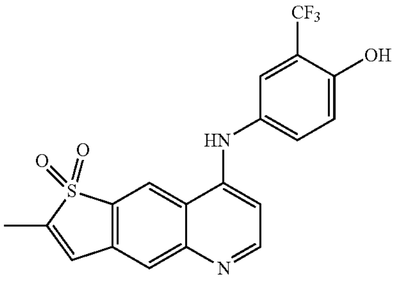
A58
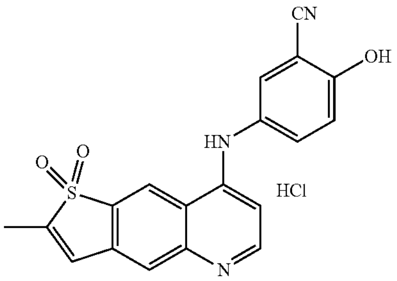
A59
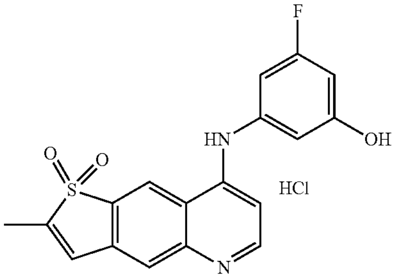
A60
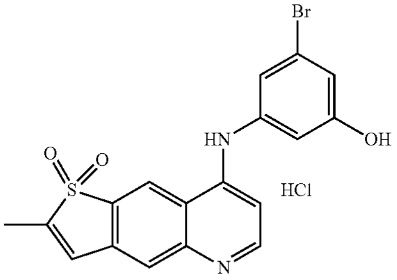
24
-continued
A61
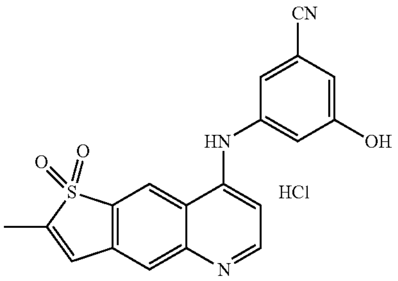
A62
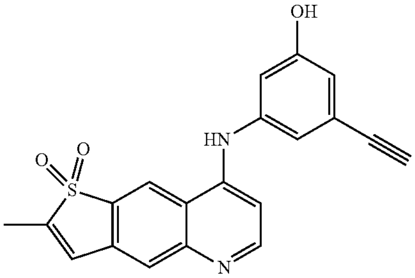
A63
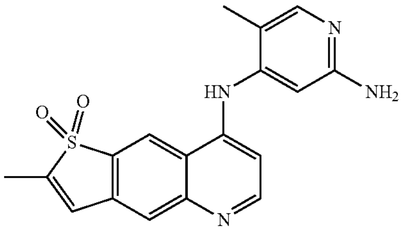
A64
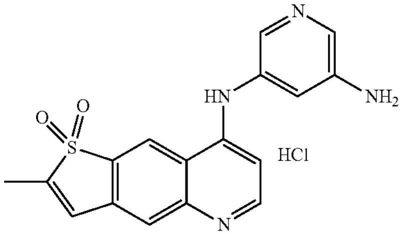
A65
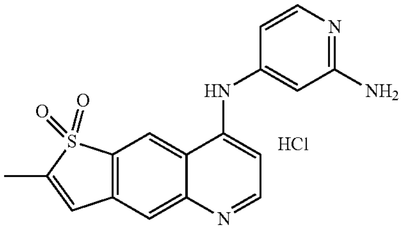
A66
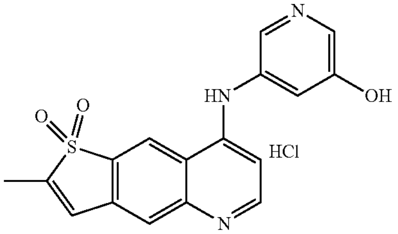

-continued
A67
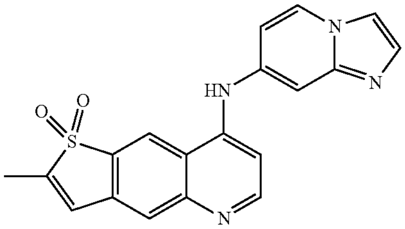
A68
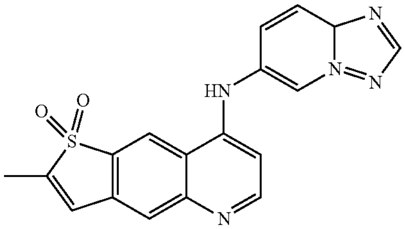
A69
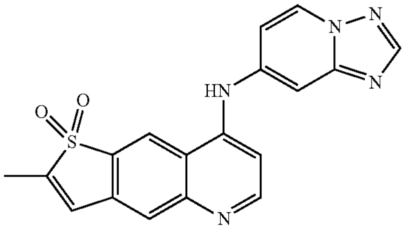
A70
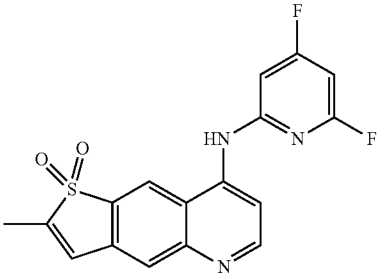
A71
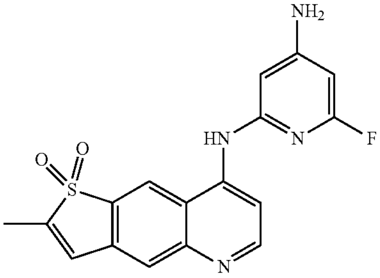
A72
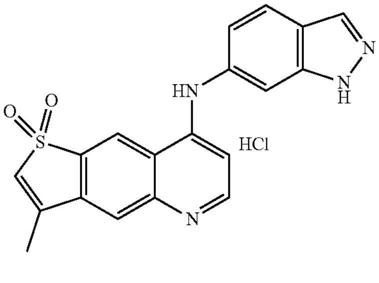
-continued
A73
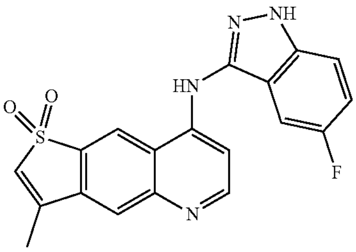
A75
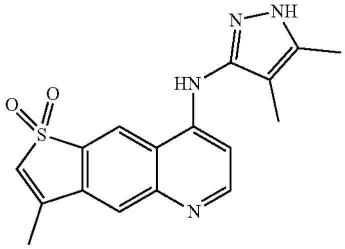
A76
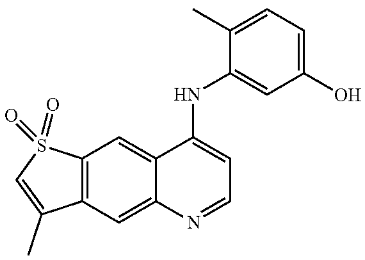
A77
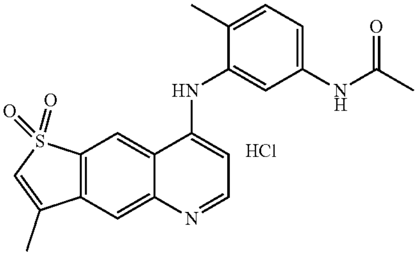
A78
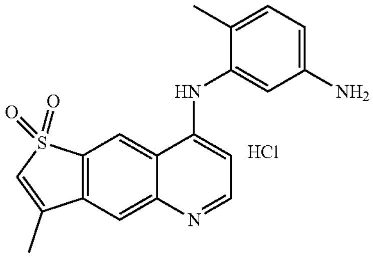
A79
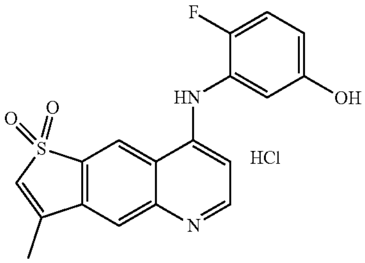

-continued
A80
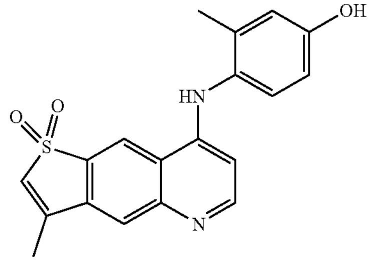
A81
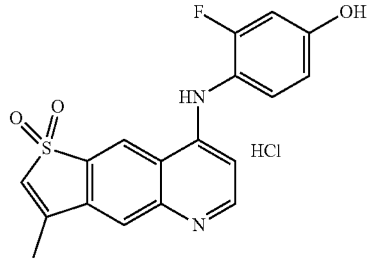
A82
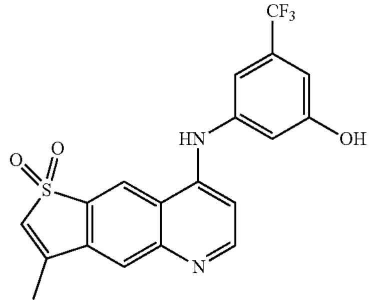
A83
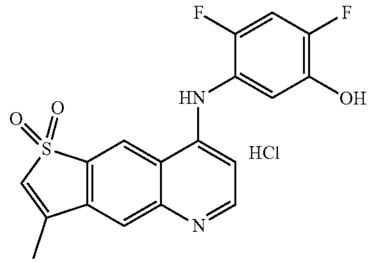
A84
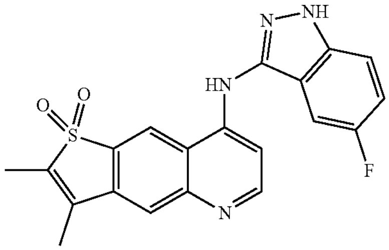
A86
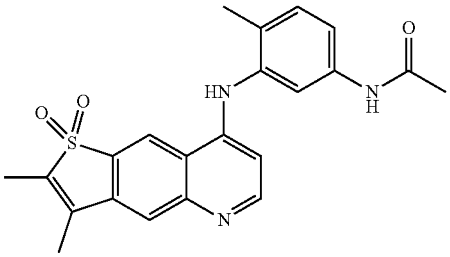
-continued
A87
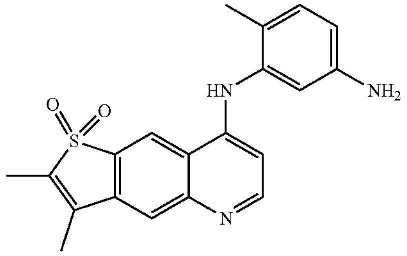
A88
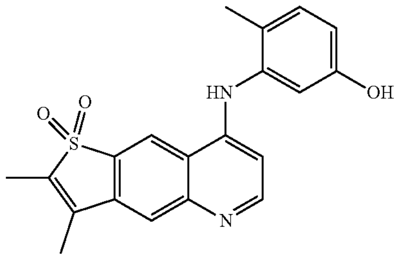
A89
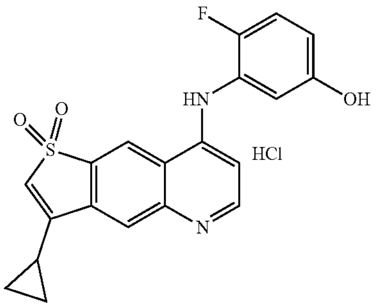
A90
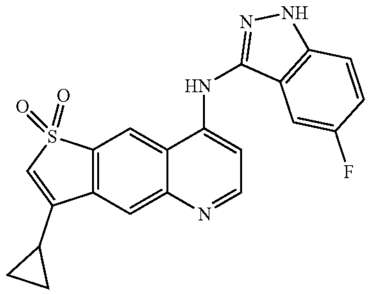
A91
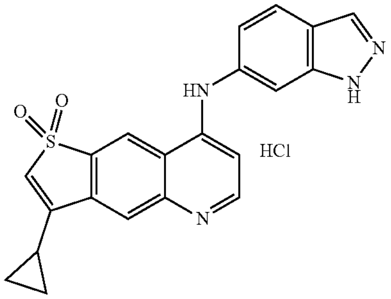

-continued
A92
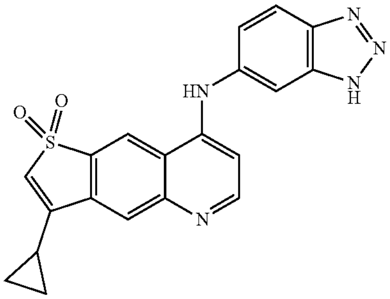
A93
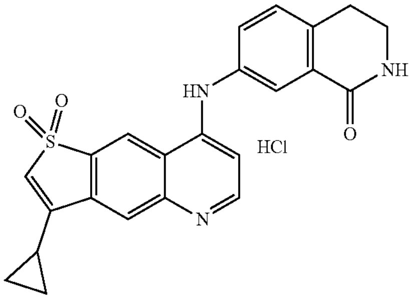
HCl
A94
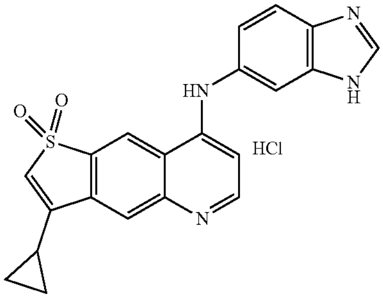
HCl
A95
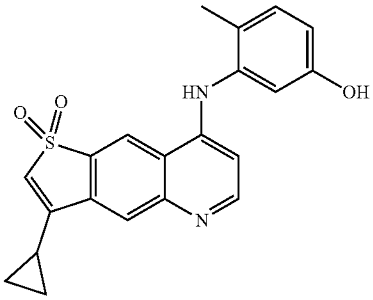
A96
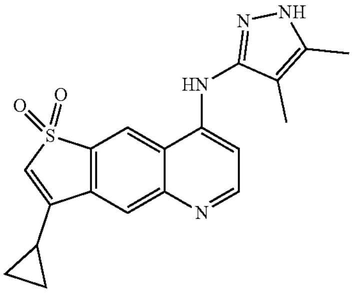
-continued
A97
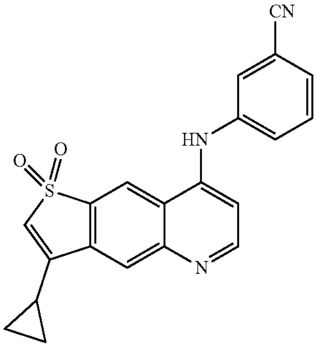
A98
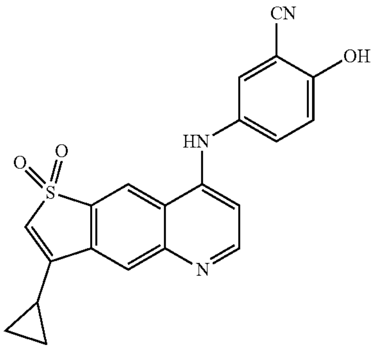
A99
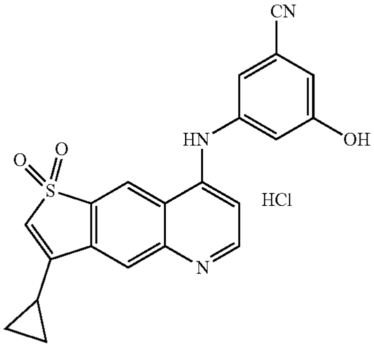
HCl
A100
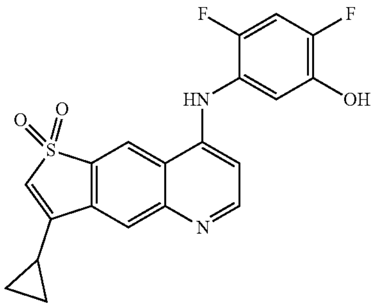

-continued
A101
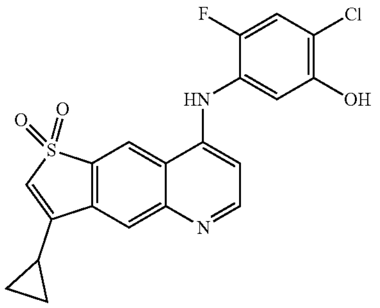
A102
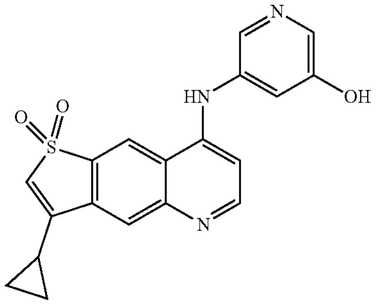
A103
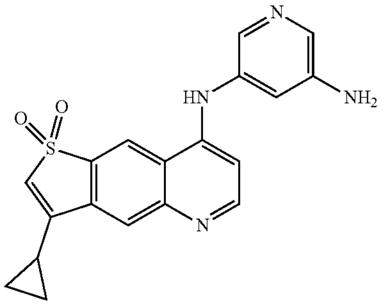
A104
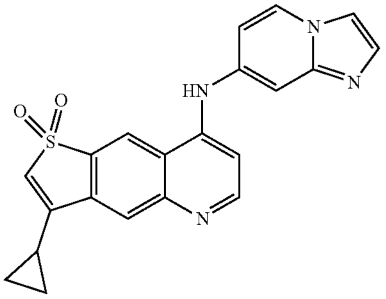
A105
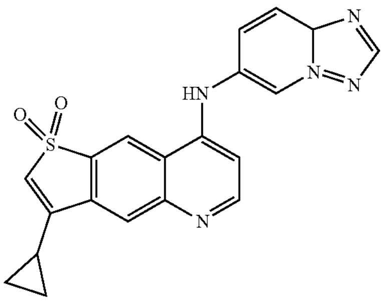
-continued
A106
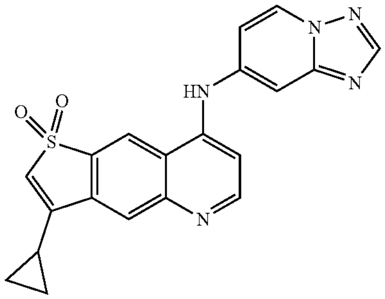
A107
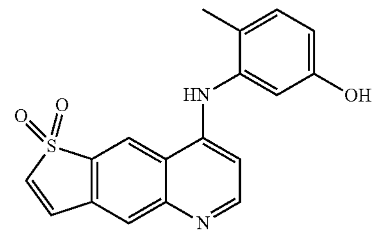
A108
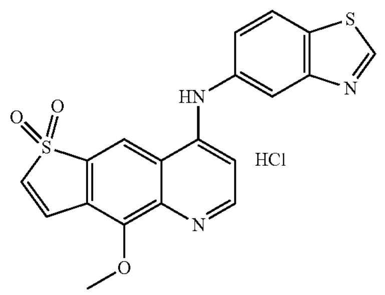
A109
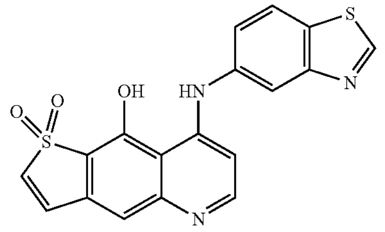
A110
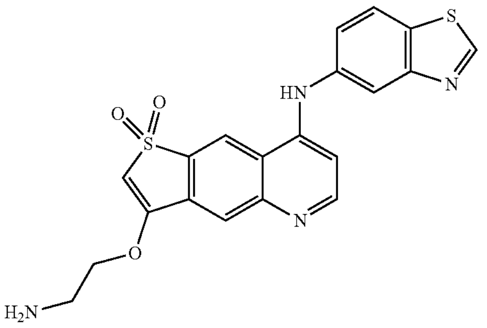

-continued

A111

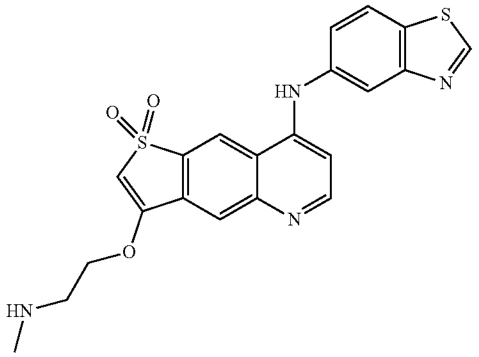

A112

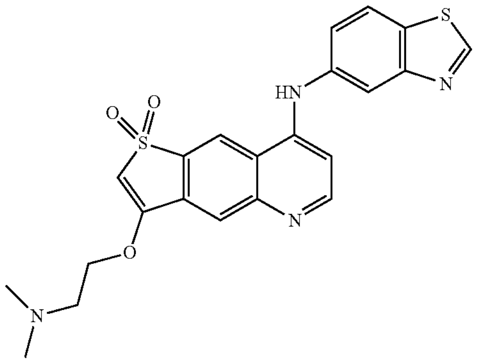

A113

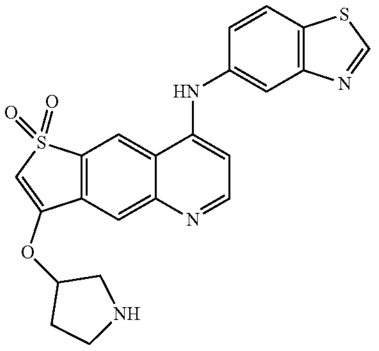

A114

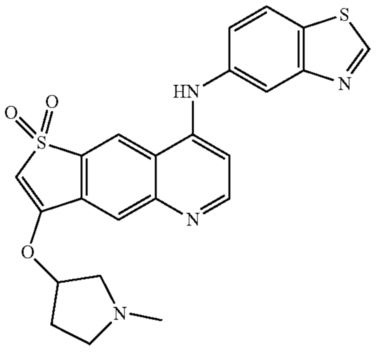

-continued

A115

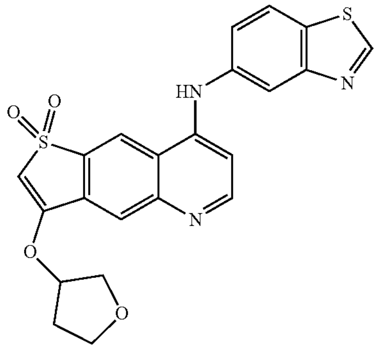

A116

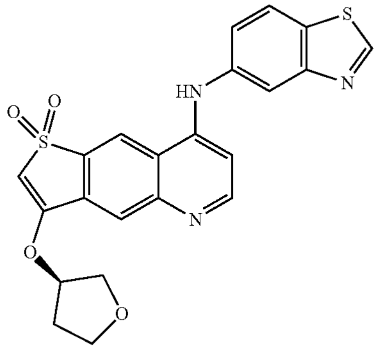

A117

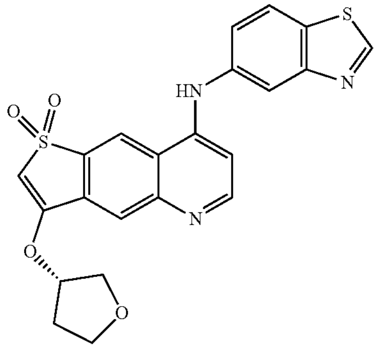

A118

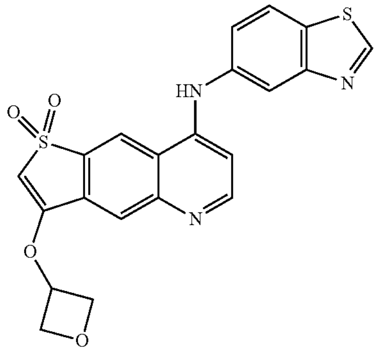

or a pharmaceutically acceptable salt, ester, solvate, prodrug, isotope-labeled derivative, stereoisomer or tautomer thereof.

In some embodiments, the compound of Formula III:

when $R_{7a}$ and $R_{8a}$ together with the carbon they attached to are C=O or C=CH or when $R_{7a}$ and $R_{8a}$ form ring C together with atoms attached to $R_{7a}$ and $R_{8a}$, each of $R_{2a}$ and $R_{3a}$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl, or $R_{2a}$ and $R_{3a}$ forming ring B together with atoms connected to $R_{2a}$ or $R_{3a}$;

or when $R_{2a}$ and $R_{3a}$ form ring B together with atoms connected to $R_{2a}$ or $R_{3a}$, $R_{8a}$ is H, deuterium, halide, amino, —OH, —$CO_2$H, —$CO_2$($C_{1-6}$ alkyl), —CN, $C_{1-6}$ alkyl, $C_{3-6}$ cycloalkyl, 3-6 membered heterocycle comprising 1-3 heteroatoms independently selected from N, O and S, $C_{1-6}$ alkoxy, —NH($C_{1-6}$ alkyl), —N($C_{1-6}$ alkyl)$_2$, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-6}$ alkoxy, $C_{3-6}$ cycloalkyl, $C_{2-6}$ alkenyl and $C_{2-6}$ alkynyl are unsubstituted or substituted with 1 to 3 groups independently selected from —OH, $C_{1-3}$ alkoxy, cyclopropyl, halide and deuterium, or $R_{8a}$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_{10a}$ groups.

In some embodiments, the compound of Formula III has ring A selected from the group consisting of:

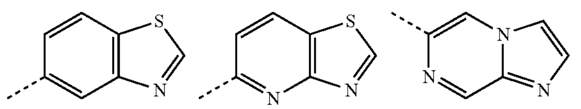
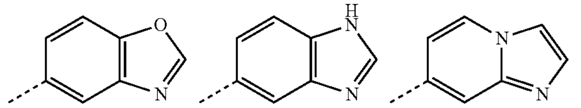
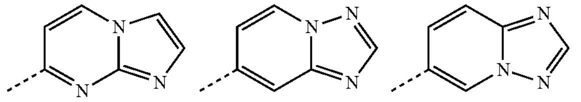
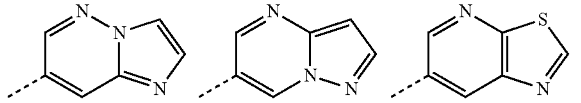
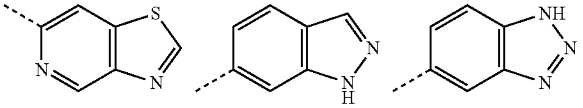
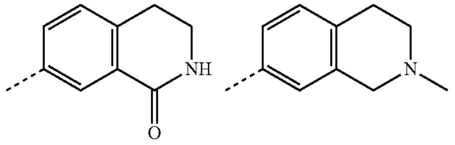
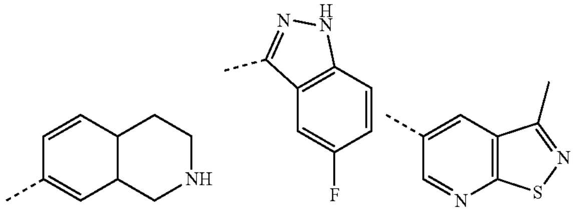
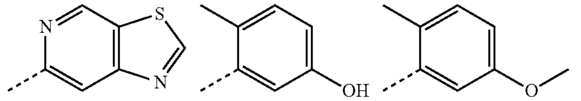

-continued

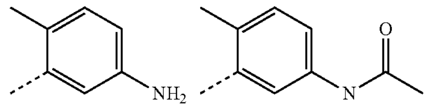
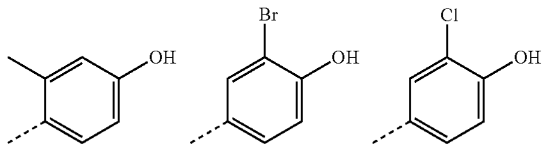
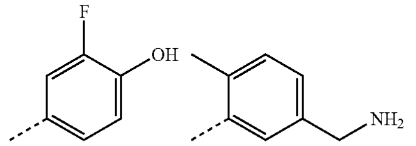
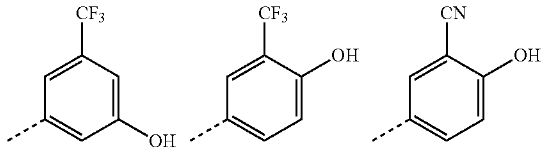
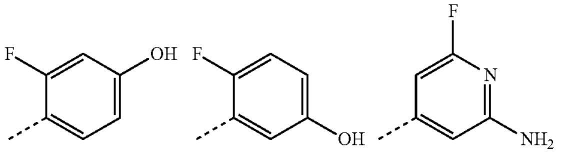
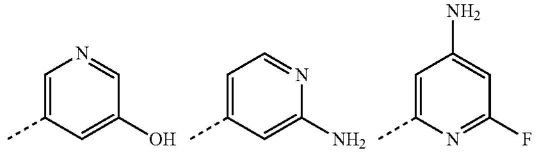
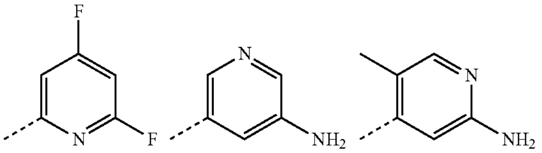
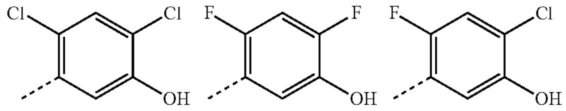
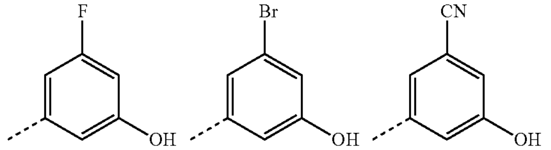
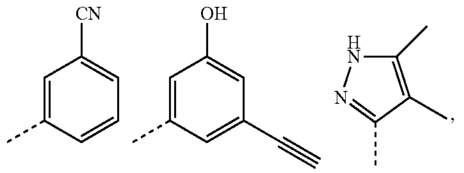

ring A is unsubstituted or substituted with 1 to 3 groups independently selected from deuterium, halide, —OH, $C_{1-3}$ alkyl and $C_{1-3}$ alkoxy.

In some embodiments, the compound of Formula III is selected from the group consisting of:
B1
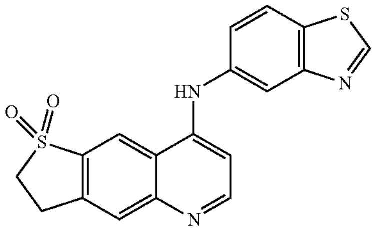
B2
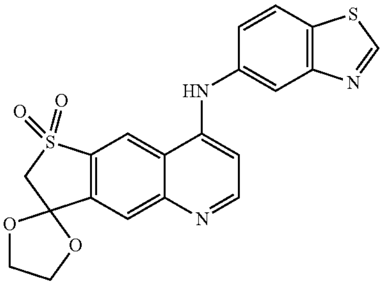
B3
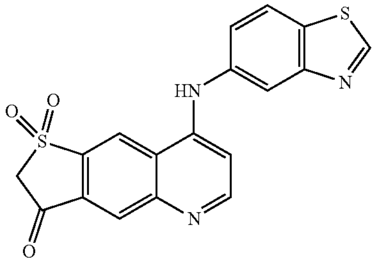
B4
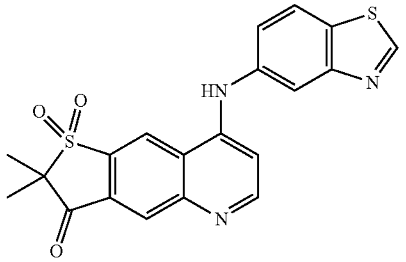
B5
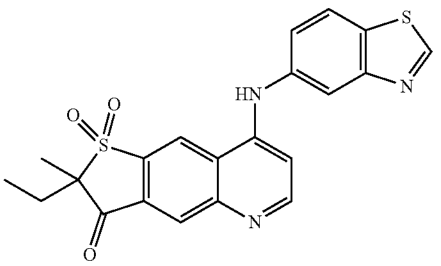
-continued
B6
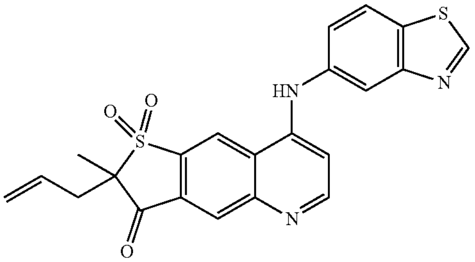
B7
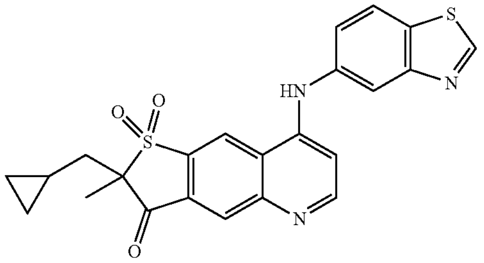
B7
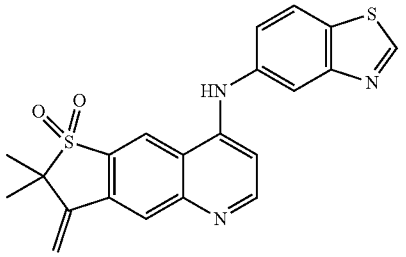
B9
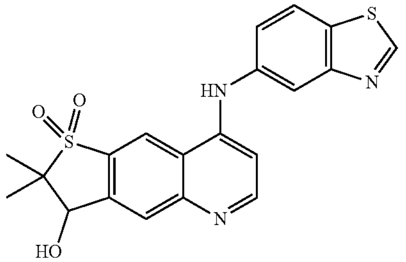
B10
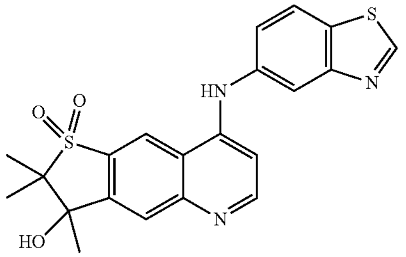
B11
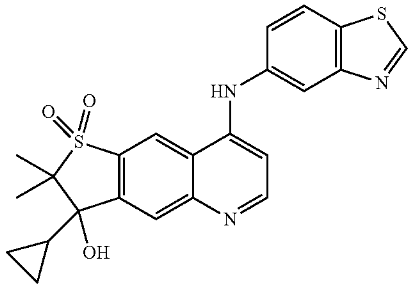

-continued
B12
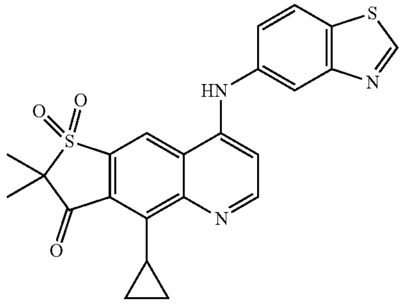
B13
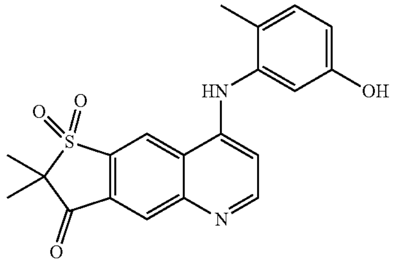
B14
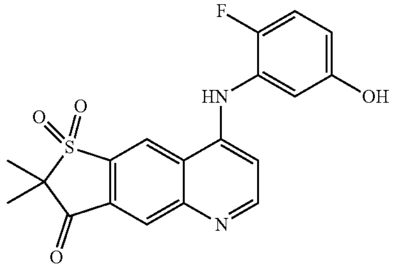
B15
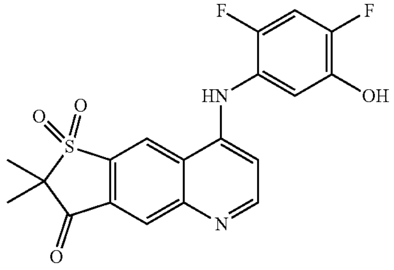
B16
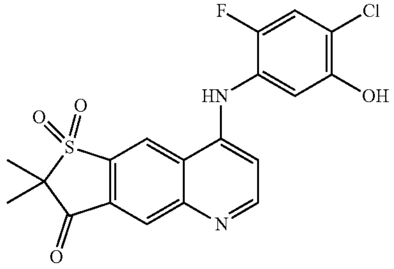
-continued
B17
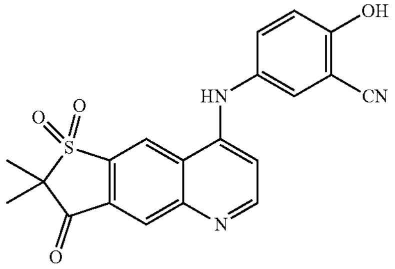
B18
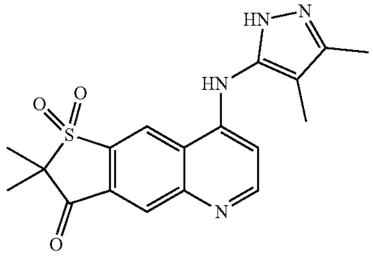
B19
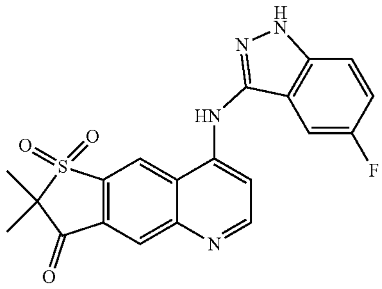
B21
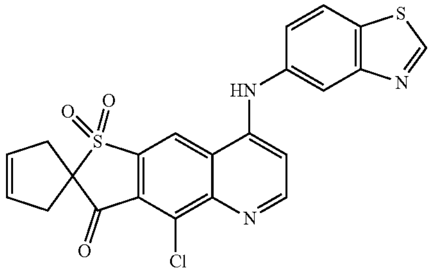
B22
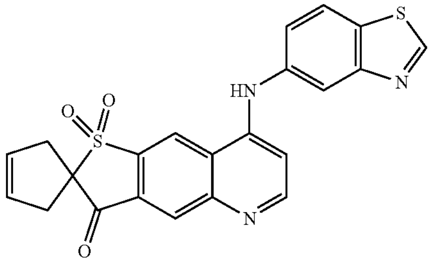

-continued

B23

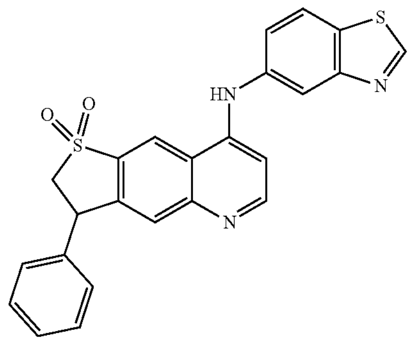

B24

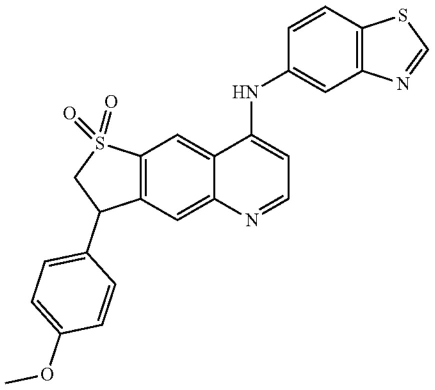

B25

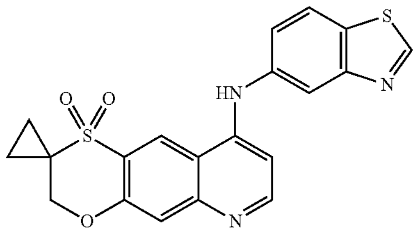

B26

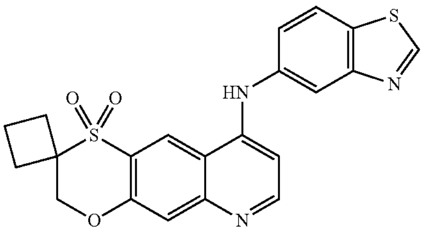

B27

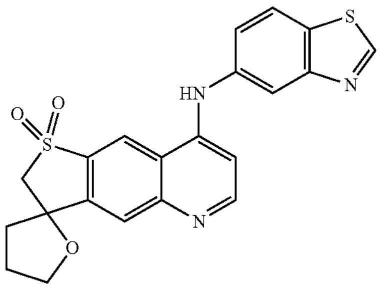

-continued

B28

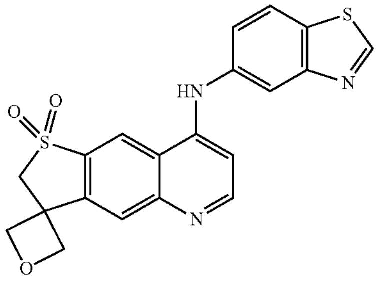

B29

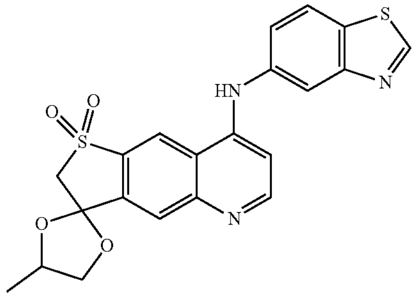

or a pharmaceutically acceptable salt, ester, solvate, prodrug, isotope-labeled derivative, stereoisomer or tautomer thereof.

In some embodiments, the compound of Formulas I, II and III: X is N.

Another aspect of the present disclosure provides a pharmaceutical composition comprising a therapeutically effective amount of a compound of any one of Formulas I, II and III or any compound disclosed herein or a pharmaceutically acceptable salt, ester, solvate, prodrug, isotope-labeled derivative, stereoisomer or tautomer thereof, and a pharmaceutically acceptable carrier.

Still another aspect of the present disclosure provides a composition comprising: (i) a compound of any one of Formulas I, II and III or any compound disclosed herein or a pharmaceutically acceptable salt, ester, solvate, prodrug, isotope-labeled derivative, stereoisomer or tautomer thereof; and (ii) at least one additional therapeutic agent selected from the group consisting of anti-tumor agent, agent treating autoimmune disease, anti-neurodegenerative agent, agent treating metabolic disease, and anti-aging agent.

Another aspect of the present disclosure provides a composition comprising: (i) a pharmaceutical composition comprising a therapeutically effective amount of a compound of any one of Formulas I, II and III or any compound disclosed herein or a pharmaceutically acceptable salt, ester, solvate, prodrug, isotope-labeled derivative, stereoisomer or tautomer thereof, and a pharmaceutically acceptable carrier; and (ii) at least one additional therapeutic agent selected from the group consisting of anti-tumor agent, agent treating autoimmune disease, anti-neurodegenerative agent, agent treating metabolic disease, and anti-aging agent.

Still another aspect of the present disclosure provides a method for treating a disease or disorder associated with programmed necrosis pathway in a mammal suffering therefrom, comprising administering to the mammal a therapeutically effective amount of at a compound of any one of Formulas I, II and III or any compound disclosed herein or a pharmaceutically acceptable salt, ester, solvate, prodrug, isotope-labeled derivative, stereoisomer or tautomer thereof, or a pharmaceutical composition thereof, wherein the cell death-related disorder is systematic inflammatory response, autoimmune diseases, tumor, cancer, metabolic diseases or neurodegenerative diseases.

Another aspect of the present disclosure provides a method for treating a disease or disorder associated with programmed necrosis pathway in a mammal suffering therefrom, comprising administering to the mammal a therapeutically effective amount of at a compound of any one of Formulas I, II and III or any compound disclosed herein or a pharmaceutically acceptable salt, ester, solvate, prodrug, isotope-labeled derivative, stereoisomer or tautomer thereof, or a pharmaceutical composition thereof, wherein the cell death-related disorder is uveitis, dermatitis, acute lung injury, type 2 diabetes mellitus, arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, alcohol steatohepatitis, autoimmune hepatitis, asthma, graft versus host disease, systemic lupus erythematosus, sarcoidosis, Blau syndrome/early-onset sarcoidosis, Wegener's granulomatosis, interstitial lung disease, lung fibrosis, kidney fibrosis, liver fibrosis, myocardial infarction, hypersensitivity pneumonitis, ankylosing spondylitis, multiple sclerosis, systemic sclerosis, polymyositis, rheumatoid arthritis, myasthenia gravis, type 1 diabetes, glomerulonephritis, autoimmune thyroiditis, transplant rejection, Crohn's disease, scleroderma, psoriasis, dermatitis, retinitis pigmentosa, proliferative vitreoretinopathy, Best vitelliform macular dystrophy, eczema, urticaria, vasculitis, eosinophilic fasciitis, wet age-related macular degeneration, dry age-related macular degeneration, diabetic retinopathy, retinopathy of prematurity (ROP), diabetic macular edema, uveitis, retinal vein occlusion, cystoid macular edema, glaucoma, Parkinson's disease, Alzheimer's disease, Huntington's disease, breast cancer, lung cancer, bladder cancer, pancreatic cancer, liver cancer, head and neck squamous cell carcinoma, thyroid cancer, sarcoma, osteosarcoma, desmoid tumor, melanoma, prostate cancer, colorectal cancer, ovarian cancer, cervical cancer, esophageal cancer, gastric cancer, myeloma, lymphoma, mantle cell lymphoma, cutaneous T-cell lymphoma, chronic and non-progressive anemia, primary or essential thrombocythemia, leukemia, acute leukemia, chronic leukemia, lymphocytic leukemia, myeloid leukemia, myelodysplastic syndrome, myeloproliferative disorder, brain tumor, astrocytoma, medulloblastoma, Schwannomor, primitive neuroectodermal tumor, or pituitary tumor Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
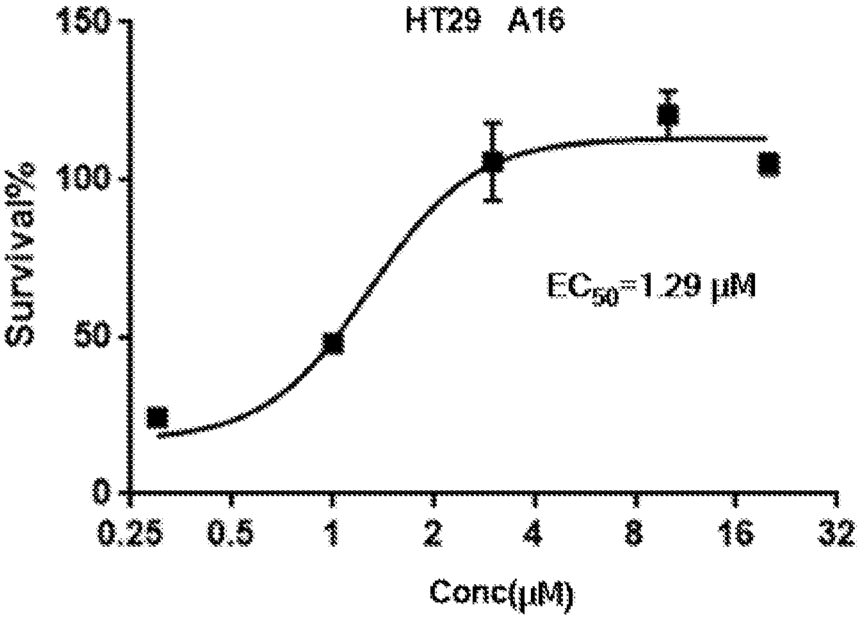
FIG. 1 depicts the inhibition of TNF-α induced-necrosis in HT-29 cells by compound A16.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/− 15%, 10%, 9%, 8%, 7%, 6%, 5%, 4%, 3%, 2%, or 1% of the designated amount.

The term "halogen" or "halide" as used herein generally refers to fluorine, chlorine, bromine, and iodine. The term "haloalkyl" as used herein generally refers to an alkyl group that is substituted with one or more independently chosen halogens (e.g., "$C_1$-$C_6$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

The term “alkyl” as used herein generally refers to a straight or branched chain saturated aliphatic hydrocarbon. Alkyl groups include groups having from 1 to 8 carbon atoms ($C_{1-8}$ alkyl), from 1 to 6 carbon atoms ($C_{1-6}$ alkyl) and from 1 to 4 carbon atoms ($C_1$-$C_4$ alkyl), including, for example, methyl, ethyl, propyl, isopropyl, n-butyl, sec-butyl, isobutyl, tert-butyl, pentyl, 2-pentyl, 3-pentyl, 2-methyl-2-butyl, 3-methyl-2-butyl, 3-methyl-1-butyl, 2-methyl-1-butyl, hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3,-dimethyl-2-butyl. In some instances, a substituent of an alkyl group is specifically indicated. For example, “cyanoalkyl” refers to an alkyl group substituted with at least one cyano substituent. In some embodiments, $C_{1-10}$ alkyl is, preferably, methyl, ethyl, n-propyl, isopropyl or tert-butyl.

The term “alkenyl” as used herein generally refers to straight or branched chain alkene groups, which comprise at least one unsaturated carbon-carbon double bond. Alkenyl groups include $C_{2-8}$ alkenyl, $C_{2-6}$ alkenyl and $C_{2-4}$ alkenyl groups, which have from 2 to 8, 2 to 6 or 2 to 4 carbon atoms, respectively, including, for example, ethenyl, allyl or isopropenyl. The term “alkynyl” as used herein generally refers to straight or branched chain alkyne groups, which have one or more unsaturated carbon-carbon bonds, at least one of which is a triple bond. Alkynyl groups include $C_{2-8}$ alkynyl, $C_{2-6}$ alkynyl and $C_{2-4}$ alkynyl groups, which have from 2 to 8, 2 to 6 or 2 to 4 carbon atoms, respectively.

The term “alkoxy” as used herein generally refers to an alkyl group as described above attached via an oxygen bridge to another chemical moiety. Alkoxy groups include different length of the alkyl groups, such as, for example, $C_{1-6}$ alkoxy and $C_{1-4}$ alkoxy groups, which have from 1 to 6 or from 1 to 4 carbon atoms, respectively. The term “$OC_{1-6}$ alkyl” as used herein generally refers to alkoxy groups include an alkyl group (with 1 to 6 carbon atoms) attached to an oxygen atom. Methoxy, ethoxy, n-propoxy, isopropoxy, n-butoxy, sec-butoxy, isobutoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term “cycloalkyl” as used herein generally refers to a group that comprises one or more saturated rings in which all ring members are carbon. For example, certain cycloalkyl groups are $C_{3-8}$ cycloalkyl, in which the cycloalkyl group contains one or more rings having from 3 to 8 ring members, all of which are carbon, including, for example, cyclopropyl, cyclobutyl, cyclopentyl, cyclohexyl, cycloheptyl, and cyclooctyl. Other example of cycloalkyl group includes adamantyl. Cycloalkyl groups do not comprise an aromatic ring or a heterocyclic ring. The term “cycloalkenyl” as used herein generally refers to a group that comprises one or more unsaturated rings in which all ring members are carbon.

The term “heterocyclic” or “heterocycle” as used herein generally refers to a ring structure containing 3-12 ring atoms (3-12 membered heterocycle), 3-8 ring atoms (3-8 membered heterocycle), 3-6 ring atoms (3-6 membered heterocycle), or 5-6 ring atoms (5-6 membered heterocycle), in which at least one ring atom is carbon and at least one ring atom is heteroatom selected from N, O, and S. A heterocycle can comprise a heteroatom group selected from C(=O), S(=O), and $S(=O)_2$. A heterocyclic group may be aromatic or non-aromatic. Piperidine and oxetane are non-limiting examples of non-aromatic heterocycles. Thiazole and pyridine are non-limiting examples of aromatic heterocycles. Other examples of heterocycle include: aziridinyl, azetidinyl, oxetanyl, pyrrolidinyl, tetrahydrofuranyl, tetrahydrothienyl, piperidinyl, morpholinyl, piperazinyl, thiomorpholinyl, tetrahydropyranyl, 1,1-dioxothiomorpholinyl, butyrolactam, valerolactam, caprolactam, butyrolactone, valerolactone and caprolactone.

“Aryl” refers to an all-carbon monocyclic or fused-ring polycyclic groups of 6 to 12 ($C_{6-12}$ aryl) or 6 to 10 carbon atoms ($C_{6-10}$ aryl) having a completely conjugated pi-electron system. Examples, without limitation, of aryl groups are phenyl, naphthalenyl, tetrahydronaphthyl, indanyl, biphenyl, and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $—NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, combined, a five- or six-membered heteroalicyclic ring. Illustrative substituted alkyl group include, but are not limited to, fluoromethyl, difluoromethyl, trifluoromethyl, aminomethyl, aminoethyl, hydoxymethyl, methoxymethyl, 2-fluoroethyl, and 2-methoxyethyl, etc.

The term “heteroaryl” as used herein generally refers to an aromatic group in which at least one aromatic ring comprises at least one heteroatom selected from N, O and S. Heteroaryls include, for example, 5-12 membered heteroaryls, 5-10 membered heteroaryls, 5-7 membered single ring structures or 7-12 membered double ring structures. The number of heteroatoms in a heteroaryl can be 1, 2, 3, 4, or more. Examples included but are not limited to, thienyl, pyridyl, pyrimidinyl, pyrazinyl, pyrazolyl, pyridazinyl, pyridine-2(1H)-keto, pyridine-4(1H)-keto, pyrrolyl, pyrazolyl, thiazolyl, 1,2,3-triazolyl, 1,2,4-triazolyl, 1,2,5-oxadiazolyl, imidazolyl, furanyl, tetrazolyl, isothiazolyl, oxazolyl, isoxazolyl, thiadiazolyl, oxadiazolyl, naphthyl, benzothienyl, indolyl, benzimidazolyl, benzothiazolyl, benzofuranyl, quinolinyl, isoquinolinyl, and quinazolinyl. The heteroaryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $—NR^XR^Y$, with $R^X$ and $R^Y$ as defined above.

The term “amino” as used herein generally refers to primary amino group ($—NH_2$), secondary amino group (—NH—), and tertiary amino group (  ).

The term “alkylamino” as used herein generally refers to a secondary or tertiary amine that has the general structure $—NH—R^1$ or $—N(R^1)(R^2)$, respectively, wherein $R^1$ and $R^2$ are selected independently from alkyl, cycloalkyl and (cycloalkyl)alkyl groups. Such groups include, but are not limited to, for example, mono- and di-($C_{1-6}$ alkyl)amino groups, in which each $C_{1-6}$ alkyl may be the same or different. It will be apparent that the definition of “alkyl” as used in the term “alkylamino” differs from the definition of "alkyl" used for all other alkyl-containing groups, in the inclusion of cycloalkyl and (cycloalkyl)alkyl groups.

The term "alkylthio" as used herein generally refers to an alkyl-substituted thio group, wherein the term alkyl is as defined above.

The terms "substituent" and "substituted," as used herein, generally denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. A straight chain substituent may be a moiety such as a halogen, alkyl group, haloalkyl group or other group that is covalently bonded to an atom (preferably a carbon or nitrogen atom) that is a member of a straight chain.

The term "bicycloheteroalkyl" as used herein generally refers to a double ring structure which shares one or two atoms and which comprise at least one hetero atom independently selected from the group consisting of N, O, and S in the ring. The term "bicycloheteroalkylene" as used herein generally refers to a di-radical of bicycloheteroalkyl group, which may bind to two other groups.

The term "cycloalkylamine" as used herein generally refers to either a ring structure with an amino group attached to a carbon atom in the ring or a ring structure with a nitrogen atom as member of the ring.

The term "cycloalkylamide" as used herein generally refers to either a ring structure with an amid group attached to a carbon atom in the ring via the amide carbon or a ring structure with both the amide nitrogen and amide carbon atoms becoming members of the ring.

The term "cyclourea" as used herein generally refers to a ring structure with the urea carbon and both urea nitrogen atoms becoming members of the ring. One example of cyclourea is oxoimidazolidine.

The term "pharmaceutically acceptable" as used herein generally refers to a form of the compound that is safe for administration to a subject. For example, a free base, a salt form, a solvate, a hydrate, a prodrug or derivative form of a compound of any one of Formulas I, II and III, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas I, II or III are the pharmaceutically acceptable salt forms of the free-base compounds. The term "pharmaceutically-acceptable salts" as used herein generally refers to salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. For example, Berge et al. describes pharmaceutically acceptable salts in detail in Pharmaceutical Sciences (1977) 66: 1-19. Pharmaceutically acceptable salts of the compounds provided herein include those derived from suitable inorganic and organic acids and bases. Inorganic acids from which salts can be derived include, but are not limited to, hydrochloric acid, hydrobromic acid, sulfuric acid, nitric acid, phosphoric acid, and the like. Organic acids from which salts can be derived include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and other amine salt. Inorganic bases from which salts can be derived include, but are not limited to, sodium, potassium, lithium, ammonium, calcium, magnesium, iron, zinc, copper, manganese, aluminum, and the like. Organic bases from which salts can be derived include, but are not limited to, primary, secondary, and tertiary amines, substituted amines, including naturally occurring substituted amines, cyclic amines, basic ion exchange resins, and the like, examples include, but are not limited to, isopropylamine, trimethylamine, diethylamine, triethylamine, tripropylamine, and ethanolamine. In some embodiments, the pharmaceutically acceptable base addition salt is ammonium, potassium, sodium, calcium, or magnesium salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e., two counterions) and higher salts (e.g., three or more counterions) are encompassed within the meaning of pharmaceutically acceptable salts.

As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Other solvates include, but are not limited to, methanol, ethanol, isopropanol, ethyl acetate, tetrahydrofuran, dimethyl sulfoxide, and N,N-dimethylformamide. Pharmaceutically acceptable solvates and hydrates are complexes that, for example, can include 1 to about 100, or 1 to about 10, or one to about 2, 3 or 4, solvent or water molecules.

As used herein, and unless otherwise specified, "prodrug" refers to a compound that can be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis. A discussion of prodrugs is provided in Higuchi, T., et al, "Pro-drugs as Novel Delivery Systems," A. C. S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active Formulas I, II, or III in vivo when such prodrug is administered to a mammalian subject. Prodrugs of an active compound, as described herein, can be prepared by modifying functional groups present in the active Formulas I, II, and III in such a way that the modifications are cleaved, either in routine manipulation or in vivo, to the parent active compound. Prodrugs include compounds wherein a hydroxy, amino or mercapto group is bonded to any group that, when the prodrug of the active Formulas I, II or III is administered to a mammalian subject, cleaves to form a free hydroxy, free amino or free mercapto group, respectively.

The terms "isotope-labelled", "isotope label", "isotope-labelled derivative" and "isotopically labelled" refer to unnatural proportions of atomic isotopes at one or more of atoms that constitute such compounds. For example, the compounds can be radiolabeled with radioactive isotopes, such as, for example, tritium ($^{3}H$), iodine-125 ($^{125}I$), carbon-14 ($^{14}C$). The compounds can also be isotope-lablled with $^{2}H$, $^{11}C$, $^{13}C$, $^{15}N$, $^{17}O$, $^{18}O$, $^{18}F$, $^{32}P$, $^{35}S$, and $^{36}Cl$. Certain isotope-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of compounds of the present disclosure, whether radioactive or not, are encompassed within the scope of the present disclosure.

The term "isomers" as used herein generally refers to different compounds that have the same molecular formula, including any and all geometric isomers and stereoisomers. "Stereoisomers" are isomers that differ only in the way the atoms are arranged in space. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure, unless specified otherwise. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa).

In some embodiments, the compound(s) of Formulas I, II or III is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient" as used herein generally refers to any pharmaceutically acceptable additive, carrier, adjuvant, or other suitable ingredient, other than the active pharmaceutical ingredient (API), which is typically included for formulation and/or administration purposes.

The term "diluent" as used herein generally refers to an agent used as filler in order to achieve the desired composition volume or weight. The diluent may be present in the pharmaceutical composition within granules in the form of a single compound or in the form of a mixture of compounds. Non-limiting examples of diluent include lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

The term "adjuvant," as used herein generally refers to any substance or mixture of substances that increases the efficacy or potency of a compound disclosed herein on a target where the adjuvant is used together with the compound disclosed herein. However, when the adjuvant is used alone, no pharmacological effect is observed on the same target.

The terms "treat", "treating," "treatment," and "therapy" as used herein generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" as used herein generally refers to quantifying the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of Formulas I, II or III, or a stereoisomer, tautomer, hydrate, solvate or pharmaceutically acceptable salt thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of Formulas I, II or III with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention may include the use of at least one compound of Formula I, II or III, which inhibits programmed necrosis in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of programmed necrosis may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

All reagents and solvents were obtained commercially unless stated otherwise. All commercial reagents and solvent were used without purification unless stated otherwise. When required, some reagents and solvents were purified by standard techniques. For example, tetrahydrofuran may be purified by distillation from sodium. All thin-layer chromatography (TLC, GF254) analyses and column purification (100-200 mesh) were performed on silica gel (Qingdao Haiyang Chemical Co. Ltd. or Yantai Chemical Co. Ltd.), using petroleum ether (b.p. 60-90° C.)/ethyl acetate (v/v) as eluent; and spots revealed by UV visualization at 254 nm and $I_2$ vapor or phosphomolybdic acid. All organic layers after extraction were dried over anhydrous $Na_2SO_4$ unless stated otherwise. All nuclear magnetic resonance spectra ($^1H$ NMR) were recorded using a Varian-400 spectrometer at 400 MHz using TMS as an internal standard. LC-MS was run using an Agilent 1100 system with LC-MSDTrap recorder, diode array detector (DAD) with detecting wavelength at 214 nm and 254 nm, and ESI source. The HPCL column is an Agela Durashell C18 3.5 μm 4.6×50 mm column. Gradients were run using 0.1 $NH_4HCO_3$ aqueous solution and acetonitrile with gradient 5/95 to 95/5 in the run time indicated (for example, 5 min), flow rate at 1.8 mL/min.

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent, such as anhydrous $Na_2SO_4$, to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

General Synthetic Routes

The following Methods A-F are embodiments for some general synthetic routes leading to compounds of Formula I, II or III. Detailed reaction conditions for each Method can be found in the examples shown vide infra.

Method AA:

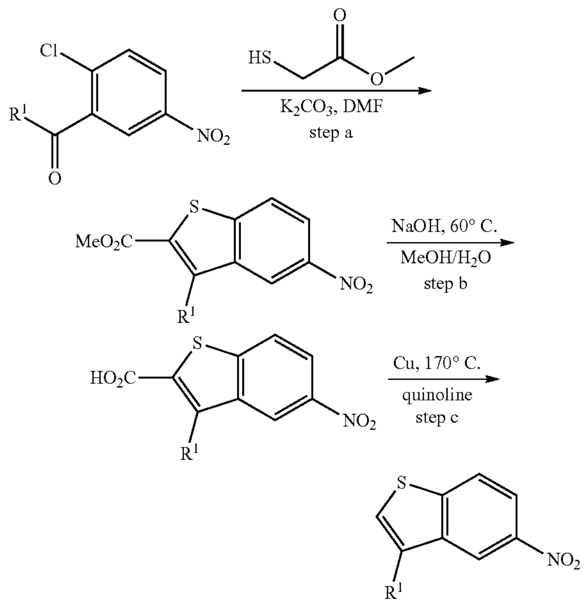

O-chloroaryl ketone or aldehyde was reacted with methyl 2-mercaptoacetate under basic condition to form substituted methyl 5-nitrobenzo[b]thiophene-2-carboxylate. Standard saponification resulted in a carboxylic acid (step b), which was subsequently decarboxylated with copper powder to give the desired product (step c).

Method AB:

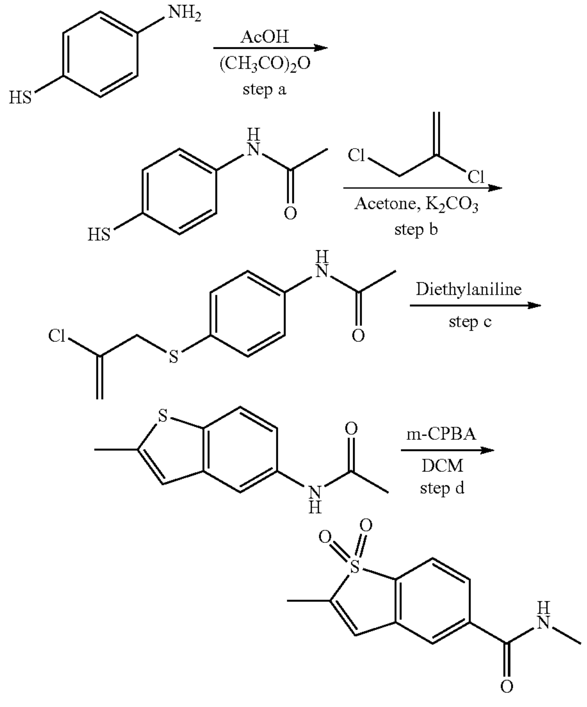

The intermediate N-(4-((2-chloroallyl)thio)phenyl)acetamide was obtaind by acetylation (step a) and alkylation (step b). Thiophene ring was made via [3,3] rearrangement. Oxidation of sulfur-containing ring via m-CPBA yielded the final product (step d).

Method AC:

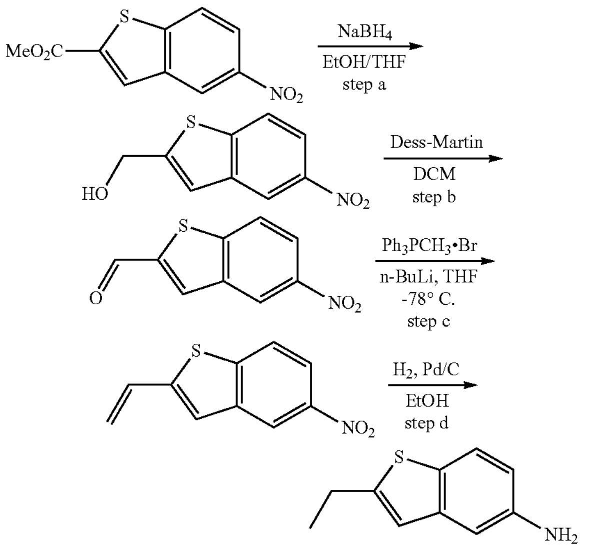

The ester of starting material was reduced to alcohol with $NaBH_4$ (step a). The alcohol was oxidized to aldehyde by Dess-Martin reagent (step b). Treatment of the aldehyde with methyltriphenylphosphonium bromide was yielded olefin containing intermediate (step c). The olefin containing intermediate was reduced with $H_2$, Pd/C to form the desired product (step d).

Method AD:

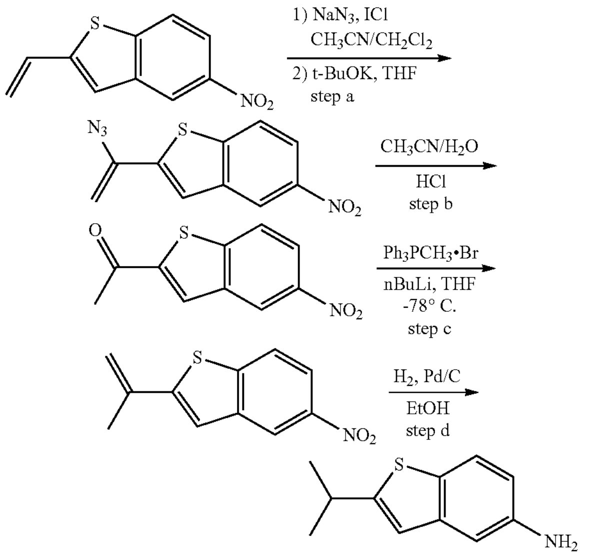

The target compound was synthesized from 5-nitro-2-vinylbenzo[b]thiophene. Alkene azide was obtained from olefin through addition reaction with $NaN_3$, ICl and elimination reaction with t-BuOK (step a). Then the ketone was obtaineded under acidic condition (step b). Treatment of the ketone with methyltriphenylphosphonium bromide yielded olefin contained intermediate via Suzuki reaction (step c). The olefin contained intermediate was reduced with $H_2$, Pd/C to form the desired product (step d).

Method AE:

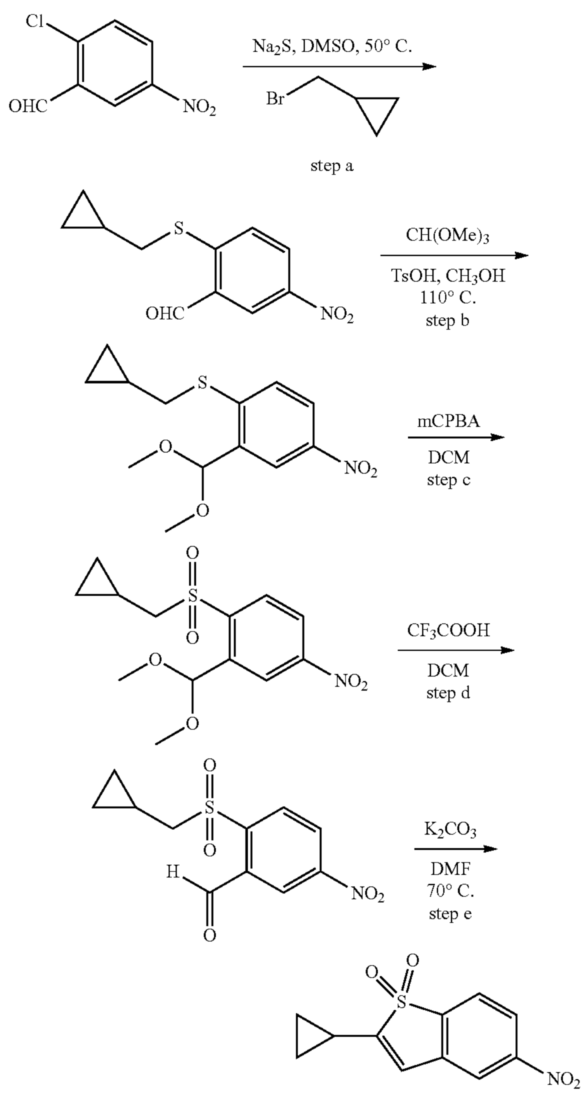

2-Chloro-5-nitrobenzaldehyde reacted with $Na_2S$ and (bromomethyl)cyclopropane to give the sulfide intermediate (step a). The aldehyde was protected as an acetal (step b) followed by oxidation via m-CPBA (step c). De-protection under TFA provided the aldehyde (step d). The final product was achieved via cyclization in the presence of $K_2CO_3$ (step e).

Method AF:

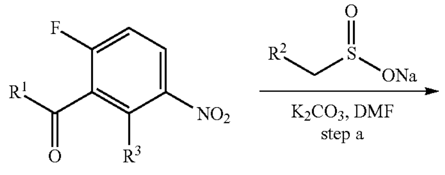

-continued

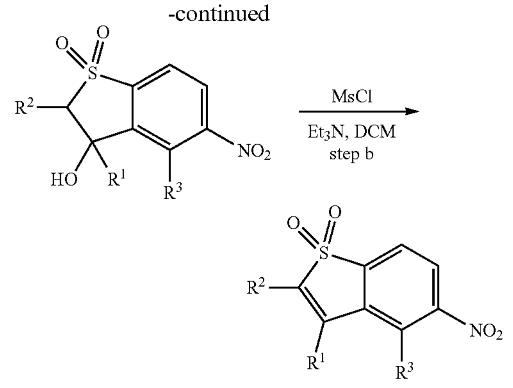

The final product was achieved by cyclization with sodium alkyl sulfonate under basic condition (step a). Followed by elimination reaction (step b).

Method AG:

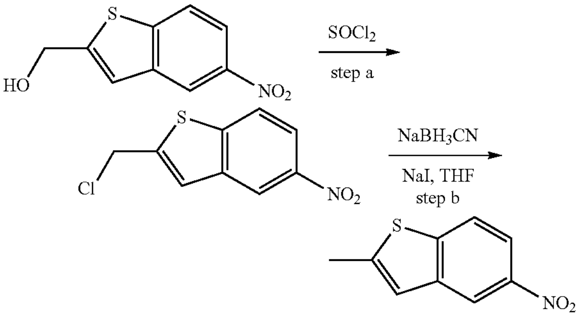

The hydroxyl was substituted with chlorine by reacting with $SOCl_2$ (step a). The chlorine contained intermediate was reduced by $NaBH_3CN$ to form the desired product (step b).

Method AH:

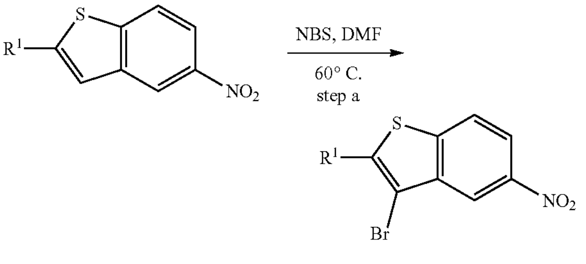

The final product was achieved by bromination with NBS (step a).

Method AI:

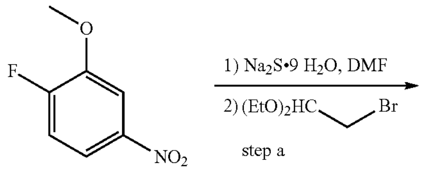

-continued

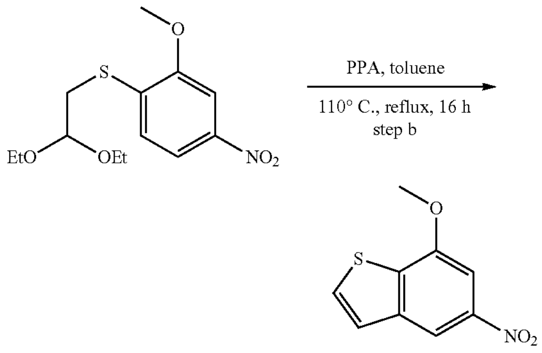

1-Fluoro-2-methoxy-4-nitrobenzene was reacted with $Na_2S$, 2-bromo-1,1-diethoxyethane to give the sulfide intermediate (step a) followed by cyclization with PPA to form the desired product (step b).

Method AJ:

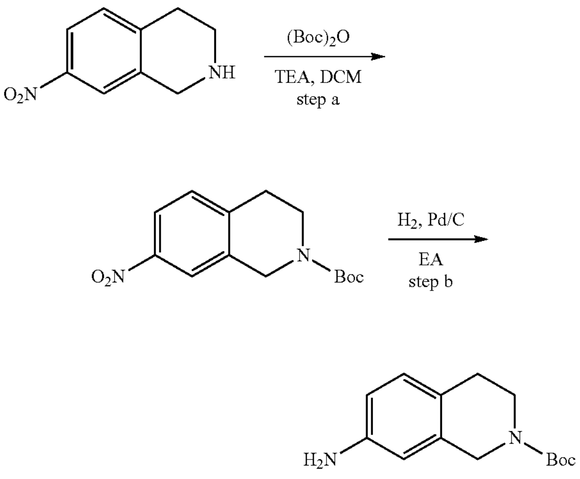

The amino group was protected by $(Boc)_2O$ (step a). Then the nitro group was reduced to amine with iron powder to form the desired product (step b).

Method AK:

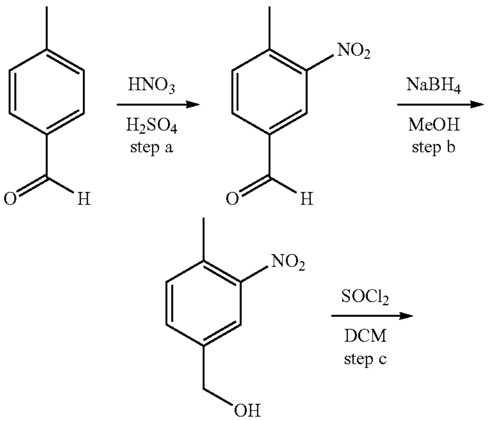

-continued

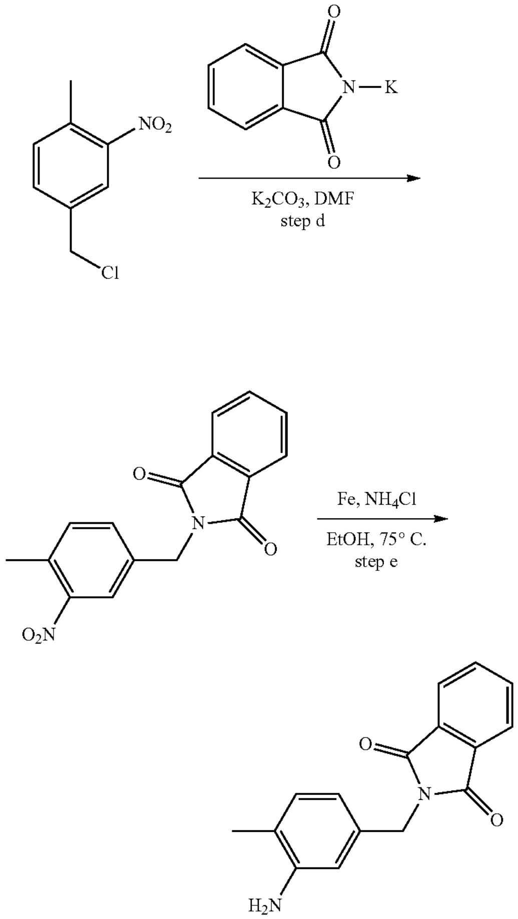

The desired compound was synthesized from 4-methylbenzaldehyde under nitration reaction with $HNO_3$, $H_2SO_4$ (step a) followed by reduction reaction with $NaBH_4$ (step b). Alcohol group was chlorinated with $SOCl_2$ (step c). Then displacement of chlorine with potassium 1,3-dioxoisoindolin-2-ide formed a protected amino contained intermediate (step d). Nitro group was reduced to an amino group with Fe, $NH_4Cl$ (step e).

Method AL:

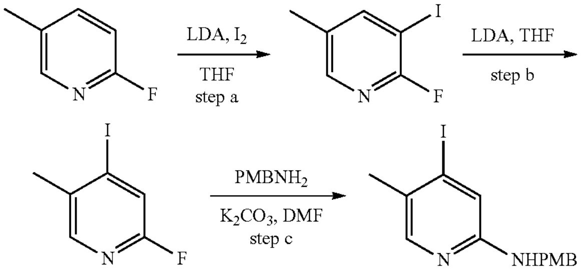

2-Fluoro-5-methylpyridine was reacted with $I_2$, LDA (step a) followed by halogen jumping reaction to form a 4-subsitited iodopyridine (step b). Fluorine of the pyridine core was substituted by $PMBNH_2$ under basic condition (step c) to form the desired compound.

Method AM:

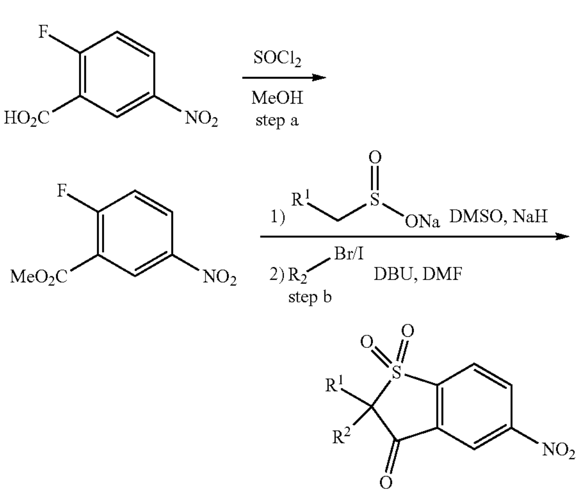

Esterification reaction with $SOCl_2$, MeOH provided substituted methyl benzoate (step a). The fluorobenzene was reacted with sodium sulfonate and NaH to form a ring and then reacted with alkyl halide to form the desired product (step b).

Method AN:

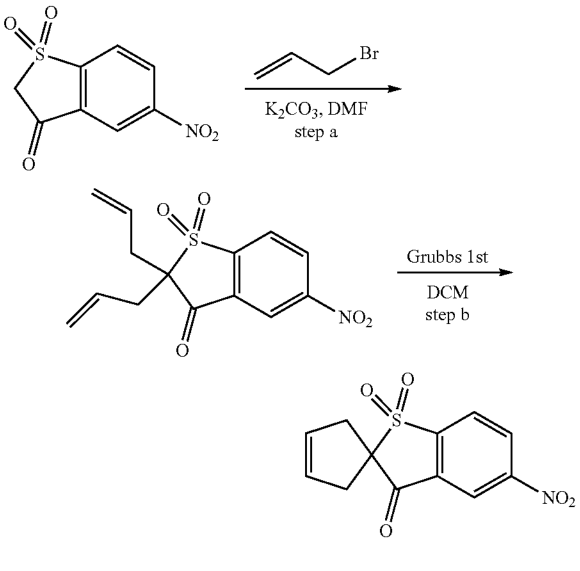

The desired product was achieved via substitution reaction with allyl bromide (step a) and Ring-Closing Metathesis (RCM) cyclization with Grubbs 1st catalyst (step b).

Method AO:

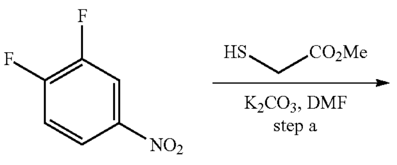

-continued

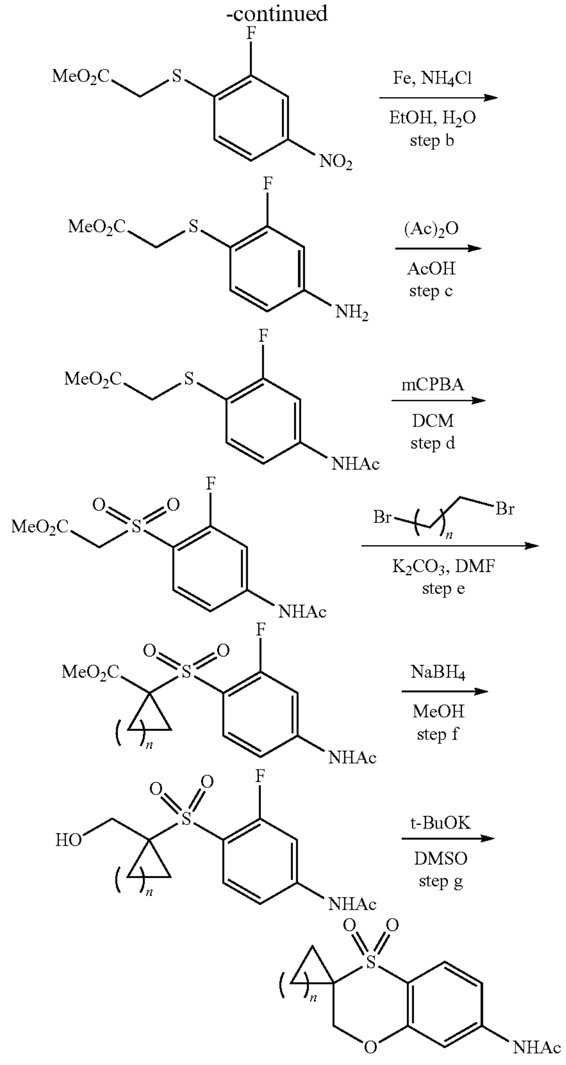

The starting material was reacted with methyl 2-sulfanylacetate (step a). Nitro group was reduced to amino group with Fe, $NH_4Cl$ (step b) then the amino group was protected by acetyl (step c). Sulfur atom was oxidized with m-CPBA (step d). Ring was made by double substitution reaction with dibromoalkane (step e). The ester group was reduced to alcohol with $NaBH_4$ (step f) followed by intramolecular cyclization to form the desired product (step g).

Method AP:

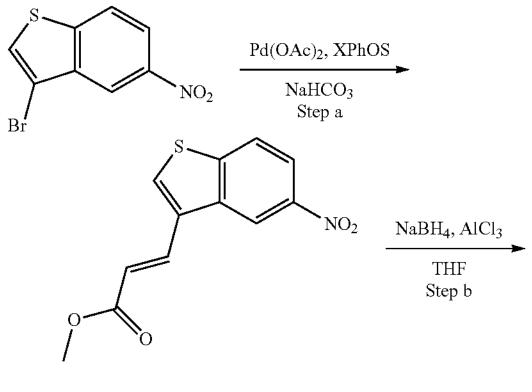

-continued
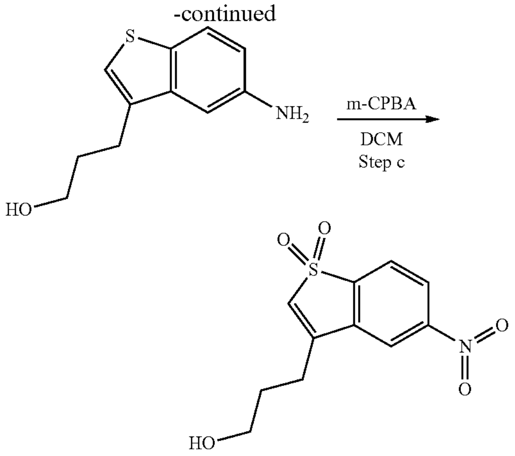
Palladium catalyzed coupling of starting material with methyl acrylate provided methyl (E)-3-(5-nitrobenzo[b]thiophen-3-yl)acrylate (step a). Both of the nitro and the ester groups were reduced by combination of $NaBH_4$ and $AlCl_3$ to provide primary alcohol (step b). Conversion of the amino to nitro and the sulfur to sulfone was done by m-CPBA (step c).
Method BA, BB:
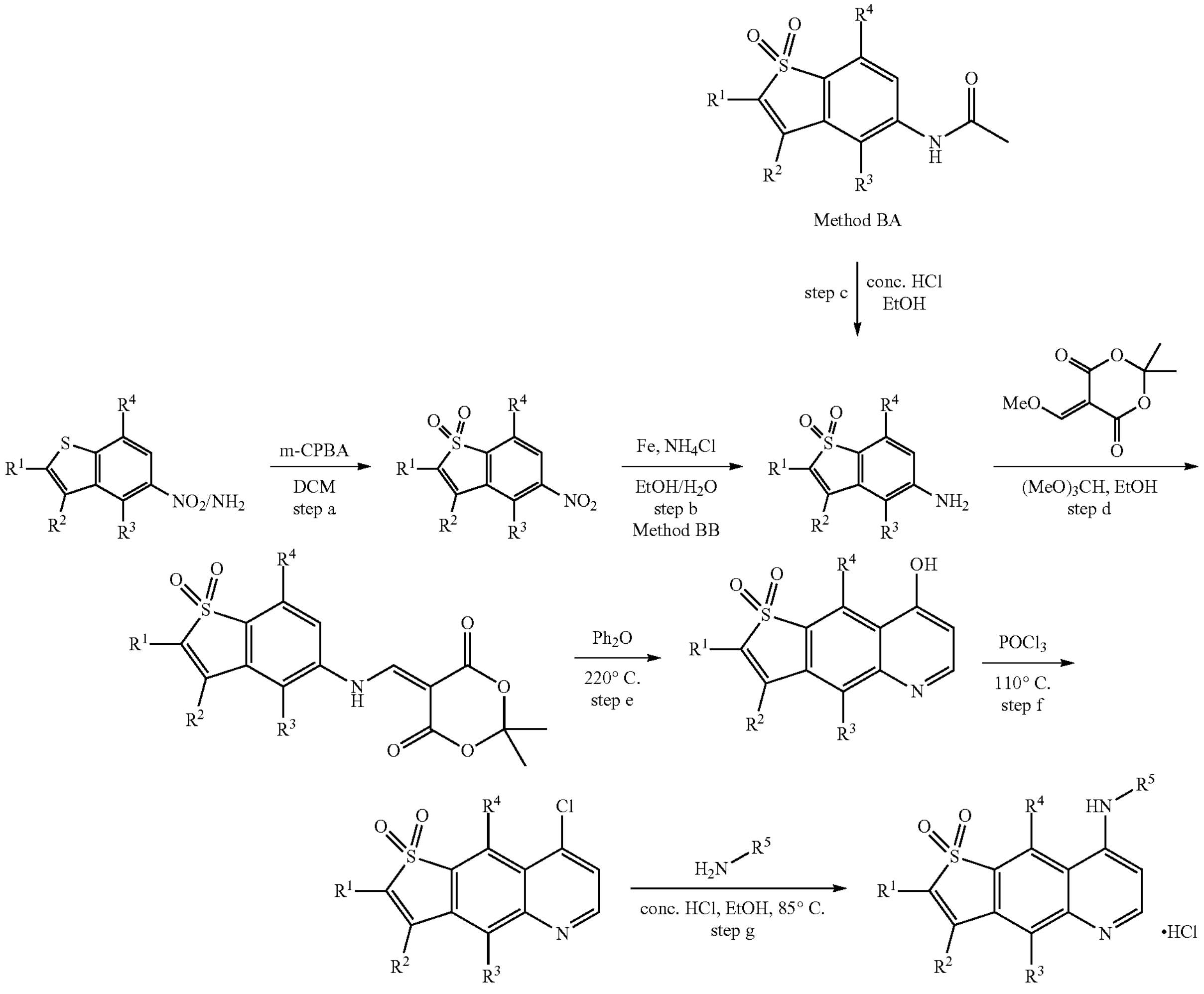

Substituted 5-aminobenzo[b]thiophene 1,1-dioxide was obtained through oxidizing sulfur atom of the thiophene ring by m-CPBA (step a) followed by converting nitro group to amino group by reduction (step b) or de-acetylation (step c) Amino group reacted with 5-(methoxymethylene)-2,2-dimethyl-1,3-dioxane-4,6-dione (step d) followed by cyclization reaction to form a pyridine ring under high temperature (step e). Chlorination with $POCl_3$ provided chlorinated heterocycle (step f), which reacted with aromatic amine to form the final product (step g).

Method BC:

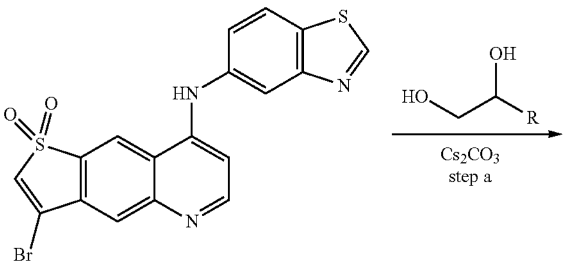

-continued

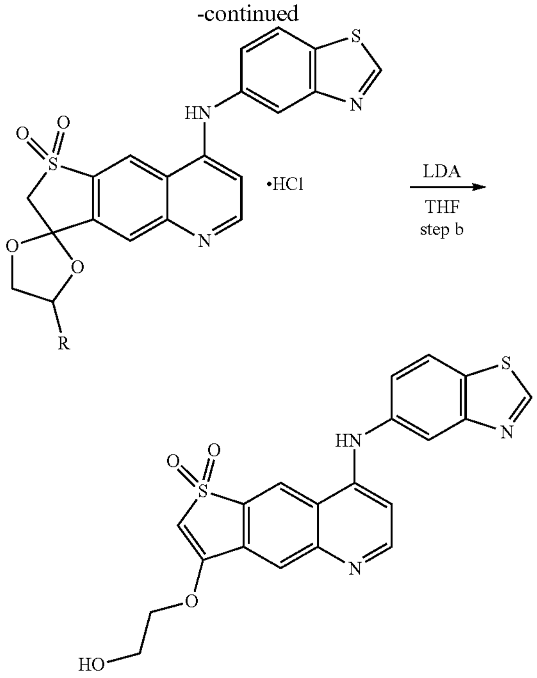

The desired compound was obtained through Michael addition reaction with ethylene glycol (step a) and ring opening under basic condition (step b).

Method BD, BE:

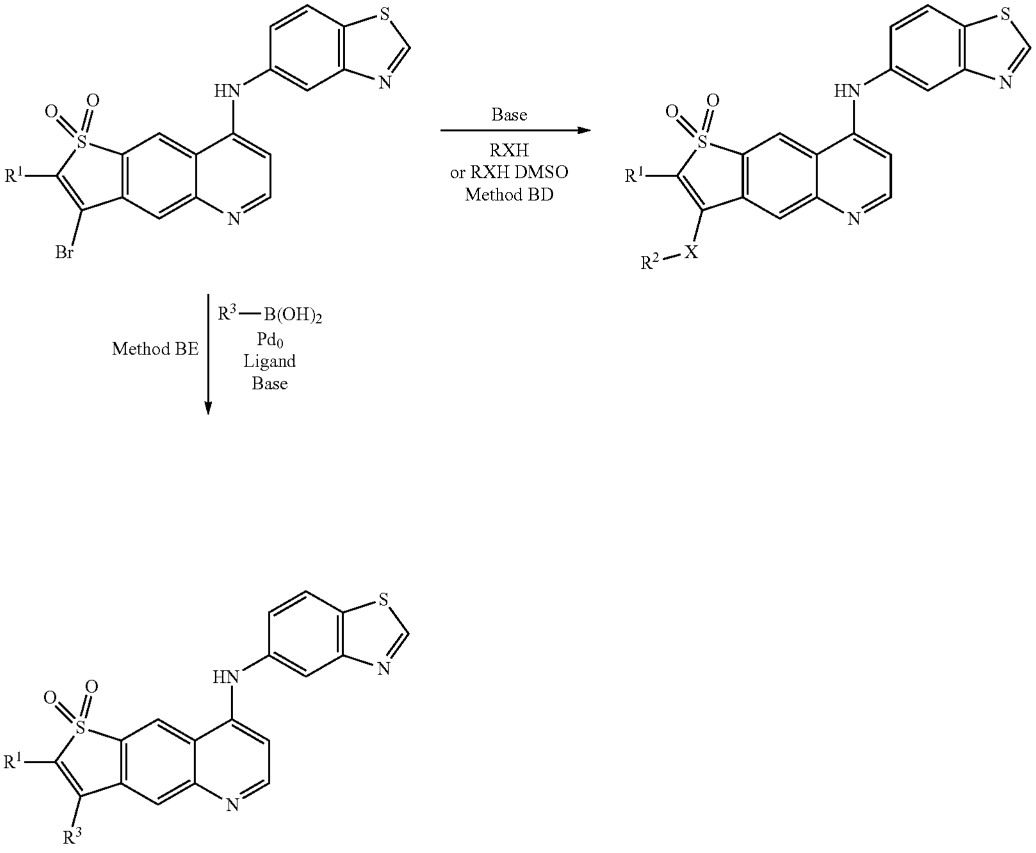

The starting material reacted with alcohol or amine under basic conditions (method BD) or a palladium catalyzed coupling with arylboronic acid to provide the desired product (method BE), respectively.

Method BF:

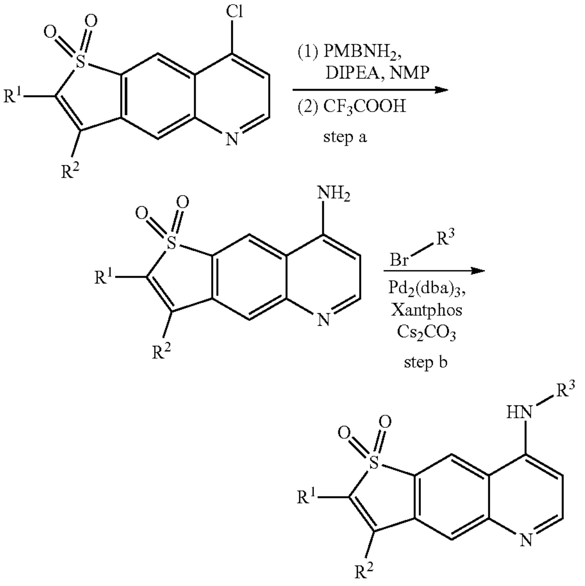

The starting material reacted with $PMBNH_2$ followed by deprotection with TFA (step a) to provide the amino group. Then the amino contained intermediate reacted with aryl halide through Buchwald reaction (step b) to form the desired product.

Method BG:

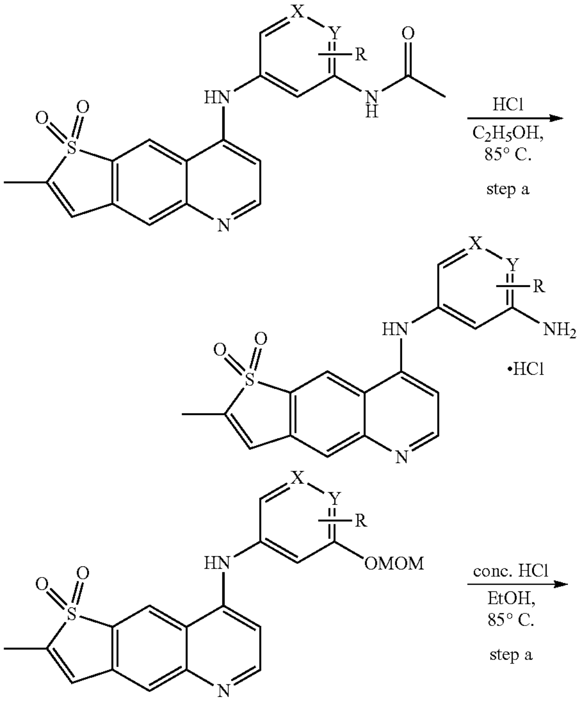

-continued

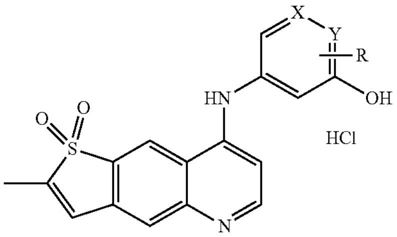

Protected alcohol or amine could be treated with conc. HCl to remove the Acetyl or MOM group to form the desired product (step a).

Method BH:

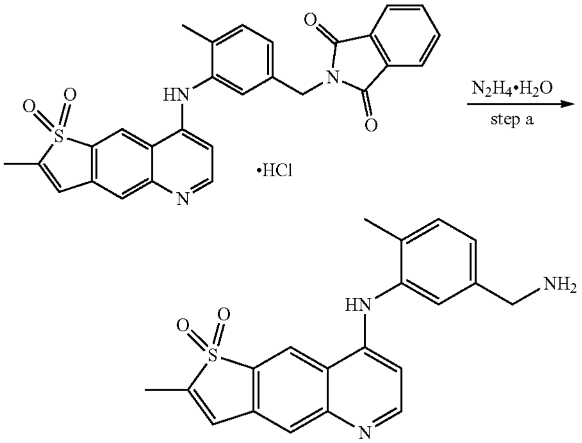

The target was obtained through hydrazinolysis reaction (step a).

Method BI:

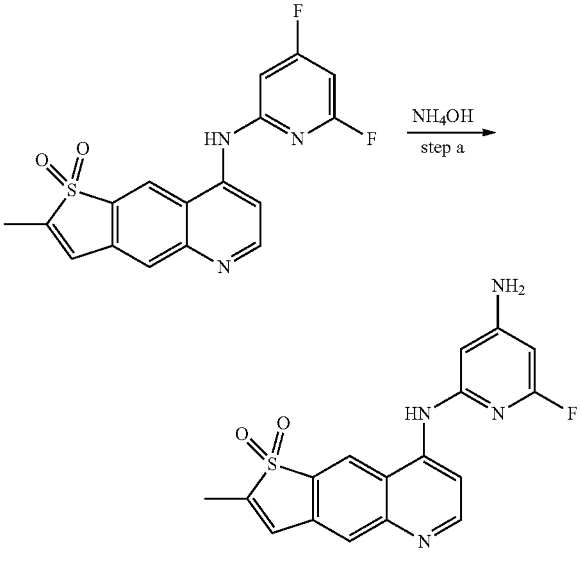

2,4-Difluoropyridine intermediate reacted with hydrazine hydrate to form the desired amino product (step a).

Method BJ:

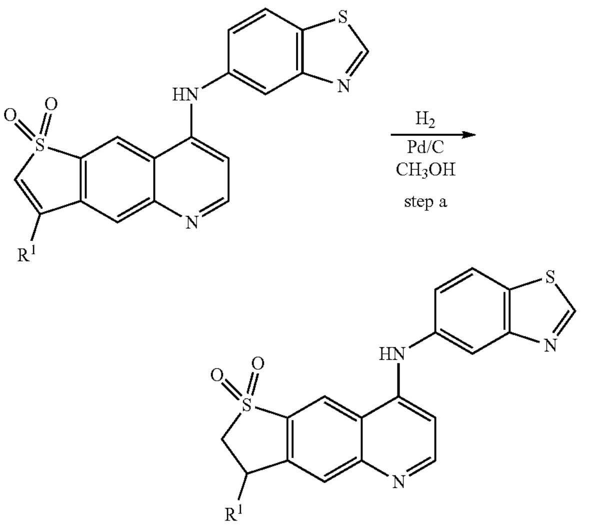

The alkene of the starting material was reduced by $H_2$, Pd/C to form the final product (step a).

Method BK:

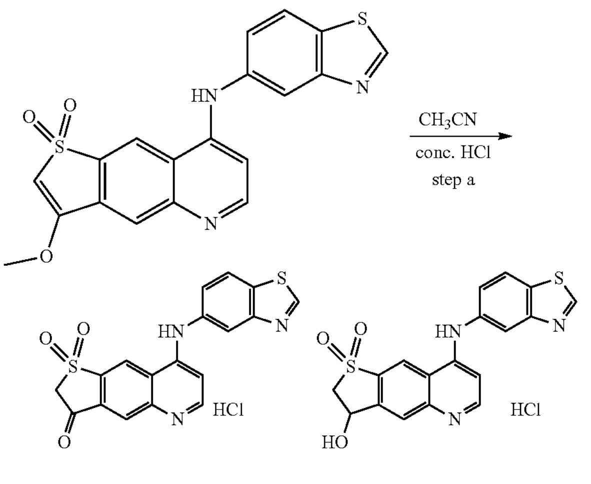

The final compound was obtained through hydrolysis reaction under acidic condition (step a).

Method BL:

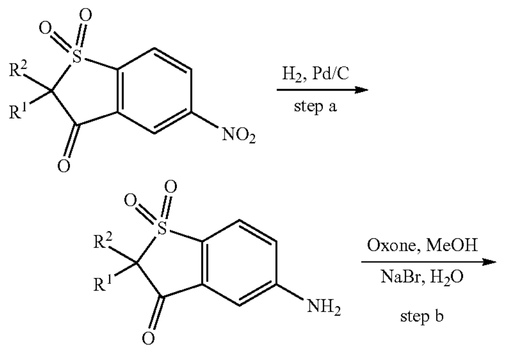

-continued

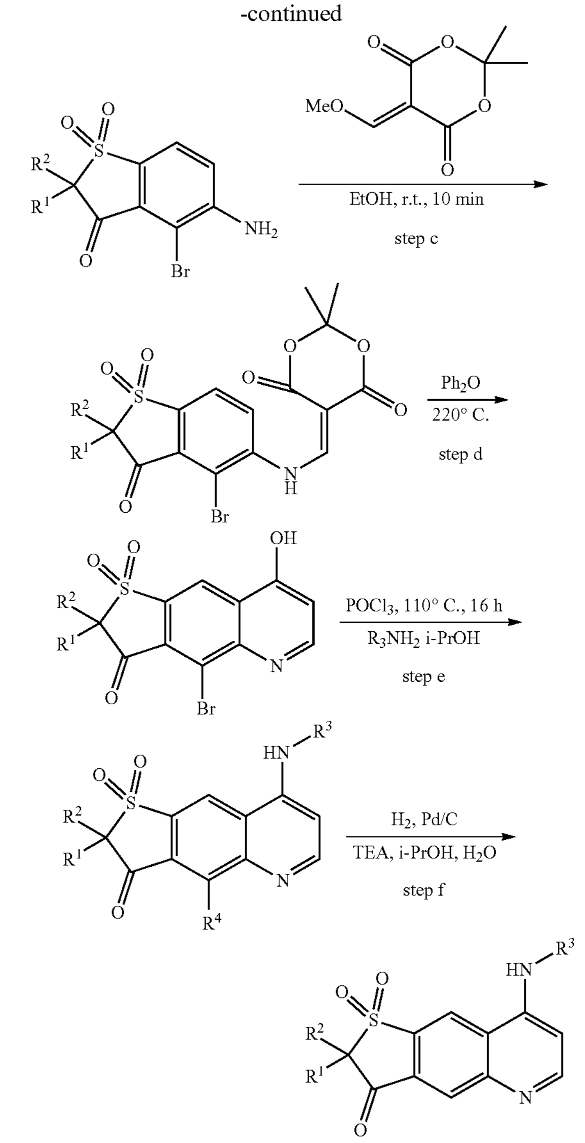

Reduction of nitro intermediate with $H_2$, Pd/C provided substituted aniline (step a) Amino intermediate reacted with NaBr, Oxone (step b), then reacted with 5-(methoxymethylene)-2,2-dimethyl-1,3-dioxane-4,6-dione to form reactive intermediate (step c), which was cyclized under high temperature (step d). Treating quinolin-4-ol with $POCl_3$ provided chloropyridine, which reacted with various aromatic amines or heterocyclic aromatic amines (step e). Dehalogenation with $H_2$, Pd/C provided the final products (step f)

Method BM:

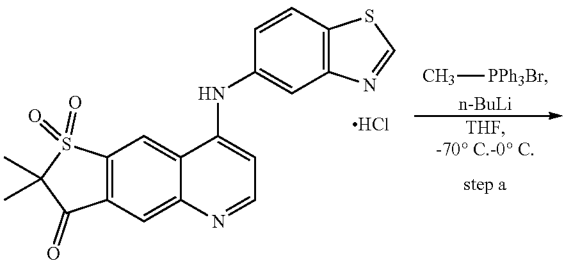

-continued

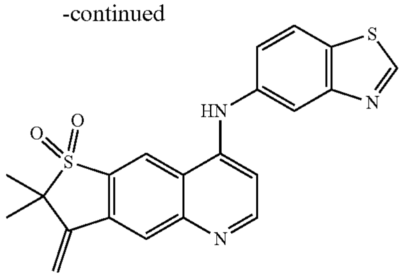

The desired product was obtained through Suzuki reaction with methyltriphenylphosphonium bromide, n-BuLi (step a).

Method BN:

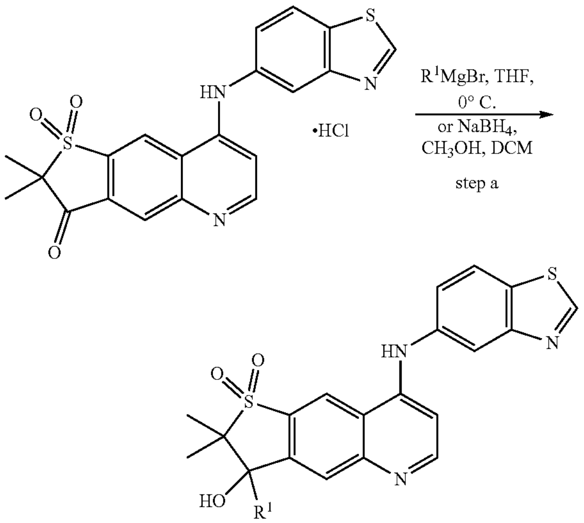

The desired product was obtained through Grignard reaction or reduction with $NaBH_4$ (step a).

Method BO:

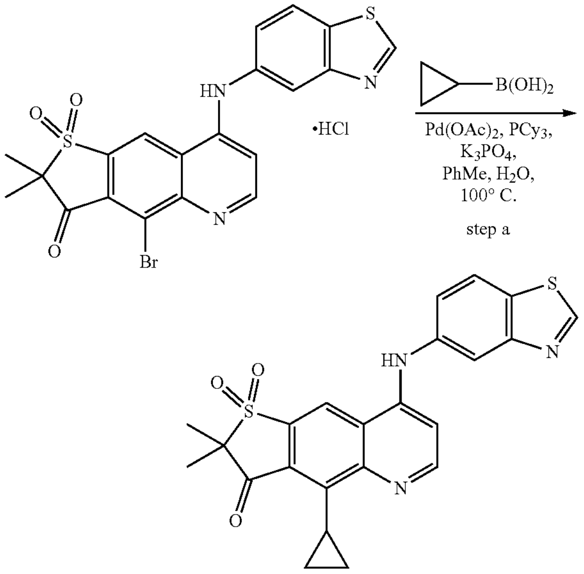

The desired product was obtained through Suzuki reaction with cyclopropylboronic acid, $Pd(OAc)_2$, $PCy_3$ and $K_3PO_4$ (step a).

Method BP:

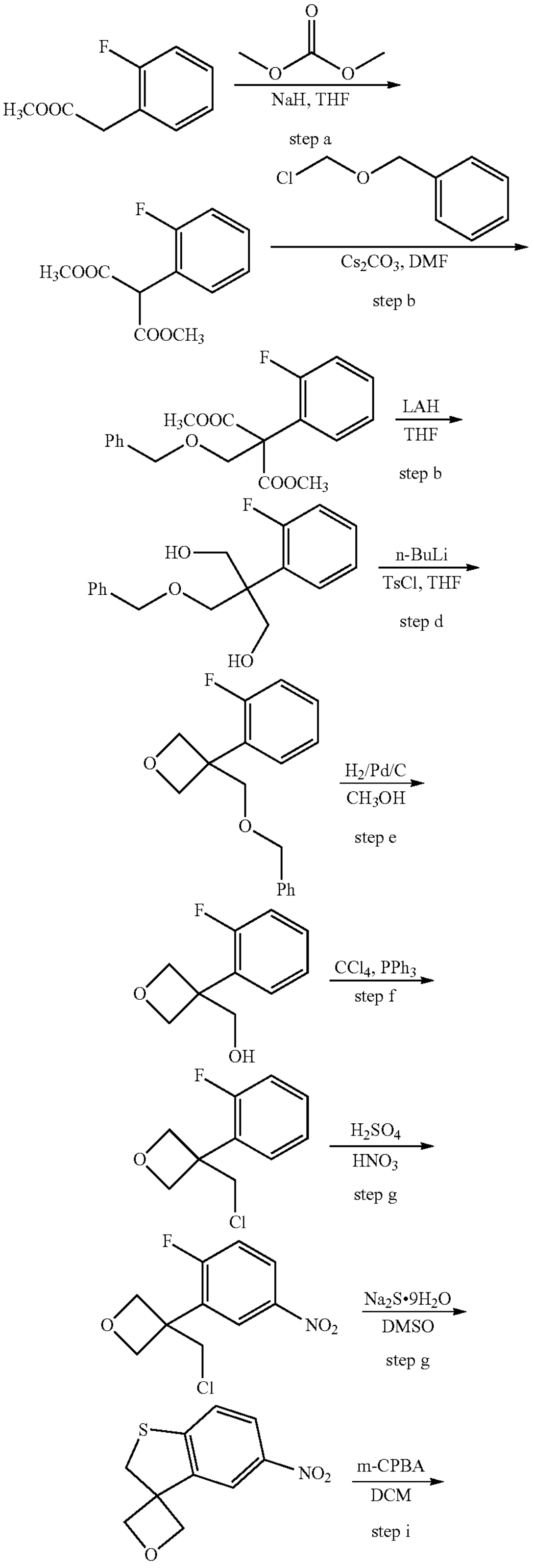

-continued

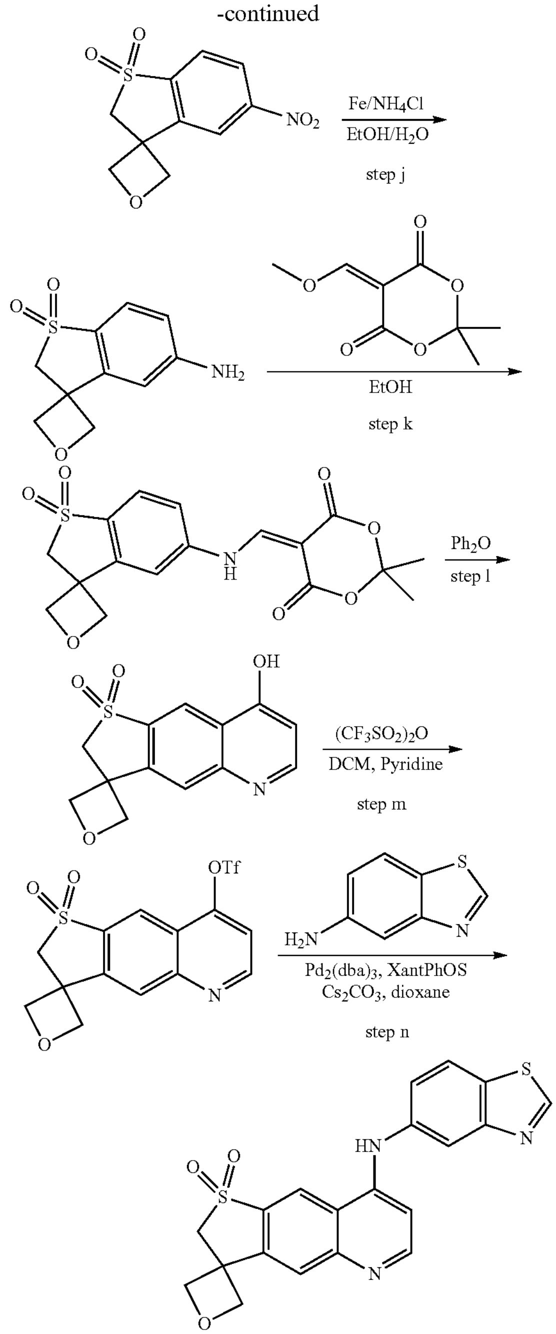

The starting material reacted with dimethyl carbonate under basic condition to give dimethyl 2-(2-fluorophenyl) malonate (step a), which reacted with ((chloromethoxy) methyl)benzene in the presence of $Cs_2CO_3$ (step b). Treatment with LAH yielded primary alcohol. Intramolecular cyclization provided oxetane derivative (step c). De-benzyl with $H_2$, Pd/C provided alcohol (step e) which was replaced by chlorine atom via Appel reaction (step f). Nitration reaction was accomplished with concentration $H_2SO_4$ and $HNO_3$ (step g), Intramolecular cyclization with $Na_2S{\cdot}9H_2O$ (step h) followed by oxidation reaction with m-CPBA (step i) provided the tricyclic intermediate. Reduction with Fe, $NH_4Cl$ (step j) gave substituted aniline, which reacted with 5-(methoxymethylene)-2,2-dimethyl-1,3-dioxane-4,6-dione (step k) followed by cyclization reaction (step l) to form the tricyclic pyridine analogues. Treatment with trifluoroacetic anhydride (step m) followed by Buchwald-Hartwig reaction afforded the desired product (step n).

EXAMPLES

General reaction progress was monitored by analytical thin layer chromatography performed on silica gel HSGF254 pre-coated plates. Organic solutions were dried over anhydrous $Na_2SO_4$, and the solvents were removed under reduced pressure. Final compounds were purified with silica gel 100-200 mesh for column chromatography. $^1H$ NMR were obtained on 400 MHz (Varian) spectrometer, and $^{13}C$ NMR were obtained on 151 MHz or 101 MHz (Varian) spectrometer. Chemical shifts were given in ppm using tetramethylsilane as internal standard. Mass spectra were obtained using an Agilent 1100 LC/MSD Trap SL version Mass Spectrometer. HRMS analysis was recorded on an Agilent 6540 UHD Accurate-Mass Q-TOF LC/MS.

Example 1: Preparation of 5-nitrobenzo[b]thiophene (Method AA)

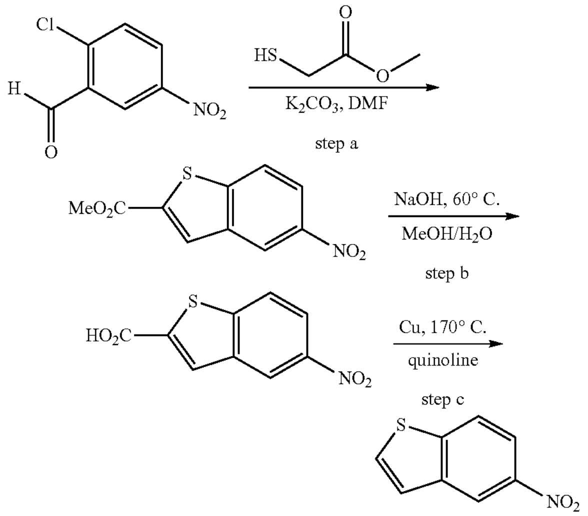

Step a: methyl 5-nitrobenzo[b]thiophene-2-carboxylate

To a solution of 2-chloro-5-nitrobenzaldehyde (64 g, 346 mmol) in DMF (600 mL) was added $K_2CO_3$ (95.5 g, 692 mmol) and ethyl thioglycolate (34 mL, 381 mmol). The mixture was stirred at room temperature overnight. The reaction solution was poured into water (3.5 L) and the resulting solid was filtered, washed with water and dried in vacuum to give the desired product (78.5 g, 96%) as a white solid. $^1H$ NMR (400 MHz, $CDCl_3$) δ 8.78 (s, 1H), 8.30 (d, J=8.8 Hz, 1H), 8.19 (s, 1H), 8.00 (d, J=8.8 Hz, 1H), 3.99 (s, 3H).

Step b: 5-nitrobenzo[b]thiophene-2-carboxylic acid

To a solution of Methyl 5-nitrobenzo[b]thiophene-2-carboxylate (78.5 g, 331 mmol) in mixture solution of MeOH (400 mL) and $H_2O$ (400 mL) was added NaOH (53.0 g, 1.3 mol). The mixture was stirred at 70° C. for 4 h. After cooling to room temperature, the solution was poured into water (4 L) and acidified with concentrated HCl. The resulting solid was filtered, washed with water, dried in vacuum to give the desired product (72.6 g, 98%) as a white solid. $^1$H NMR (400 MHz, DMSO-$d_6$) δ 8.97 (s, 1H), 8.49-8.19 (m, 3H).

Step c: 5-nitrobenzo[b]thiophene

To a solution of Methyl 5-nitrobenzo[b]thiophene-2-carboxylate (65 g, 291 mmol) in quinoline (500 mL) was added copper powder (18.6 g, 291 mmol). The reaction was stirred at 170° C. under $N_2$ atmosphere for 4 h. The solid was removed via filtration and washed with EA (400 mL). Another EA (2 L) was added to the filtrate to dilute the solution and then the solution was acidified with concentrated HCl with an ice bath. The organic layer was separated, and washed with 2N HCl (400 mL), saturate $NaHCO_3$ aqueous solution (400 mL), then The organic layer was dried over $Na_2SO_4$, filtered and concentrated. The residue was rinsed with EA (200 mL) and dried in vacuum to give the desired product (48 g, 78%) as a white solid. $^1$H NMR (400 MHz, DMSO-$d_6$) δ 8.84 (s, 1H), 8.29 (d, J=9.2 Hz, 1H), 8.17 (d, J=8.8 Hz, 1H), 8.05 (d, J=5.2 Hz, 1H), 7.72 (d, J=5.6 Hz, 1H).

Example 2: Preparation of N,2-dimethylbenzo[b]thiophene-5-carboxamide 1,1-dioxid (Method AB)

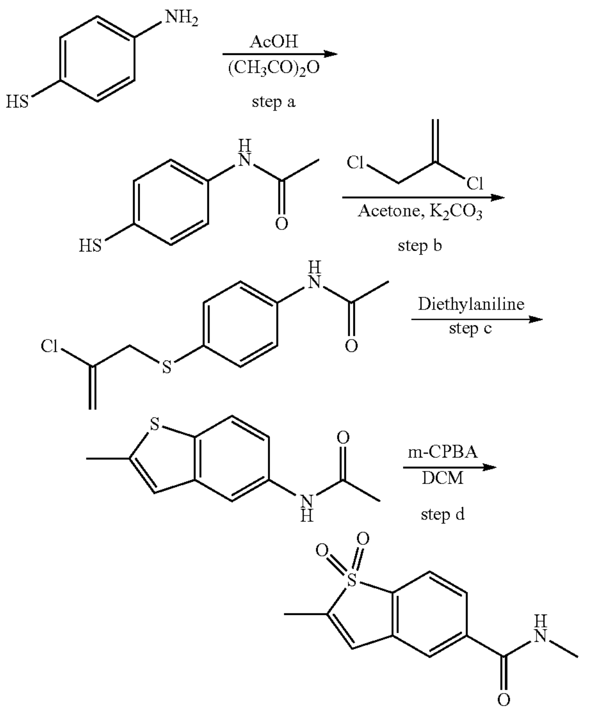

Step a: N-(4-mercaptophenyl)acetamide

To a solution of 4-aminobenzenethiol (25.0 g, 200 mmol) in AcOH (120 mL) was added $Ac_2O$ (22.4 g, 220 mmol). The reaction was stirred at room temperature for 10 min. The reaction was poured into water (1 L) and the resulting solid was collected via filtration, the cake was washed with water and dried in vacuum to give the desired product (31 g, 90%) as white solid. $^1$H NMR (400 MHz, DMSO-$d_6$) δ 9.90 (s, 1H), 7.46 (d, J=8.4 Hz, 2H), 7.20 (d, J=8.4 Hz, 2H), 5.23 (s, 1H), 2.01 (s, 3H).

Step b: N-(4-((2-chloroallyl)thio)phenyl)acetamide

To a solution of N-(4-mercaptophenyl)acetamide (31.0 g, 186 mmol) and $K_2CO_3$ (5.0 g, 36 mmol) in acetone (50 mL) was added 2,3-dichloroprop-1-ene (22.6 g, 205 mmol). The reaction was stirred at room temperature for 1 h. the precipitation was filtered off and the filtrate was concentrated. The residue was purified by silica gel column chromatography (DCM/MeOH=50/1) to give the desired product (42 g, 94%) as a white solid. $^1$H NMR (400 MHz, DMSO-$d_6$) δ 10.00 (s, 1H), 7.55 (d, J=8.4 Hz, 2H), 7.34 (d, J=8.8 Hz, 2H), 5.32 (s, 1H), 5.21 (s, 1H), 3.83 (s, 2H), 2.03 (s, 3H). LCMS (ESI/APCI) m/z: 239.8 $[M-H]^-$.

Step c: 8-hydroxy-2-methylthieno[2,3-g]quinoline1, 1-dioxide

Intermediate N-(4-((2-chloroallyl)thio)phenyl)acetamide (20.0 g, 8.3 mmol) was added to N, N-diethylaniline (150 mL). The mixture solution was stirred at 220° C. for 26 h under $N_2$ atmosphere. The reaction solution was acidified with 6 N HCl. EA (200 mL) was added to dilute the solvent and stirred for 30 min. The organic layer was separated and the aqueous layer was extracted with EA (200 mL×2). The combined organic phase was washed with 6 N HCl (150 mL), dried over $Na_2SO_4$, filtered and concentrated. The residue was purified by silica gel column chromatography (PE/EA=3:1) to give a crude product. The crude was rinsed with EtOH/$H_2O$ (100 mL/200 mL) to give the desired product (5.0 g, 29%) as a yellow solid. $^1$H NMR (400 MHz, DMSO-$d_6$) δ7.96 (s, 1H), 7.63 (d, J=8.4 Hz, 1H), 7.36 (s, 1H), 7.21 (d, J=8.4 Hz, 1H), 6.91 (s, 1H), 2.56 (s, 3H), 2.19 (s, 3H). LC-MS (ESI/APCI) m/z: 205.9 $[M+H]^+$.

Step d: N-(2-methyl-1,1-dioxidobenzo[b]thiophen-5-yl)acetamide

To a solution of 8-hydroxy-2-methylthieno[2,3-g]quinoline 1,1-dioxide (5.0 g, 24.4 mmol) in MeOH/$H_2O$ (75 mL/75 mL) was added Oxone (22.5 g, 36.6 mmol). The mixture solution was stirred at room temperature for 2 h. The reaction was quenched with saturated $Na_2SO_3$ aqueous solution and extracted with DCM (100 mL×3). The combined organic phase was dried over $Na_2SO_4$, filtered and concentrated. The residue was rinsed with EA (70 mL) to give the desired product (4.3 g, 76%) as a white solid. $^1$H NMR (400 MHz, DMSO-$d_6$) δ 10.40 (s, 1H), 7.82 (s, 1H), 7.76 (d, J=8.4 Hz, 1H), 7.60 (d, J=8.4 Hz, 1H), 7.24 (s, 1H), 2.09 (s, 6H). LC-MS (ESI/APCI) m/z: 237.8 $[M+H]^+$.

Example 3: Preparation of 2-ethylbenzo[b]thiophen-5-amine (Method AC)

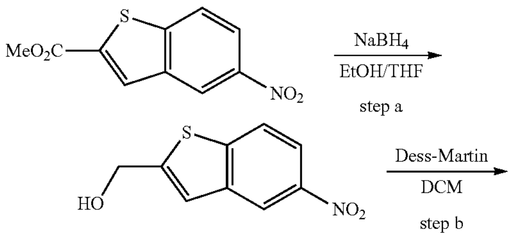

-continued

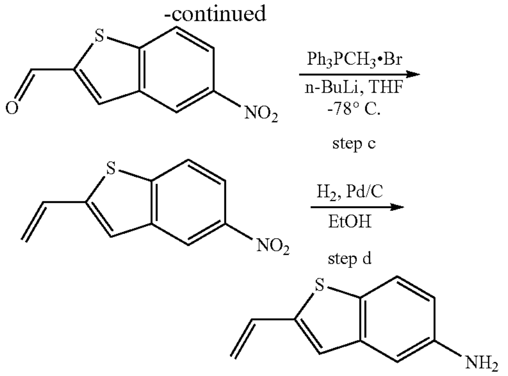

Step a: (5-nitrobenzo[b]thiophen-2-yl)methanol

To a solution of methyl 5-nitrobenzo[b]thiophene-2-carboxylate (3.0 g, 12.6 mmol) in EtOH/THF (80 mL/40 mL) was added Sodium borohydride (1.87 g, 50.6 mmol) slowly. The reaction mixture was stirred at room temperature for 24 h. The reaction mixture was quenched with saturated $NH_4Cl$ aqueous solution and extracted with dichloromethane (80 mL×3). The combined organic layer was dried over $Na_2SO_4$, filtered and evaporated to give the desired product (2.0 g, 75%). $^1H$ NMR (400 MHz, DMSO-$d_6$) δ 9.90 (s, 1H), 7.46 (d, J=8.4 Hz, 2H), 7.20 (d, J=8.4 Hz, 2H), 5.23 (s, 1H), 2.01 (s, 3H).

Step b: 5-nitrobenzo[b]thiophene-2-carbaldehyde

To a solution of (5-nitrobenzo[b]thiophen-2-yl)methanol (2.0 g, 10 mmol) in dichloromethane (50 mL) was slowly added Dess-Martin (4.2 g, 10 mmol). The reaction mixture was stirred at room temperature for 4 h. The reaction mixture was quenched with saturated $NaHCO_3$ aqueous solution and extracted with dichloromethane (50 mL×3). The combined organic layer was dried over $Na_2SO_4$, filtered and evaporated. The residue was purified by silica gel column chromatography (petroleum ether/dichloromethane=1/1) to give the desired product (850 mg, 41%). $^1H$ NMR (400 MHz, DMSO-$d_6$) δ 10.21 (s, 1H), 9.10 (d, J=2.0 Hz, 1H), 8.64 (s, 1H), 8.40 (d, J=9.2 Hz, 1H), 8.35 (dd, J=8.8, 2.4 Hz, 1H).

Step c: 5-nitro-2-vinylbenzo[b]thiophene

To a solution of methyltriphenylphosphonium bromide (2.94 g, 8.2 mmol) in dried tetrahydrofuran (30 mL) was slowly added n-BuLi (4.6 mL, 7.4 mmol) at −78° C. under $N_2$ atmosphere. The reaction mixture was stirred under the ice bath for another 1 h. The reaction mixture was added the solution of 5-nitrobenzo[b]thiophene-2-carbaldehyde (850 mg, 4.1 mmol) in dried tetrahydrofuran (20 mL) at −78° C. Then the reaction mixture was stirred at room temperature overnight. The reaction mixture was quenched with saturated $NH_4Cl$ aqueous solution, and extracted with ethyl acetate (50 mL×3). The combined organic layer was dried over $Na_2SO_4$, filtered and evaporated. The residue was purified by silica gel column chromatography (petroleum ether/ethyl acetate=20/1) to give the desired product (400 mg, 48%). $^1H$ NMR (400 MHz, DMSO-$d_6$) δ 8.74 (d, J=2.0 Hz, 1H), 8.22 (d, J=8.8 Hz, 1H), 8.16 (dd, J=8.8, 2.0 Hz, 1H), 7.67 (s, 1H), 7.11 (dd, J=17.2, 10.8 Hz, 1H), 5.77 (d, J=17.2 Hz, 1H), 5.49 (d, J=10.8 Hz, 1H).

Step d: 2-ethylbenzo[b]thiophen-5-amine

To a solution of 5-nitro-2-vinylbenzo[b]thiophene (400 mg, 1.95 mmol) in EtOH (25 mL) was added Pd/C (11 mg, 0.1 mmol) under $H_2$ atmosphere. The reaction was stirred at room temperature overnight. The reaction mixture was filtered and evaporated to give the desired product (300 mg, 87%). $^1H$ NMR (400 MHz, $CDCl_3$) δ 7.51 (d, J=8.4 Hz, 1H), 6.97 (s, 1H), 6.83 (s, 1H), 6.69 (d, J=7.6 Hz, 1H), 2.89 (q, J=7.6 Hz, 2H), 1.35 (t, J=7.6 Hz, 3H)

Example 4: Preparation of 2-isopropylbenzo[b]thiophen-5-amine (Method AD)

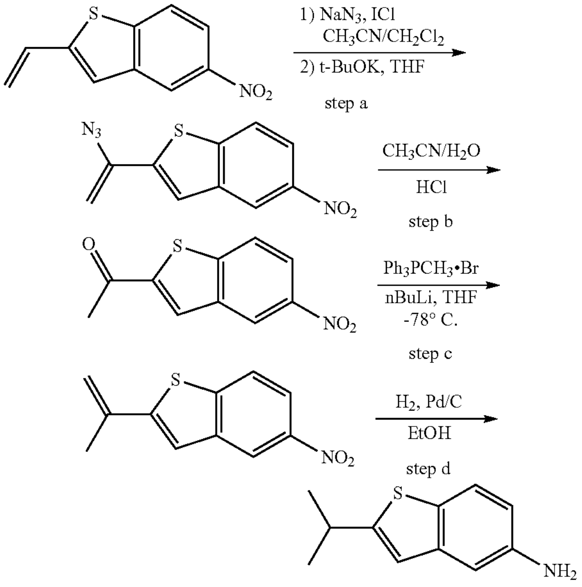

Step a: 2-(1-azidovinyl)-5-nitrobenzo[b]thiophene

To a solution of $NaN_3$ (553 mg, 8.2 mmol) in $CH_3CN$ was added ICl (810 mg, 5.0 mmol) in DCM (3 mL) at −20° C. The mixture was stirred for 30 min. 5-nitro-2-vinylbenzo[b]thiophene (680 mg, 3.3 mmol) dissolved in DCM (3 mL) was added to the reaction solution. the mixture was recovered to room temperature, and stirred for 1 h. Saturated $Na_2S_2O_3$ aqueous solution was added to quench the reaction. The aqueous layer was extracted with DCM (10 mL×3). The combined organic layer was dried over $Na_2SO_4$, filtered and concentrated. The resulting residue was dissolved in dry THF (10 mL). t-BuOK (443 mg, 4.0 mmol) was added at 0° C. The mixture was stirred for 30 min. Saturated $NH_4Cl$ aqueous solution was added to quench the reaction. The aqueous layer was extracted with EA (10 mL×3). The combined organic layer was dried over $Na_2SO_4$, filtered and concentrated. The residue was purified by silica gel column chromatography (petroleum ether/ethyl acetate=20/1) to give the desired product (450 mg, 55%) as a white solid. $^1H$ NMR (400 MHz, $CDCl_3$) δ 8.63 (s, 1H), 8.19 (d, J=9.2 Hz, 1H), 7.89 (d, J=8.8 Hz, 1H), 7.58 (s, 1H), 5.56 (s, 1H), 5.10 (s, 1H).

Step b: 1-(5-nitrobenzo[b]thiophen-2-yl)ethan-1-one

To a solution of 2-(1-azidovinyl)-5-nitrobenzo[b]thiophene (450 mg, 1.8 mmol) in $CH_3CN/H_2O$ (4 mL/1 mL) was added conc. HCl (1 mL). the mixture was stirred at 50° C. for 1 h. The mixture was extracted with DCM (10 mL×2). The combined organic layer was dried over $Na_2SO_4$, filtered and concentrated. The residue was purified by silica gel column chromatography (petroleum ether/ethyl acetate=5/1) to give the desired product (380 mg, 95%) as a yellow solid. $^1H$ NMR (400 MHz, $CDCl_3$) δ 8.81 (d, J=2.0 Hz, 1H), 8.31 (dd, J=9.2, 2.4 Hz, 1H), 8.07 (s, 1H), 8.01 (d, J=8.8 Hz, 1H), 2.71 (s, 3H).

Step c: 5-nitro-2-(prop-1-en-2-yl)benzo[b]thiophene

To a solution of Methyltriphenylphosphonium bromide (1.97 g, 4.1 mmol) in THF (15 mL) under N2 atmosphere was added n-Buli (2.3 mL, 5.8 mmol) at −78° C. The mixture was stirred for 1 h. 1-(5-nitrobenzo[b]thiophen-2-yl)ethan-1-one (380 mg, 1.7 mmol) dissolved in dry THF (10 mL) was added to the solution dropwise. Recovering to room temperature, the mixture was stirred overnight. Saturated $NH_4Cl$ aqueous solution was added to quench the reaction. The aqueous layer was extracted with EA (25 mL×3). The combined organic layer was dried over $Na_2SO_4$, filtered and concentrated. The residue was purified by silica gel column chromatography (petroleum ether/ethyl acetate=20/1) to give the desired product (225 mg, 60%) as a yellow solid. $^1H$ NMR (400 MHz, $CDCl_3$) δ 8.58 (d, J=2.4 Hz, 1H), 8.15 (dd, J=8.8, 2.4 Hz, 1H), 7.85 (d, J=8.8 Hz, 1H), 7.33 (s, 1H), 5.55 (s, 1H), 5.23 (s, 1H), 2.24 (s, 3H).

Step d: 2-isopropylbenzo[b]thiophen-5-amine

To a solution of 5-nitro-2-(prop-1-en-2-yl)benzo[b]thiophene (225 mg, 1.05 mmol) in EtOH (15 mL) was added Pd/C (5 mg, 0.05 mmol). The mixture was stirred at room temperature under $H_2$ atmosphere overnight. the solution was filtered and the resulting filtrate was concentrated to give the desired product (187 mg, 98%) as a yellow solid. $^1H$ NMR (400 MHz, $CDCl_3$) δ 7.52 (d, J=8.4 Hz, 1H), 6.99 (s, 1H), 6.84 (s, 1H), 6.70 (d, J=8.4 Hz, 1H), 3.84 (br s, 2H), 3.26-3.12 (m, 1H), 1.37 (d, J=6.8 Hz, 6H).

Example 5: reparation of 2-cyclopropyl-5-nitrobenzo[b]thiophene 1,1-dioxide (Method AE)

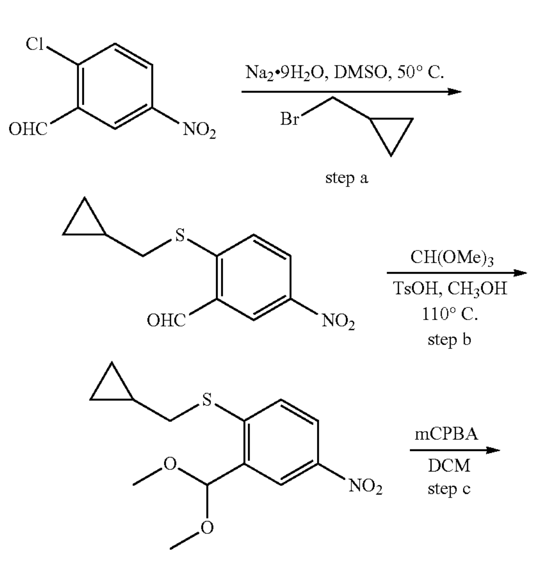

-continued

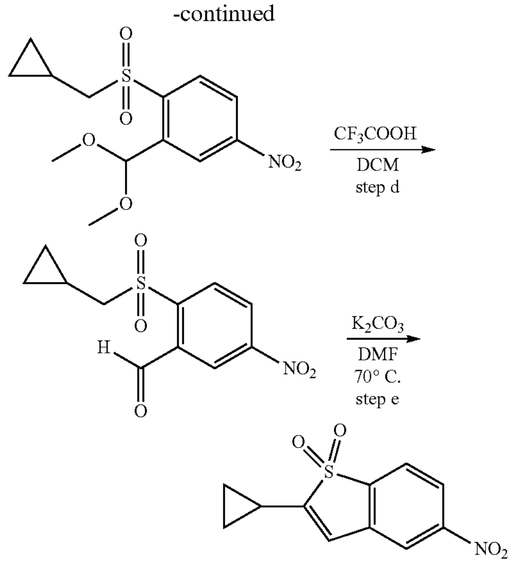

Step a: 2-((cyclopropylmethyl)thio)-5-nitrobenzaldehyde

To a solution of 2-chloro-5-nitrobenzaldehyde (1.85 g, 10.0 mmol) in DMSO (40 mL) was added $Na_2S·9H_2O$ (4.04 g, 10.0 mmol). The mixture was stirred at 50° C. for 30 min. (bromomethyl)cyclopropane (1.35 g, 10.0 mmol) was added and the mixture was stirred for 1 h. water (200 mL) was added to dilute the solution and the aqueous layer was extracted with EA (50 mL×3). The combined organic layer was dried over $Na_2SO_4$, filtered and concentrated. The residue was purified by silica gel column chromatography (petroleum ether/ethyl acetate=50/1) to give the desired product (2.0 g, 84%). $^1H$ NMR (400 MHz, $CDCl_3$) δ 10.29 (s, 1H), 8.64 (s, 1H), 8.30 (d, J=8.8 Hz, 1H), 7.49 (d, J=8.8 Hz, 1H), 3.01 (d, J=6.8 Hz, 2H), 1.17-1.02 (m, 1H), 0.71 (d, J=7.2 Hz, 2H), 0.38 (d, J=4.8 Hz, 2H).

Step b: (cyclopropylmethyl)(2-(dimethoxymethyl)-4-nitrophenyl)sulfane

To a solution of 2-((cyclopropylmethyl)thio)-5-nitrobenzaldehyde (2.0 g, 8.4 mmol) in trimethyl orthoformate (6 mL) and CH3OH (20 mL) was added p-toluenesulfonic acid (80 mg, 0.42 mmol). The mixture was stirred at 110° C. for 2 h. The solvent was removed in vacuum. The residue (2.3 g, 97%) was used for next step. $^1H$ NMR (400 MHz, $CDCl_3$) δ 8.68 (s, 1H), 8.34 (d, J=8.8 Hz, 1H), 8.30 (d, J=8.4 Hz, 1H), 6.24 (s, 1H), 3.47 (s, 6H), 3.28 (d, J=7.2 Hz, 2H), 1.04-0.91 (m, 1H), 0.55 (d, J=7.2 Hz, 2H), 0.15 (d, J=4.8 Hz, 2H).

Step c: 1-((cyclopropylmethyl)sulfonyl)-2-(dimethoxymethyl)-4-nitrobenzene

To a solution of (cyclopropylmethyl)(2-(dimethoxymethyl)-4-nitrophenyl)sulfane (2.3 g, 8.1 mmol) in DCM (60 mL) was added m-CPBA (4.2 g, 21.0 mmol). The mixture was stirred at room temperature for 24 h. Saturated $Na_2SO_3$ aqueous solution was added to quench the solution. The aqueous layer was extracted with DCM (60 mL×3). The combined organic layer was dried over $Na_2SO_4$, filtered and concentrated to give the crude product (2.7 g).

Step d: 2-((cyclopropylmethyl)sulfonyl)-5-nitrobenzaldehyde

To a solution of 1-((cyclopropylmethyl)sulfonyl)-2-(dimethoxymethyl)-4-nitrobenzene (2.7 g, 8.6 mmol) in DCM (30 mL) was added $CF_3COOH$ (3 mL). The mixture was stirred at room temperature for 24 h. the solvent was removed in vacuum and the residue was purified by silica gel column chromatography (DCM) to give the desired product (1.6 g, 73%) as a yellow solid. $^1H$ NMR (400 MHz, $CDCl_3$) δ 10.87 (s, 1H), 8.88 (s, 1H), 8.59 (d, J=8.4 Hz, 1H), 8.36 (d, J=8.4 Hz, 1H), 3.25 (d, J=6.8 Hz, 2H), 1.11-0.91 (m, 1H), 0.62 (d, J=7.2 Hz, 2H), 0.18 (d, J=3.2 Hz, 2H).

Step e: 2-cyclopropyl-5-nitrobenzo[b]thiophene 1,1-dioxide

To a solution of 2-((cyclopropylmethyl)sulfonyl)-5-nitrobenzaldehyde (1.0 g, 3.7 mmol) in N,N-dimethylformamide (40 mL) was added $K_2CO_3$ (1.0 g, 0.74 mmol). The mixture was stirred at 60° C. for 8 h. Water (100 mL) was added to dilute the solution and the aqueous layer was extracted with EA (30 mL×3). The combined organic layer was dried over $Na_2SO_4$, filtered and concentrated. The residue was purified by silica gel column chromatography (petroleum ether/ethyl acetate=20/1) to give the desired product (285 mg, 29%) as a yellow solid. $^1H$ NMR (400 MHz, $CDCl_3$) δ 8.30 (d, J=8.0 Hz, 1H), 8.09 (s, 1H), 7.84 (d, J=8.4 Hz, 1H), 6.70 (s, 1H), 1.94-1.83 (m, 1H), 1.21-1.14 (m, 2H), 1.12-1.05 (m, 2H).

Example 6: Preparation of 3-cyclopropyl-5-nitrobenzo[b]thiophene 1,1-dioxide (Method AF)

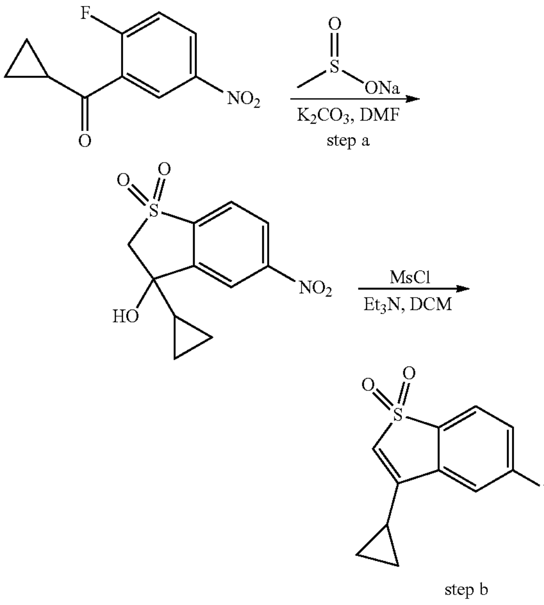

Step a: 3-cyclopropyl-3-hydroxy-5-nitro-2,3-dihydrobenzo[b]thiophene 1,1-dioxide To a solution of cyclopropyl(2-fluoro-5-nitrophenyl) methanone (3.7 g, 17.7 mmol) in N, N-dimethylformamide (10 mL) was added sodium methanesulfinate (1.8 g, 17.7 mmol). The mixture was stirred at room temperature for 1 h. $K_2CO_3$ (49 g, 35.4 mmol) was added and the mixture was stirred at 70° C. overnight. Water (50 mL) was added and the solution was extracted with ethyl acetate (100 mL×2). The combined organic layer was dried over $Na_2SO_4$ and concentrated to give the desired product (4.7 g).

Step b: 3-cyclopropyl-5-nitrobenzo[b]thiophene 1,1-dioxide

To a solution of 3-cyclopropyl-3-hydroxy-5-nitro-2,3-dihydrobenzo[b]thiophene 1,1-dioxide (4.7 g, 17.7 mmol) in DCM (200 mL) was added Triethylamine (7.2 g, 70.8 mmol) and methanesulfonyl chloride (4.0 g, 35.4 mmol). The mixture was stirred at room temperature overnight. The organic layer was removed and the residue was purified by silica gel column chromatography (petroleum ether/ethyl acetate=2/1) to give the desired product (2.7 g, 62%) as a yellow solid. $^1H$ NMR (400 MHz, $CDCl_3$) δ 8.53-8.42 (m, 2H), 7.89 (d, J=8.8 Hz, 1H), 6.33 (d, J=1.2 Hz, 1H), 1.96-1.88 (m, 1H), 1.29-1.25 (m, 2H), 0.92-0.85 (m, 2H).

Example 7: Preparation of 2-methyl-5-nitrobenzo[b]thiophene (Method AG)

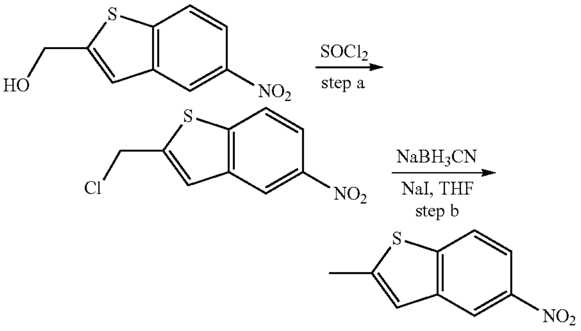

Step a: 2-(chloromethyl)-5-nitrobenzo[b]thiophene

Intermediate (5-nitrobenzo[b]thiophen-2-yl)methanol (4.8 g, 23.0 mmol) was dissolved in $SOCl_2$ (40 mL). The mixture was stirred at room temperature for 8 h. The solvent was removed in vacuum and the residue was purified by silica gel column chromatography (petroleum ether/ethyl acetate=10/1) to give the desired product (2.1 g, 40%) as a yellow solid. $^1H$ NMR (400 MHz, $CDCl_3$) δ 8.63 (s, 1H), 8.20 (d, J=8.4 Hz, 1H), 7.92 (d, J=8.8 Hz, 1H), 7.46 (s, 1H), 4.88 (s, 2H).

Step b: 2-methyl-5-nitrobenzo[b]thiophene

To a solution of 2-(chloromethyl)-5-nitrobenzo[b]thiophene (2.1 g, 9.2 mmol) in THF (40 mL) was added NaI (1.4 g, 9.2 mmol) and $NaBH_3CN$ (2.3 g, 36.8 mmol). The mixture was stirred at 70° C. for 4 h. the solvent was removed in vacuum. Water (40 mL) was added and the aqueous layer was extracted with DCM (20 mL×3). The combined organic layer was dried over $Na_2SO_4$, filtered and concentrated. The residue was purified by silica gel column chromatography (petroleum ether/ethyl acetate=20/1) to give the desired product as a yellow solid (900 mg, 51%). $^1H$ NMR (400 MHz, $CDCl_3$) δ 8.54 (s, 1H), 8.11 (d, J=7.2 Hz, 1H), 7.84 (d, J=8.8 Hz, 1H), 7.13 (s, 1H), 2.64 (s, 3H).

Example 8: Preparation of 3-bromo-2-methyl-5-nitrobenzo[b]thiophene (Method AH)

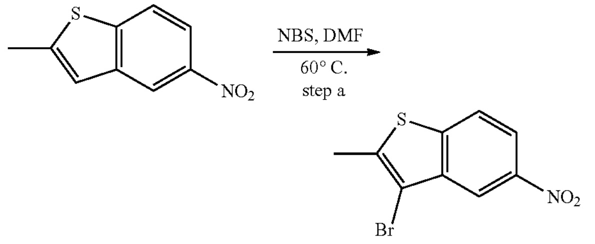

Step a: 3-bromo-2-methyl-5-nitrobenzo[b]thiophene

To a solution of 2-methyl-5-nitrobenzo[b]thiophene (900 mg, 4.7 mmol) in N, N-dimethylformamide (20 mL) was added NBS (872 mg, 4.9 mmol). The mixture was stirred at 60° C. for 48 h. the mixture was removed in vacuum. The residue was rinsed with EA to give the desired product (800 mg, 63%).

Example 9: Preparation of 7-methoxy-5-nitrobenzo[b]thiophene (Method AI)

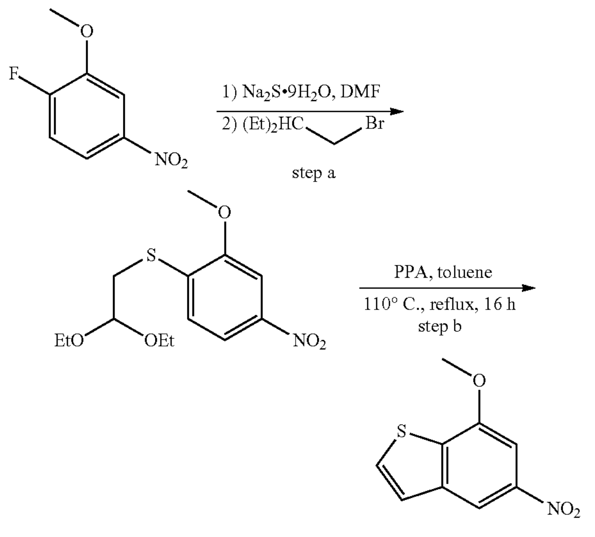

Step a: (2,2-diethoxyethyl)(2-methoxy-4-nitrophenyl)sulfane

To a solution 1-fluoro-2-methoxy-4-nitrobenzene (3.42 g, 20.0 mmol) in N, N-dimethylformamide (30 mL) was added $Na_2S·9H_2O$ (5.12 g, 21.6 mmol). The mixture was stirred at room temperature for 4 h. 2-bromo-1,1-diethoxyethane (5.12 g, 21.6 mmol) was added and the mixture was stirred at room temperature overnight. Water (100 mL) was added to quench the reaction. The aqueous layer was extracted with EA (100 mL). The organic layer was dried over $Na_2SO_4$, filtered and concentrated. The residue was purified by silica gel column chromatography (petroleum ether/ethyl acetate=20/1) to give the desired product as a yellow oil (5.00 g, 83%). $^1$H NMR (400 MHz, $CDCl_3$) δ7.83 (dd, J=8.4, 2.4 Hz, 1H), 7.65 (d, J=2.4 Hz, 1H), 7.34 (d, J=8.8 Hz, 1H), 4.72 (t, J=5.6 Hz, 1H), 3.98 (s, 3H), 3.76-3.66 (m, 2H), 3.62-3.52 (m, 2H), 3.19 (d, J=5.2 Hz, 2H), 1.21 (t, J=7.2 Hz, 6H).

Step b: 7-methoxy-5-nitrobenzo[b]thiophene

To a solution of (2,2-diethoxyethyl)(2-methoxy-4-nitrophenyl)sulfane (5.0 g, 16.6 mmol) in $PhCH_3$ (150 mL) was added PPA (15 mL). The mixture was stirred at reflux overnight. Saturated $NaHCO_3$ aqueous solution was added to adjust pH to 7. The solution was extracted with EA (100 mL×2). The combined organic layer was dried over $Na_2SO_4$, filtered and concentrated. The residue was purified by silica gel column chromatography (petroleum ether/ethyl acetate=20/1) to give the desired product as a colorless oil (1.1 g, 32%).

Example 10: Preparation of tert-butyl 7-amino-3,4-dihydroisoquinoline-2(1H)-carboxylate (Method AJ)

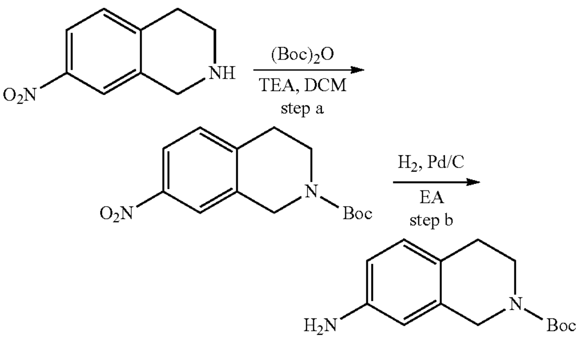

Step a: tert-butyl 7-nitro-3,4-dihydroisoquinoline-2(1H)-carboxylate

To a solution of 7-nitro-1,2,3,4-tetrahydroisoquinoline (200 mg, 1.1 mmol) in DCM (10 mL) was added Di-tert-butyl dicarbonate (260 mg, 1.2 mmol), $Et_3N$ (280 mg, 2.75 mol). The mixture was stirred at room temperature for 8 h. the solvent was removed in vacuum and the residue was purified by silica gel column chromatography (DCM/MeOH=20/1) to give the desired product (250 mg, 80%) as a yellowish solid. $^1$H NMR (400 MHz, $CDCl_3$) δ 8.03-8.01 (m, 2H), 7.30 (d, J=8.4 Hz, 1H), 4.66 (s, 2H), 3.69 (s, 2H), 2.93 (s, 2H), 1.52-1.48 (m, 9H).

Step b: tert-butyl 7-amino-3,4-dihydroisoquinoline-2(1H)-carboxylate

To a solution of tert-butyl 7-nitro-3,4-dihydroisoquinoline-2(1H)-carboxylate (190 mg, 0.68 mmol) in EA (10 mL) was added Pd/C (200 mg). The mixture was stirred under $H_2$ atmosphere at room temperature. The solution was filtrated and the resulting filtrate was purified by silica gel column chromatography (DCM/MeOH=25/1) to give the desired product (100 mg) as a yellow solid. $^1$H NMR (400 MHz, DMSO-$d_6$) δ 6.79 (d, J=8.4 Hz, 1H), 6.39 (d, J=8.4 Hz, 1H), 6.30 (s, 1H), 4.88 (s, 2H), 4.32 (s, 2H), 3.47 (d, J=5.6 Hz, 2H), 2.57 (d, J=5.6 Hz, 2H), 1.42 (s, 9H).

Example 11: Preparation of 2-(3-amino-4-methylbenzyl)isoindoline-1,3-dione (Method AK)

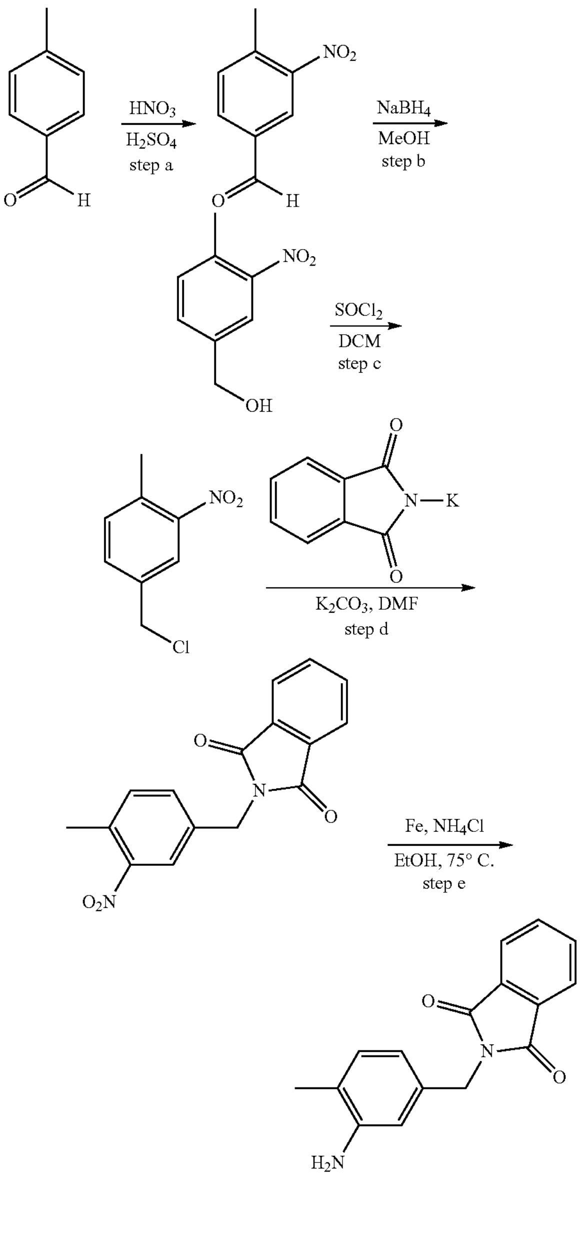

Step a: 4-methyl-3-nitrobenzaldehyde

To a solution of 4-methylbenzaldehyde (1.0 g, 8.3 mmol) in conc. $H_2SO_4$ (4 mL) was added conc. $HNO_3$ dropwise at 0° C. The mixture was stirred at room temperature for 3 h. The solution was poured into ice water and the resulting solid was collected via filtration, and dried in vacuum to give the desired product (750 mg, 55%) as a white solid. $^1H$ NMR (400 MHz, $CDCl_3$) δ10.04 (s, 1H), 8.46 (s, 1H), 8.03 (d, J=7.2 Hz, 1H), 7.50 (d, J=6.4 Hz, 1H), 2.70 (s, 3H).

Step b: (4-methyl-3-nitrophenyl)methanol

To a solution of 4-methyl-3-nitrobenzaldehyde (730 mg, 4.3 mmol) in $CH_3OH$ (15 mL) was added $NaBH_4$ (490 mg, 12.9 mmol) slowly. The mixture was stirred at room temperature for 3 h. EA (100 mL) and saturated $NaHCO_3$ aqueous solution (40 mL) was added. The organic layer was separated, dried over $Na_2SO_4$, filtered and concentrated to give the desired product (600 mg, 84%). $^1H$ NMR (400 MHz, $CDCl_3$) δ7.98 (s, 1H), 7.50 (d, J=7.6 Hz, 1H), 7.33 (d, J=7.6 Hz, 1H), 4.75 (s, 2H), 2.59 (s, 3H).

Step c: 4-(chloromethyl)-1-methyl-2-nitrobenzene

To a solution of (4-methyl-3-nitrophenyl)methanol (600 mg, 3.6 mmol) in DCM (4 mL) was added $SOCl_2$ (2 mL). The mixture was stirred at 40° C. for 12 h. The solvent was removed in vacuum and the residue was purified by silica gel column chromatography (PE/EA=30/1) to give the desired product (600 mg, 90%) as a yellow solid. $^1H$ NMR (400 MHz, $CDCl_3$) δ8.01 (s, 1H), 7.53 (d, J=7.6 Hz, 1H), 7.35 (d, J=8.0 Hz, 1H), 4.60 (s, 2H), 2.61 (s, 3H).

Step d: 2-(4-methyl-3-nitrobenzyl)isoindoline-1,3-dione

To a solution of 4-(chloromethyl)-1-methyl-2-nitrobenzene (200 mg, 1.1 mmol) in N,N-dimethylformamide (3 mL) was added $K_2CO_3$ (45 mg, 0.33 mmol) and potassium phthalimide (206 mg, 1.1 mmol). The mixture was stirred at 50° C. overnight. Cooling to room temperature. EA (75 mL) was added to dilute the solution. The organic layer was washed with saturated NaCl aqueous solution (30 mL×2), dried over $Na_2SO_4$, filtered and concentrated to give the desired product (300 mg, 92%) as a yellow solid. $^1H$ NMR (400 MHz, $CDCl_3$) δ8.01 (s, 1H), 7.90-7.81 (m, 2H), 7.76-7.70 (m, 2H), 7.56 (d, J=7.6 Hz, 1H), 7.29 (d, J=7.6 Hz, 1H), 4.87 (s, 2H), 2.55 (s, 3H).

Step e: 2-(3-amino-4-methylbenzyl)isoindoline-1,3-dione

To a solution of 2-(4-methyl-3-nitrobenzyl)isoindoline-1,3-dione (296 mg, 1.0 mmol) in EtOH (5 mL) and water (5 mL) was added $NH_4Cl$ (212 mg, 4.0 mmol) and iron powder (224 mg, 4.0 mmol). The mixture was stirred at reflux for 2 h. The solution was filtered via diatomite. The filtrate was extracted with dichloromethane (20 mL×3). The combined organic layer was dried over $Na_2SO_4$ and concentrated. The residue was purified by silica gel column chromatography (petroleum ether/ethyl acetate=1/1) to give the desired product (140 mg, 53%) as a yellow solid. $^1H$ NMR (400 MHz, $CDCl_3$) δ7.83 (s, 2H), 7.69 (s, 2H), 6.98 (d, J=7.6 Hz, 1H), 6.83-6.75 (m, 2H), 4.74 (s, 2H), 2.12 (s, 3H).

Example 12: Preparation of 4-iodo-N-(4-methoxybenzyl)-5-methylpyridin-2-amine (Method AL)

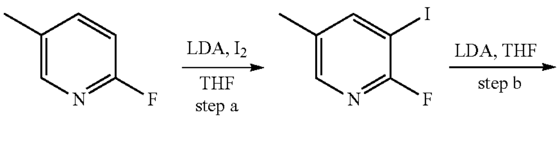

-continued

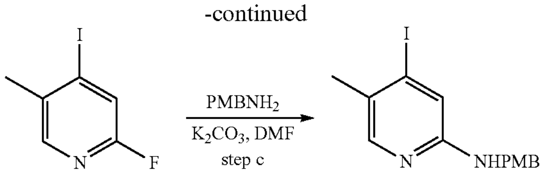

Step a: 2-fluoro-3-iodo-5-methylpyridine

To a solution of LDA (2 M, 10 mL) in THF (30 mL) was added dropwise 2-fluoro-5-methylpyridine (2.2 g, 19.8 mmol) in THF (5 mL) at −78° C. under $N_2$ atmosphere. The reaction mixture was stirred at −78° C. for 2 h. A solution of $I_2$ (2.5 g, 19.8 mmol) in THF (5 mL) was added dropwise at −78° C. and the mixture was stirred for 2 h. The reaction mixture was quenched with water (30 mL) and extracted with ethyl acetate (30 mL). The organic layer was dried over $Na_2SO_4$, filtered and evaporated. The residue was purified by silica gel column chromatography (petroleum ether/ethyl acetate=200/1) to give the desired product (800 mg, 17%). $^1H$ NMR (400 MHz, $CDCl_3$) δ 8.00-7.96 (m, 1H), 7.95 (s, 1H), 2.30 (s, 3H).

Step b: 2-fluoro-4-iodo-5-methylpyridine

To a solution of 2-fluoro-3-iodo-5-methylpyridine (800 mg, 3.4 mmol) in THF (30 mL) was added LDA (2 M, 2.6 mL) dropwise at −78° C. The reaction mixture was stirred at −78° C. for 2 h. The reaction was quenched with water (30 mL) and extracted with ethyl acetate (30 mL). The organic layer was dried over $Na_2SO_4$, filtered and evaporated, the residue was purified by silica gel column chromatography (petroleum ether/ethyl acetate=50/1) to give the desired product (590 mg, 74%). $^1H$ NMR (400 MHz, $CDCl_3$) δ 7.98 (s, 1H), 7.42 (d, J=3.2 Hz, 1H), 2.38 (s, 3H).

Step c: 4-iodo-N-(4-methoxybenzyl)-5-methylpyridin-2-amine

To a solution of 2-fluoro-4-iodo-5-methylpyridine (200 mg, 0.84 mmol), (4-methoxyphenyl)methanamine and $K_2CO_3$ in DMF (30 mL) was stirred at 90° C. overnight. Ethyl acetate (20 mL) was added and the organic layer was washed with saturated NaCl aqueous solution (10 mL×3). The organic layer was dried over $Na_2SO_4$, filtered and evaporated. The residue was purified by silica gel column chromatography (petroleum ether/ethyl acetate=10/1) to give the desired product (90 mg, 30%). $^1H$ NMR (400 MHz, $CDCl_3$) δ 7.84 (s, 1H), 7.25-7.23 (m, 2H), 6.93 (s, 1H), 6.87 (d, J=8.4 Hz, 2H), 4.37 (d, J=5.6 Hz, 2H), 3.80 (s, 3H), 2.24 (s, 3H).

Example 13: Preparation of 2,2-dimethyl-5-nitrobenzo[b]thiophen-3(2H)-one 1,1-dioxide (Method AM)

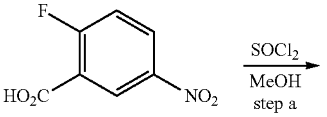

-continued

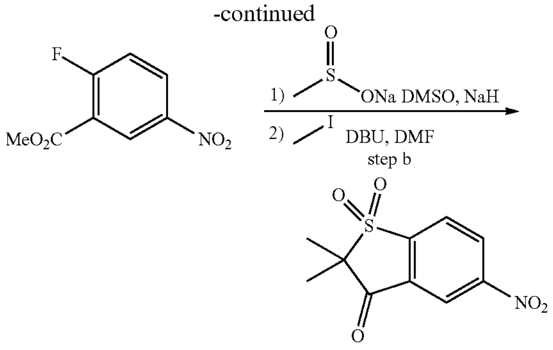

Step a: methyl 2-fluoro-5-nitrobenzoate

To a solution of 2-fluoro-5-nitrobenzoic acid (37 g, 200 mmol) in methanol (500 mL) was dripped sulfoxide dichloride (36 mL, 500 mmol) at room temperature and stirred at 60° C. overnight. The mixture was concentrated to give the desired product methyl 2-fluoro-5-nitrobenzoate (40.0 g, crude) as a white solid. $^1H$ NMR (400 MHz, $CDCl_3$) δ 8.91-8.81 (m, 1H), 8.46-8.37 (m, 1H), 7.39-7.28 (m, 1H), 3.99 (s, 3H).

Step b: 2,2-dimethyl-5-nitrobenzo[b]thiophen-3(2H)-one 1,1-dioxide

To a solution of methyl 2-fluoro-5-nitrobenzoate (20.0 g, 100 mmol) in DMSO (200 mL) was added sodium ethanesulfinate (11.7 g, 100 mmol) and stirred at room temperature overnight. Then, the mixture was added NaH (4.0 g, 100 mmol) and stirred at room temperature for 5 hours. Subsequently, the mixture was added $CH_3I$ (21.4 g, 150 mmol) and stirred at room temperature for 6 hours. The reaction mixture was added 1N HCl solution (250 mL) to adjust pH to 2 and extracted with ethyl acetate (500 mL). The organic layer was washed with water (250 mL×3), dried over anhydrous $Na_2SO_4$, filtered and concentrated to give the crude product. The residue was subsequently stirred in the suspension of MeOH (100 mL) and DCM (100 mL) at room temperature overnight. The suspension was filtered to give the desired product 2,2-dimethyl-5-nitrobenzo[b]thiophen-3(2H)-one 1,1-dioxide (11 g, 43%) as a yellow solid. $^1H$ NMR (400 MHz, DMSO-$d_6$) δ 8.83 (d, J=8.0 Hz, 1H), 8.62 (s, 1H), 8.52 (d, J=8.8 Hz, 1H), 1.56 (s, 6H).

Example 14: Preparation of 5-nitro-3H-spiro[benzo[b]thiophene-2,1'-cyclopentan]-3'-en-3-one 1,1-dioxide (Method AN)

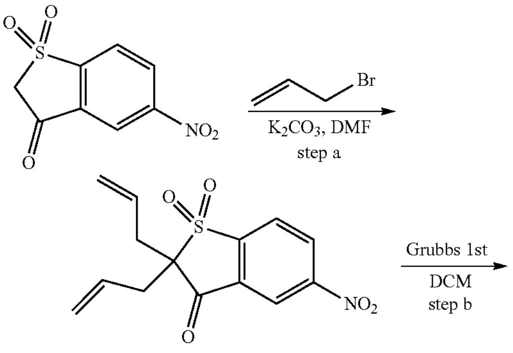

-continued

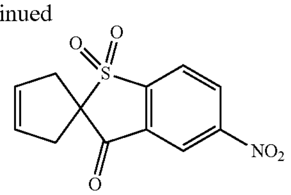

Step a: 2,2-diallyl-5-nitrobenzo[b]thiophen-3(2H)-one 1,1-dioxide

To a solution of 5-nitrobenzo[b]thiophen-3(2H)-one 1,1-dioxide (3.565 g, 15.7 mmol) in N, N-dimethylformamide (35 mL) was added allyl bromide (7.59 g, 62.7 mmol) and potassium carbonate (8.66 g, 62.7 mmol) and stirred at room temperature overnight. The mixture reaction was quenched with 3N HCl solution (20 mL) and extracted with ethyl acetate (50 mL×2). The combined organic layer was washed with brine (20 mL), dried over anhydrous $Na_2SO_4$, filtered and concentrated to give the crude product. The residue was purified by the silica gel column chromatography (petroleum ether/ethyl acetate=10/1) to give the desired product 2,2-diallyl-5-nitrobenzo[b]thiophen-3(2H)-one 1,1-dioxide (2.09 g, 43%) as a yellow solid. $^1H$ NMR (400 MHz, $CDCl_3$) δ 8.79-8.69 (m, 2H), 8.20 (d, J=8.4 Hz, 1H), 5.83-5.71 (m, 2H), 5.27-5.18 (m, 4H), 2.91-2.78 (m, 4H).

Step b: 5-nitro-3H-spiro[benzo[b]thiophene-2,1'-cyclopentan]-3'-en-3-one 1,1-dioxide To a solution of first generation Grubbs catalyst (212 mg, 0.258 mmol) in dichloromethane (200 mL) was slowly dripped the dichloromethane (50 mL) solution of 2,2-diallyl-5-nitrobenzo[b]thiophen-3(2H)-one 1,1-dioxide (2.09 g, 6.8 mmol) and the mixture was stirred at room temperature overnight. The mixture reaction was filtered and concentrated. The residue was purified by silica gel column chromatography (petroleum ether/ethyl acetate=10/1) to give the desired product 5-nitro-3H-spiro[benzo[b]thiophene-2,1'-cyclopentan]-3'-en-3-one 1,1-dioxide (1.88 g, 99%) as a yellow solid. $^1H$ NMR (400 MHz, $CDCl_3$) δ 8.83 (s, 1H), 8.76 (d, J=8.8 Hz, 1H), 8.24 (d, J=8.4 Hz, 1H), 5.77 (s, 2H), 3.46 (d, J=17.2 Hz, 2H), 3.01 (d, J=17.2 Hz, 2H).

Example 15: Preparation of N-(4,4-dioxido-2H-spiro[benzo[b][1,4]oxathiine-3,1'-cyclobutan]-7-yl) acetamide (Method AO)

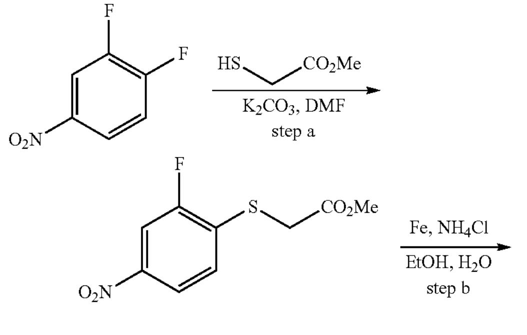

-continued

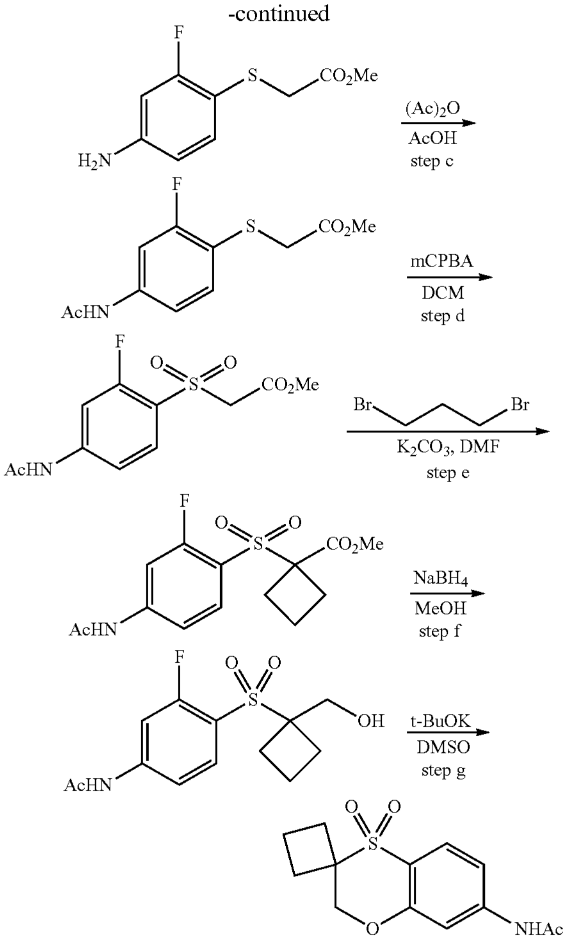

Step a: methyl 2-((2-fluoro-4-nitrophenyl)thio)acetate

To a solution of 1,2-difluoro-4-nitrobenzene (3.18 g, 20 mmol) and potassium carbonate (5.52 g, 40 mmol) in N,N-dimethylformamide (30 mL) was added methyl 2-mercaptoacetate (2.33 g, 22 mmol) at 0° C. and stirred at room temperature overnight. Then, the reaction mixture was poured into water (200 mL) and the suspension was filtered. The residue was subsequently washed with water (20 mL×2) and dried to yield the product methyl 2-((2-fluoro-4-nitrophenyl)thio)acetate (3.5 g, 71%) as a white solid. $^1H$ NMR (400 MHz, $CDCl_3$) δ 8.02 (d, J=8.4 Hz, 1H), 7.93 (d, J=9.6 Hz, 1H), 7.50 (t, J=8.0 Hz, 1H), 3.79 (s, 2H), 3.76 (s, 3H).

Step b: methyl 2-((4-amino-2-fluorophenyl)thio)acetate

To a solution of methyl 2-((2-fluoro-4-nitrophenyl)thio) acetate (3.5 g, 14 mmol) in ethanol (50 mL) and water (10 mL) was added Fe (3.2 g, 57 mmol) and $NH_4Cl$ (3.8 g, 71 mmol) at room temperature and stirred at 75° C. for 3 hours. The mixture reaction was filtered and the residue was subsequently washed with DCM (100 mL×3). The filtrate was washed with brine (200 mL), dried over anhydrous $Na_2SO_4$, filtered and concentrated to give the crude product. The residue was subsequently stirred in the suspension of $Et_2O$ (20 mL) at room temperature for 1 hour. The suspension was filtered to give the desired product methyl 2-((4- amino-2-fluorophenyl)thio)acetate (2.4 g, 78%) as a white solid. $^1$H NMR (400 MHz, $CDCl_3$) δ7.31-7.27 (m, 1H), 6.48-6.30 (m, 2H), 3.89 (s, 2H), 3.67 (s, 3H), 3.44 (s, 2H).

Step c: methyl 2-((4-acetamido-2-fluorophenyl)thio)acetate

To a solution of methyl 2-((4-amino-2-fluorophenyl)thio) acetate (2.0 g, 11 mmol) in acetic acid (14 mL) was added acetic anhydride (1.4 g, 13 mmol) at 0° C. and stirred at room temperature for 4 hours. Then, the reaction mixture was poured into water (150 mL) and the suspension was filtered. The residue was subsequently dried to yield the product methyl 2-((4-acetamido-2-fluorophenyl)thio)acetate (2.0 g, crude) as a white solid (2.1 g,71%).

Step d: methyl 2-((4-acetamido-2-fluorophenyl)sulfonyl)acetate

To a solution of methyl 2-((4-acetamido-2-fluorophenyl) thio)acetate (1.8 g, 7 mmol) in dichloromethane (130 mL) was added mCPBA (3.8 g, 19 mmol) at 0° C. and the mixture reaction was stirred at room temperature overnight. The mixture reaction was quenched with saturated $Na_2SO_3$ aqueous solution (20 mL) and subsequently washed with saturated $NaHCO_3$ aqueous solution (60 mL). The organic layer was dried over anhydrous $Na_2SO_4$, filtered and concentrated to give the crude product. The residue was subsequently stirred in the suspension of EA (20 mL) at room temperature for 2 hours. The suspension was filtered to give the desired product methyl 2-((4-acetamido-2-fluorophenyl)sulfonyl) acetate (1.2 g, 60%) as a white solid. $^1$H NMR (400 MHz, $CDCl_3$) δ 7.90-7.77 (m, 2H), 7.65 (s, 1H), 7.19 (d, J=8.4 Hz, 1H), 4.28 (s, 2H), 3.70 (s, 3H), 2.23 (s, 3H).

Step e: methyl 1-((4-acetamido-2-fluorophenyl) sulfonyl)cyclobutane-1-carboxylate To a solution of methyl 2-((4-acetamido-2-fluorophenyl) sulfonyl)acetate (1.2 g, 4.2 mmol) in DMF (40 mL) was added 1,3-dibromopropane (1.3 g, 6.8 mmol) and $K_2CO_3$ (1.2 g, 8.5 mmol) at room temperature and stirred at 60° C. for 3 hours. The mixture reaction was added brine (100 mL) and extracted with ethyl acetate (200 mL). The organic layer dried over anhydrous $Na_2SO_4$, filtered and concentrated to give the crude product. The residue was subsequently stirred in the suspension of $Et_2O$ (15 mL) at room temperature for 1 hour. The suspension was filtered to give the desired product methyl 1-((4-acetamido-2-fluorophenyl)sulfonyl) cyclobutane-1-carboxylate (0.96 g, 69%) as a white solid. $^1$H NMR (400 MHz, $CDCl_3$) δ7.80-7.65 (m, 2H), 7.51 (s, 1H), 7.21 (d, J=8.4 Hz, 1H), 3.68 (s, 3H), 3.10-2.95 (m, 2H), 2.70-2.60 (m, 2H), 2.23 (s, 3H), 2.15-1.95 (m, 2H).

Step f: N-(3-fluoro-4-((1-(hydroxymethyl)cyclobutyl)sulfonyl)phenyl)acetamide

To a solution of methyl 1-((4-acetamido-2-fluorophenyl) sulfonyl)cyclobutane-1-carboxylate (940 mg, 2.86 mmol) in methanol (40 mL) was added $NaBH_4$ (435 mg, 11.4 mmol) at 0° C. and stirred at room temperature overnight. The mixture reaction was quenched with saturated $NaHCO_3$ aqueous solution (200 mL) and extracted with DCM (100 mL×2). The combined organic layer was dried over anhydrous $Na_2SO_4$, filtered and concentrated to give the crude product N-(3-fluoro-4-((1-(hydroxymethyl)cyclobutyl) sulfonyl)phenyl)acetamide (630 mg, 73%) as a yellow solid. $^1$H NMR (400 MHz, $CDCl_3$) δ7.84-7.72 (m, 2H), 7.64 (s, 1H), 7.23 (d, J=8.8 Hz, 1H), 3.87 (d, J=6.4 Hz, 2H), 2.85-2.74 (m, 2H), 2.23 (s, 3H), 2.10-1.90 (m, 4H).

Step g: N-(4,4-dioxido-2H-spiro[benzo[b][1,4]oxathiine-3,1'-cyclobutan]-7-yl)acetamide To a solution of N-(3-fluoro-4-((1-(hydroxymethyl)cyclobutyl)sulfonyl)phenyl)-acetamide (613 mg, 2.0 mmol) in DMSO (10 mL) was added t-BuOK (246 mg, 2.2 mmol) at room temperature and stirred at 80° C. for 1.5 hours. The mixture reaction was added brine (100 mL) and extracted with ethyl acetate (200 mL). The organic layer dried over anhydrous $Na_2SO_4$, filtered and concentrated to give the crude product N-(4,4-dioxido-2H-spiro[benzo[b][1,4]-oxathiine-3,1'-cyclobutan]-7-yl)acetamide (500 mg, crude) as a white solid.

Example 16: Preparation of 5-nitro-4',5'-dihydro-2H,3'H-spiro[benzo[b]thiophene-3,2'-furan] 1,1-dioxide (Method AP)

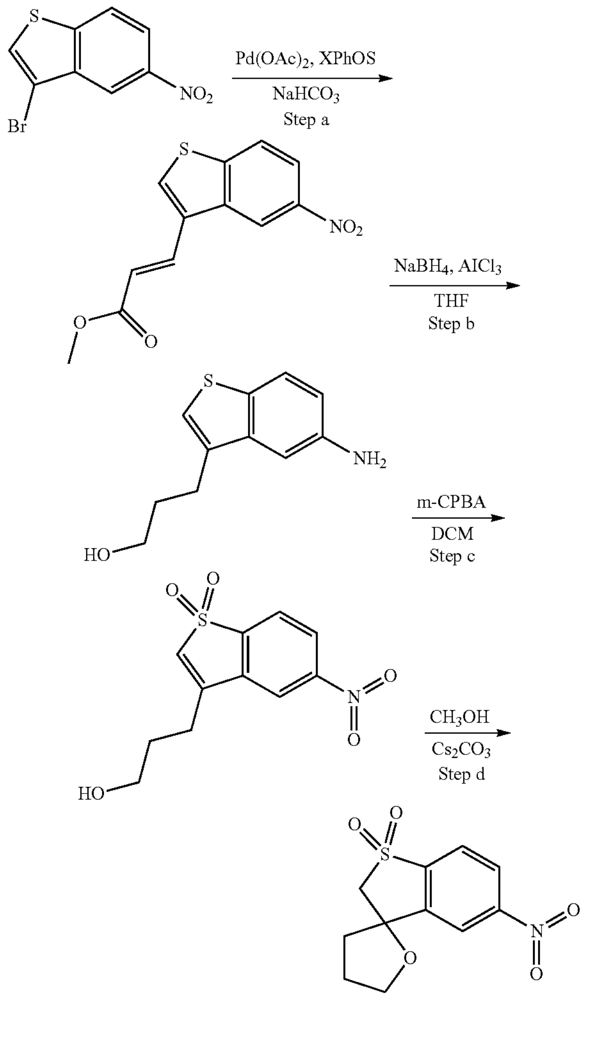

Step a: Methyl (E)-3-(5-nitrobenzo[b]thiophen-3-yl) acrylate

To a solution of 3-bromo-5-nitrobenzo[b]thiophene (5.0 g, 19.4 mmol) in DMF (50 mL) was added $NaHCO_3$ (3.3 g, 3.9 mmol), Xphos (954 mg, 2.0 mmol), $Pd(OAc)_2$ (220 mg, 1.0 mmol). The reaction was stirred at 120° C. under $N_2$ atmosphere for 4 h. The solvent was removed in vacuum and the residue was purified by silica gel column chromatography (DCM) to give the desired product (3.6 g, 71%) as a yellow solid. $^1H$ NMR (400 MHz, $CDCl_3$) δ 8.89 (s, 1H), 8.28 (d, J=8.0 Hz, 1H), 8.07-7.87 (m, 3H), 6.58 (d, J=16.0 Hz, 1H), 3.87 (s, 3H).

Step b: 3-(5-aminobenzo[b]thiophen-3-yl)propan-1-ol

To a solution of Methyl (E)-3-(5-nitrobenzo[b]thiophen-3-yl)acrylate (3.6 g, 13.7 mmol) in dry THF (100 mL) with an ice bath was added $NaBH_4$ (4.2 g, 109.6 mmol) slowly. The reaction was stirred at room temperature overnight. $AlCl_3$ (3.6 g, 27.4 mmol) was added with an ice bath and the reaction was stirred at reflux temperature for 2 day. The reaction was quenched by saturated $NH_4Cl$ aqueous solution under ice bath. The solid was filtered off, washed with EA (50 mL) and the resulting filtrate was extracted with EA (50 mL×3). The combined organic phase was dried over $Na_2SO_4$, filtrated and concentrated. The residue was purified by silica gel column chromatography (DCM/MeOH=50/1) to give the desired product (1.8 g. 64%) as a yellow solid. $^1H$ NMR (400 MHz, DMSO-$d_6$) δ 8.07 (s, 1H), 8.02 (d, J=8.4 Hz, 1H), 7.47 (d, J=8.4 Hz, 1H), 5.10 (s, 1H), 3.73-3.53 (m, 4H), 3.44-3.37 (m, 2H). LCMS (ESI/APCI) m/z: 207.9 $[M+H]^+$.

Step c: 3-(3-hydroxypropyl)-5-nitrobenzo[b]thiophene 1,1-dioxide

To a solution of 3-(5-aminobenzo[b]thiophen-3-yl)propan-1-ol (1.8 g, 8.7 mmol) in DCM (50 mL) with an ice bath was added 85% m-CPBA (4.4 g, 21.8 mmol). The mixture was stirred at room temperature overnight. The mixture was filtered and the filtrate was quenched with $Na_2SO_3$, washed with saturated $NaHCO_3$ aqueous solution, extracted with DCM (40 mL×3). The combined organic phase was dried over $Na_2SO_4$, filtered and concentrated. The residue was purified by silica gel column chromatography (DCM/MeOH=50/1) to give the desired product (800 mg, 34%) as a yellow solid. $^1H$ NMR (400 MHz, $CDCl_3$) δ 8.43 (d, J=7.6 Hz, 1H), 8.31 (s, 1H), 7.90 (d, J=8.0 Hz, 1H), 6.66 (s, 1H), 3.90-3.76 (m, 2H), 2.84 (t, J=6.8 Hz, 2H), 2.04-1.91 (m, 2H). LCMS (ESI/APCI) m/z: 267.8 $[M-H]^-$.

Step d: 5-nitro-4',5'-dihydro-2H,3'H-spiro[benzo[b]thiophene-3,2'-furan] 1,1-dioxide To a solution of 3-(3-hydroxypropyl)-5-nitrobenzo[b]thiophene 1,1-dioxide (800 mg, 3.0 mmol) in MeOH (40 mL) was added $Cs_2CO_3$ (1.47 g, 4.5 mmol). The mixture was turned into dark yellow quickly and stirred at room temperature for 2 h. The solvent was removed in vacuum and the residue was purified by silica gel column chromatography (PE/EA=5/1) to give the desired product (200 mg, 25%) as a yellow solid. $^1H$ NMR (400 MHz, $CDCl_3$) δ 8.45-8.32 (m, 2H), 7.90 (d, J=8.4 Hz, 1H), 4.36-4.12 (m, 2H), 3.61 (q, J=13.0 Hz, 2H), 2.63-2.25 (m, 2H), 2.25-2.07 (m, 2H).

Example 17: Preparation of 8-(benzo[d]thiazol-5-ylamino)-3-bromothieno[2,3-g]quinoline 1,1-dioxide (A1) (Method BB)

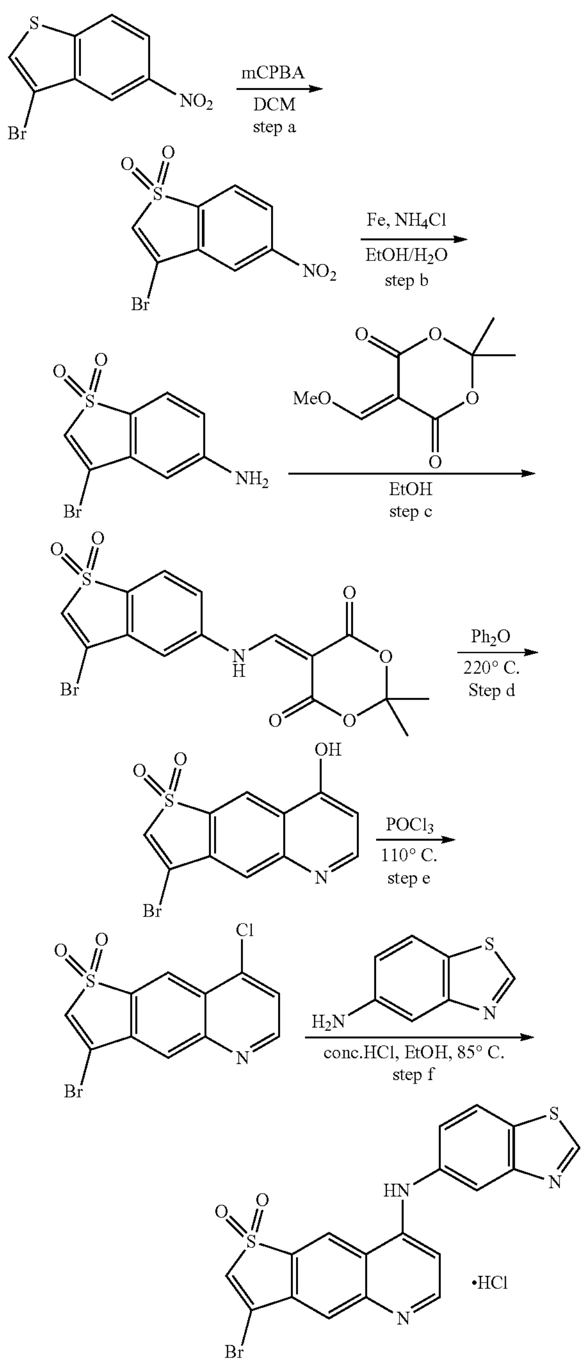

Step a: 3-bromo-5-nitrobenzo[b]thiophene 1,1-dioxide

To a solution of 3-bromo-5-nitrobenzo[b]thiophene (21.0 g, 81.4 mmol) in DCM (300 mL) with an ice bath was added 85% m-CPBA (42.0 g, 203.5 mmol). The mixture was stirred at room temperature overnight. The resulting solid was filtered off and the filtrate was quenched with $Na_2SO_3$ aqueous solution, and washed with saturated $NaHCO_3$ aqueous solution, the aqueous layer was extracted with DCM (200 mL×2). The combined organic phase was dried over $Na_2SO_4$, filtered and concentrated. The residue was rinsed with EA and dried in vacuum to give the desired product (20.8 g, 99%) as a white solid. $^1H$ NMR (400 MHz, DMSO-$d_6$) δ8.56 (dd, J=8.4 Hz, J=1.2 Hz, 1H), 8.34 (s, 1H), 8.30 (d, J=8.4 Hz, 1H), 8.20 (d, J=1.6 Hz, 1H).

Step b: 5-amino-3-bromobenzo[b]thiophene 1,1-dioxide

To a solution of 3-bromo-5-nitrobenzo[b]thiophene 1,1-dioxide (20.8 g, 71.7 mmol) in EtOH (300 mL) and $H_2O$ (100 mL) was added iron powder (16.1 g, 287 mmol) and $NH_4Cl$ (15.3 g, 287 mmol). The mixture was stirred at 85° C. for 2 h. The reaction was filtered through diatomaceous earth and the cake was washed with DCM. The resulting filtrate was extracted with DCM (500 mL×3). The combined organic phase was dried over $Na_2SO_4$, filtered and concentrated. The residue was rinsed with EA, dried in vacuum to give the desired product (15.0 g, 81%) as a yellow solid. $^1H$ NMR (400 MHz, DMSO-$d_6$) δ 7.84 (s, 1H), 7.47 (s, 1H), 6.89-6.59 (m, 2H), 6.44 (s, 2H). LCMS (ESI/APCI) m/z 257.7 $[M-H]^-$.

Step c: 5-(((3-bromo-1,1-dioxidobenzo[b]thiophen-5-yl)amino)methylene)-2,2-dimethyl-1,3-dioxane-4,6-dione To a solution of 5-amino-3-bromobenzo[b]thiophene 1,1-dioxide (13.5 g, 51.9 mmol) in EtOH (120 mL) was added 5-(methoxymethylene)-2,2-dimethyl-1,3-dioxane-4,6-dione (14.3 g, 77.9 mmol). The mixture was stirred at room temperature for 30 min. The resulting solid was collected via filtration, washed with EtOH (20 mL) and dried in vacuum to give the desired product (18.0 g, 86%) as a yellow solid. $^1H$ NMR (400 MHz, DMSO-$d_6$) δ11.42 (d, J=12.8 Hz, 1H), 8.68 (d, J=13.6 Hz, 1H), 8.13 (s, 1H), 7.99 (s, 1H), 7.90 (s, 2H), 1.69 (s, 6H).

Step d: 3-bromo-8-hydroxythieno[2,3-g]quinoline 1,1-dioxide

The diphenyl ether (720 mL) was added to a round-bottomed flask and the solvent was heated to 240° C. for 5 min. Intermediate 5-(((3-bromo-1,1-dioxidobenzo[b]thiophen-5-yl)amino)methylene)-2,2-dimethyl-1,3-dioxane-4,6-dione (18.0 g, 43.6 mmol) was added slowly to the solution. The mixture was stirred for 5 min. After cooling to room temperature, the resulting solid was collected via filtration, washed with ether (100 mL) and dried in vacuum to give the desired product (5.5 g, 41%) as a grey solid. $^1H$ NMR (400 MHz, DMSO-$d_6$) δ12.31 (s, 1H), 8.35 (s, 1H), 8.25 (s, 1H), 8.08 (d, J=7.2 Hz, 1H), 7.77 (s, 1H), 6.23 (d, J=6.8 Hz, 1H). LCMS (ESI/APCI) m/z 311.6 $[M+H]^+$.

Step e. 3-bromo-8-chlorothieno[2,3-g]quinoline 1,1-dioxide

Intermediate 3-bromo-8-hydroxythieno[2,3-g]quinoline 1,1-dioxide (5.5 g, 17.7 mmol) was added to $POCl_3$ (50 mL) and then the mixture was stirred at reflux for 2 hours to afford a light brown solution. After cooling to room temperature, the excess $POCl_3$ was removed in vacuum. The residue was used directly for next step.

Step f: 8-(benzo[d]thiazol-5-ylamino)-3-bromothieno[2,3-g]quinoline 1,1-dioxide

3-Bromo-8-chlorothieno[2,3-g]quinoline 1,1-dioxide (5.8 g, 17.7 mmol) was dissolved in EtOH (20 mL) and benzo[d]thiazol-5-amine (3.2 g, 21.3 mmol) was added subsequently. The mixture was stirred at reflux for 1 h. After cooling to room temperature. The resulting solid was collected via filtration, washed with EtOH and dried in vacuum to give the desired product as a hydrochloride salt (6.0 g, 77%). $^1H$ NMR (400 MHz, DMSO-$d_6$) δ 11.37 (s, 1H), 9.55 (s, 1H), 9.43 (s, 1H), 8.63 (d, J=6.8 Hz, 1H), 8.50 (s, 1H), 8.40 (d, J=8.8 Hz, 1H), 8.27-8.21 (m, 2H), 7.62 (d, J=8.8 Hz, 1H), 7.04 (d, J=7.2 Hz, 1H). LC-MS (ESI/APCI) m/z: 443.5 $[M+H]^+$.

Example 18: Preparation of 8-(benzo[d]thiazol-5-ylamino)-2H-spiro[thieno[2,3-g]quinoline-3,2'-[1,3]dioxolane]1,1-dioxide (B2) and 8-(benzo[d]thiazol-5-ylamino)-3-(2-hydroxyethoxy)thieno[2,3-g]quinoline 1,1-dioxide (A16) (Method BC)

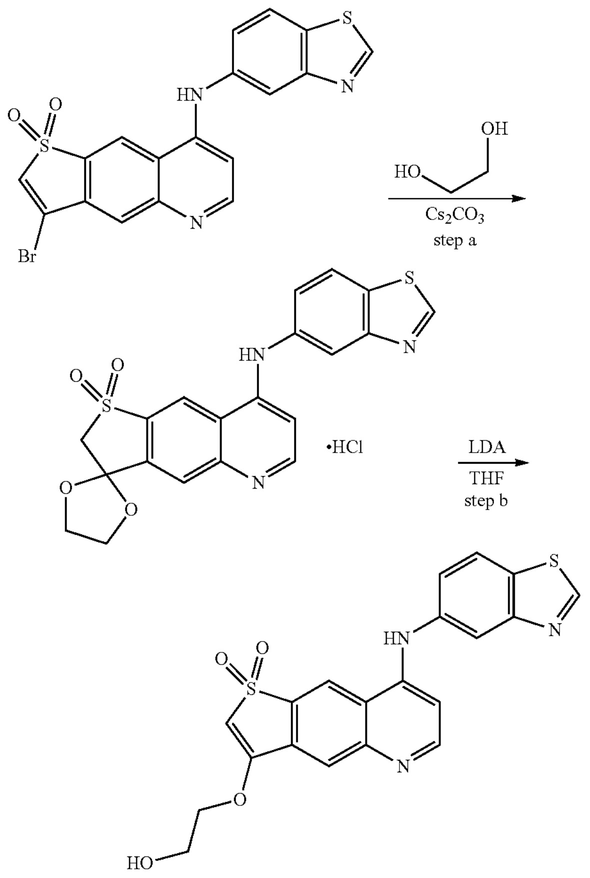

Step a: 8-(benzo[d]thiazol-5-ylamino)-2H-spiro[thieno[2,3-g]quinoline-3,2'-[1,3]dioxolane] 1,1-dioxide (B2)

To a solution of 8-(benzo[d]thiazol-5-ylamino)-3-bromothieno[2,3-g]quinoline 1,1-dioxide (450 mg, 0.9 mmol) in Ethylene glycol (10 mL) was added $Cs_2CO_3$ (826 mg, 2.5 mmol). The mixture was stirred at 60° C. for 5 h. The solvent was removed in vacuum and the residue was purified by silica gel column chromatography (DCM/MeOH=100/1) to give the crude product. Which was dissolved in acetone (50 mL). 2N EA/HCl (2 mL) was added. The resulting solid was collected via filtration, washed with EtOH and dried in vacuum to give the desired product (55 mg, 13%) as a hydrochloride. $^1$H NMR (400 MHz, DMSO-$d_6$) δ 15.02 (s, 1H), 11.48 (s, 1H), 9.55 (s, 1H), 9.46 (s, 1H), 8.63 (d, J=6.8 Hz, 1H), 8.43-8.36 (m, 2H), 8.25 (s, 1H), 7.63 (d, J=8.4 Hz, 1H), 6.99 (d, J=6.4 Hz, 1H), 4.33 (s, 2H), 4.25 (s, 2H), 4.14 (s, 2H). LCMS (ESI/APCI) m/z: 425.6 [M+H]$^+$.

Step b: 8-(benzo[d]thiazol-5-ylamino)-3-(2-hydroxyethoxy)thieno[2,3-g]quinoline 1,1-dioxide (A16)

To a solution of 8-(benzo[d]thiazol-5-ylamino)-2H-spiro[thieno[2,3-g]quinoline-3,2'-[1,3]dioxolane] 1,1-dioxide (12 mg, 0.03 mmol) in dry THF (3 mL) was added LDA (0.06 mL, 0.12 mmol) at −78° C. The mixture was stirred at room temperature for 3 h. Saturated $NH_4Cl$ aqueous solution was added to quench the reaction. The aqueous layer was extracted with DCM (10 mL×3). The combined organic layer was dried over $Na_2SO_4$, filtered and concentrated. The residue was purified by silica gel column chromatography (DCM/MeOH=20/1) to give the desired product (4 mg, 31%) as a yellow solid. $^1$H NMR (400 MHz, DMSO-$d_6$) δ 9.47 (s, 1H), 9.08 (s, 1H), 8.59 (d, J=5.6 Hz, 1H), 8.27 (d, J=8.8 Hz, 1H), 8.10 (s, 1H), 8.06 (s, 1H), 7.57 (d, J=8.8 Hz, 1H), 7.08 (d, J=5.6 Hz, 1H), 6.95 (s, 1H), 5.14 (s, 1H), 4.25 (s, 2H), 3.83 (s, 2H). LCMS (ESI/APCI) m/z: 425.7 [M+H]$^+$.

Example 19: Preparation of 8-(benzo[d]thiazol-5-ylamino)-3-methoxythieno[2,3-g]quinoline 1,1-dioxide (A12) (Method BD)

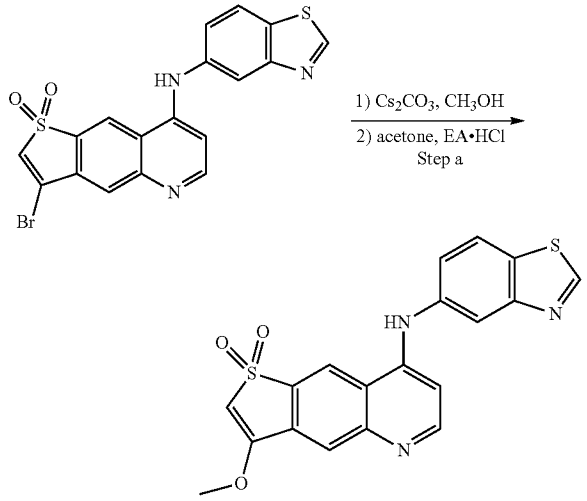

Step a: 8-(benzo[d]thiazol-5-ylamino)-3-methoxythieno[2,3-g]quinoline 1,1-dioxide To a solution of 8-(benzo[d]thiazol-5-ylamino)-3-bromothieno[2,3-g]quinoline 1,1-dioxide (300 mg, 0.63 mmol) in $CH_3OH$ was added $Cs_2CO_3$ (462 mg, 4.42 mmol). The mixture was stirred at room temperature for 20 h. the solvent was removed in vacuum and the residue was purified by silica gel column chromatography (DCM/MeOH=100/1) to give the crude product. Then the crude product was dissolved in acetone (50 mL). 2N EA/HCl (2 mL) was added. The mixture was stirred for 10 min. The resulting solid was collected via filtration, dried over vacuum to give the desired product as hydrochloride salt (105 mg, 39%). $^1$H NMR (400 MHz, DMSO-$d_6$) δ14.88 (s, 1H), 11.25 (s, 1H), 9.54 (s, 1H), 9.34 (s, 1H), 8.60 (d, J=6.8 Hz, 1H), 8.40 (d, J=8.4 Hz, 1H), 8.23 (s, 1H), 8.17 (s, 1H), 7.62 (d, J=8.4 Hz, 1H), 7.16 (s, 1H), 7.01 (d, J=7.2 Hz, 1H), 4.07 (s, 3H). LCMS (ESI/APCI) m/z: 395.7 [M+H]$^+$.

Example 20: Preparation of 8-(benzo[d]thiazol-5-ylamino)-3-(4-fluorophenyl)thieno[2,3-g]quinoline 1,1-dioxide (A25) (Method BE)

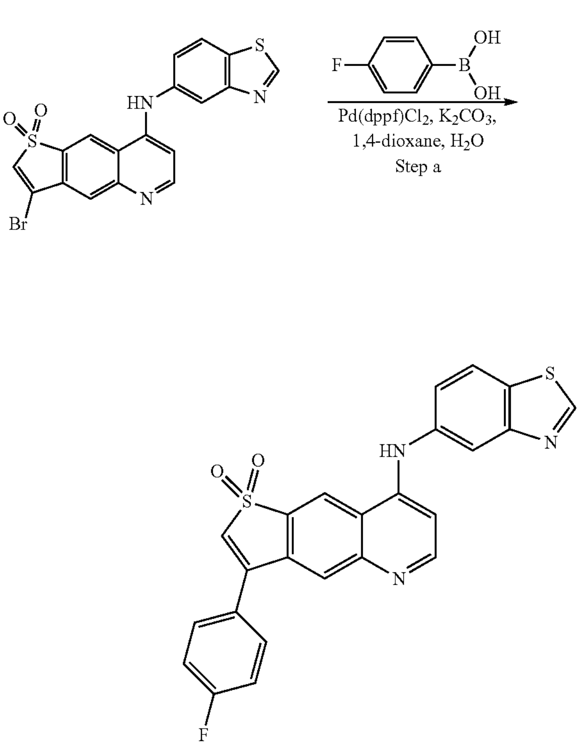 [SMILES: O=S1(=O)C=C(Br)c2cc3nccc(Nc4ccc5scnc5c4)c3cc21 ; OB(O)c1ccc(F)cc1 ; O=S1(=O)C=C(c2ccc(F)cc2)c2cc3nccc(Nc4ccc5scnc5c4)c3cc21]

Step a: 8-(benzo[d]thiazol-5-ylamino)-3-(4-fluorophenyl)thieno[2,3-g]quinoline 1,1-dioxide To a solution of 8-(benzo[d]thiazol-5-ylamino)-3-bromothieno[2,3-g]quinoline 1,1-dioxide (50 mg, 0.11 mmol) in dioxane/$H_2O$ (10 mL/1 mL) was added (4-fluorophenyl)boronic acid (24 mg, 0.17 mmol), $Pd(dppf)Cl_2$ (10 mg, 0.01 mmol) and $K_2CO_3$ (40 mg, 0.34 mmol). The mixture was stirred at 100° C. under $N_2$ atmosphere overnight. The solvent was removed in vacuum and the residue was purified by silica gel column chromatography (DCM/MeOH=40/1) to give the desired product (30 mg, 58%) as a yellow solid. $^1$H NMR (400 MHz, DMSO-$d_6$) δ 11.32 (s, 1H), 9.55 (s, 1H), 9.43 (s, 1H), 8.61 (d, J=6.8 Hz, 1H), 8.41 (d, J=8.4 Hz, 1H), 8.25 (s, 1H), 8.19 (s, 1H), 8.00 (s, 1H), 7.89-7.85 (m, 2H), 7.64 (d, J=8.0 Hz, 1H), 7.54 (t, J=8.8 Hz, 2H), 7.04 (d, J=6.4 Hz, 1H)LCMS (ESI/APCI) m/z: 459.6 [M+H]$^+$.

Example 21: Preparation of 8-(imidazo[1,2-a]pyridin-7-ylamino)-2-methylthieno[2,3-g]quinoline 1,1-dioxide (A67) (Method BF)

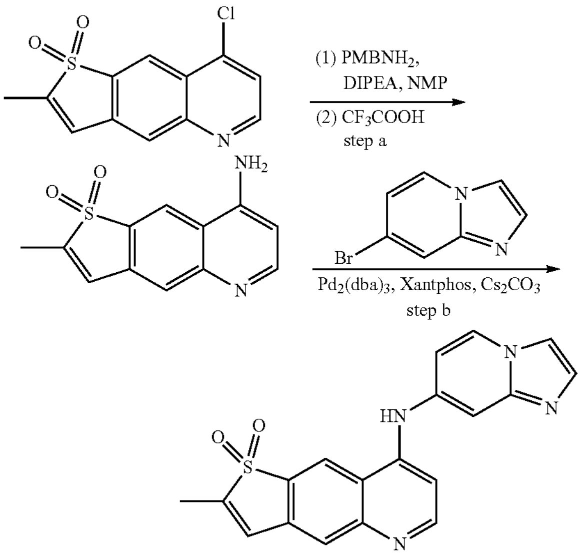

Step a: 8-amino-2-methylthieno[2,3-g]quinoline 1,1-dioxide

To a solution of 8-chloro-2-methylthieno[2,3-g]quinoline 1,1-dioxide (300 mg, 1.1 mmol) in N-methyl pyrrolidone (10 mL) was added 4-methoxybenzylamine (233 mg, 1.7 mmol) and DIPEA (636 mg, 3.3 mmol). The mixture was stirred at 120° C. under the microwave for 2 h. EA (20 mL) was added to dilute the solution and the organic layer was washed with saturated NaCl aqueous solution (10 mL×3). The organic layer was dried over $Na_2SO_4$, filtered and concentrated. The residue was dissolved in $CF_3COOH$ (5 mL). the mixture was stirred at reflux for 1 h. the solvent was removed in vacuum. Saturated $NaHCO_3$ aqueous solution was added to adjust pH to 8. $Et_2O$ (10 mL) was added and the resulting solid was collected via filtration, dried in vacuum to give the desired product (110 mg, 41%) as a yellow solid. $^1H$ NMR (400 MHz, DMSO-$d_6$) δ 8.77 (s, 1H), 8.36 (d, J=5.6 Hz, 1H), 7.76 (s, 1H), 7.38 (s, 1H), 7.17 (s, 2H), 6.62 (d, J=5.2 Hz, 1H), 2.18 (s, 3H).

Step b: 8-(imidazo[1,2-a]pyridin-7-ylamino)-2-methylthieno[2,3-g]quinoline 1,1-dioxide To a solution of 8-amino-2-methylthieno[2,3-g]quinoline 1,1-dioxide (100 mg, 0.41 mmol) in dioxane (15 mL) was added 7-bromoimidazo[1,2-a]pyridine (223 mg, 1.1 mmol), $Pd_2(dba)_3$, Xantphos (55 mg, 0.09 mmol) and $Cs_2CO_3$ (390 mg, 1.2 mmol). The mixture was stirred at 100° C. under $N_2$ atmosphere overnight. the solvent was removed in vacuum and the residue was purified by silica gel column chromatography (DCM/MeOH=50/1) to give the desired product (23 mg. 16%) as a yellow solid. $^1H$ NMR (400 MHz, DMSO-$d_6$) δ 9.58 (s, 1H), 8.94 (s, 1H), 8.66 (d, J=5.6 Hz, 1H), 8.59 (d, J=7.2 Hz, 1H), 7.97 (s, 1H), 7.94 (s, 1H), 7.56 (s, 1H), 7.47 (s, 2H), 7.30 (s, 1H), 7.07 (d, J=7.6 Hz, 1H), 2.22 (s, 3H). LC-MS (m/z): 362.8 $[M+H]^+$.

Example 22: Preparation of 8-((2-aminopyridin-4-yl)amino)-2-methylthieno[2,3-g]quinoline 1,1-dioxide (A65) (Method BG)

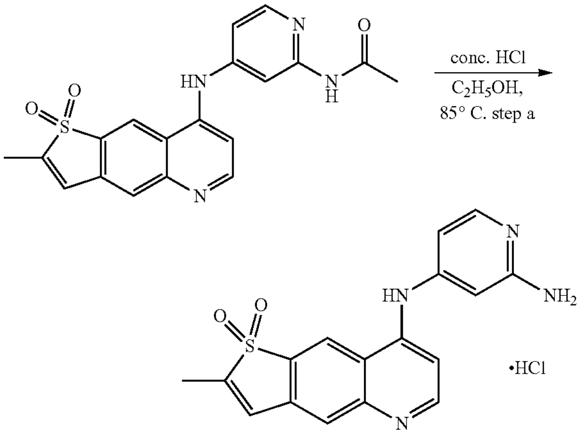

Step a: 8-((2-aminopyridin-4-yl)amino)-2-methylthieno[2,3-g]quinoline 1,1-dioxide To a solution of N-(4-((2-methyl-1,1-dioxidothieno[2,3-g]quinolin-8-yl)amino)pyridin-2-yl)acetamide (60 mg, 0.16 mmol) in EtOH (4 mL) was added conc. HCl (1 mL). the mixture was stirred at reflux for 1 h. The resulting solid was collected via filtration, washed with EtOH and dried in vacuum to give the desired product (30 mg, 56%) as a white solid. $^1H$ NMR (400 MHz, DMSO-$d_6$) δ 13.17 (s, 1H), 10.96 (s, 1H), 9.07 (s, 1H), 8.96 (d, J=5.6 Hz, 1H), 8.21 (s, 1H), 7.93 (d, J=6.8 Hz, 1H), 7.88 (s, 2H), 7.65 (d, J=5.6 Hz, 1H), 7.59 (s, 1H), 6.87 (d, J=6.4 Hz, 1H), 6.81 (s, 1H), 2.25 (s, 3H). LC-MS (m/z): 338.8 $[M+H]^+$.

Example 23: Preparation of 8-((5-(aminomethyl)-2-methylphenyl)amino)-2-methylthieno[2,3-g]quinoline 1,1-dioxide (A50) (Method BH)

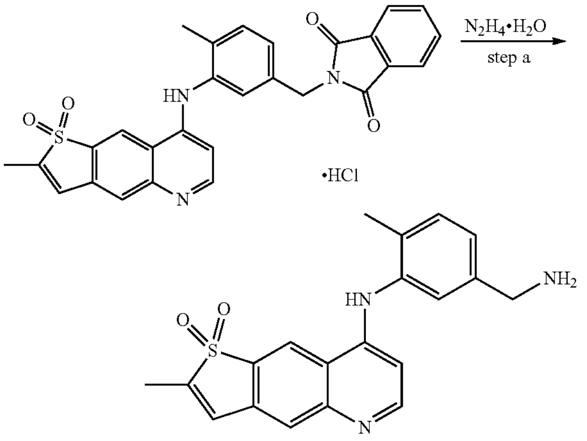

Step a: 8-((5-(aminomethyl)-2-methylphenyl)amino)-2-methylthieno[2,3-g]quinoline 1,1-dioxide To a solution of 2-(4-methyl-3-((2-methyl-1,1-dioxidothieno[2,3-g]quinolin-8-yl)amino)benzyl)isoindoline-1,3-dione (49 mg, 0.1 mmol) in EtOH (3 mL) was added hydrazine hydrate (2 mL). The mixture was stirred at room temperature for 4 h. The resulting solid was collected via filtration, washed with acetone, dried in vacuum to give the desired product as a white solid (10 mg, 27%). $^1$H NMR (400 MHz, DMSO-$d_6$) δ 9.08 (s, 2H), 8.44 (s, 1H), 8.13-7.81 (m, 3H), 7.54-7.23 (m, 4H), 6.28 (s, 1H), 4.02 (s, 2H), 2.21 (s, 6H). LC-MS (m/z): 365.8 $[M+H]^+$.

Example 24: Preparation of 8-((4-amino-6-fluoropyridin-2-yl)amino)-2-methylthieno[2,3-g]quinoline 1,1-dioxide (A71) (Method BH)

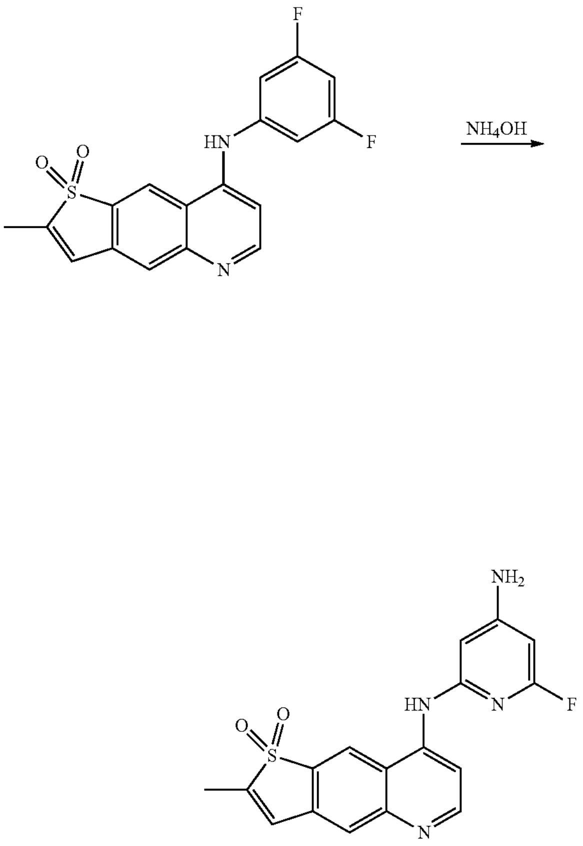

Step a: 8-((4-amino-6-fluoropyridin-2-yl)amino)-2-methylthieno[2,3-g]quinoline 1,1-dioxide To a solution of 8-((4,6-difluoropyridin-2-yl)amino)-2-methylthieno[2,3-g]quinoline 1,1-dioxide (200 mg, 0.56 mmol) in DMSO (3 mL) was added ammonium hydroxide (10 mL). The mixture was stirred at 120° C. overnight. Saturated NaCl aqueous solution (10 mL) was added and the solution was extracted with DCM (10 mL×3). The combined organic layer was dried over $Na_2SO_4$, filtered and concentrated. The residue was purified by silica gel column chromatography (DCM/MeOH=20/1) to give the desired product (6 mg, 3%) as a yellow solid. $^1$H NMR (400 MHz, DMSO-$d_6$) δ 9.50 (s, 1H), 9.06 (s, 1H), 8.69 (s, 1H), 8.21 (s, 1H), 7.94 (s, 1H), 7.45 (s, 1H), 6.51 (s, 2H), 6.35 (s, 1H), 5.82 (s, 1H), 2.21 (s, 3H). LC-MS (m/z): 356.7 $[M+H]^+$.

Example 25: Preparation of 8-(benzo[d]thiazol-5-ylamino)-2,3-dihydrothieno[2,3-g]quinoline 1,1-dioxide (B1) (Method BJ)

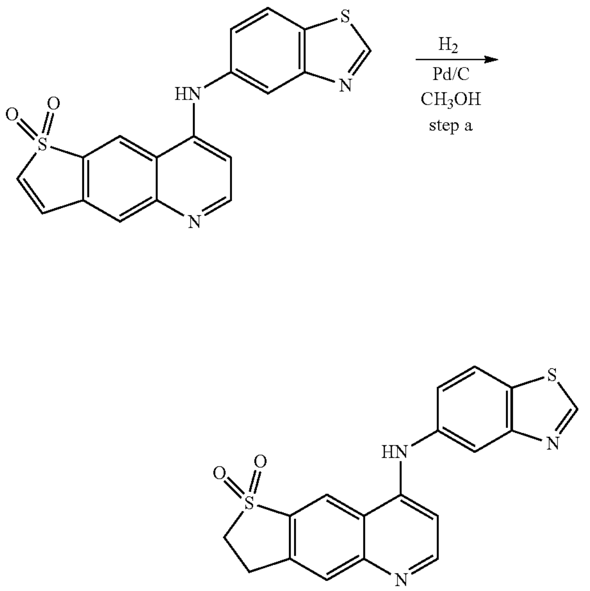

Step a: 8-(benzo[d]thiazol-5-ylamino)-2,3-dihydrothieno[2,3-g]quinoline 1,1-dioxide To a solution of 8-(benzo[d]thiazol-5-ylamino)thieno[2,3-g]quinoline 1,1-dioxide (50 mg, 0.14 mmol) in methanol (30 mL) was added 5% Pd/C (5 mg, 0.05 mmol) and stirred at room temperature under $H_2$ atmosphere for 24 h. The mixture was filtered and concentrated. The residue was purified by silica gel column chromatography (dichloromethane/methanol=50/1) to give the desired product 8-(benzo[d]thiazol-5-ylamino)-2,3-dihydrothieno[2,3-g]quinoline 1,1-dioxide (24 mg, 47%) as a yellow solid. $^1$H NMR (400 MHz, DMSO-$d_6$) δ 9.57 (s, 1H), 9.45 (s, 1H), 9.00 (s, 1H), 8.57 (d, J=5.6 Hz, 1H), 8.22 (d, J=8.8 Hz, 1H), 8.06 (s, 1H), 7.98 (s, 1H), 7.56 (d, J=8.4 Hz, 1H), 7.05 (d, J=5.2 Hz, 1H), 3.72 (t, J=6.8 Hz, 2H), 3.54 (t, J=6.4 Hz, 2H).

Example 26: Preparation of 8-(benzo[d]thiazol-5-ylamino)thieno[2,3-g]quinolin-3(2H)-one 1,1-dioxide hydrochloride (B3) (Method BK)

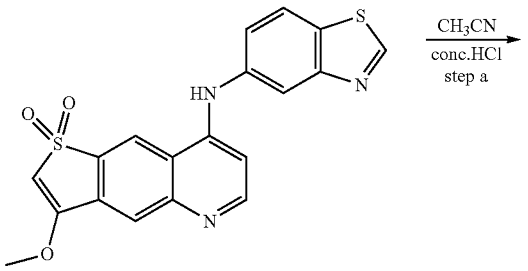

-continued

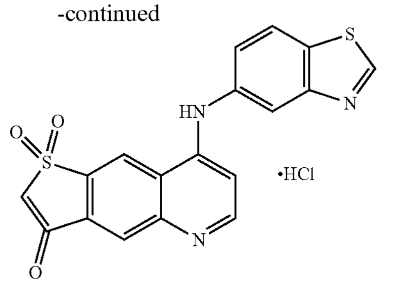

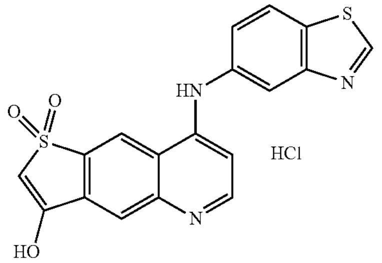

Step a: 8-(benzo[d]thiazol-5-ylamino)thieno[2,3-g]quinolin-3(2H)-one 1,1-dioxide hydrochloride To a solution of 8-(benzo[d]thiazol-5-ylamino)-3-methoxythieno[2,3-g]quinoline 1,1-dioxide (15 mg, 0.04 mmol) in acetonitrile (2 mL) was added concentrated hydrochloric acid (0.5 mL) and stirred at 80° C. overnight. Then water (20 mL) was added to the reaction mixture and the suspension was filtered. The residue was subsequently washed with isopropanol (5 mL) and dried to yield the isomers as hydrochloride (12 mg, 83%) as a yellow solid. $^1$H NMR (400 MHz, DMSO-$d_6$) δ 14.97 (s, 1H), 11.64 (s, 0.67H), 11.30 (s, 0.33H), 9.70 (s, 0.67H), 9.55 (s, 1H), 9.30 (s, 0.33H), 8.72 (d, J=6.4 Hz, 0.67H), 8.63 (s, 0.67H), 8.59 (d, J=4.8 Hz, 0.33H), 8.43 (d, J=8.8 Hz, 1H), 8.28 (s, 0.67H), 8.24 (s, 0.33H), 8.20 (s, 0.33H), 7.70-7.58 (m, 1H), 7.07 (d, J=6.4 Hz, 0.67H), 7.00 (d, J=4.4 Hz, 0.33H), 6.58 (s, 0.33H), 4.85 (s, 1.33H).

Example 27: Preparation of 8-(benzo[d]thiazol-5-ylamino)-2,2-dimethylthieno[2,3-g]quinolin-3(2H)-one 1,1-dioxide (B4) (Method BL)

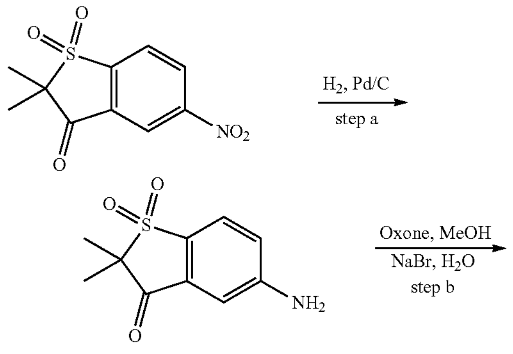

-continued

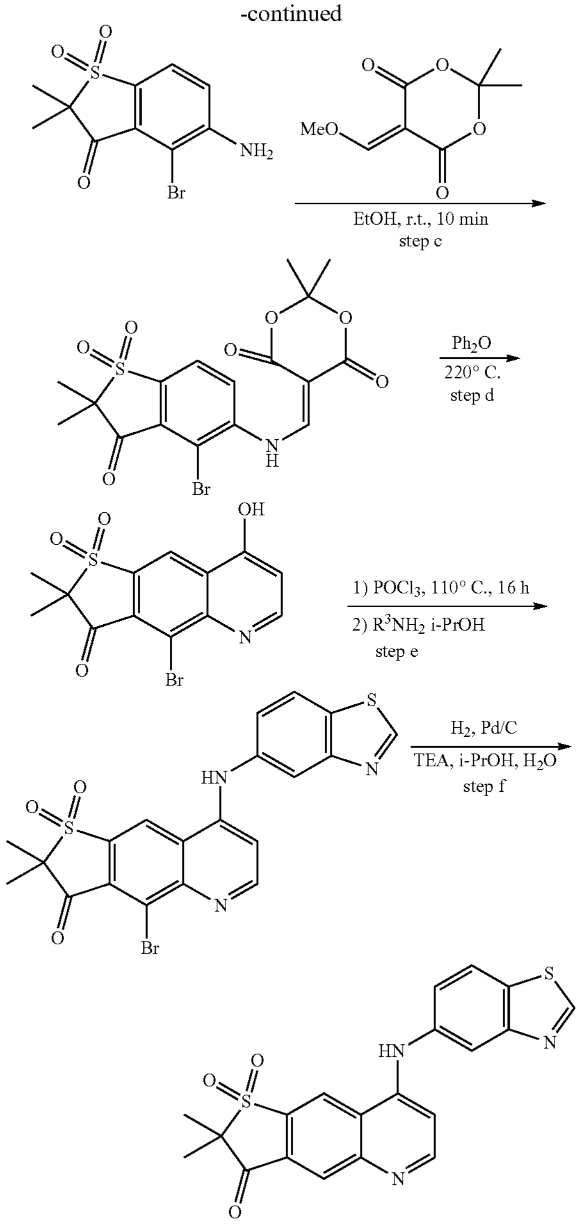

Step a: 5-amino-2,2-dimethylbenzo[b]thiophen-3(2H)-one 1,1-dioxide

To a solution of 2,2-dimethyl-5-nitrobenzo[b]thiophen-3(2H)-one 1,1-dioxide (11 g, 43 mmol) in isopropanol (15 mL) was added 10% Pd/C (1.3 g) and concentrated HCl solution (16 mL) and stirred at room temperature under $H_2$ atmosphere overnight. The mixture reaction was filtered and the filtrate was added saturated $NaHCO_3$ aqueous solution to adjust pH to 8. The mixture was extracted with ethyl acetate (200 mL×2), the combined organic layer was dried over anhydrous $Na_2SO_4$, filtered and concentrated. The residue was purified by silica gel column chromatography (petroleum ether/ethyl acetate=5/1) to give the desired 5-amino-2,2-dimethylbenzo[b]thiophen-3(2H)-one 1,1-dioxide (8.7 g, 90%) as a yellow solid. $^1$H NMR (400 MHz, DMSO-$d_6$) δ 7.75 (d, J=8.4 Hz, 1H), 7.13 (d, J=8.8 Hz, 1H), 6.95 (s, 1H), 6.53 (br s, 2H), 1.43 (s, 6H).

Step b: 5-amino-4-bromo-2,2-dimethylbenzo[b]thiophen-3(2H)-one 1,1-dioxide

To a solution of 5-amino-2,2-dimethylbenzo[b]thiophen-3(2H)-one 1,1-dioxide (8.7 g, 38.7 mmol) in methanol (250 mL) and water (110 mL) was added Oxone (23.8 g, 38.7 mmol) and NaBr (4 g, 38.7 mmol) and the mixture was stirred at room temperature for 3 hours. The mixture reaction was quenched by adding saturated $Na_2SO_3$ aqueous solution. The mixture was extracted with ethyl acetate (200 mL×2), the combined organic layer was dried over anhydrous $Na_2SO_4$, filtered and concentrated. The residue was purified by silica gel column chromatography (dichloromethane/methanol=100/1) to give the desired 5-amino-4-bromo-2,2-dimethylbenzo[b]thiophen-3(2H)-one 1,1-dioxide (10 g, 85%) as a yellow solid. $^1$H NMR (400 MHz, DMSO-$d_6$) δ 7.82 (d, J=8.8 Hz, 1H), 7.31 (d, J=8.4 Hz, 1H), 6.74 (br s, 2H), 1.45 (s, 6H).

Step c. 5-(((4-bromo-2,2-dimethyl-1,1-dioxido-3-oxo-2,3-dihydrobenzo[b]thiophen-5-yl)amino)methylene)-2,2-dimethyl-1,3-dioxane-4,6-dione To a solution of 5-amino-4-bromo-2,2-dimethylbenzo[b]thiophen-3(2H)-one 1,1-dioxide (10 g, 32.9 mmol) in methanol (150 mL) was added 5-(methoxymethylene)-2,2-dimethyl-1,3-dioxane-4,6-dione (9.2 g, 49.3 mmol) and stirred at room temperature for 30 minutes. The suspension was filtered. The residue was subsequently washed with EtOH (50 mL) and dried to yield the product 5-(((4-bromo-2,2-dimethyl-1,1-dioxido-3-oxo-2,3-dihydrobenzo[b]thiophen-5-yl)amino)methylene)-2,2-dimethyl-1,3-dioxane-4,6-dione (13 g, 86%) as a white solid. $^1$H NMR (400 MHz, DMSO-$d_6$) δ 11.84 (d, J=13.6 Hz, 1H), 8.92 (d, J=13.6 Hz, 1H), 8.54 (d, J=8.4 Hz, 1H), 8.31 (d, J=8.8 Hz, 1H), 1.71 (s, 6H), 1.53 (s, 6H).

Step d: 4-bromo-8-hydroxy-2,2-dimethylthieno[2,3-g]quinolin-3(2H)-one 1,1-dioxide A mixture of 5-(((4-bromo-2,2-dimethyl-1,1-dioxido-3-oxo-2,3-dihydrobenzo[b]thiophen-5-yl)amino)methylene)-2,2-dimethyl-1,3-dioxane-4,6-dione (13 g, 28.4 mmol) in diphenyl ether (200 mL) was stirred at 220° C. for 5 minutes. The mixture was cooled to room temperature and was added petroleum ether (200 mL). The suspension was filtered and the residue was subsequently dried to yield the product 4-bromo-8-hydroxy-2,2-dimethylthieno[2,3-g]quinolin-3(2H)-one 1,1-dioxide (6 g, 60%) as a brown solid. $^1$H NMR (400 MHz, DMSO-$d_6$) δ 11.78 (s, 1H), 8.60 (s, 1H), 8.06 (t, J=6.0 Hz, 1H), 6.34 (d, J=7.2 Hz, 1H), 1.54 (s, 6H).

Step e: 8-(benzo[d]thiazol-5-ylamino)-4-bromo-2,2-dimethylthieno[2,3-g]quinolin-3(2H)-one 1,1-dioxide A mixture of 4-bromo-8-hydroxy-2,2-dimethylthieno[2,3-g]quinolin-3(2H)-one 1,1-dioxide (30 mg, 0.084 mmol) in $POCl_3$ (6 mL) was stirred at 110° C. overnight. The mixture was concentrated and the residue was dissolved in isopropanol (6 mL). Then, the mixture reaction was added benzo[d]thiazol-5-amine (15 mg, 0.101 mmol) and stirred at 90° C. overnight. The suspension was cooled to room temperature and filtered. The residue was subsequently washed with isopropanol (6 mL) and dried to yield the crude product 8-(benzo[d]thiazol-5-ylamino)-4-bromo-2,2-dimethylthieno[2,3-g]quinolin-3(2H)-one 1,1-dioxide (45 mg, crude) as a yellow solid.

Step f: 8-(benzo[d]thiazol-5-ylamino)-2,2-dimethylthieno[2,3-g]quinolin-3(2H)-one 1,1-dioxide To a solution of 8-(benzo[d]thiazol-5-ylamino)-4-bromo-2,2-dimethylthieno[2,3-g]quinolin-3(2H)-one 1,1-dioxide (45 mg, 0.084 mmol) in isopropanol (6 mL) and water (0.5 mL) was added 10% Pd/C (100 mg), triethylamine (0.5 mL) and stirred at 90° C. under $H_2$ atmosphere overnight. The mixture was filtered and concentrated. The residue was purified by silica gel column chromatography (dichloromethane/methanol=25/1) to give the desired product 8-(benzo[d]thiazol-5-ylamino)-2,2-dimethylthieno[2,3-g]quinolin-3(2H)-one 1,1-dioxide (5 mg, 14%) as a yellow solid. $^1$H NMR (400 MHz, $CDCl_3$) δ 9.10 (s, 1H), 8.87 (s, 1H), 8.75 (d, J=5.2 Hz, 1H), 8.69 (s, 1H), 8.14 (s, 1H), 8.06 (d, J=8.4 Hz, 1H), 7.50-7.39 (m, 2H), 7.14 (d, J=5.2 Hz, 1H), 1.66 (s, 6H).

Example 28: Preparation of 8-(benzo[d]thiazol-5-ylamino)-2,2-dimethyl-3-methylene-2,3-dihydrothieno[2,3-g]quinoline 1,1-dioxide (B8) (Method BM)

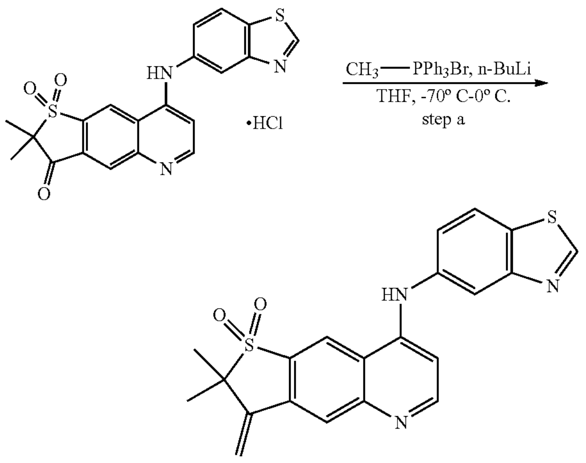

Step a: 8-(benzo[d]thiazol-5-ylamino)-2,2-dimethyl-3-methylene-2,3-dihydrothieno[2,3-g]quinoline 1,1-dioxide A mixture of methyl triphenylphosphorus bromide (260 mg, 0.73 mmol) in tetrahydrofuran (5 mL) was stirred at −70° C. under $N_2$ atmosphere for 15 minutes. Then the mixture solution was added n-BuLi (0.33 mL, 0.83 mmol) at −70° C. and stirred at 0° C. for 1.5 hours. Subsequently, 8-(benzo[d]thiazol-5-ylamino)-2,2-dimethylthieno[2,3-g]quinolin-3(2H)-one 1,1-dioxide hydrochloride (100 mg, 0.22 mmol) in tetrahydrofuran (5 mL) was added to the mixture solution at −70° C. and stirred at room temperature overnight. The mixture was quenched with water (1 mL) and concentrated. The residue was purified by silica gel column chromatography (dichloromethane/methanol=30/1) to give the desired product 8-(benzo[d]thiazol-5-ylamino)-2,2-dimethyl-3-methylene-2,3-dihydrothieno[2,3-g]quinoline 1,1-dioxide (10 mg, 11%) as a yellow solid. $^1$H NMR (400 MHz, DMSO-$d_6$) δ 9.63 (s, 1H), 9.45 (s, 1H), 9.13 (s, 1H), 8.60 (d, J=5.2 Hz, 1H), 8.42 (s, 1H), 8.23 (d, J=8.4 Hz, 1H), 8.07 (s, 1H), 7.56 (d, J=7.6 Hz, 1H), 7.06 (d, J=5.2 Hz, 1H), 6.36 (s, 1H), 5.68 (s, 1H), 1.55 (s, 6H).

Example 29: Preparation of 8-(benzo[d]thiazol-5-ylamino)-3-hydroxy-2,2,3-trimethyl-2,3-dihydrothieno[2,3-g]quinoline 1,1-dioxide (B10) (Method BN)

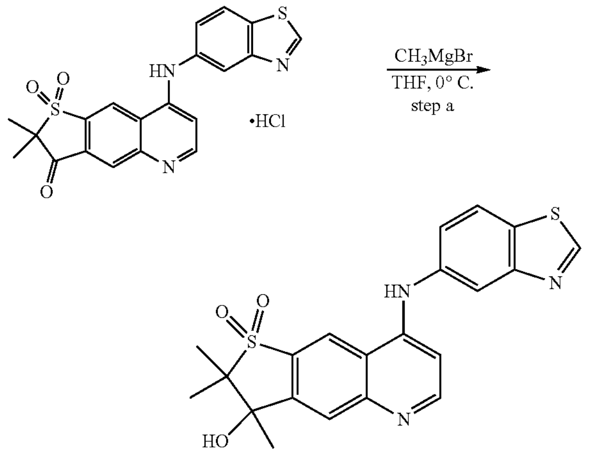

Step a: 8-(benzo[d]thiazol-5-ylamino)-3-hydroxy-2,2,3-trimethyl-2,3-dihydrothieno[2,3-g]quinoline 1,1-dioxide A mixture of 8-(benzo[d]thiazol-5-ylamino)-2,2-dimethylthieno[2,3-g]quinolin-3(2M-one 1,1-dioxide hydrochloride (60 mg, 0.13 mmol) in tetrahydrofuran (5 mL) was stirred at 0° C. under $N_2$ atmosphere for 30 minutes. Then, the mixture solution was added magnesium methyl bromide (0.4 mL, 0.40 mmol) at 0° C. and stirred at room temperature for 1 hour. The mixture was quenched with water (1 mL) and concentrated. The residue was purified by silica gel column chromatography (dichloromethane/methanol=50/1) to give the desired product 8-(benzo[d]thiazol-5-ylamino)-3-hydroxy-2,2,3-trimethyl-2,3-dihydrothieno[2,3-g]quinoline 1,1-dioxide (30 mg, 52%) as a yellow solid. $^1$H NMR (400 MHz, DMSO-$d_6$) δ 9.57 (s, 1H), 9.45 (s, 1H), 9.02 (s, 1H), 8.59 (d, J=5.6 Hz, 1H), 8.22 (d, J=8.8 Hz, 1H), 8.09 (s, 1H), 8.06 (s, 1H), 7.55 (d, J=8.4 Hz, 1H), 7.06 (d, J=5.2 Hz, 1H), 6.19 (s, 1H), 1.60 (s, 3H), 1.40 (s, 3H), 1.27 (s, 3H).

Example 30: Preparation of 8-(benzo[d]thiazol-5-ylamino)-4-cyclopropyl-2,2-dimethylthieno[2,3-g]quinolin-3(2H)-one 1,1-dioxide (B12) (Method BO)

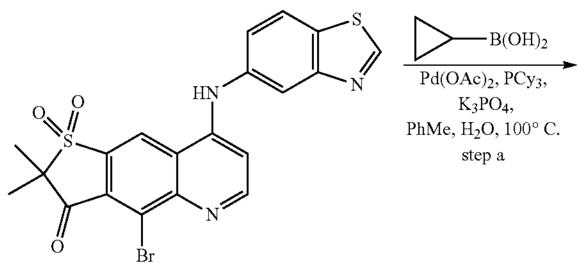

-continued

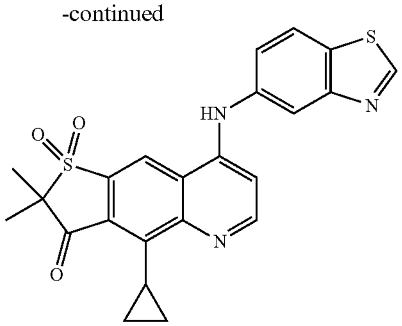

Step a: 8-(benzo[d]thiazol-5-ylamino)-4-cyclopropyl-2,2-dimethylthieno[2,3-g]quinolin-3(2H)-one 1,1-dioxide To a solution of 8-(benzo[d]thiazol-5-ylamino)-4-bromo-2,2-dimethylthieno[2,3-g]quinolin-3(2H)-one 1,1-dioxide (49 mg, 0.1 mmol) in toluene (3 mL) and water (0.2 mL) was added cyclopropylboric acid (17 mg, 0.2 mmol), potassium phosphate trihydrate (83 mg, 0.35 mmol), potassium acetate (2 mg, 0.005 mmol) and cyclohexylphosphine (3 mg, 0.01 mmol) and stirred at 100° C. under $N_2$ atmosphere overnight. The mixture reaction was filtered and concentrated. The residue was purified by silica gel column chromatography (dichloromethane/methanol=100/1) to give the desired product 8-(benzo[d]thiazol-5-ylamino)-4-cyclopropyl-2,2-dimethylthieno[2,3-g]quinolin-3(2H)-one 1,1-dioxide (4 mg, 9%) as a yellow solid. $^1$H NMR (400 MHz, $CDCl_3$) δ 9.10 (s, 1H), 8.69-8.59 (m, 2H), 8.10 (s, 1H), 8.03 (d, J=8.4 Hz, 1H), 7.42 (d, J=8.4 Hz, 1H), 7.11 (d, J=5.2 Hz, 1H), 3.38-3.23 (m, 1H), 1.78-1.70 (m, 2H), 1.63 (s, 6H), 1.34-1.28 (m, 2H).

Example 31: Preparation of 8'-(benzo[d]thiazol-5-ylamino)-2'H-spiro[oxetane-3,3'-thieno[2,3-g]quinoline] 1', 1'-dioxide (B28) (Method BP)

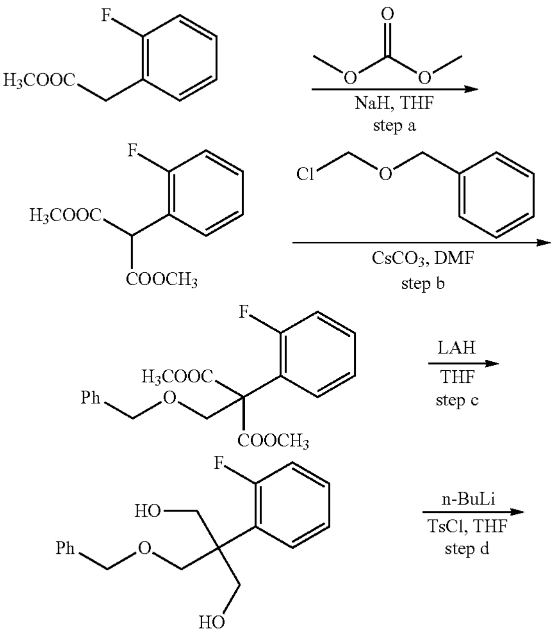

-continued

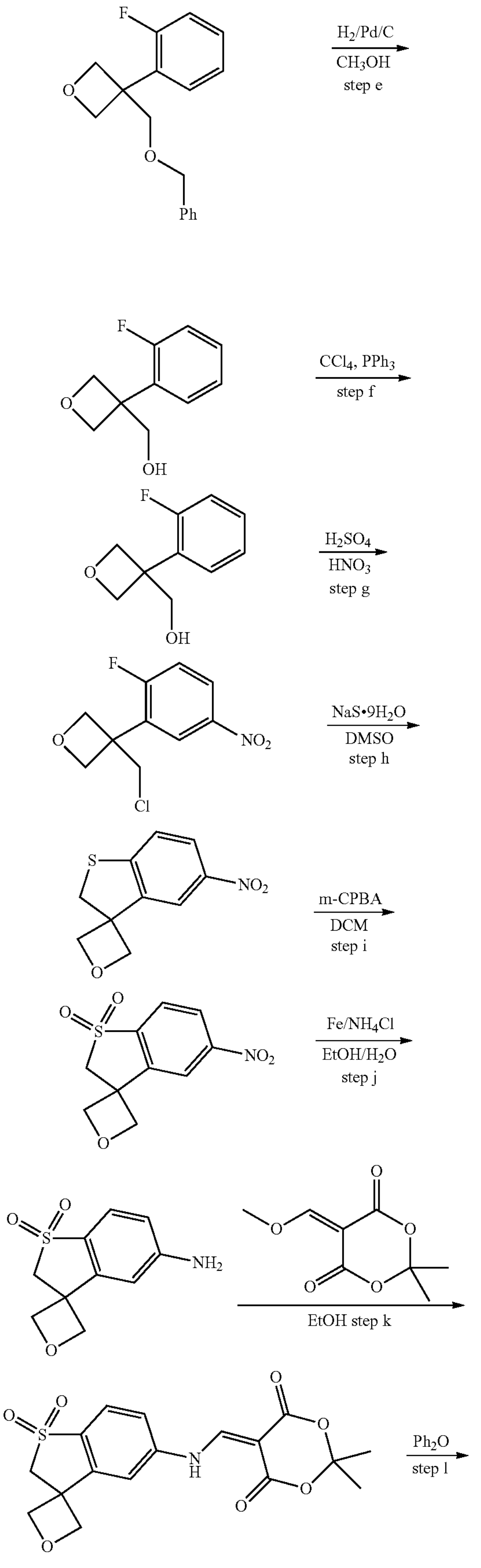

-continued

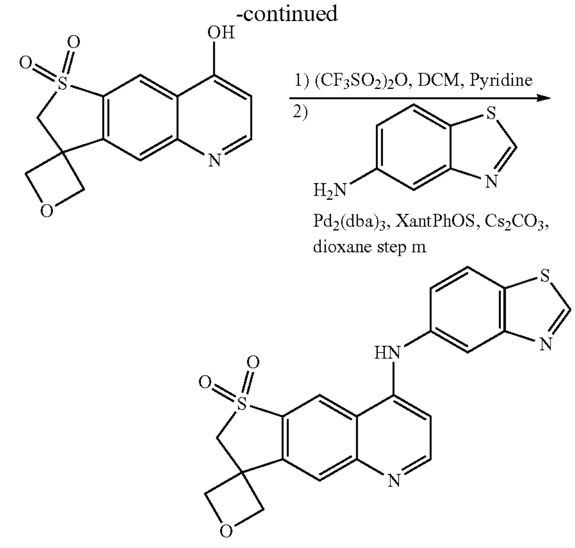

Step a: Dimethyl 2-(2-fluorophenyl)malonate

To a solution of methyl 2-(2-fluorophenyl)acetate (10.3 g, 61.3 mmol) and dimethyl carbonate (16.6 g, 183.9 mmol) in dry THF (200 ml) with an ice bath was added 60% NaH (9.8 g, 245.2 mmol). The mixture was stirred at 70° C. overnight. The reaction was quenched by saturated $NH_4Cl$ aqueous solution with an ice bath. The aqueous layer was extracted with DCM (100 mL×3). The combined organic phase was dried over $Na_2SO_4$, filtered and concentrated. The residue was purified by silica gel column chromatography (PE/EA=20/1) to give the desired product (11.2 g, 81%) as a yellow oil. $^1H$ NMR (400 MHz, $CDCl_3$) δ 7.50-7.39 (m, 1H), 7.37-7.27 (m, 1H), 7.20-7.12 (m, 1H), 7.12-7.01 (m, 1H), 5.01 (s, 1H), 3.77 (s, 6H).

Step b: Dimethyl 2-((benzyloxy)methyl)-2-(2-fluorophenyl)malonate

To a solution of dimethyl 2-(2-fluorophenyl)malonate (11.2 g, 49.6 mmol) and $Cs_2CO_3$ (32.3 g, 99.2 mmol) in DMF (130 mL) with an ice bath was added benzylchloromethyl ether (11.7 g, 74.4 mmol) dropwise. The mixture was stirred at room temperature for 1 h. The solvent was concentrated and water (400 mL) was added. The aqueous layer was extracted with EA (200 mL×3). The combined organic phase was dried over $Na_2SO_4$, filtered and concentrated. The residue was purified by silica gel column chromatography (PE/EA=20/1) to give the desired product (12.6 g, 73%) as a colorless oil. $^1H$ NMR (400 MHz, $CDCl_3$) δ 7.51-7.41 (m, 1H), 7.35-7.27 (m, 3H), 7.25-7.18 (m, 3H), 7.16-7.09 (m, 1H), 7.07-6.98 (m, 1H), 4.58 (s, 2H), 4.19 (s, 2H), 3.78 (s, 6H). LCMS (ESI/APCI) m/z: 346.8 $[M+H]^+$.

Step c: 2-((benzyloxy)methyl)-2-(2-fluorophenyl) propane-1,3-diol

To a solution of Dimethyl 2-((benzyloxy)methyl)-2-(2-fluorophenyl)malonate (8.6 g, 24.9 mmol) in dry THF (100 mL) with an ice bath was added $LiAlH_4$ (3.8 g, 99.6 mmol) slowly. The reaction was stirred at room temperature for 2 h. The reaction mixture was cooled to 0° C. and $H_2O$ (3.8 mL) was added dropwise and stirred for 5 min. then 15% NaOH solution (3.8 mL) was added and stirred for 10 min. $H_2O$ (11.4 mL) was added and stirred for 10 min. Precipitate was filtered off and washed with MeOH. The resulting filtrate was evaporated. The residue was purified by silica gel column chromatography (PE/EA=2/1) to give the desired product (1.8 g, 25%) as a colorless oil. $^1$H NMR (400 MHz, $CDCl_3$) δ 7.47-7.38 (m, 1H), 7.38-7.29 (m, 3H), 7.29-7.20 (m, 3H), 7.17-7.08 (m, 1H), 7.07-6.96 (m, 1H), 4.53 (s, 2H), 4.16 (d, J=11.2 Hz, 2H), 4.07 (d, J=10.4 Hz, 2H), 3.94 (s, 2H). LCMS (ESI/APCI) m/z: 290.9 $[M+H]^+$.

Step d: 3-((benzyloxy)methyl)-3-(2-fluorophenyl)oxetane

To a solution of 2-((benzyloxy)methyl)-2-(2-fluorophenyl)propane-1,3-diol (1.8 g, 6.2 mmol) in dry THF (20 mL) with an ice bath under $N_2$ atmosphere was added n-BuLi (2.5 mL, 6.2 mmol) dropwise. The reaction was stirred at 0° C. for 10 min. A solution of p-TsCl (1.2 g, 6.2 mmol) in the THF (5 mL) was added and the mixture was stirred for 10 min at 0° C. A solution of n-BuLi in hexanes (2.5 mL, 6.2 mmol) was added dropwise and the reaction was stirred at 55° C. overnight. The reaction mixture was cooled to 0° C. and saturated $NH_4Cl$ aqueous solution was added to quench the reaction. The mixture was extracted with EA (30 mL×3). The combined organic phase was dried over $Na_2SO_4$, filtered and concentrated. The residue was purified by silica gel column chromatography (PE/EA=20/1) to give the desired product (1.1 g, 61%) as a colorless oil. $^1$H NMR (400 MHz, $CDCl_3$) δ 7.32-7.21 (m, 4H), 7.21-7.15 (m, 2H), 7.15-7.08 (m, 1H), 7.08-6.96 (m, 2H), 5.00 (d, J=5.6 Hz, 2H), 4.79 (d, J=5.2 Hz, 2H), 4.52 (s, 2H), 3.88 (s, 2H). LCMS (ESI/APCI) m/z: 272.9 $[M+H]^+$.

Step e: (3-(2-fluorophenyl)oxetan-3-yl)methanol

To a solution of 3-((benzyloxy)methyl)-3-(2-fluorophenyl)oxetane (1.1 g, 4.0 mmol) in MeOH (20 mL) was added 10% Pd/C (21 mg, 0.2 mmol). The reaction was stirred under $H_2$ atmosphere for 12 h. The Pd/C was filtered off and the cake was washed with MeOH. The resulting filtrate was concentrated to give the desired product as a colorless oil (650 mg, 89%). $^1$H NMR (400 MHz, $CDCl_3$) δ 7.32-7.27 (m, 1H), 7.20-7.12 (m, 1H), 7.10-6.96 (m, 2H), 5.01 (d, J=6.0 Hz, 2H), 4.76 (d, J=6.0 Hz, 2H), 4.10 (s, 2H).

Step f: 3-(chloromethyl)-3-(2-fluorophenyl)oxetane

To a solution of (3-(2-fluorophenyl)oxetan-3-yl)methanol (420 mg, 2.3 mmol) in $CCl_4$ (20 mL) was added $PPh_3$ (1.2 g, 4.6 mmol). The reaction was stirred at 90° C. for 24 h. The solvent was removed in vacuum and the residue was purified by silica gel column chromatography (PE/EA=40/1) to give the desired product (440 mg, 96%) as a colorless oil. $^1$H NMR (400 MHz, $CDCl_3$) δ 7.34-7.27 (m, 1H), 7.16 (t, J=7.6 Hz, 1H), 7.10-6.99 (m, 2H), 5.02 (d, J=6.4 Hz, 2H), 4.74 (d, J=6.4 Hz, 2H), 4.11 (s, 2H).

Step g: 3-(chloromethyl)-3-(2-fluoro-5-nitrophenyl)oxetane

To a solution of 3-(chloromethyl)-3-(2-fluorophenyl)oxetane (440 mg, 2.2 mmol) in conc. $H_2SO_4$ (5 mL) with an ice bath was added fuming nitric acid (1 mL) dropwise. The reaction was stirred at room temperature for 5 min. The mixture was poured into cooled water (50 mL). The aqueous was extracted with EA (10 mL×3). The combined organic phase was dried over $Na_2SO_4$, filtered and concentrated to give the desired product (520 mg, 93%) as a yellow solid. $^1$H NMR (400 MHz, $CDCl_3$) δ 8.30-8.19 (m, 1H), 8.03-7.95 (m, 1H), 7.24-7.18 (m, 1H), 5.03 (d, J=5.2 Hz, 2H), 4.75 (d, J=5.6 Hz, 2H), 4.16 (s, 2H).

Step h: 5-nitro-2H-spiro[benzo[b]thiophene-3,3'-oxetane]

To a solution of 3-(chloromethyl)-3-(2-fluoro-5-nitrophenyl)oxetane (520 mg, 2.0 mmol) in DMSO (30 mL) was added $Na_2S \cdot 9H_2O$ (768 mg, 3.2 mmol). The reaction was stirred at room temperature for 3 h. Water (80 mL) was added to the reaction and the aqueous layer was extracted with EA (20 mL×2). The combined organic phase was dried over $Na_2SO_4$, filtered and concentrated. The residue was purified by silica gel column chromatography (PE/EA=10/1) to give the desired product (240 mg, 51%) as a yellow sold. $^1$H NMR (400 MHz, $CDCl_3$) δ 8.43 (s, 1H), 8.11 (d, J=8.8 Hz, 1H), 7.31 (d, J=8.8 Hz, 1H), 4.85 (d, J=6.4 Hz, 2H), 4.82 (d, J=6.4 Hz, 2H), 3.78 (s, 2H).

Step i: 5-nitro-2H-spiro[benzo[b]thiophene-3,3'-oxetane] 1,1-dioxide

To a solution of 5-nitro-2H-spiro[benzo[b]thiophene-3,3'-oxetane] (240 mg, 1.08 mmol) in DCM (15 mL) with an ice bath was added 85% m-CPBA (543 mg, 2.69 mmol). The mixture was stirred at room temperature overnight. The solid was filtered off and the filtrate was quenched with $Na_2SO_3$, extracted with DCM (20 mL×3). The combined organic phase was washed with saturated $NaHCO_3$ aqueous solution, dried over $Na_2SO_4$, filtered and concentrated. The residue was purified by silica gel column chromatography (DCM/MeOH=50/1) to give the desired product 5-nitro-2H-spiro[benzo[b]thiophene-3,3'-oxetane] 1,1-dioxide (220 mg, 80%) as a white solid. $^1$H NMR (400 MHz, $CDCl_3$) δ 8.85 (s, 1H), 8.44 (d, J=7.6 Hz, 1H), 7.92 (d, J=8.4 Hz, 1H), 5.04 (d, J=6.8 Hz, 2H), 4.95 (d, J=6.8 Hz, 2H), 3.91 (s, 2H).

Step j: 5-amino-2H-spiro[benzo[b]thiophene-3,3'-oxetane] 1,1-dioxide

To a solution of 5-nitro-2H-spiro[benzo[b]thiophene-3,3'-oxetane] 1,1-dioxide (220 mg, 0.86 mmol) in EtOH (8 mL) and $H_2O$ (3 mL) was added iron powder (193 mg, 3.44 mmol) and $NH_4Cl$ (182 mg, 3.44 mmol). The mixture was stirred at 85° C. for 2 h. The solid was filtered through diatomaceous earth and the cake was washed with DCM. The resulting filtrate was extracted with DCM (20 mL×2). The combined organic phase was dried over $Na_2SO_4$, filtered and concentrated to give the desired product 5-amino-2H-spiro[benzo[b]thiophene-3,3'-oxetane] 1,1-dioxide (200 mg, 93%) as a yellow solid. $^1$H NMR (400 MHz, $CDCl_3$) δ 7.47 (d, J=8.4 Hz, 1H), 7.10 (s, 1H), 6.74 (d, J=8.0 Hz, 1H), 4.95 (d, J=6.4 Hz, 2H), 4.87 (d, J=6.0 Hz, 2H), 4.30 (s, 2H), 3.75 (s, 2H). LCMS (ESI/APCI) m/z: 225.8 $[M+H]^+$.

Step k: 5-(((1,1-dioxido-2H-spiro[benzo[b]thiophene-3,3'-oxetan]-5-yl)amino)methylene)-2,2-dimethyl-1,3-dioxane-4,6-dione To a solution of 5-amino-2H-spiro[benzo[b]thiophene-3,3'-oxetane] 1,1-dioxide (200 mg, 0.8 mmol) in EtOH (4 mL) was added 5-(methoxymethylene)-2,2-dimethyl-1,3-dioxane-4,6-dione (223 mg, 1.2 mmol). The mixture was stirred at room temperature for 20 min. The resulting solid was collected via filtration, washed with EtOH (5 mL) and dried in vacuum to give the desired product (240 mg, 79%) as a yellow solid. $^1$H NMR (400 MHz, $CDCl_3$) δ 11.47 (d, J=12.8 Hz, 1H), 8.76 (d, J=13.6 Hz, 1H), 7.87-7.74 (m, 2H), 7.43 (d, J=6.8 Hz, 1H), 5.03 (d, J=6.0 Hz, 2H), 4.89 (d, J=6.0 Hz, 2H), 3.84 (s, 2H), 1.79 (s, 6H).

Step l: 8'-hydroxy-2'H-spiro[oxetane-3,3'-thieno[2,3-g]quinoline] 1',1'-dioxide

The diphenyl ether (6 mL) was added to a round-bottomed flask and the solvent was heated to 240° C. for 10 minutes. Intermediate 5-(((1,1-dioxido-2H-spiro[benzo[b]thio-phene-3,3'-oxetan]-5-yl)amino)methylene)-2,2-dimethyl-1,3-dioxane-4,6-dione (240 mg, 0.63 mmol) was added slowly to the solution. The mixture was stirred for 5 min. After cooling to room temperature, the resulting suspension was then filtered, washed with ether (2 mL) and dried in vacuum to give the desired product (110 mg, 63%) as a yellow solid. $^1$H NMR (400 MHz, DMSO-$d_6$) δ 12.34 (s, 1H), 8.27 (s, 1H), 8.17 (s, 1H), 8.05 (d, J=7.6 Hz, 1H), 6.15 (d, J=7.2 Hz, 1H), 4.96 (d, J=6.0 Hz, 2H), 4.77 (d, J=6.4 Hz, 2H), 4.13 (s, 2H). LCMS (ESI/APCI) m/z: 277.8 $[M+H]^+$.

Step m: 8'-(benzo[d]thiazol-5-ylamino)-2'H-spiro[oxetane-3,3'-thieno[2,3-g]quinoline] 1',1'-dioxide To a solution of 8'-hydroxy-2'H-spiro[oxetane-3,3'-thieno[2,3-g]quinoline] 1',1'-dioxide (30 mg, 0.11 mmol) and pyridine (0.1 mL, 1.0 mmol) in dry DCM (4 mL) was added trifluoromethanesulfonic anhydride (0.1 mL, 0.6 mmol) dropwise at 0° C. the reaction was stirred at room temperature for 10 min. The solvent was removed in vacuum and the residue was dissolved in dioxane (4 mL) subsequently. $Pd_2(dba)_3$ (18 mg, 0.02 mmol), Xantphos (12 mg, 0.02 mmol), $Cs_2CO_3$ (359 mg, 1.1 mmol) was added. The reaction was stirred at 100° C. for 1 h under $N_2$ atmosphere. The solvent was removed in vacuum and the resulting residue was purified by silica gel column chromatography (DCM/MeOH=20/1) to give the desired product (15 mg, 33%) as a yellow solid. $^1$H NMR (400 MHz, DMSO-$d_6$) δ 9.59 (s, 1H), 9.45 (s, 1H), 8.99 (s, 1H), 8.63 (d, J=5.6 Hz, 1H), 8.47 (s, 1H), 8.23 (d, J=8.8 Hz, 1H), 8.07 (d, J=1.7 Hz, 1H), 7.56 (dd, J=8.8, 1.6 Hz, 1H), 7.09 (d, J=5.6 Hz, 1H), 4.97 (d, J=6.4 Hz, 2H), 4.94 (d, J=6.4 Hz, 2H), 4.23 (s, 2H). $^{13}$C NMR (151 MHz, DMSO-$d_6$) δ 157.5, 154.1, 153.6, 151.5, 149.2, 141.2, 138.5, 135.2, 129.4, 124.9, 123.2, 121.5, 119.6, 116.7, 116.4, 102.1, 80.7, 59.3, 43.9, 39.9, 39.8, 39.7, 39.5, 39.5, 39.4, 39.2, 39.1. HRMS (ESI) calcd for $C_{20}H_{15}N_3O_3S_2$, $[M+H]^+$, 410.0628, found, 410.0628.

Table 1 shows selected compounds that were prepared according to the methods disclosed herein. The method used for each compound is indicated in the third column of the table.

TABLE 1

Selected compounds synthesized (A1-A118, B1-B29)

| No. | Structure | Method | $^1$H NMR & LC-MS |
|---|---|---|---|
| A1 | 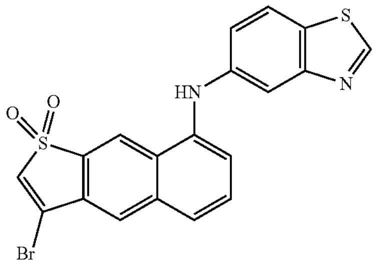 [SMILES: O=S1(=O)C=C(Br)c2cc3cccc(Nc4ccc5scnc5c4)c3cc21] | AA, AH, BB | $^1$H NMR (400 MHz, DMSO-$d_6$) δ 11.37 (s, 1H), 9.55 (s, 1H), 9.43 (s, 1H), 8.63 (d, J = 6.8 Hz, 1H), 8.50 (s, 1H), 8.40 (d, J = 8.8 Hz, 1H), 8.27-8.21 (m, 2H), 7.62 (d, J = 8.8 Hz, 1H), 7.04 (d, J = 7.2 Hz, 1H). |
| A2 | 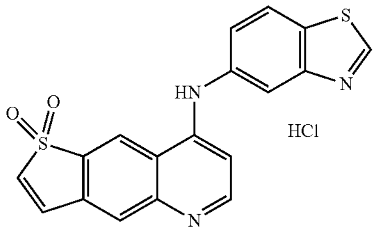 [SMILES: O=S1(=O)C=Cc2cc3nccc(Nc4ccc5scnc5c4)c3cc21 ; Cl] HCl | AA, BB | $^1$H NMR (400 MHz, DMSO-$d_6$) δ 14.79 (br s, 1H), 11.15 (s, 1H), 9.54 (s, 1H), 9.31 (s, 1H), 8.56 (d, J = 7.2 Hz, 1H), 8.39 (d, J = 8.4 Hz, 1H), 8.22 (s, 1H), 8.16 (s, 1H), 8.00 (d, J = 7.6 Hz, 1H), 7.81 (d, J = 6.8 Hz, 1H), 7.61 (d, J = 8.4 Hz, 1H), 7.00 (d, J = 6.8 Hz, 1H). LCMS (ESI/APCI) m/z: 365.7 $[M + H]^+$. |
| A3 | 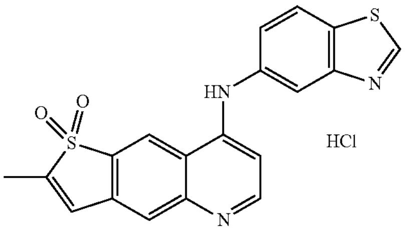 [SMILES: CC1=Cc2cc3nccc(Nc4ccc5scnc5c4)c3cc2S1(=O)=O ; Cl] HCl | AB, BA | $^1$H NMR (400 MHz, DMSO-$d_6$) δ 9.72 (s, 1H), 9.46 (s, 1H), 9.06 (s, 1H), 8.55 (d, J = 5.2 Hz, 1H), 8.25 (d, J = 8.8 Hz, 1H), 8.08 (s, 1H), 7.94 (s, 1H), 7.55 (d, J = 8.4 Hz, 1H), 7.48 (s, 1H), 7.06 (d, J = 52 Hz, 1H), 2.22 (s, 3H). LCMS (ESEAPCI) m/z: 379.7 $[M + H]^+$. |

TABLE 1-continued

Selected compounds synthesized (A1-A118, B1-B29)

| No. | Structure | Method | $^1H$ NMR & LC-MS |
|---|---|---|---|
| A4 | 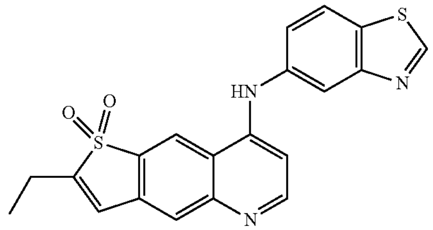 [SMILES: CCC1=Cc2cc3nccc(Nc4ccc5scnc5c4)c3cc2S1(=O)=O] | AC, BB | $^1H$ NMR (400 MHz, DMSO-$d_6$) δ 9.50 (s, 1H), 9.45 (s, 1H), 9.01 (s, 1H), 8.55 (d, J = 52 Hz, 1H), 8.23 (d, J = 8.4 Hz, 1H), 8.06 (s, 1H), 7.94 (s, 1H), 7.55 (d, J = 8.4 Hz, 1H), 7.47 (s, 1H), 7.07 (d, J = 52 Hz, 1H), 2.60 (q, J = 7.2 Hz, 2H), 1.32 (t, J = 7.2 Hz, 3H). LCMS (ESI/APCI) m/z: 393.7 $[M + H]^+$. |
| A5 | 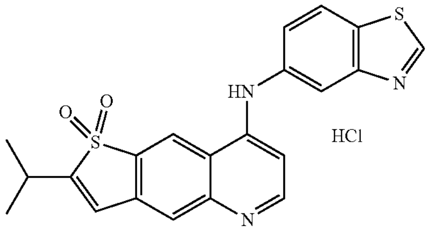 [SMILES: CC(C)C1=Cc2cc3nccc(Nc4ccc5scnc5c4)c3cc2S1(=O)=O ; Cl] | AD, BB | $^1H$ NMR (400 MHz, DMSO-$d_6$) δ 15.03 (br s, 1H), 11.13 (s, 1H), 9.54 (s, 1H), 9.32 (s, 1H), 8.54 (s, 1H), 8.38 (d, J = 8.8 Hz, 1H), 8.22 (s, 1H), 8.13 (s, 1H), 7.69 (s, 1H), 7.61 (d, J = 8.4 Hz, 1H), 6.98 (s, 1H), 3.11-2.90 (m, 1H), 1.36 (d, J = 6.4 Hz, 6H). LCMS (ESEAPCI) m/z: 407.7 $[M + H]^+$. |
| A6 | 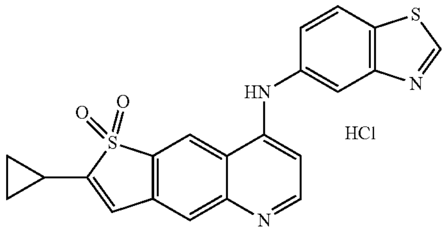 [SMILES: O=S1(=O)C(C2CC2)=Cc2cc3nccc(Nc4ccc5scnc5c4)c3cc21 ; Cl] | AE, BB | $^1H$ NMR (400 MHz, DMSO-$d_6$) δ 14.76 (br s, 1H), 11.25 (s, 1H), 9.55 (s, 1H), 9.32 (s, 1H), 8.53 (d, J = 7.2 Hz, 1H), 8.40 (d, J = 8.8 Hz, 1H), 8.23 (s, 1H), 8.01 (s, 1H), 7.61 (d, J = 8.4 Hz, 1H), 7.51 (s, 1H), 6.96 (d, J = 7.2 Hz, 1H), 2.02-1.89 (m, 1H), 1.22-1.15 (m, 2H), 1.11-1.05 (m, 2H). LCMS (ESEAPCI) m/z: 405.7 $[M + H]^+$. |
| A7 | 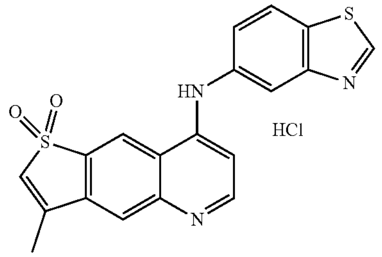 [SMILES: CC1=CS(=O)(=O)c2cc3c(Nc4ccc5scnc5c4)ccnc3cc21 ; Cl] | AA, BB | $^1H$ NMR (400 MHz, DMSO-$d_6$) δ 14.95 (br s, 1H), 11.32 (s, 1H), 9.54 (s, 1H), 9.35 (s, 1H), 8.58 (d, J = 6.8 Hz, 1H), 8.40 (d, J = 8.8 Hz, 1H), 8.24 (s, 1H), 8.17 (s, 1H), 7.63 (d, J = 8.4 Hz, 1H), 7.59 (s, 1H), 7.00 (d, J = 6.8 Hz, 1H), 2.41 (s, 3H). LCMS (ESEAPCI) m/z: 379.8 $[M + H]^+$. |
| A8 | 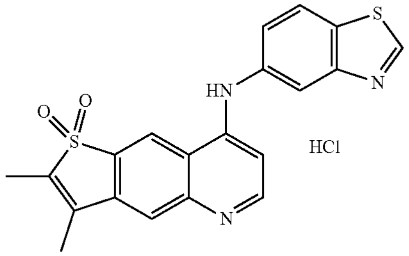 [SMILES: CC1=C(C)S(=O)(=O)c2cc3c(Nc4ccc5scnc5c4)ccnc3cc21 ; Cl] | AF, BB | $^1H$ NMR (400 MHz, DMSO-$d_6$) δ 14.69 (s, 1H), 11.23 (s, 1H), 9.54 (s, 1H), 9.35 (s, 1H), 8.57 (d, J = 6.8 Hz, 1H), 8.40 (d, J = 8.4 Hz, 1H), 8.24 (s, 1H), 8.08 (s, 1H), 7.62 (d, J = 8.4 Hz, 1H), 7.00 (d, J = 6.8 Hz, 1H), 2.32 (s, 3H), 2.22 (s, 3H). LC-MS (m/z): 393.7 $[M + H]^+$. |
| A9 | 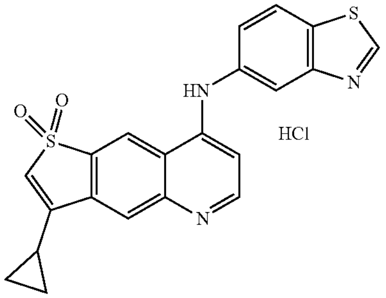 [SMILES: O=S1(=O)C=C(C2CC2)c2cc3nccc(Nc4ccc5scnc5c4)c3cc21 ; Cl] | AF, BB | $^1H$ NMR (400 MHz, $CDCl_3$) δ 7.80-7.69 (m, 1H), 7.54-7.45 (m, 1H), 7.23-7.19 (m, 1H), 7.19-7.14 (m, 1H), 2.73-2.59 (m, 1H), 1.34-1.21 (m, 2H), 1.16-1.00 (m, 2H). LC-MS (m/z): 164.9 $[M + H]^+$. |

TABLE 1-continued

Selected compounds synthesized (A1-A118, B1-B29)

| No. | Structure | Method | $^1$H NMR & LC-MS |
| --- | --- | --- | --- |
| A10 | 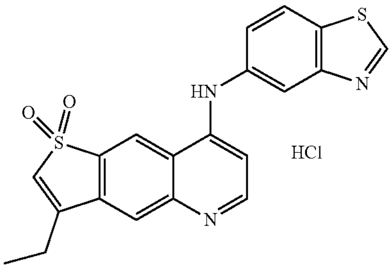 [SMILES: CCC1=CS(=O)(=O)c2cc3c(Nc4ccc5scnc5c4)ccnc3cc21 ; Cl] HCl | AF, BB | $^1$H NMR (400 MHz, DMSO-$d_6$) δ 14.72 (s, 1H), 11.25 (s, 1H), 9.55 (s, 1H), 9.32 (s, 1H), 8.59 (d, J = 6.8 Hz, 1H), 8.40 (d, J = 8.4 Hz, 1H), 8.24 (s, 1H), 8.15 (s, 1H), 7.63-7.60 (m, 2H), 7.01 (d, J = 6.8 Hz, 1H), 2.86-2.77 (m, 2H), 1.30 (t, J = 7.2 Hz, 3H). LC-MS (m/z): 393.7 [M + H]$^+$. |
| A11 | 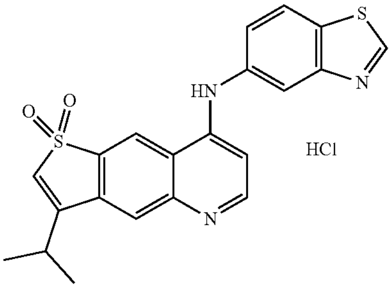 [SMILES: CC(C)C1=CS(=O)(=O)c2cc3c(Nc4ccc5scnc5c4)ccnc3cc21 ; Cl] HCl | AF, BB | $^1$H NMR (400 MHz, DMSO-$d_6$) δ 14.56 (br s, 1H), 11.17 (s, 1H), 9.54 (s, 1H), 9.30 (s, 1H), 8.60 (d, J = 6.8 Hz, 1H), 8.40 (d, J = 8.4 Hz, 1H), 8.25-8.20 (m, 2H), 7.65-7.60 (m, 2H), 7.02 (d, J = 6.8 Hz, 1H), 3.25-3.15 (m, 1H), 1.32 (d, J = 6.8 Hz, 6H). LCMS (ESI/APCI) m/z: 407.7 [M + H]$^+$. |
| A12 | 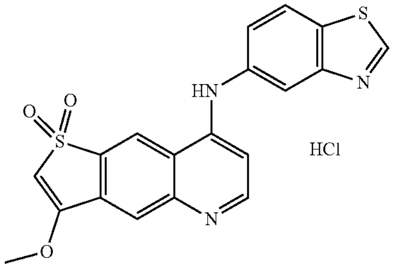 [SMILES: COC1=CS(=O)(=O)c2cc3c(Nc4ccc5scnc5c4)ccnc3cc21 ; Cl] HCl | AA, AH, BB, BD | $^1$H NMR (400 MHz, DMSO-$d_6$) δ14.88 (s, 1H), 11.25 (s, 1H), 9.54 (s, 1H), 9.34 (s, 1H), 8.60 (d, J = 6.8 Hz, 1H),8.40 (d, J = 8.4 Hz, 1H), 8.23 (s, 1H), 8.17 (s, 1H), 7.62 (d, J = 8.4 Hz, 1H),7.16 (s, 1H), 7.01 (d, J = 7.2 Hz, 1H), 4.07 (s, 3H). LCMS (ESI/APCI) m/z: 395.7 [M + H]$^+$. |
| A13 | 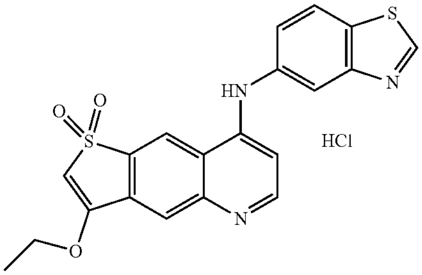 [SMILES: CCOC1=CS(=O)(=O)c2cc3c(Nc4ccc5scnc5c4)ccnc3cc21 ; Cl] HCl | AA, AH, BB, BD | $^1$H NMR (400 MHz, DMSO-$d_6$) δ14.79 (s, 1H), 11.25 (s, 1H), 9.54 (s, 1H), 9.34 (s, 1H), 8.60 (d, J = 6.8 Hz, 1H), 8.40 (d, J = 8.4 Hz, 1H), 8.23 (s, 1H), 8.18 (s, 1H), 7.62 (d, J = 8.0 Hz, 1H), 7.14 (s, 1H), 7.01 (d, J = 6.4 Hz, 1H), 4.40-4.26 (m, 2H), 1.47 (t, J = 6.0 Hz, 3H). LCMS (ESEAPCI) m/z: 409.6 [M + H]$^+$. |
| A14 | 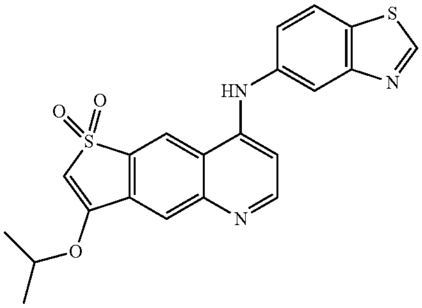 [SMILES: CC(C)OC1=CS(=O)(=O)c2cc3c(Nc4ccc5scnc5c4)ccnc3cc21] | AA, AH, BB, BD | $^1$H NMR (400 MHz, DMSO-$d_6$) δ 9.58 (s, 1H), 9.45 (s, 1H), 9.01 (s, 1H), 8.58 (d, J = 5.6 Hz, 1H), 8.23 (d, J = 8.4 Hz, 1H), 8.07 (s, 1H), 7.90 (s, 1H), 7.55 (d, J = 8.0 Hz, 1H), 7.10 (d, J = 5.2 Hz, 1H), 6.93 (s, 1H), 4.78-4.64 (m, 1H), 1.43 (d, J = 6.0 Hz, 6H). LCMS (ESEAPCI) m/z: 423.7 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| A15 | 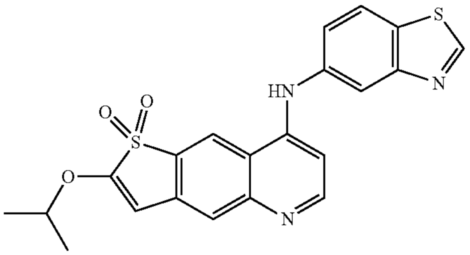 [SMILES: CC(C)OC1=Cc2cc3nccc(Nc4ccc5scnc5c4)c3cc2S1(=O)=O] | AA, AH, BB, BD | $^1$H NMR (400 MHz, DMSO-d$_6$) δ 9.45 (s, 2H), 8.92 (s, 1H), 8.50 (d, J = 5.2 Hz, 1H), 8.22 (d, J = 8.4 Hz, 1H), 8.04 (s, 1H), 7.73 (s, 1H), 7.53 (d, J = 8.4 Hz, 1H), 7.01 (d, J = 5.2 Hz, 1H), 6.80 (s, 1H), 4.81-4.67 (m, 1H), 1.42 (d, J = 6.0 Hz, 6H). LCMS (ESEAPCI) m/z: 423.7 [M + H]$^+$. |
| A16 | 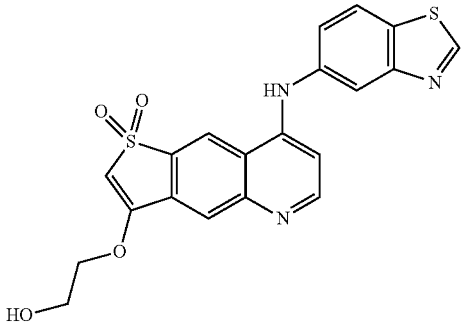 [SMILES: O=S1(=O)C=C(OCCO)c2cc3nccc(Nc4ccc5scnc5c4)c3cc21] | AA, AH, BB, BC | $^1$H NMR (400 MHz, DMSO-d$_6$) δ 9.47 (s, 1H), 9.08 (s, 1H), 8.59 (d, J = 5.6 Hz, 1H), 8.27 (d, J = 8.8 Hz, 1H), 8.10 (s, 1H), 8.06 (s, 1H), 7.57 (d, J = 8.8 Hz, 1H), 7.08 (d, J = 5.6 Hz, 1H), 6.95 (s, 1H), 5.14 (s, 1H), 4.25 (s, 2H), 3.83 (s, 2H). LCMS (ESI/APCI) m/z: 425.7 [M + H]$^+$. |
| A17 | 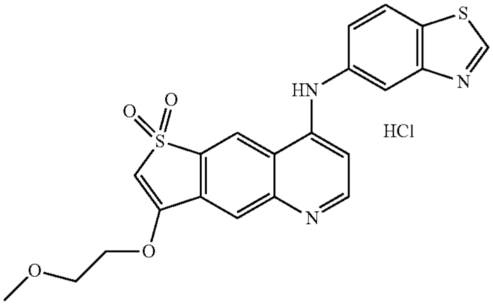 [SMILES: COCCOC1=CS(=O)(=O)c2cc3c(Nc4ccc5scnc5c4)ccnc3cc21 ; Cl] HCl | AA, AH, BB, BD | $^1$H NMR (400 MHz, DMSO-d$_6$) δ14.90 (s, 1H), 11.31 (s, 1H), 9.54 (s, 1H), 9.36 (s, 1H), 8.60 (d, J = 6.8 Hz, 1H), 8.40 (d, J = 8.4 Hz, 1H), 8.23 (s, 1H), 8.20 (s, 1H), 7.62 (d, J = 8.4 Hz, 1H), 7.17 (s, 1H), 7.00 (d, J = 6.8 Hz, 1H), 4.41 (s, 2H), 3.79 (s, 2H), 3.37 (s, 3H). LCMS (ESEAPCI) m/z: 439.6 [M + H]$^+$. |
| A18 | 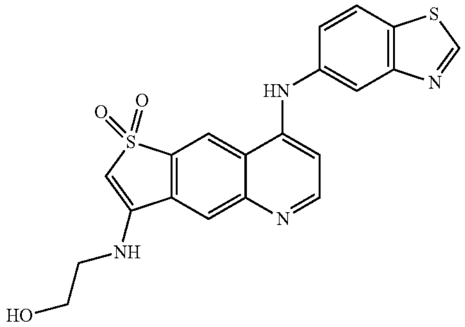 [SMILES: O=S1(=O)C=C(NCCO)c2cc3nccc(Nc4ccc5scnc5c4)c3cc21] | AA, AH, BB, BD | $^1$H NMR (400 MHz, DMSO-d$_6$) δ 9.51 (s, 1H), 9.44 (s, 1H), 8.89 (s, 1H), 8.57 (d, J = 5.2 Hz, 1H), 8.48 (s, 1H), 8.22 (d, J = 8.4 Hz, 1H), 8.06 (s, 1H), 7.77 (s, 1H), 7.56 (d, J = 8.1 Hz, 1H), 7.09 (d, J = 5.2 Hz, 1H), 5.88 (s, 1H), 4.87 (t, J = 4.8 Hz, 1H), 3.66 (d, J = 4.8 Hz, 2H), 3.31-3.27 (m, 2H). LCMS (ESEAPCI) m/z: 424.6 [M + H]$^+$. |
| A19 | 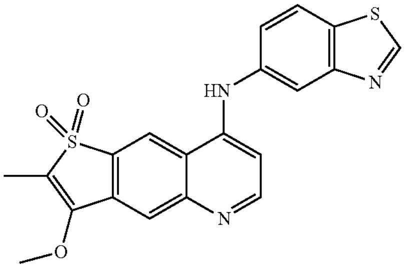 [SMILES: COC1=C(C)S(=O)(=O)c2cc3c(Nc4ccc5scnc5c4)ccnc3cc21] | AG, AH, BB, BD | $^1$H NMR (400 MHz, DMSO-d$_6$) δ 9.51 (s, 1H), 9.45 (s, 1H), 9.03 (s, 1H), 8.56 (d, J = 5.6 Hz, 1H), 8.23 (d, J = 8.4 Hz, 1H), 8.06 (s, 1H), 7.87 (s, 1H), 7.55 (d, J = 8.8 Hz, 1H), 7.09 (d, J = 52 Hz, 1H), 4.28 (s, 3H), 2.32 (s, 3H). LCMS (ESEAPCI) m/z: 409.7 [M + H]$^+$. |

TABLE 1-continued

Selected compounds synthesized (A1-A118, B1-B29)

| No. | Structure | Method | $^1$H NMR & LC-MS |
|---|---|---|---|
| A20 | 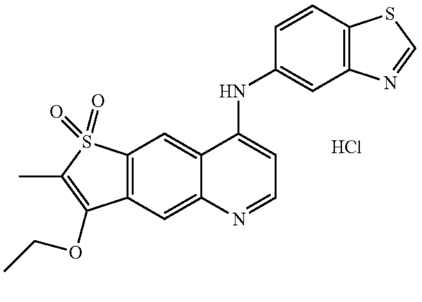 [SMILES: CCOC1=C(C)S(=O)(=O)c2cc3c(Nc4ccc5scnc5c4)ccnc3cc21 ; Cl] HCl | AF, BB | $^1$H NMR (400 MHz, DMSO-$d_6$) δ 14.94 (s, 1H), 11.29 (s, 1H), 9.54 (s, 1H), 9.39 (s, 1H), 8.57 (d, J = 6.8 Hz, 1H), 8.40 (d, J = 8.4 Hz, 1H), 8.23 (s, 1H), 8.16 (s, 1H), 7.62 (d, J = 8.4 Hz, 1H), 6.99 (d, J = 6.8 Hz, 1H), 4.65 (q, J = 6.8 Hz, 2H), 2.33 (s, 3H), 1,44 (t, J = 6.8 Hz, 3H). LCMS (ESEAPCI) m/z: 423.7 $[M + H]^+$. |
| A21 | 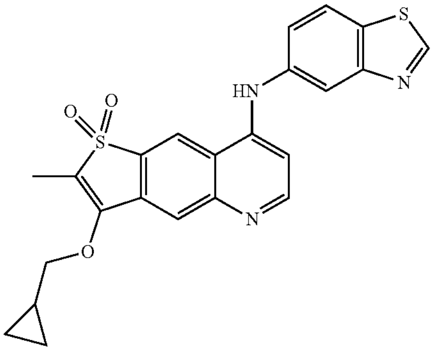 [SMILES: CC1=C(OCC2CC2)c2cc3nccc(Nc4ccc5scnc5c4)c3cc2S1(=O)=O] | AF, BB | $^1$H NMR (400 MHz, DMSO-$d_6$) δ 9.60 (s, 1H), 9.46 (s, 1H), 9.05 (s, 1H), 8.57 (d, J = 5.2 Hz, 1H), 8.24 (d, J = 8.4 Hz, 1H), 8.07 (s, 1H), 7.90 (s, 1H), 7.55 (d, J = 7.6 Hz, 1H), 7.09 (d, J = 5.6 Hz, 1H), 4.40 (d, J = 7.2 Hz, 2H), 2.25 (s, 3H), 1.35-1.26 (m, 1H), 0.70-0.65 (m, 2H), 0.47-0.39 (m, 2H). LCMS (ESEAPCI) m/z: 449.7 $[M + H]^+$. |
| A22 | 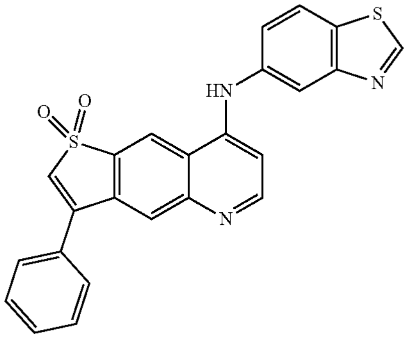 [SMILES: O=S1(=O)C=C(c2ccccc2)c2cc3nccc(Nc4ccc5scnc5c4)c3cc21] | AA, AH, BB, BE | $^1$H NMR (400 MHz, DMSO-$d_6$) δ 9.61 (s, 1H), 9.46 (s, 1H), 9.12 (s, 1H), 8.57 (d, J = 5.2 Hz, 1H), 8.24 (d, J = 8.8 Hz, 1H), 8.08 (s, 1H), 7.90 (s, 1H), 7.81-7.76 (m, 2H), 7.74 (s, 1H), 7.69-7.62 (m, 3H), 7.57 (d, J = 8.8 Hz, 1H), 7.11 (d, J = 5.2 Hz, 1H). LCMS (ESEAPCI) m/z: 441.6 $[M + H]^+$. |
| A23 | 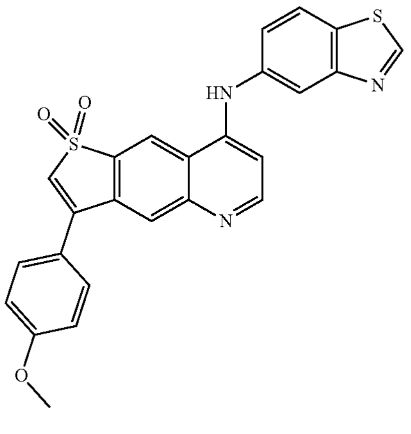 [SMILES: COc1ccc(C2=CS(=O)(=O)c3cc4c(Nc5ccc6scnc6c5)ccnc4cc32)cc1] | AA, AH, BB, BE | $^1$H NMR (400 MHz, DMSO-$d_6$) δ 14.79 (s, 1H), 11.36 (s, 1H), 9.55 (s, 1H), 9.43 (s, 1H), 8.60 (d, J = 6.8 Hz, 1H), 8.41 (d, J = 8.8 Hz, 1H), 8.30 (s, 1H), 8.26 (s, 1H), 7.89 (s, 1H), 7.76 (d, J = 8.4 Hz, 2H), 7.64 (d, J = 8.4 Hz, 1H), 7.21 (d, J = 8.0 Hz, 2H), 7.03 (d, J = 6.8 Hz, 1H), 3.89 (s, 3H). LCMS (ESI/APCI) m/z: 471.7 $[M + H]^+$ |

TABLE 1-continued

| Selected compounds synthesized (A1-A118, B1-B29) | | | |
|---|---|---|---|
| No. | Structure | Method | $^{1}$H NMR & LC-MS |
| A24 | 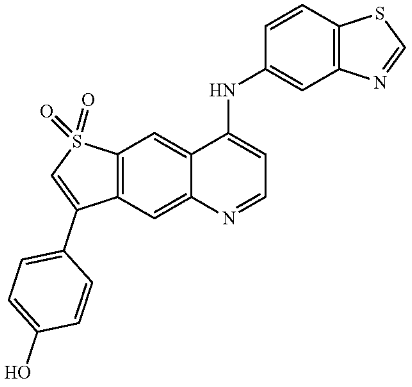 | AA, AH, BB, BE | $^{1}$H NMR (400 MHz, DMSO-$d_6$) δ 9.60 (s, 1H), 9.45 (s, 1H), 9.07 (s, 1H), 8.57 (d, J = 5.2 Hz, 1H), 8.23 (d, J = 8.4 Hz, 1H), 8.07 (s, 1H), 7.99 (s, 1H), 7.63 (s, 1H), 7.61 (s, 1H), 7.56 (d, J = 8.4 Hz, 1H), 7.50 (s, 1H), 7.11 (d, J = 52 Hz, 1H), 6.95 (d, J = 8.0 Hz, 2H). LCMS (ESEAPCI) m/z: 457.6 $[M + H]^+$. |
| A25 | 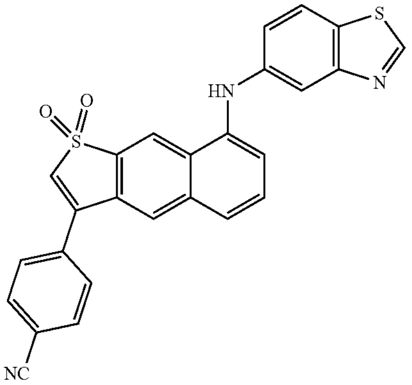 [SMILES: N#Cc1ccc(C2=CS(=O)(=O)c3cc4c(Nc5ccc6scnc6c5)cccc4cc32)cc1] | AA, AH, BB, BE | $^{1}$H NMR (400 MHz, DMSO-$d_6$) δ 9.67 (s, 1H), 9.45 (s, 1H), 9.14 (s, 1H), 8.57 (d, J = 5.2 Hz, 1H), 8.24 (d, J = 8.4 Hz, 1H), 8.16-8.05 (m, 3H), 8.03-7.94 (m, 2H), 7.90 (s, 1H), 7.85 (s, 1H), 7.56 (d, J = 7.6 Hz, 1H),7.11 (d, J = 5.6 Hz, 1H). LCMS (ESEAPCI) m/z: 466.6 $[M + H]^+$. |
| A26 | 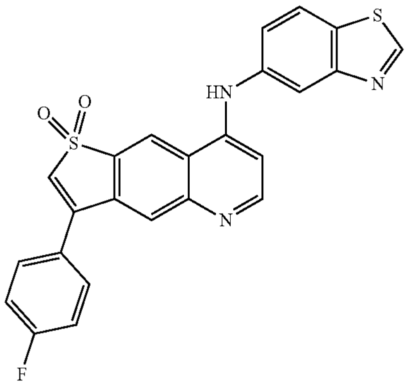 [SMILES: O=S1(=O)C=C(c2ccc(F)cc2)c2cc3nccc(Nc4ccc5scnc5c4)c3cc21] | AA, AH, BB, BE | $^{1}$H NMR (400 MHz, DMSO-$d_6$) δ 11.32 (s, 1H), 9.55 (s, 1H), 9.43 (s, 1H), 8.61 (d, J = 6.8 Hz, 1H), 8.41 (d, J = 8.4 Hz, 1H), 8.25 (s, 1H), 8.19 (s, 1H), 8.00 (s, 1H), 7.89-7.85 (m, 2H), 7.64 (d, J = 8.0 Hz, 1H), 7.54 (t, J = 8.8 Hz, 2H), 7.04 (d, J = 6.4 Hz, 1H). LCMS (ESEAPCI) m/z: 459.6 $[M + H]^+$. |
| A27 | 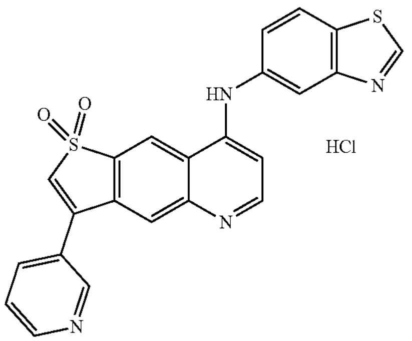 [SMILES: O=S1(=O)C=C(c2cccnc2)c2cc3nccc(Nc4ccc5scnc5c4)c3cc21 ; Cl] | AA, AH, BB, BE | $^{1}$H NMR (400 MHz, DMSO-$d_6$) δ9.62 (s, 1H), 9.45 (s, 1H), 9.14 (s, 1H), 8.96 (s, 1H), 8.81 (d, J = 4.4 Hz, 1H), 8.58 (d, J = 5.6 Hz, 1H), 8.28-8.22 (m, 2H), 8.08 (s, 1H), 7.88 (s, 1H), 7.86 (s, 1H), 7.71-7.65 (m, 1H), 7.59-7.54 (m, 1H), 7.12 (d, J = 5.6 Hz, 1H). LC-MS (m/z): 442.6 $[M + H]^+$. |

TABLE 1-continued

Selected compounds synthesized (A1-A118, B1-B29)

| No. | Structure | Method | $^1$H NMR & LC-MS |
|---|---|---|---|
| A28 | 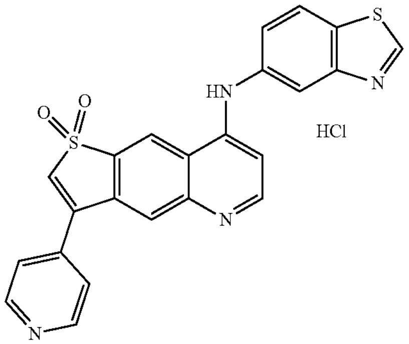 [SMILES: O=S1(=O)C=C(c2ccncc2)c2cc3nccc(Nc4ccc5scnc5c4)c3cc21 ; Cl] HCl | AA, AH, BB, BE | $^1$H NMR (400 MHz, DMSO-$d_6$) δ 11.57 (s, 1H), 9.56 (d, J = 7.2 Hz, 2H), 9.01 (d, J = 4.8 Hz, 2H), 8.60 (d, J = 6.8 Hz, 1H), 8.41 (d, J = 8.4 Hz, 1H), 8.29 (s, 1H), 8.26 (s, 2H), 8.01 (d, J = 4.8 Hz, 2H), 7.65 (d, J = 8.0 Hz, 1H), 7.03 (d, J = 6.8 Hz, 1H). LCMS (ESEAPCI) m/z: 442.6 $[M + H]^+$. |
| A29 | 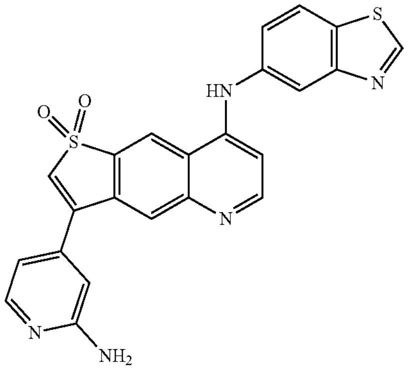 [SMILES: Nc1cc(C2=CS(=O)(=O)c3cc4c(Nc5ccc6scnc6c5)ccnc4cc32)ccn1] | AA, AH, BB, BE | $^1$H NMR (400 MHz, DMSO-$d_6$) δ 9.61 (s, 1H), 9.46 (s, 1H), 9.12 (s, 1H), 8.58 (d, J = 5.2 Hz, 1H), 8.24 (d, J = 8.8 Hz, 1H), 8.14 (d, J = 4.8 Hz, 1H), 8.08 (s, 1H), 7.93 (s, 1H), 7.82 (s, 1H), 7.53 (d, J = 8.0 Hz, 1H), 7.12 (d, J = 52 Hz, 1H), 6.78-6.76 (m, 2H), 6.34 (s, 2H). LCMS (ESI/APCI) m/z: calcd for 457.6 $[M + H]^+$. |
| A30 | 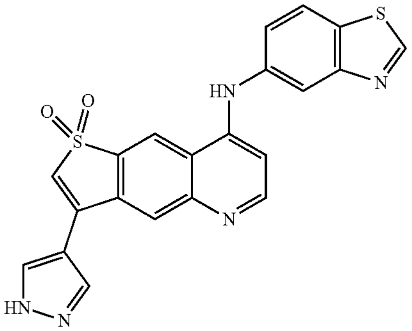 [SMILES: O=S1(=O)C=C(c2cn[nH]c2)c2cc3nccc(Nc4ccc5scnc5c4)c3cc21] | AA, AH, BB, BE | $^1$H NMR (400 MHz, DMSO-$d_6$) δ 11.39 (s, 1H), 9.55 (s, 1H), 9.41 (s, 1H), 8.77 (s, 1H), 8.65 (d, J = 6.8 Hz, 1H), 8.42 (s, 2H), 8.40 (s, 1H), 8.26 (s, 1H), 7.91 (s, 1H), 7.64 (d, J = 7.6 Hz, 1H), 7.55-7.51 (m, 1H), 7.37 (s, 1H), 7.03 (d, J = 6.8 Hz, 1H). LCMS (ESEAPCI) m/z: 431.6 $[M + H]^+$. Purity: 95.7%, t = 7.728 |
| A31 | 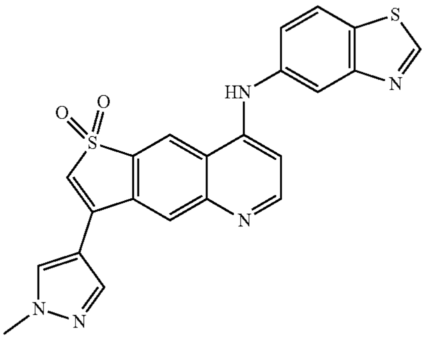 [SMILES: Cn1cc(C2=CS(=O)(=O)c3cc4c(Nc5ccc6scnc6c5)ccnc4cc32)cn1] | AA, AH, BB, BE | $^1$H NMR (400 MHz, DMSO-$d_6$) δ 10.52 (s, 1H), 9.50 (s, 1H), 9.24 (s, 1H), 8.66 (s, 1H), 8.63 (d, J = 6.0 Hz, 1H), 8.48 (d, J = 16.4 Hz, 1H), 8.33 (d, J = 8.8 Hz, 1H), 8.17 (s, 2H), 7.77 (s, 1H), 7.60 (d, J = 8.0 Hz, 1H), 7.08 (s, 1H), 4.00 (s, 3H). LCMS (ESEAPCI) m/z: 445.6 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A32 | 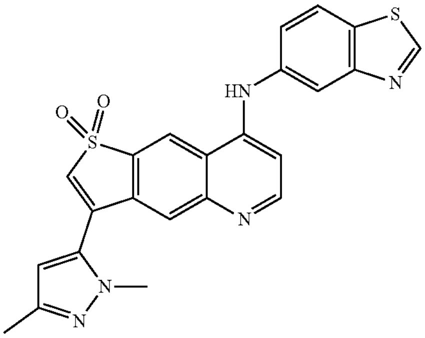 [SMILES: Cc1cc(C2=CS(=O)(=O)c3cc4c(Nc5ccc6scnc6c5)ccnc4cc32)n(C)n1] | AA, AH, BB, BE | $^1$H NMR (400 MHz, DMSO-$d_6$) δ 9.63 (s, 1H), 9.46 (s, 1H), 9.14 (s, 1H), 8.59 (d, J = 52 Hz, 1H), 8.24 (d, J = 8.4 Hz, 1H), 8.08 (s, 1H), 7.94 (s, 1H), 7.91 (s, 1H), 7.56 (d, J = 8.0 Hz, 1H), 7.12 (d, J = 5.2 Hz, 1H), 6.76 (s, 1H), 3,91 (s, 3H), 2.29 (s, 3H). LCMS (ESEAPCI) m/z: 459.6 $[M + H]^+$. |
| A33 | 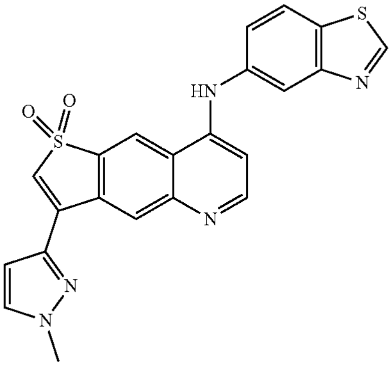 [SMILES: Cn1ccc(C2=CS(=O)(=O)c3cc4c(Nc5ccc6scnc6c5)ccnc4cc32)n1] | AA, AH, BB, BE | $^1$H NMR (400 MHz, DMSO-$d_6$) δ 9.63 (s, 1H), 9.46 (s, 1H), 9.10 (s, 1H), 9.08 (s, 1H), 8.59 (d, J = 5.2 Hz, 1H), 8.24 (d, J = 8.4 Hz, 1H), 8.08 (s, 1H), 7.97 (s, 1H), 7.95 (s, 1H), 7.57 (d, J = 8.4 Hz, 1H), 7.11 (d, J = 52 Hz, 1H), 7.05 (s, 1H), 4.07 (s, 3H). LCMS (ESEAPCI) m/z: 445.6 $[M + H]^+$. |
| A34 | 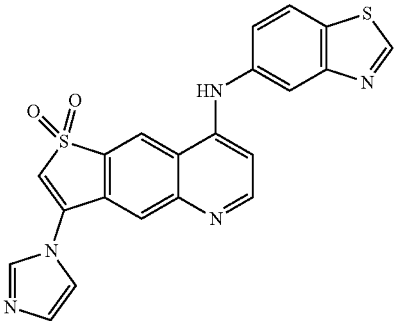 [SMILES: O=S1(=O)C=C(n2ccnc2)c2cc3nccc(Nc4ccc5scnc5c4)c3cc21] | AA, AH, BB, BD | $^1$H NMR (400 MHz, DMSO-$d_6$) $^1$H NMR (400 MHz, DMSO-d) 5 11.12 (s, 1H), 9.54 (s, 1H), 9.43 (s, 1H), 8.64 (d, J = 6.0 Hz, 1H), 8.48 (s, 1H), 8.39 (d, J = 8.8 Hz, 1H), 8.33 (s, 1H), 8.24 (s, 1H), 8.13 (s, 1H), 7.93 (s, 1H), 7.63 (d, J = 8.4 Hz, 1H), 7.38 (s, 1H), 7.08 (d, J = 6.4 Hz, 1H). LCMS (ESEAPCI) m/z: 431.6 $[M + H]^+$. |
| A35 | 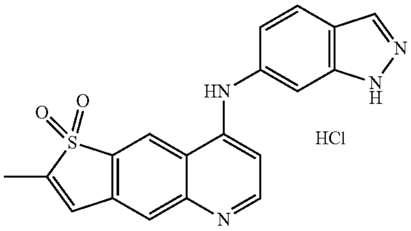 [SMILES: CC1=Cc2cc3nccc(Nc4ccc5cn[nH]c5c4)c3cc2S1(=O)=O ; Cl] HCl | AB, BA | $^1$H NMR (400 MHz, DMSO-$d_6$) δ 14.87 (br s, 1H), 13.33 (s, 1H), 11.22 (s, 1H), 9.36 (s, 1H), 8.57-8.46 (m, 1H), 8.19 (s, 1H), 8.10 (s, 1H), 8.00-7.90 (m, 1H), 7.70-7.58 (m, 2H), 7.25-7.18 (m, 1H), 6.98-6.87 (m, 1H), 2.27 (s, 3H). LCMS (ESI/APCI m/z: 362.8 $[M + H]^+$. |
| A36 | 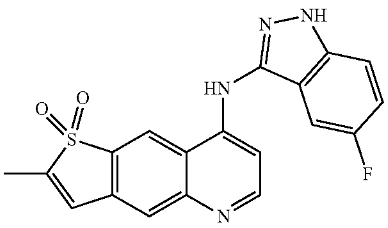 [SMILES: CC1=Cc2cc3nccc(Nc4n[nH]c5ccc(F)cc45)c3cc2S1(=O)=O] | AB, BA | $^1$H NMR (400 MHz, DMSO-$d_6$) δ 12.90 (s, 1H), 9.56 (s, 1H), 9.26 (s, 1H), 8.62 (s, 1H), 7.95 (s, 1H), 7.75 (s, 1H), 7.67 (s, 1H), 7.56 (s, 1H), 7.46 (s, 1H), 7.32 (s, 1H), 2.22 (s, 3H). LCMS (ESI/APCI) m/z: 380.7 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A37 | 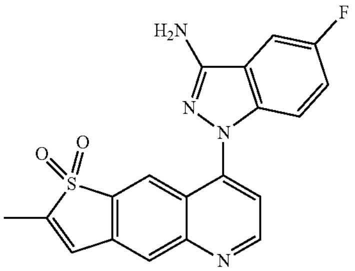 [SMILES: CC1=Cc2cc3nccc(-n4nc(N)c5cc(F)ccc54)c3cc2S1(=O)=O] | AB, BA | $^1$H NMR (400 MHz, DMSO-$d_6$) δ 9.07 (s, 1H), 9.00 (s, 1H), 8.15 (s, 1H), 7.75 (s, 3H), 7.51 (s, 1H), 7.39 (s, 1H), 6.42 (s, 2H), 2.22 (s, 3H). LCMS (ESI/APCI) m/z: 380.7 [M + H]$^+$. |
| A38 | 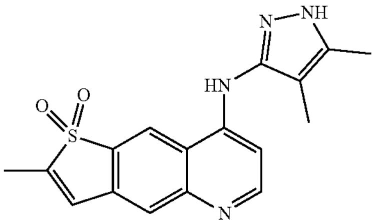 | AB, BA | $^1$H NMR (400 MHz, DMSO-$d_6$) δ 12.28 (s, 1H), 9.07 (s, 1H), 9.01 (s, 1H), 8.47 (d, J = 5.6 Hz, 1H), 7.87 (s, 1H), 7.43 (s, 1H), 6.75 (s, 1H), 2.20 (s, 6H), 1.82 (s, 3H). LCMS (ESEAPCI) m/z: 340.8 [M + H]$^+$. |
| A39 | 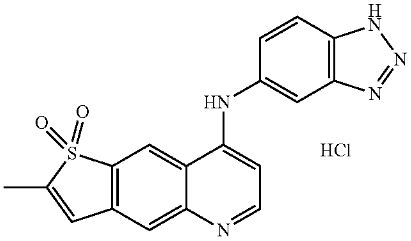 [SMILES: CC1=Cc2cc3nccc(Nc4ccc5[nH]nnc5c4)c3cc2S1(=O)=O ; Cl] HCl | AB, BA | $^1$H NMR (400 MHz, DMSO-$d_6$) δ 14.90 (br s, 1H), 11.23 (s, 1H), 9.35 (s, 1H), 8.54 (d, J = 6.8 Hz, 1H), 8.20-7.90 (m, 3H), 7.64 (s, 1H), 7.54 (d, J = 10.0 Hz, 1H), 6.95 (d, J = 6.4 Hz, 1H), 2.27 (s, 3H). LCMS (ESEAPCI) m/z: 363.8 [M + H]$^+$. |
| A40 | 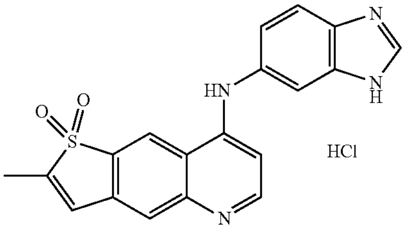 [SMILES: CC1=Cc2cc3nccc(Nc4ccc5nc[nH]c5c4)c3cc2S1(=O)=O ; Cl] HCl | AB, BA | $^1$H NMR (400 MHz, DMSO-$d_6$) δ 13.84 (br s, 1H), 11.01 (s, 1H), 9.31 (s, 1H), 8.55-8.40 (m, 2H), 8.05 (s, 1H), 7.80 (d, J = 8.8 Hz, 1H), 7.73 (s, 1H), 7.61 (s, 1H), 7.32 (d, J = 8.4 Hz, 1H), 6.82 (d, J = 7.2 Hz, 1H), 2.26 (s, 3H). LCMS (ESEAPCI) m/z: 362.8 [M + H]$^+$. |
| A41 | 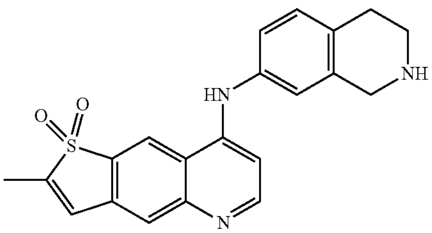 [SMILES: CC1=Cc2cc3nccc(Nc4ccc5c(c4)CNCC5)c3cc2S1(=O)=O] | AB, AJ, BA | $^1$H NMR (400 MHz, DMSO-$d_6$) δ 9.22 (s, 1H), 8.98 (s, 1H), 8.48 (d, J = 5.6 Hz, 1H), 7.89 (s, 1H), 7.43 (s, 1H), 7.18-7.10 (m, 2H), 7.04 (s, 1H), 6.90 (d, J = 5.6 Hz, 1H), 3.90 (s, 2H), 3.05-2.95 (m, 2H), 2.76-2.70 (m, 2H), 2.20 (s, 3H). LC-MS (m/z): 377.8 [M + H]$^+$. |
| A42 | 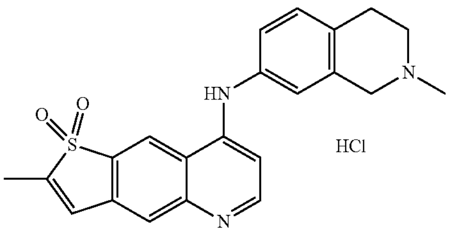 HCl | AB, BA | $^1$H NMR (400 MHz, DMSO-$d_6$) δ 15.15 (s, 1H), 11.27-11.00 (m, 2H), 9.36 (s, 1H), 8.60-8.50 (m, 1H), 8.13 (s, 1H), 7.63 (s, 1H), 7.50-7.38 (m, 2H), 7.32 (s, 1H), 6.90-6.83 (m, 1H), 4.60-4.20 (m, 2H), 3.67 (s, 1H), 3.30-3.23 (m, 2H), 3.15-3.05 (m, 1H), 2.92 (s, 3H), 2.26 (s, 3H). LC-MS (m/z): 391.8 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| A43 | 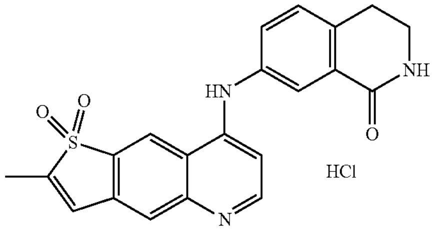 [SMILES: CC1=Cc2cc3nccc(Nc4ccc5c(c4)C(=O)NCC5)c3cc2S1(=O)=O ; Cl] HCl | AB, BA | $^1$H NMR (400 MHz, DMSO-$d_6$) δ 14.93 (br s, 1H), 11.13 (s, 1H), 9.33 (s, 1H), 8.58-8.46 (m, 1H), 8.16-8.06 (m, 2H), 7.92 (s, 1H), 7.64-7.49 (m, 3H), 6.95-6.84 (m, 1H), 3.43 (s, 2H), 2.99 (s, 2H), 2.26 (s, 3H). LC-MS (m/z): 391.7 [M + H]$^+$. |
| A44 | 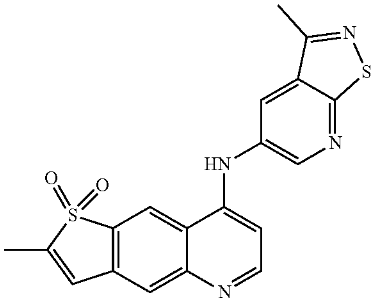 [SMILES: CC1=Cc2cc3nccc(Nc4cnc5snc(C)c5c4)c3cc2S1(=O)=O] | AB, BA | $^1$H NMR (400 MHz, DMSO-$d_6$) δ 9.61 (s, 1H), 9.01 (s, 1H), 8.89 (d, J = 2.4 Hz, 1H), 8.59 (d, J = 5.2 Hz, 1H), 8.53 (d, J = 2.4 Hz, 1H), 7.96 (s, 1H), 7.47 (s, 1H), 7.13 (d, J = 52 Hz, 1H), 2.72 (s, 3H), 2.22 (s, 3H). LC-MS (m/z): 394.7 [M + H]$^+$. |
| A45 | 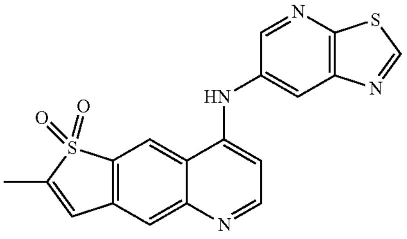 [SMILES: CC1=Cc2cc3nccc(Nc4cnc5scnc5c4)c3cc2S1(=O)=O] | AB, BA, BF | $^1$H NMR (400 MHz, DMSO-$d_6$) δ 9.62 (s, 2H), 9.01 (s, 1H), 8.76 (s, 1H), 8.58 (s, 1H), 8.49 (s, 1H), 7.96 (s, 1H), 7.48 (s, 1H), 7.11 (s, 1H), 2.22 (s, 3H). LCMS (ESI/APCI) m/z: 380.7 [M + H]$^+$. |
| A46 | 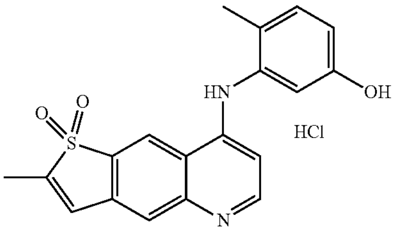 [SMILES: CC1=Cc2cc3nccc(Nc4cc(O)ccc4C)c3cc2S1(=O)=O ; Cl] HCl | AB, BA | $^1$H NMR (400 MHz, DMSO-$d_6$) δ 14.59 (br s, 1H), 10.88 (s, 1H), 9.76 (s, 1H), 9.30 (s, 1H), 8.49 (d, J = 6.8 Hz, 1H), 8.05 (s, 1H), 7.62 (s, 1H), 7.27 (d, J = 8.4 Hz, 1H), 6.84 (d, J = 8.0 Hz, 1H), 6.76 (s, 1H), 6.36 (d, J = 7.2 Hz, 1H), 2.26 (s, 3H), 2.08 (s, 3H). LCMS (ESI/APCI) m/z: 352.8 [M + H]$^+$. |
| A47 | 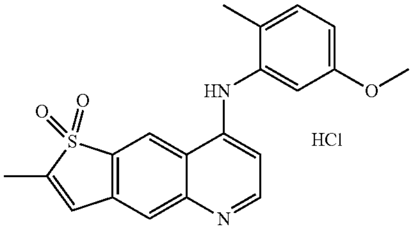 HCl | AB, BA | $^1$H NMR (400 MHz, DMSO-$d_6$) δ 14.96 (br s, 1H), 11.03 (s, 1H), 9.36 (s, 1H), 8.48 (d, J = 6.8 Hz, 1H), 8.12 (s, 1H), 7.63 (s, 1H), 7.40 (d, J = 8.0 Hz, 1H), 7.05-6.97 (m, 2H), 6.36 (d, J = 6.8 Hz, 1H), 3.76 (s, 3H), 2.26 (s, 3H), 2.14 (s, 3H). LC-MS (m/z): 366.8 [M + H]$^+$. |
| A48 | 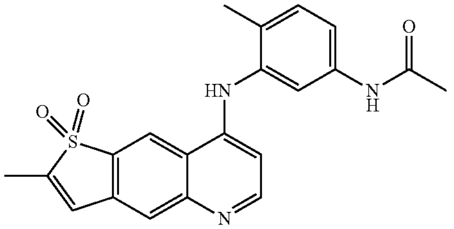 [SMILES: CC(=O)Nc1ccc(C)c(Nc2ccnc3cc4c(cc23)S(=O)(=O)C(C)=C4)c1] | AB, BA | $^1$H NMR (400 MHz, DMSO-$d_6$) δ 10.00 (s, 1H), 9.09 (s, 1H), 9.03 (s, 1H), 8.43 (d, J = 5.2 Hz, 1H), 7.89 (s, 1H), 7.64 (s, 1H), 7.44 (s, 1H), 7.40 (d, J = 8.0 Hz, 1H), 7.30 (d, J = 8.0 Hz, 1H), 6.22 (d, J = 52 Hz, 1H), 2.21 (s, 3H), 2.11 (s, 3H), 2.03 (s, 3H). LC-MS (m/z): 393.8 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| A49 | 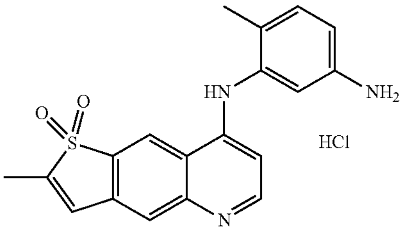 [SMILES: CC1=Cc2cc3nccc(Nc4cc(N)ccc4C)c3cc2S1(=O)=O ; Cl] HCl | AB, BA, BG | $^1$H NMR (400 MHz, DMSO-$d_6$) δ 11.07 (s, 1H), 9.36 (s, 1H), 8.53 (d, J = 6.8 Hz, 1H), 8.11 (s, 1H), 7.64 (s, 1H), 7.43 (s, J = 7.6 Hz, 1H), 7.13 (s, 1H), 7.08 (s, 1H), 6.36 (d, J = 6.8 Hz, 1H), 2.27 (s, 3H), 2.16 (s, 3H). LC-MS (m/z): 351.8 $[M + H]^+$. |
| A50 | 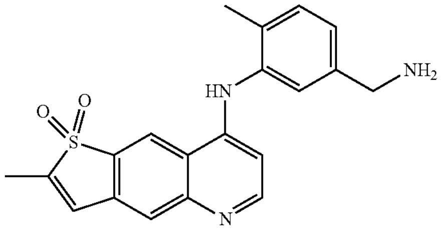 [SMILES: CC1=Cc2cc3nccc(Nc4cc(CN)ccc4C)c3cc2S1(=O)=O] | AB, AK, BA, BH | $^1$H NMR (400 MHz, DMSO-$d_6$) δ 9.08 (s, 2H), 8.44 (s, 1H), 8.13-7.81 (m, 3H), 7.54-7.23 (m, 4H), 6.28 (s, 1H), 4.02 (s, 2H), 2.21 (s, 6H). LC-MS (m/z): 365.8 $[M + H]^+$ |
| A51 | 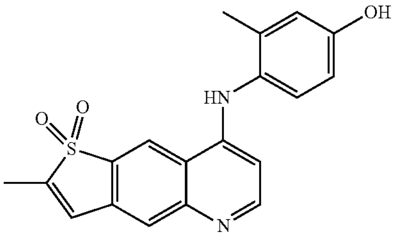 [SMILES: CC1=Cc2cc3nccc(Nc4ccc(O)cc4C)c3cc2S1(=O)=O] | AB, BA | $^1$H NMR (400 MHz, DMSO-$d_6$) δ 9.49 (s, 1H), 9.00 (s, 1H), 8.91 (s, 1H), 8.37 (d, J = 4.8 Hz, 1H), 7.85 (s, 1H), 7.42 (s, 1H), 7.06 (d, J = 8.4 Hz, 1H), 6.78 (s, 1H), 6.71 (d, J = 7.6 Hz, 1H), 6.08 (d, J = 52 Hz, 1H), 2.20 (s, 3H), 2.08 (s, 3H). LCMS (ESEAPCI) m/z: 352.8 $[M + H]^+$. |
| A52 | 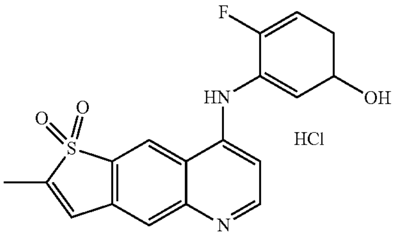 [SMILES: CC1=Cc2cc3nccc(NC4=CC(O)CC=C4F)c3cc2S1(=O)=O ; Cl] HCl | AB, BA | $^1$H NMR (400 MHz, DMSO-$d_6$) δ 14.76 (br s, 1H), 10.57 (s, 1H), 9.90 (s, 1H), 9.23 (s, 1H), 8.58 (s, 1H), 8.05 (s, 1H), 7.59 (s, 1H), 7.29 (s, 1H), 6.90 (s, 1H), 6.86 (s, 1H), 6.64 (s, 1H), 2.25 (s, 3H). LC-MS (m/z): 356.8 $[M + H]^+$. |
| A53 | 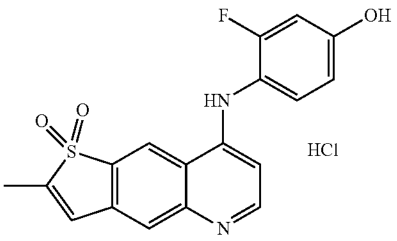 [SMILES: CC1=Cc2cc3nccc(Nc4ccc(O)cc4F)c3cc2S1(=O)=O ; Cl] HCl | AB, BA | $^1$H NMR (400 MHz, DMSO-$d_6$) δ 14.94 (br s, 1H), 10.80 (s, 1H), 10.45 (s, 1H), 9.29 (s, 1H), 8.54 (d, J = 6.8 Hz, 1H), 8.09 (s, 1H), 7.62 (s, 1H), 7.39-7.32 (m, 1H), 6.88 (d, J = 12.0 Hz, 1H), 6.83 (d, J = 8.4 Hz, 1H), 6.55 (d, J = 6.4 Hz, 1H), 2.26 (s, 3H). LC-MS (m/z): 356.8 $[M + H]^+$. |
| A54 | 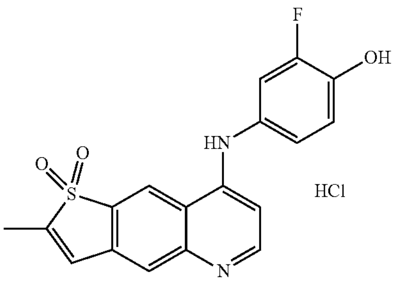 [SMILES: CC1=Cc2cc3nccc(Nc4ccc(O)c(F)c4)c3cc2S1(=O)=O ; Cl] HCl | AB, BA | $^1$H NMR (400 MHz, DMSO-$d_6$) δ 14.60 (br s, 1H), 10.88 (s, 1H), 10.35 (s, 1H), 9.24 (s, 1H), 8.51 (d, J = 6.0 Hz, 1H), 8.04 (s, 1H), 7.61 (s, 1H), 7.34 (d, J = 11.2 Hz, 1H), 7.29-6.93 (m, 2H), 6.82 (d, J = 6.0 Hz, 1H), 2.26 (s, 3H). LCMS (ESI/APCI) m/z: 356.7 $[M + H]^+$. |

TABLE 1-continued

Selected compounds synthesized (A1-A118, B1-B29)

| No. | Structure | Method | $^1$H NMR & LC-MS |
|---|---|---|---|
| A55 | 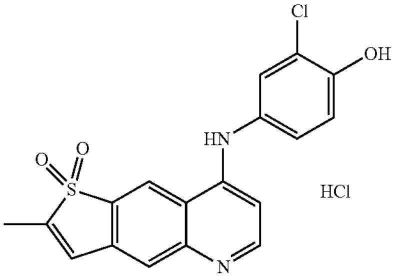 [SMILES: CC1=Cc2cc3nccc(Nc4ccc(O)c(Cl)c4)c3cc2S1(=O)=O ; Cl] HCl | AB, BA | $^1$H NMR (400 MHz, DMSO-$d_6$) δ 14.57 (br s, 1H), 10.75 (s, 1H), 10.64 (s, 1H), 9.21 (s, 1H), 8.50 (d, J = 6.0 Hz, 1H), 8.02 (s, 1H), 7.59 (s, 1H), 7.48 (s, 1H), 7.26 (d, J = 7.2 Hz, 1H), 7.16 (d, J = 8.0 Hz, 1H), 6.79 (d, J = 6.4 Hz, 1H), 2.25 (s, 3H). LCMS (ESI/APCI) m/z: 372.7 $[M + H]^+$. |
| A56 | 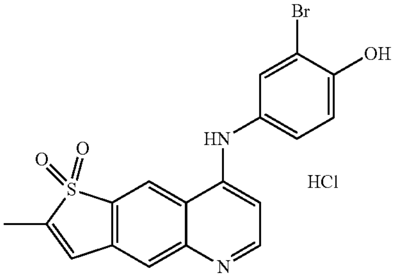 [SMILES: CC1=Cc2cc3nccc(Nc4ccc(O)c(Br)c4)c3cc2S1(=O)=O ; Cl] HCl | AB, BA | $^1$H NMR (400 MHz, DMSO-$d_6$) δ 14.81 (brs, 1H), 10.96 (s, 1H), 10.79 (s, 1H), 9.26 (s, 1H), 8.50 (d, J = 6.8 Hz, 1H), 8.08 (s, 1H), 7.62 (d, J = 5.6 Hz, 2H), 7.31 (d, J = 7.6 Hz, 1H), 7.17 (d, J = 8.4 Hz, 1H), 6.78 (d, J = 6.8 Hz, 1H), 2.25 (s, 3H). LC-MS (m/z): 416.6 $[M + H]^+$ |
| A57 | 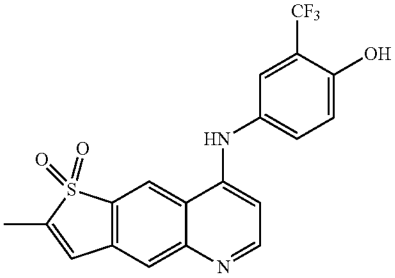 [SMILES: CC1=Cc2cc3nccc(Nc4ccc(O)c(C(F)(F)F)c4)c3cc2S1(=O)=O] | AB, BA | $^1$H NMR (400 MHz, DMSO-$d_6$) δ 14.89 (br s, 1H), 11.16 (s, 1H), 11.03 (s, 1H), 9.28 (s, 1H), 8.50 (d, J = 6.8 Hz, 1H), 8.09 (s, 1H), 7.66-7.60 (m, 2H), 7.58 (d, J = 8.8 Hz, 1H), 7.27 (d, J = 8.8 Hz, 1H), 6.78 (d, J = 6.8 Hz, 1H), 2.26 (s, 3H). LC-MS (m/z): 406.7 $[M + H]^+$. |
| A58 | 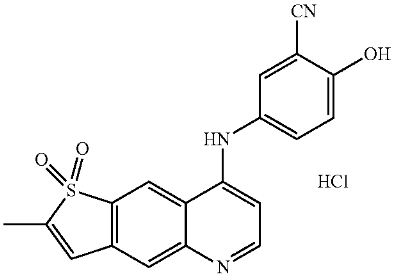 [SMILES: CC1=Cc2cc3nccc(Nc4ccc(O)c(C#N)c4)c3cc2S1(=O)=O ; Cl] HCl | AB, BA | $^1$H NMR (400 MHz, DMSO-$d_6$) δ 14.87 (br s, 1H), 11.67 (s, 1H), 11.00 (s, 1H), 9.28 (s, 1H), 8.52 (d, J = 7.2 Hz, 1H), 8.09 (s, 1H), 7.77 (s, 1H), 7.66-7.54 (m, 2H), 7.25 (d, J = 8.8 Hz, 1H), 6.82 (d, J = 6.8 Hz, 1H), 2.26 (s, 3H). LCMS (ESEAPCI) m/z: 363.7 $[M + H]^+$. |
| A59 | 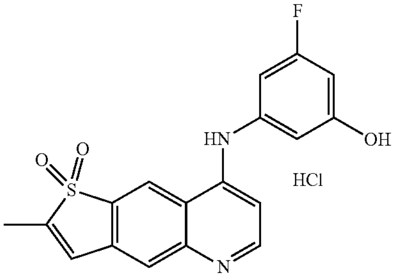 [SMILES: CC1=Cc2cc3nccc(Nc4cc(O)cc(F)c4)c3cc2S1(=O)=O ; Cl] HCl | AB, BA | $^1$H NMR (400 MHz, DMSO-$d_6$) δ14.90 (brs, 1H), 10.92 (s, 1H), 10.51 (s, 1H), 9.27 (s, 1H), 8.58 (d, J = 7.2 Hz, 1H), 8.08 (s, 1H), 7.62 (s, 1H), 7.05 (d, J = 6.8 Hz, 1H), 6.80 (d, J = 9.2 Hz, 1H), 6.75 (s, 1H), 6.65 (d, J = 10.8 Hz, 1H), 2.26 (s, 3H). LCMS (ESEAPCI) m/z: 356.7 $[M + H]^+$. |

TABLE 1-continued

Selected compounds synthesized (A1-A118, B1-B29)

| No. | Structure | Method | $^1$H NMR & LC-MS |
|---|---|---|---|
| A60 | 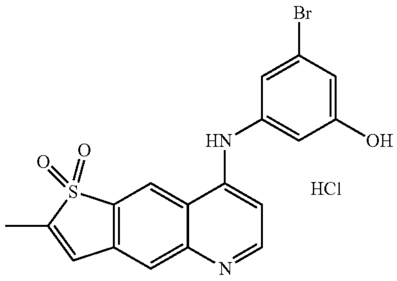 [SMILES: CC1=Cc2cc3nccc(Nc4cc(O)cc(Br)c4)c3cc2S1(=O)=O ; Cl] | AB, BA | $^1$H NMR (400 MHz, DMSO-$d_6$) δ14.85 (brs, 1H), 10.91 (s, 1H), 10.49 (s, 1H), 9.24 (s, 1H), 8.58 (d, J = 6.8 Hz, 1H), 8.07 (s, 1H), 7.62 (s, 1H), 7.12 (s, 1H), 7.02 (s, 2H), 6.90 (s, 1H), 2.26 (s, 3H). LCMS (ESI/APCI) m/z: 416.6 [M + H]$^+$. |
| A61 | 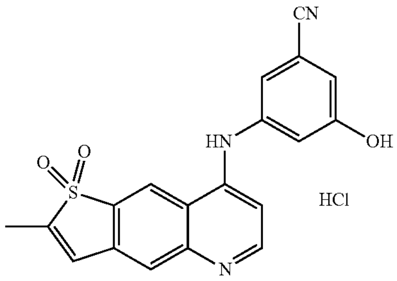 [SMILES: CC1=Cc2cc3nccc(Nc4cc(O)cc(C#N)c4)c3cc2S1(=O)=O ; Cl] | AB, BA | $^1$H NMR (400 MHz, DMSO-$d_6$) δ10.88 (s, 1H), 10.74 (s, 1H), 9.23 (s, 1H), 8.61 (d, J = 6.8 Hz, 1H), 8.06 (s, 1H), 7.62 (s, 1H), 7.40 (s, 1H), 7.20 (s, 2H), 7.09 (d, J = 6.8 Hz, 1H), 2.62 (s, 3H). LCMS (ESI/APCI) m/z: 363.7 [M + H]$^+$. |
| A62 | 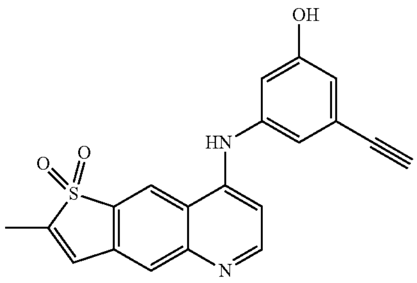 [SMILES: C#Cc1cc(O)cc(Nc2ccnc3cc4c(cc23)S(=O)(=O)C(C)=C4)c1] | AB, BA | $^1$H NMR (400 MHz, DMSO-$d_6$) δ 9.24 (s, 1H), 8.92 (s, 1H), 8.57 (s, 1H), 7.91 (s, 1H), 7.44 (s, 1H), 7.08 (s, 1H), 6.88-6.84 (m, 2H), 6.64 (s, 1H), 4.17 (s, 1H), 2.21 (s, 3H). LCMS (ESI/APCI) m/z: 362.8 [M + H]$^+$. |
| A63 | 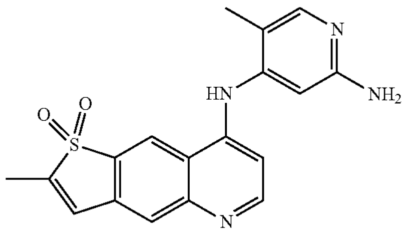 [SMILES: CC1=Cc2cc3nccc(Nc4cc(N)ncc4C)c3cc2S1(=O)=O] | AB, BA, BF, BG | $^1$H NMR (400 MHz, DMSO-$d_6$) δ 9.00-8.80 (m, 2H), 8.67 (s, 1H), 7.97 (s, 1H), 7.81 (s, 1H), 7.53-7.42 (m, 1H), 6.84 (s, 1H), 6.27 (s, 1H), 6.07 (s, 2H), 2.21 (s, 3H), 2.05 (s, 3H). LC-MS (m/z): 352.8 [M + H]$^+$. |
| A64 | 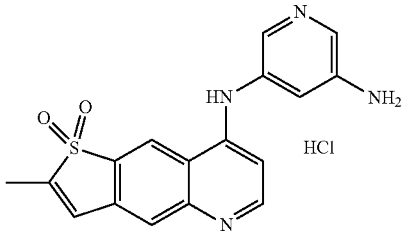 | AB, BA, BF, BG | $^1$H NMR (400 MHz, DMSO-$d_6$) δ 11.10 (s, 1H), 9.29 (s, 1H), 8.69 (d, J = 6.8 Hz, 1H), 8.13 (s, 1H), 8.06 (s, 1H), 8.00 (s, 1H), 7.63 (s, 1H), 7.42 (s, 1H), 7.17 (d, J = 6.4 Hz, 1H), 6.51 (br s, 2H), 2.26 (s, 3H). LCMS (ESEAPCI) m/z: 405.7 [M + H]$^+$. |

TABLE 1-continued

Selected compounds synthesized (A1-A118, B1-B29)

| No. | Structure | Method | $^1$H NMR & LC-MS |
|---|---|---|---|
| A65 | 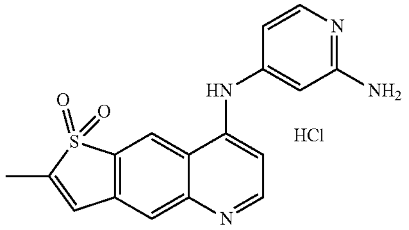 [SMILES: CC1=Cc2cc3nccc(Nc4ccnc(N)c4)c3cc2S1(=O)=O ; Cl] | AB, BA, BF, BG | $^1$H NMR (400 MHz, DMSO-$d_6$) δ 13.17 (s, 1H), 10.96 (s, 1H), 9.07 (s, 1H), 8.96 (d, J = 5.6 Hz, 1H), 8.21 (s, 1H), 7.93 (d, J = 6.8 Hz, 1H), 7.88 (s, 2H), 7.65 (d, J = 5.6 Hz, 1H), 7.59 (s, 1H), 6.87 (d, J = 6.4 Hz, 1H), 6.81 (s, 1H), 2.25 (s, 3H). LCMS (ESEAPCI) m/z: 338.8 $[M + H]^+$. |
| A66 | 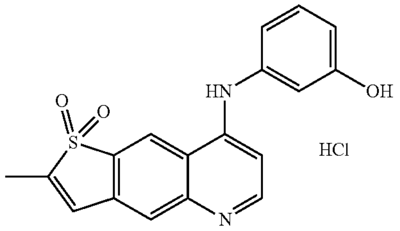 [SMILES: CC1=Cc2cc3nccc(Nc4cccc(O)c4)c3cc2S1(=O)=O ; Cl] | AB, BA, BF, BG | $^1$H NMR (400 MHz, DMSO-$d_6$) δ 11.28 (s, 1H), 11.17 (s, 1H), 9.36 (s, 1H), 8.64 (d, J = 6.8 Hz, 1H), 8.33 (s, 1H), 8.29 (s, 1H), 8.16 (s, 1H), 7.64 (s, 1H), 7.60 (s, 1H), 7.11 (d, J = 6.8 Hz, 1H), 2.26 (s, 3H). LCMS (ESEAPCI) m/z: 339.8 $[M + H]^+$. |
| A67 | 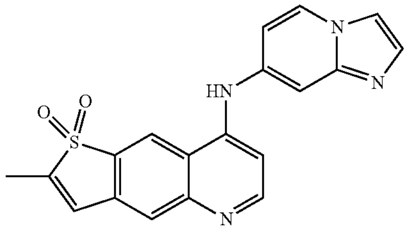 [SMILES: CC1=Cc2cc3nccc(Nc4ccn5ccnc5c4)c3cc2S1(=O)=O] | AB, BA | $^1$H NMR (400 MHz, DMSO-$d_6$) δ 9.58 (s, 1H), 8.94 (s, 1H), 8.66 (d, J = 5.6 Hz, 1H), 8.59 (d, J = 7.2 Hz, 1H), 7.97 (s, 1H), 7.94 (s, 1H), 7.56 (s, 1H), 7.47 (s, 2H), 7.30 (s, 1H), 7.07 (d, J = 7.6 Hz, 1H), 2.22 (s, 3H). LCMS (ESEAPCI) m/z: 362.8 $[M + H]^+$. |
| A68 | 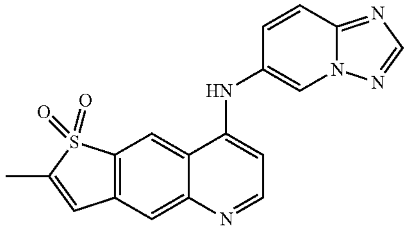 [SMILES: CC1=Cc2cc3nccc(Nc4ccc5ncnn5c4)c3cc2S1(=O)=O] | AB, BA | $^1$H NMR (400 MHz, DMSO-$d_6$) δ 11.35 (s, 1H), 9.40 (s, 1H), 9.31 (s, 1H), 8.66 (s, 1H), 8.61 (d, J = 6.8 Hz, 1H), 8.17 (s, 1H), 8.08 (d, J = 9.2 Hz, 1H), 7.90-7.75 (m, 1H), 7.65 (s, 1H), 7.02 (d, J = 6.8 Hz, 1H), 2.27 (s, 3H). LCMS (ESI/APCI) m/z: 363.8 $[M + H]^+$. |
| A69 | 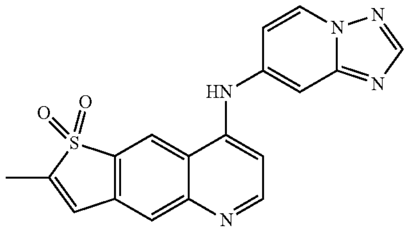 [SMILES: CC1=Cc2cc3nccc(Nc4ccn5ncnc5c4)c3cc2S1(=O)=O] | AB, BA | $^1$H NMR (400 MHz, DMSO-$d_6$) δ 9.70 (s, 1H), 8.95-8.97 (m, 2H), 8.74 (d, J = 5.2 Hz, 1H), 8.39 (s, 1H), 8.01 (s, 1H), 7.58 (s, 1H), 7.52-7.45 (m, 2H), 7.26-7.20 (m, 1H), 2.22 (s, 3H). LCMS (ESI/APCI) m/z: 363.7 $[M + H]^+$. |
| A70 | 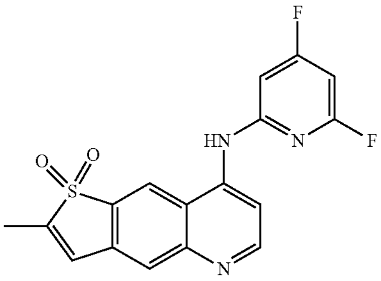 [SMILES: CC1=Cc2cc3nccc(Nc4cc(F)cc(F)n4)c3cc2S1(=O)=O] | AB, BA | $^1$H NMR (400 MHz, DMSO-$d_6$) δ 10.02 (s, 1H), 9.01 (s, 1H), 8.85 (d, J = 5.2 Hz, 1H), 8.31 (d, J = 5.6 Hz, 1H), 8.02 (s, 1H), 7.47 (s, 1H), 7.06 (d, J = 10.0 Hz, 1H), 6.82 (d, J = 92 Hz, 1H), 2.22 (s, 3H). LC-MS (m/z): 359.7 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A71 | 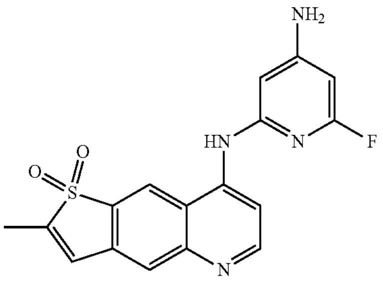 [SMILES: CC1=Cc2cc3nccc(Nc4cc(N)cc(F)n4)c3cc2S1(=O)=O] | AB, BA, BI | $^1$H NMR (400 MHz, DMSO-$d_6$) δ 9.50 (s, 1H), 9.06 (s, 1H), 8.69 (s, 1H), 8.21 (s, 1H), 7.94 (s, 1H), 7.45 (s, 1H), 6.51 (s, 2H), 6.35 (s, 1H), 5.82 (s, 1H), 2.21 (s, 3H). LC-MS (m/z): 356.7 $[M + H]^+$. |
| A72 | 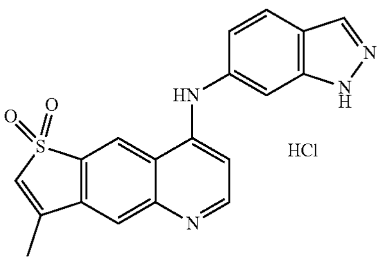 [SMILES: CC1=CS(=O)(=O)c2cc3c(Nc4ccc5cn[nH]c5c4)ccnc3cc21 ; Cl] | AA, BB | $^1$H NMR (400 MHz, DMSO-$d_6$) δ 13.00 (s, 1H), 9.47 (s, 1H), 8.96 (s, 1H), 8.57 (d, J = 5.2 Hz, 1H), 8.06 (s, 1H), 8.02 (s, 1H), 7.81 (d, J = 8.4 Hz, 1H), 7.48 (s, 1H), 7.31 (s, 1H), 7.17 (d, J = 8.4 Hz, 1H), 7.09(d, J = 5.2 Hz, 1H), 2.40 (s, 3H). LC-MS (m/z): 363.7 $[M + H]^+$. |
| A73 | 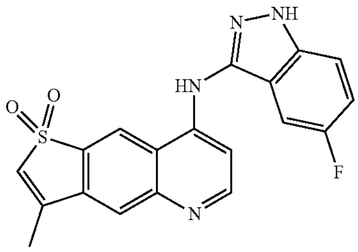 [SMILES: CC1=CS(=O)(=O)c2cc3c(Nc4n[nH]c5ccc(F)cc45)ccnc3cc21] | AA, BB | $^1$H NMR (400 MHz, DMSO-$d_6$) δ 12.91 (s, 1H), 9.60 (s, 1H), 9.22 (s, 1H), 8.66 (d, J = 5.2 Hz, 1H), 8.05 (s, 1H), 7.75 (d, J = 8.8 Hz, 1H), 7.70 (d, J = 5.2 Hz, 1H), 7.57 (dd, J = 8.8, 4.0 Hz, 1H), 7.36-7.28 (m, 2H), 2.41 (s, 3H). LC-MS (m/z): 380.7 $[M + H]^+$. |
| A74 | 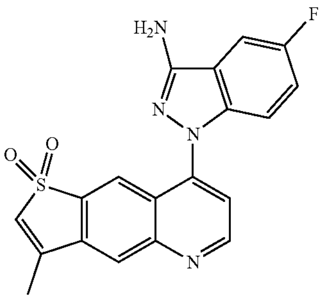 [SMILES: CC1=CS(=O)(=O)c2cc3c(-n4nc(N)c5cc(F)ccc54)ccnc3cc21] | AA, BB | $^1$H NMR (400 MHz, DMSO-$d_6$) δ 9.05-9.00 (m, 2H), 8.24 (s, 1H), 7.79-7.72 (m, 3H), 7.42-7.36 (m, 2H), 6.42 (s, 2H), 2.43 (s, 3H). LCMS (ESEAPCI) m/z: 380.7 $[M + H]^+$. |
| A75 | 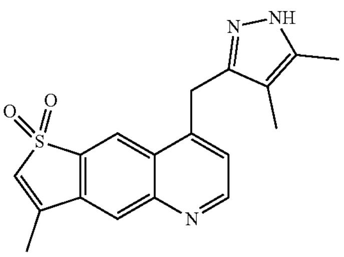 [SMILES: CC1=CS(=O)(=O)c2cc3c(Cc4n[nH]c(C)c4C)ccnc3cc21] | AA, BB | $^1$H NMR (400 MHz, DMSO-$d_6$) δ 12.72 ( br s, 1H), 10.87 (s, 1H), 9.34 (s, 1H), 8.62 (d, J = 7.2 Hz, 1H), 8.14 (s, 1H), 7.59 (s, 1H), 7.01 (d, J = 6.8 Hz, 1H), 2.40 (s, 3H), 2.24 (s, 3H), 1.89 (s, 3H). LC-MS (m/z): 340.8 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A76 | 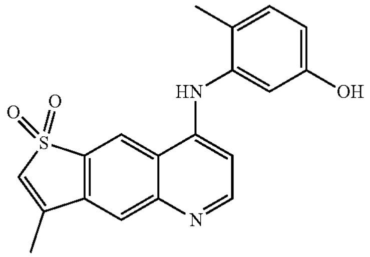 [SMILES: CC1=CS(=O)(=O)c2cc3c(Nc4cc(O)ccc4C)ccnc3cc21] | AA, BB | $^1$H NMR (400 MHz, DMSO-$d_6$) δ 9.46 (s, 1H), 9.08 (s, 1H), 8.97 (s, 1H), 8.46 (d, J = 5.6 Hz, 1H), 7.98 (s, 1H), 7.30 (s, 1H), 7.17 (d, J = 8.0 Hz, 1H), 6.72-6.65 (m, 2H), 6.25 (d, J = 52 Hz, 1H), 2.39 (s, 3H), 2.04 (s, 3H). LC-MS (m/z): 352.8 [M + H]$^+$. |
| A77 | 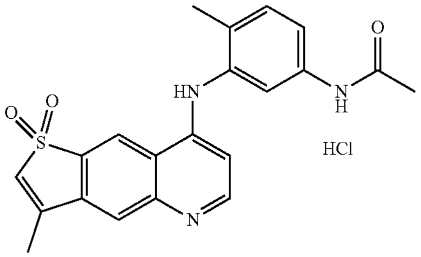 [SMILES: CC(=O)Nc1ccc(C)c(Nc2ccnc3cc4c(cc23)S(=O)(=O)C=C4C)c1 ; Cl] HCl | AA, BB | $^1$H NMR (400 MHz, DMSO-$d_6$) δ 14.69 (s, 1H), 11.02 (s, 1H), 10.23 (s, 1H), 9.29 (s, 1H), 8.54 (d, J = 6.8 Hz, 1H), 8.11 (s, 1H), 7.79 (s, 1H), 7.58 (s, 1H), 7.48 (d, J = 8.0 Hz, 1H), 7.40 (d, J = 8.4 Hz, 1H), 6.38 (d, J = 6.8 Hz, 1H), 2.40 (s, 3H), 2.15 (s, 3H), 2.05 (s, 3H). LCMS (ESI/APCI) m/z: 393.8 [M + H]$^+$. |
| A78 | 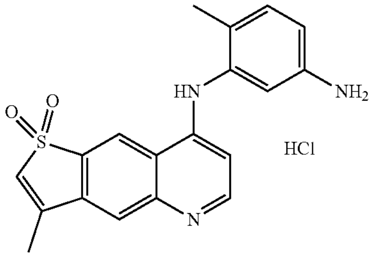 [SMILES: CC1=CS(=O)(=O)c2cc3c(Nc4cc(N)ccc4C)ccnc3cc21 ; Cl] HCl | AA, BB, BG | $^1$H NMR (400 MHz, DMSO-$d_6$) δ 11.03 (s, 1H), 9.29 (s, 1H), 8.56 (d, J = 7.2 Hz, 1H), 8.11 (s, 1H), 7.59 (s, 1H), 7.37 (s, 1H), 7.17-6.88 (m, 2H), 6.39 (d, J = 6.8 Hz, 1H), 2.40 (s, 3H), 2.13 (s, 3H). LCMS (ESI/APCI) m/z: 351.8 [M + H]$^+$. |
| A79 | 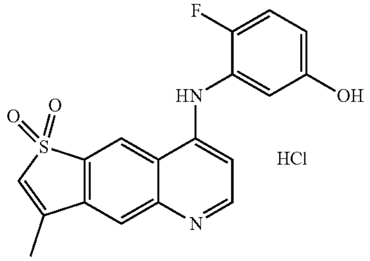 [SMILES: CC1=CS(=O)(=O)c2cc3c(Nc4cc(O)ccc4F)ccnc3cc21 ; Cl] HCl | AA, BB | $^1$H NMR (400 MHz, DMSO-$d_6$) δ 14.88 (br s, 1H), 10.92 (s, 1H), 9.96 (s, 1H), 9.25 (s, 1H), 8.64 (d, J = 6.8 Hz, 1H), 8.12 (s, 1H), 7.58 (s, 1H), 7.35-7.28 (m, 1H), 6.97-6.85 (m, 2H), 6.70 (d, J = 4.8 Hz, 1H), 2.40 (s, 3H). LC-MS (m/z): 356.8 [M + H]$^+$. |
| A80 | 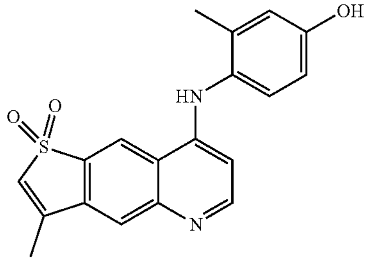 [SMILES: CC1=CS(=O)(=O)c2cc3c(Nc4ccc(O)cc4C)ccnc3cc21] | AA, BB | $^1$H NMR (400 MHz, DMSO-$d_6$) δ 14.53 (br s, 1H), 10.76 (s, 1H), 9.81 (s, 1H), 9.24 (s, 1H), 8.49 (d, J = 6.8 Hz, 1H), 8.07 (s, 1H), 7.57 (s, 1H), 7.16 (d, J = 8.4 Hz, 1H), 6.85 (s, 1H), 6.79 (d, J = 8.4 Hz, 1H), 6.35 (d, J = 6.8 Hz, 1H), 2.40 (s, 3H), 2.13 (s, 3H). LC-MS (m/z): 352.8 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| A81 | 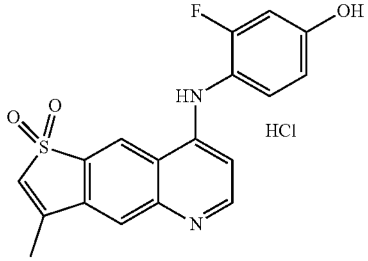 [SMILES: CC1=CS(=O)(=O)c2cc3c(Nc4ccc(O)cc4F)ccnc3cc21 ; Cl] | AA, BB | $^1$H NMR (400 MHz, DMSO-$d_6$) δ 14.95 (br s, 1H), 10.87 (s, 1H), 10.47 (s, 1H), 9.27 (s, 1H), 8.58 (s, 1H), 8.15 (s, 1H), 7.58 (s, 1H), 7.37 (s, 1H), 6.95-6.75 (m, 2H), 6.59 (s, 1H), 2.40 (s, 3H). |
| A82 | 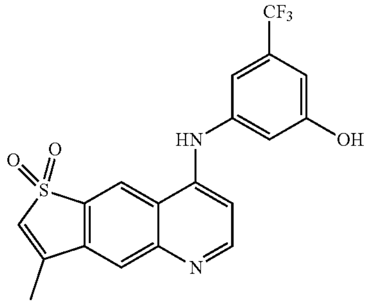 [SMILES: CC1=CS(=O)(=O)c2cc3c(Nc4cc(O)cc(C(F)(F)F)c4)ccnc3cc21] | AA, BB | $^1$H NMR (400 MHz, DMSO-$d_6$) δ 14.78 (br s, 1H), 10.59 (s, 1H), 10.51 (br s, 1H), 9.11 (s, 1H), 8.65 (d, J = 6.4 Hz, 1H), 8.09 (s, 1H), 7.50 (s, 1H), 7.22 (s, 1H), 7.16 (s, 1H), 7.12 (d, J = 6.4 Hz, 1H), 7.02 (s, 1H), 2.40 (s, 3H). LC-MS (m/z): 406.7 $[M + H]^+$ |
| A83 | 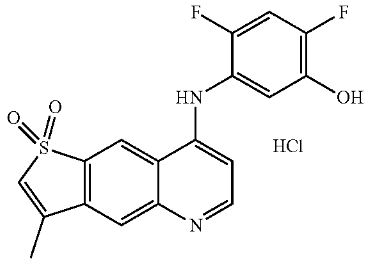 [SMILES: CC1=CS(=O)(=O)c2cc3c(Nc4cc(O)c(F)cc4F)ccnc3cc21 ; Cl] | AA, BB | $^1$H NMR (400 MHz, DMSO-$d_6$) δ 14.95 (br s, 1H), 10.94 (s, 1H), 10.48 (s, 1H), 9.25 (s, 1H), 8.64 (d, J = 6.8 Hz, 1H), 8.13 (s, 1H), 7.66-7.50 (m, 2H), 7.16 (s, 1H), 6.70 (d, J = 5.6 Hz, 1H), 2.40 (s, 3H). LC-MS (m/z): 374.7 $[M + H]^+$. |
| A84 | 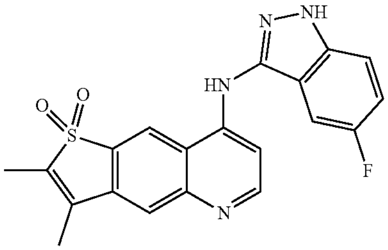 [SMILES: CC1=C(C)S(=O)(=O)c2cc3c(Nc4n[nH]c5ccc(F)cc45)ccnc3cc21] | AF, BB | $^1$H NMR (400 MHz, DMSO-$d_6$) δ 12.90 (s, 1H), 9.58 (s, 1H), 9.26 (s, 1H), 8.65 (d, J = 4.0 Hz, 1H), 8.00 (s, 1H), 7.77 (d, J = 8.8 Hz, 1H), 7.70 (d, J = 4.8 Hz, 1H), 7.60-7.53 (m, 1H), 7.36-7.28 (m, 1H), 2.32 (s, 3H), 2.16 (s, 3H). LC-MS (m/z): 394.7 $[M + H]^+$ |
| A85 | 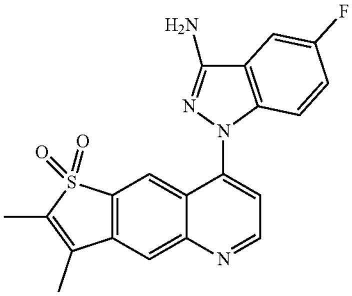 [SMILES: CC1=C(C)S(=O)(=O)c2cc3c(-n4nc(N)c5cc(F)ccc54)ccnc3cc21] | AF, BB | $^1$H NMR (400 MHz, DMSO-$d_6$) δ 9.06 (s, 1H), 9.02 (d, J = 4.4 Hz, 1H), 8.19 (s, 1H), 7.80-7.73 (m, 3H), 7.55-7.35 (m, 1H), 6.42 (s, 2H), 2.34 (s, 3H), 2.15 (s, 3H). LC-MS (m/z): 394.8 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A86 | 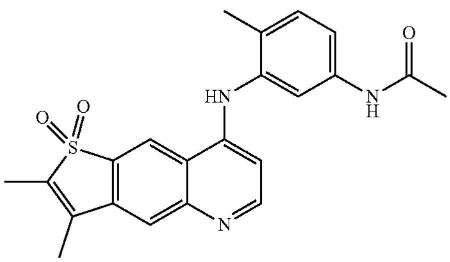 [SMILES: CC(=O)Nc1ccc(C)c(Nc2ccnc3cc4c(cc23)S(=O)(=O)C(C)=C4C)c1] | AF, BB | $^1$H NMR (400 MHz, DMSO-$d_6$) δ 10.00 (s, 1H), 9.17 (s, 1H), 9.03 (s, 1H), 8.45 (d, J = 5.2 Hz, 1H), 7.94 (s, 1H), 7.65 (s, 1H), 7.41 (d, J = 8.0 Hz, 1H), 7.30 (d, J = 8.4 Hz, 1H), 6.24 (d, J = 5.6 Hz, 1H), 2.30 (s, 3H), 2.18-2.10 (m, 6H), 2.03 (s, 3H). LC-MS (m/z): 407.8 $[M + H]^+$. |
| A87 | 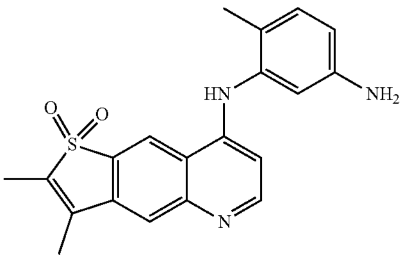 [SMILES: CC1=C(C)S(=O)(=O)c2cc3c(Nc4cc(N)ccc4C)ccnc3cc21] | AF, BB, BG | $^1$H NMR (400 MHz, DMSO-$d_6$) δ 9.10-9.00 (m, 2H), 8.43 (d, J = 5.6 Hz, 1H), 7.92 (s, 1H), 7.02 (d, J = 8.0 Hz, 1H), 6.55-6.45 (m, 2H), 6.24 (d, J = 5.2 Hz, 1H), 5.32 (br s, 2H), 2.29 (s, 3H), 2.14 (s, 3H), 1.99 (s, 3H). LC-MS (m/z): 365.8 $[M + H]^+$. |
| A88 | 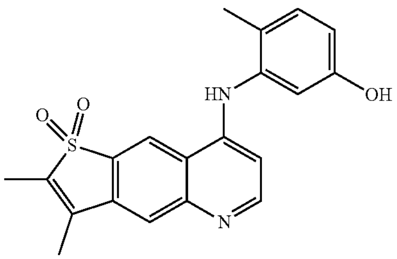 [SMILES: CC1=C(C)S(=O)(=O)c2cc3c(Nc4cc(O)ccc4C)ccnc3cc21] | AF, BB, BG | $^1$H NMR (400 MHz, DMSO-$d_6$) δ 14.63 (br s, 1H), 10.91 (s, 1H), 9.76 (s, 1H), 9.30 (s, 1H), 8.51 (d, J = 7.2 Hz, 1H), 8.06 (s, 1H), 7.27 (d, J = 8.0 Hz, 1H), 6.84 (d, J = 8.8 Hz, 1H), 6.77 (s, 1H), 6.38 (d, J = 6.8 Hz, 1H), 2.31 (s, 3H), 2.21 (s, 3H), 2.09 (s, 3H). LC-MS (m/z): 366.8 $[M + H]^+$. |
| A89 | 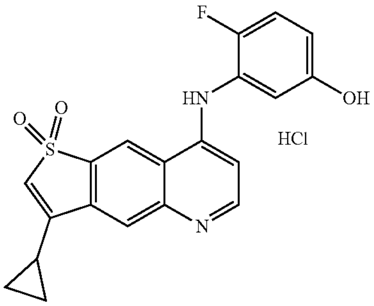 [SMILES: O=S1(=O)C=C(C2CC2)c2cc3nccc(Nc4cc(O)ccc4F)c3cc21 ; Cl] | AF, BB | $^1$H NMR (400 MHz, DMSO-$d_6$) δ 14.91 (br s, 1H), 10.90 (s, 1H), 9.96 (s, 1H), 9.24 (s, 1H), 8.64 (s, 1H), 8.34 (s, 1H), 7.40 (s, 1H), 7.36-7.27 (m, 1H), 6.96-6.83 (m, 2H), 6.69 (s, 1H), 2.13 (s, 1H), 1.06-1.03 (m, 2H), 0.97 (s, 2H).LCMS (ESI/APCI) m/z: 382.7 $[M + H]^+$. |
| A90 | 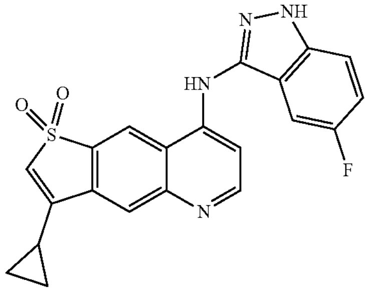 [SMILES: O=S1(=O)C=C(C2CC2)c2cc3nccc(Nc4n[nH]c5ccc(F)cc45)c3cc21] | AF, BB | $^1$H NMR (400 MHz, DMSO-$d_6$) δ 13.05 (s, 1H), 9.99 (s, 1H), 9.27 (s, 1H), 8.68 (d, J = 5.6 Hz, 1H), 8.28 (s, 1H), 7.75 (d, J = 8.8 Hz, 1H), 7.68 (d, J = 5.6 Hz, 1H), 7.63-7.57 (m, 1H), 7.38-7.30 (m, 1H), 7.20 (s, 1H), 2.28 (s, 1H), 1.21-1.56 (m, 2H), 0.99-0.93 (m, 2H). LCMS (ESI/APCI) m/z: 406.7 $[M + H]^+$. |

TABLE 1-continued

Selected compounds synthesized (A1-A118, B1-B29)

| No. | Structure | Method | $^1$H NMR & LC-MS |
|---|---|---|---|
| A91 | 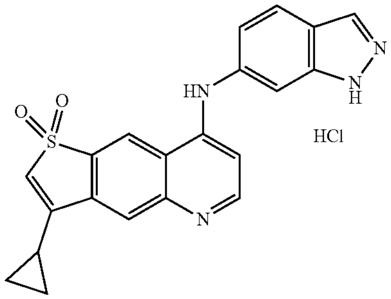 [SMILES: O=S1(=O)C=C(C2CC2)c2cc3nccc(Nc4ccc5cn[nH]c5c4)c3cc21 ; Cl] | AF, BB | $^1$H NMR (400 MHz, DMSO-$d_6$) δ 14.68 (br s, 1H), 13.33 (s, 1H), 11.19 (s, 1H), 9.28 (s, 1H), 8.58 (s, 1H), 8.33 (s, 1H), 8.19 (s, 1H), 7.97 (d, J = 8.0 Hz, 1H), 7.67 (s, 1H), 7.40 (s, 1H), 7.22 (d, J = 8.0 Hz, 1H), 6.99 (s, 1H), 2.15 (s, 1H), 1.24-1.20 (m, 2H), 0.98 (s, 2H). LCMS (ESEAPCI) m/z: 388.7 $[M + H]^+$. |
| A92 | 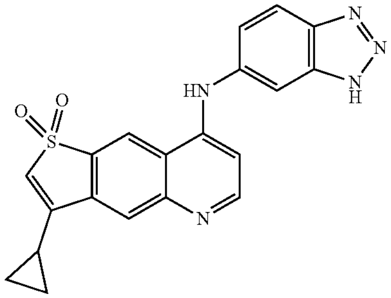 [SMILES: O=S1(=O)C=C(C2CC2)c2cc3nccc(Nc4ccc5nn[nH]c5c4)c3cc21] | AF, BB | $^1$H NMR (400 MHz, DMSO-$d_6$) δ 9.57 (s, 1H), 8.96 (s, 1H), 8.59 (d, J = 5.6 Hz, 1H), 8.25 (s, 1H), 8.01 (d, J = 8.4 Hz, 1H), 7.78 (s, 1H), 7.47 (d, J = 8.4 Hz, 1H), 7.13-7.08 (m, 2H), 2.35-2.27 (m, 1H), 1.21-1.17 (m, 2H), 0.97-0.91 (m, 2H). LCMS (ESI/APCI) m/z: 389.8 $[M + H]^+$. |
| A93 | 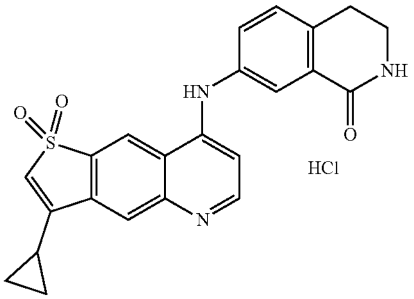 [SMILES: O=C1NCCc2ccc(Nc3ccnc4cc5c(cc34)S(=O)(=O)C=C5C3CC3)cc21 ; Cl] | AF, BB | $^1$H NMR (400 MHz, DMSO-$d_6$) δ 14.61 (br s, 1H), 11.01 (s, 1H), 9.22 (s, 1H), 8.60 (d, J = 6.8 Hz, 1H), 8.31 (s, 1H), 8.12 (s, 1H), 7.92 (s, 1H), 7.60 (d, J = 6.0 Hz, 1H), 7.55 (d, J = 8.0 Hz, 1H), 7.39 (s, 1H), 6.97 (d, J = 7.2 Hz, 1H), 3.46-3.42 (m, 2H), 2.99 (t, J = 6.2 Hz, 2H), 2.19-2.11 (m, 1H), 1.28-1.19 (m, 2H), 1.01-0.93 (m, 2H). LCMS (ESI/APCI) m/z: 417.7 $[M + H]^+$. |
| A94 | 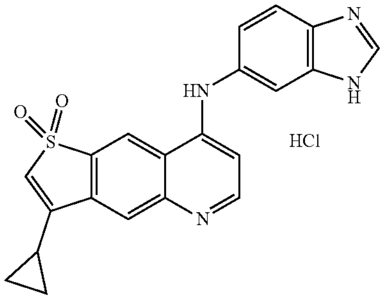 [SMILES: O=S1(=O)C=C(C2CC2)c2cc3nccc(Nc4ccc5nc[nH]c5c4)c3cc21 ; Cl] | AF, BB | $^1$H NMR (400 MHz, DMSO-$d_6$) δ 12.68 (br s, 1H), 9.50 (s, 1H), 9.00 (s, 1H), 8.49 (d, J = 52 Hz, 1H), 8.26 (s, 1H), 8.21 (s, 1H), 7.68 (d, J = 8.0 Hz, 1H), 7.57 (s, 1H), 7.23 (d, J = 8.4 Hz, 1H), 7.10 (s, 1H), 6.85 (s, 1H), 2.28 (s, 1H), 1.21-1.16 (m, 2H), 0.97-0.90 (m, 2H). LCMS (ESEAPCI) m/z: found 388.7 $[M + H]^+$. |
| A95 | 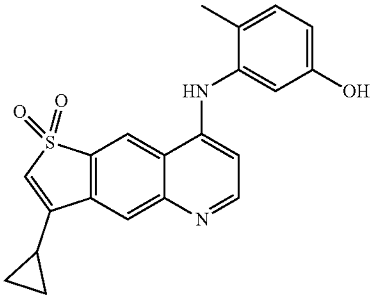 [SMILES: Cc1ccc(O)cc1Nc1ccnc2cc3c(cc12)S(=O)(=O)C=C3C1CC1] | AF, BB | $^1$H NMR (400 MHz, DMSO-$d_6$) δ 9.51 (s, 1H), 9.08 (s, 1H), 8.97 (s, 1H), 8.46 (d, J = 5.2 Hz, 1H), 8.20 (s, 1H), 7.16 (d, J = 8.4 Hz, 1H), 7.09 (s, 1H), 6.73-6.67 (m, 2H), 6.24 (d, J = 5.2 Hz, 1H), 2.32-2.25 (s, 1H), 1.20-1.15 (m, 2H), 0.96-0.90 (m, 2H). LCMS (ESEAPCI) m/z: 378.7 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A96 | 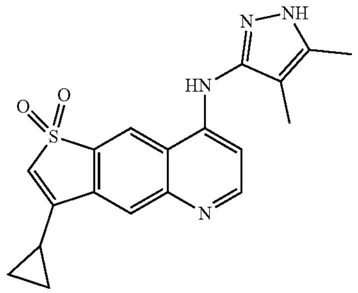 [SMILES: Cc1[nH]nc(Nc2ccnc3cc4c(cc23)S(=O)(=O)C=C4C2CC2)c1C] | AF, BB | $^1$H NMR (400 MHz, DMSO-$d_6$) δ 12.29 (s, 1H), 9.07-9.00 (m, 2H), 8.51 (d, J = 5.2 Hz, 1H), 8.20 (s, 1H), 7.08 (s, 1H), 6.78 (d, J = 5.2 Hz, 1H), 2.32-2.25 (m, 1H), 2.20 (s, 3H), 1.83 (s, 3H), 1.20-1.15 (m, 2H), 0.95-0.90 (m, 2H). LCMS (ESEAPCI) m/z: 366.8 [M + H]$^+$. |
| A97 | 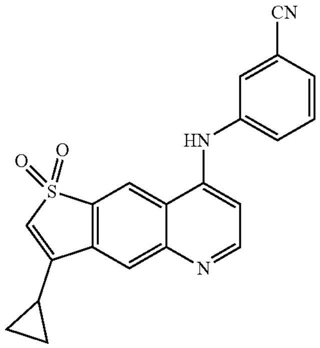 [SMILES: N#Cc1cccc(Nc2ccnc3cc4c(cc23)S(=O)(=O)C=C4C2CC2)c1] | AF, BB | $^1$H NMR (400 MHz, DMSO-$d_6$) δ 9.52 (s, 1H), 8.89 (s, 1H), 8.69-8.61 (m, 1H), 8.28 (s, 1H), 7.82 (s, 1H), 7.77-7.63 (m, 1H), 7.66-7.56 (m, 2H), 7.24-7.18 (m, 1H), 7.13 (s, 1H), 2.32 (s, 1H), 1.22-1.15 (m, 2H), 0.94(s, 2H). LCMS (ESEAPCI) m/z: found 373.7 [M + H]$^+$. |
| A98 | 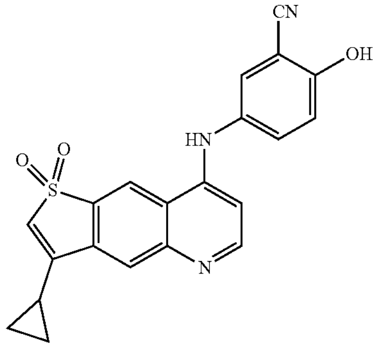 [SMILES: N#Cc1cc(Nc2ccnc3cc4c(cc23)S(=O)(=O)C=C4C2CC2)ccc1O] | AF, BB | $^1$H NMR (400 MHz, DMSO-$d_6$) 8.89-8.83 (m, 2H), 8.40 (d, J = 5.2 Hz, 1H), 8.12 (s, 1H), 7.05 (s, 1H), 6.94 (s, 1H), 6.87 (d, J = 9.2 Hz, 1H), 6.48 (d, J = 5.6 Hz, 1H), 6.22 (d, J = 8.8 Hz, 1H), 2.30-2.22 (m, 1H), 1.20-1.12 (m, 2H), 0.95-0.88 (m, 2H). LCMS (ESEAPCI) m/z: 389.7 [M + H]$^+$. |
| A99 | 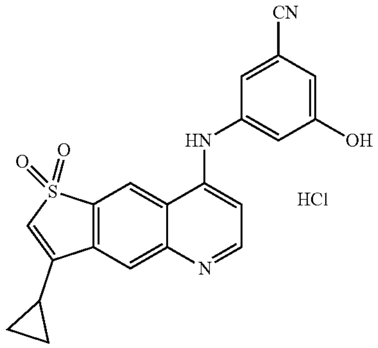 [SMILES: N#Cc1cc(O)cc(Nc2ccnc3cc4c(cc23)S(=O)(=O)C=C4C2CC2)c1 ; Cl] | AF, BB | $^1$H NMR (400 MHz, DMSO-$d_6$) δ 14.78 (br s, 1H), 10.87 (s, 1H), 10.77 (s, 1H), 9.18 (s, 1H), 8.65 (s, 1H), 8.33 (s, 1H), 7.43-7.36 (m, 2H), 7.24-7.17 (m, 2H), 7.13 (d, J = 6.4 Hz, 1H), 2.16 (s, 1H), 1.23-1.19 (m, 2H), 1.00-0.94 (m, 2H). LCMS (ESI/APCI) m/z: 389.6 [M + H]$^+$. |

TABLE 1-continued

Selected compounds synthesized (A1-A118, B1-B29)

| No. | Structure | Method | $^1$H NMR & LC-MS |
|---|---|---|---|
| A100 | 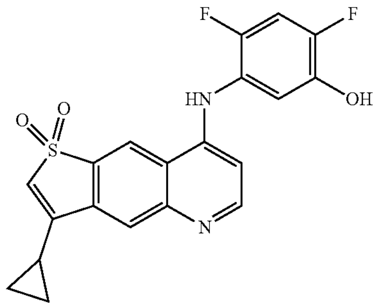 [SMILES: O=S1(=O)C=C(C2CC2)c2cc3nccc(Nc4cc(O)c(F)cc4F)c3cc21] | AF, BB | $^1$H NMR (400 MHz, DMSO-d$_6$) δ 10.15 (s, 1H), 9.19 (s, 1H), 8.91 (s, 1H), 8.55 (d, J = 5.2 Hz, 1H), 8.24 (s, 1H), 7.41 (t, J = 10.8 Hz, 1H), 7.11 (s, 1H), 7.03 (t, J = 8.4 Hz, 1H), 6.49 (s, 1H), 2.34-2.25 (s, 1H), 1.20-1.15 (m, 2H), 0.96-0.89 (m, 2H). LCMS (ESI/APCI) m/z: 400.7 [M + H]$^+$. |
| A101 | 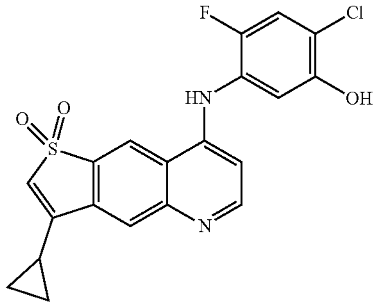 | AF, BB | $^1$H NMR (400 MHz, DMSO-d$_6$) δ 10.44 (s, 1H), 9.26 (s, 1H), 8.90 (s, 1H), 8.58 (d, J = 5.2 Hz, 1H), 8.25 (s, 1H), 7.51 (d, J = 10.0 Hz, 1H), 7.11 (s, 1H), 7.03 (d, J = 7.2 Hz, 1H), 6.59 (s, 1H), 2.35-2.26 (m, 1H), 2.12-1.15 (m, 2H), 0.96-0.91 (m, 2H). LCMS (ESEAPCI) m/z: 416.7 [M + H]$^+$. |
| A102 | 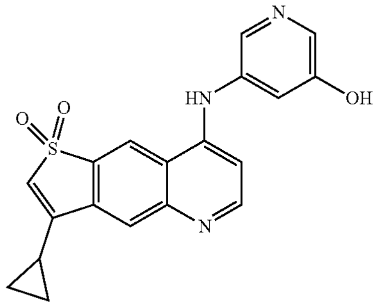 [SMILES: O=S1(=O)C=C(C2CC2)c2cc3nccc(Nc4cncc(O)c4)c3cc21] | AF, BB, BF, BG | $^1$H NMR (400 MHz, DMSO-d$_6$) δ 11.10 (s, 1H), 10.81 (s, 1H), 9.24 (s, 1H), 8.66 (d, J = 6.8 Hz, 1H), 8.37 (s, 1H), 8.28-8.20 (m, 2H), 7.44 (s, 1H), 7.40 (s, 1H), 7.08 (d, J = 6.8 Hz, 1H), 2.17-2.11 (m, 1H), 1.25-1.20 (m, 2H), 1.00-0.94 (m, 2H). LCMS (ESEAPCI) m/z: 365.7 [M + H]$^+$. |
| A103 | 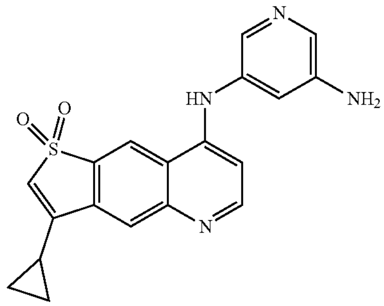 [SMILES: Nc1cncc(Nc2ccnc3cc4c(cc23)S(=O)(=O)C=C4C2CC2)c1] | AF, BB, BF, BG | $^1$H NMR (400 MHz, DMSO-d$_6$) δ 11.16 (br s, 1H), 9.27 (s, 1H), 8.73 (d, J = 6.8 Hz, 1H), 8.45 (s, 1H), 8.08 (s, 1H), 7.99 (s, 1H), 7.48 (s, 1H), 7.38 (s, 1H), 7.22 (d, J = 6.4 Hz, 1H), 2.19-2.08 (m, 1H), 1.24-1.20 (m, 2H), 1.00-0.90 (m, 2H). LCMS (ESEAPCI) m/z: 364.7 [M + H]$^+$. |
| A104 | 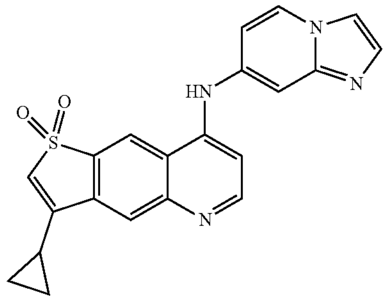 [SMILES: O=S1(=O)C=C(C2CC2)c2cc3nccc(Nc4ccn5ccnc5c4)c3cc21] | AF, BB | $^1$H NMR (400 MHz, DMSO-d$_6$) δ 9.94 (s, 1H), 8.85 (s, 1H), 8.81 (s, 1H), 8.67 (d, J = 7.2 Hz, 1H), 8.34 (s, 1H), 8.04 (s, 1H),7.76 (s, 1H), 7.49 (s, 2H), 7.28 (d, J = 7.2 Hz, 1H), 7.14 (s, 1H), 2.32 (s, 1H), 1.25-1.20 (m, 2H), 0.97-0.92 (m, 2H). 388.8 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| A105 | 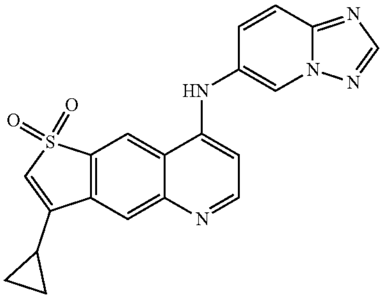 [SMILES: O=S1(=O)C=C(C2CC2)c2cc3nccc(Nc4ccc5ncnn5c4)c3cc21] | AF, BB | $^1$H NMR (400 MHz, DMSO-$d_6$) δ 9.50 (s, 1H), 9.06 (s, 1H), 8.93 (s, 1H), 8.58 (d, J = 4.8 Hz, 1H), 8.54 (s, 1H), 8.26 (s, 1H), 7.95 (d, J = 9.2 Hz, 1H), 7.73 (d, J = 92 Hz, 1H), 7.11 (s, 1H), 6.92 (d, J = 52 Hz, 1H), 2.35-2.27 (m, 1H), 1.22-1.17 (m, 2H), 0.98-0.91 (m, 2H). LCMS (ESEAPCI) m/z: 389.8 $[M + H]^+$. |
| A106 | 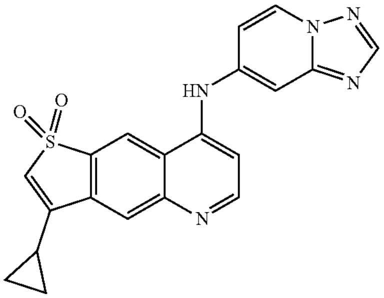 [SMILES: O=S1(=O)C=C(C2CC2)c2cc3nccc(Nc4ccn5ncnc5c4)c3cc21] | AF, BB | $^1$H NMR (400 MHz, DMSO-$d_6$) δ 9.61 (s, 1H), 9.07 (s, 1H), 8.96 (s, 1H), 8.58 (s, 1H), 8.54 (s, 1H), 8.27 (s, 1H), 7.96 (d, J = 9.2 Hz, 1H), 7.78 (d, J = 9.2 Hz, 1H), 7.13 (s, 1H), 6.95-6.89 (m, 1H), 2.33-2.27 (m, 1H), 1.22-1.17 (m, 2H), 0.96-0.92 (m, 2H). LCMS (ESI/APCI) m/z: 389.7 $[M + H]^+$. |
| A107 | 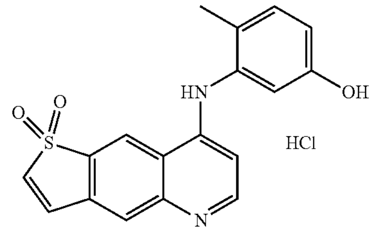 [SMILES: Cc1ccc(O)cc1Nc1ccnc2cc3c(cc12)S(=O)(=O)C=C3 ; Cl] HCl | AA, BB | $^1$H NMR (400 MHz, DMSO-$d_6$) δ 9.46 (s, 1H), 9.07 (s, 1H), 9.00 (s, 1H), 8.45 (d, J = 5.6 Hz, 1H), 7.96 (s, 1H), 7.82 (d, J = 6.4 Hz, 1H), 7.54 (d, J = 6.8 Hz, 1H), 7.17 (d, J = 8.0 Hz, 1H), 6.75-6.53 (m, 2H), 6.24 (d, J = 5.6 Hz, 1H), 2.04 (s, 3H). LCMS (ESI/APCI) m/z: 338.8 $[M + H]^+$. |
| A108 | 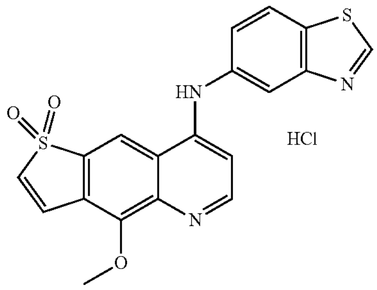 [SMILES: COc1c2c(cc3c(Nc4ccc5scnc5c4)ccnc13)S(=O)(=O)C=C2 ; Cl] HCl | AF, BB | $^1$H NMR (400 MHz, DMSO-$d_6$) δ 14.07 (s, 1H), 11.42 (s, 1H), 9.55 (s, 1H), 9.08 (s, 1H), 8.43-8.39 (m, 2H), 8.21 (d, J = 8.0 Hz, 2H), 7.79 (d, J = 7.2 Hz, 1H), 7.61 (d, J = 8.8 Hz, 1H), 7.01 (d, J = 7.2 Hz, 1H), 4.31 (s, 3H). LCMS (ESEAPCI) m/z: 395.7 $[M + H]^+$. |
| A109 | 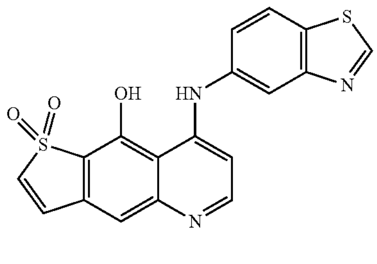 [SMILES: O=S1(=O)C=Cc2cc3nccc(Nc4ccc5scnc5c4)c3c(O)c21] | AI, BB | $^1$H NMR (400 MHz, DMSO-$d_6$) δ 15.35 (s, 1H), 13.14 (s, 1H), 9.50 (s, 1H), 8.31 (d, J = 8.4 Hz, 1H), 8.13 (s, 1H), 8.03 (s, 1H), 7.52 (d, J = 8.8 Hz, 1H), 7.34 (d, J = 6.8 Hz, 1H), 7.18 (d, J = 6.8 Hz, 1H), 6.63 (d, J = 6.4 Hz, 1H), 6.48 (s, 1H). LCMS (ESEAPCI) m/z: 381.6 $[M + H]^+$. |

TABLE 1-continued

Selected compounds synthesized (A1-A118, B1-B29)

| No. | Structure | Method | $^1$H NMR & LC-MS |
|---|---|---|---|
| A110 | 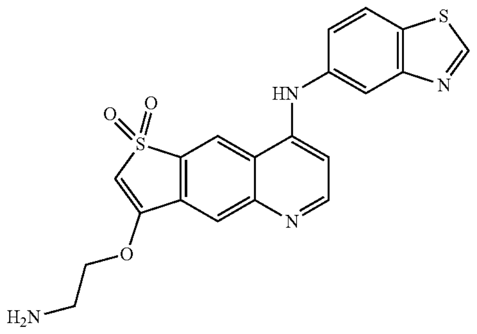 [SMILES: NCCOC1=CS(=O)(=O)c2cc3c(Nc4ccc5scnc5c4)ccnc3cc21] | AA, AH, BB, BD | $^1$H NMR (400 MHz, DMSO-d6) δ 9.57 (s, 1H), 9.45 (s, 1H), 9.02 (s, 1H), 8.59 (d, J = 4.8 Hz, 1H), 8.23 (d, J = 8.0 Hz, 2H), 8.06 (s, 1H), 7.55 (d, J = 8.0 Hz, 1H), 7.10 (s, 1H), 6.94 (s, 1H), 4.32-4.23 (m, 2H), 3.19-3.10 (m, 2H). LCMS (ESEAPCI) m/z: 424.6 $[M + H]^+$. |
| A111 | 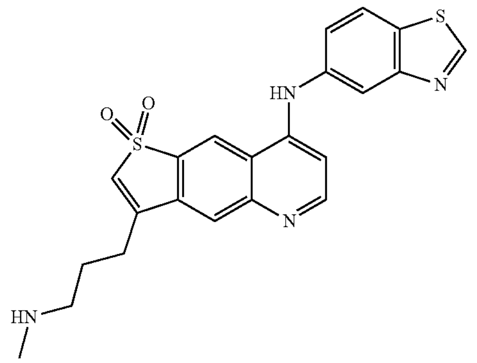 [SMILES: CNCCCC1=CS(=O)(=O)c2cc3c(Nc4ccc5scnc5c4)ccnc3cc21] | AA, AH, BB, BD | $^1$H NMR (400 MHz, DMSO-d6) δ 9.59 (s, 1H), 9.44 (s, 1H), 9.03 (s, 1H), 8.58 (d, J = 5.2 Hz, 1H), 8.23 (d, J = 8.4 Hz, 1H), 8.06 (s, 2H), 7.55 (d, J = 8.0 Hz, 1H), 7.10 (d, J = 52 Hz, 1H), 6.94 (s, 1H), 4.48-4.36 (m, 2H), 3.49 (s, 3H), 2.58-2.53 (m, 2H). LCMS (ESEAPCI) m/z: found 438.7 $[M + H]^+$. |
| A112 | 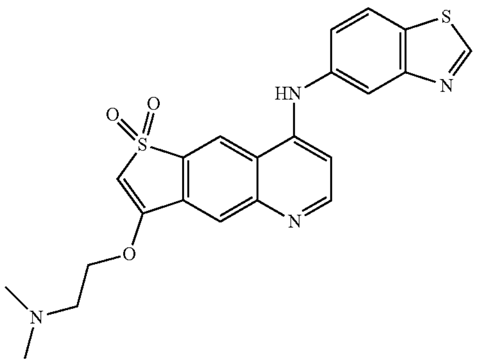 [SMILES: CN(C)CCOC1=CS(=O)(=O)c2cc3c(Nc4ccc5scnc5c4)ccnc3cc21] | AA, AH, BB, BD | $^1$H NMR (400 MHz, DMSO-d6) δ 9.40 (s, 1H), 8.99 (s, 1H), 8.55 (d, J = 4.8 Hz, 1H), 8.21 (d, J = 8.8 Hz, 1H), 8.07 (s, 1H), 8.04 (s, 1H), 7.54 (d, J = 8.4 Hz, 1H), 7.10 (d, J = 4.4 Hz, 1H), 6.86 (s, 1H), 4.46-4.31 (m, 2H), 3.20-3.06 (m, 2H), 2.53 (s, 3H), 2.07 (s, 3H). LCMS (ESEAPCI) m/z: 452.7 $[M + H]^+$. |
| A113 | 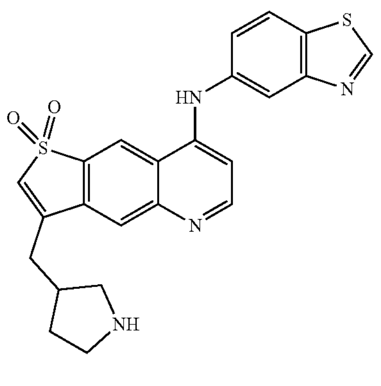 [SMILES: O=S1(=O)C=C(CC2CCNC2)c2cc3nccc(Nc4ccc5scnc5c4)c3cc21] | AA, AH, BB, BD | $^1$H NMR (400 MHz, DMSO-d6) δ 9.58 (s, 1H), 9.45 (s, 1H), 9.03 (s, 1H), 8.58 (d, J = 4.0 Hz, 1H), 8.23 (d, J = 8.4 Hz, 1H), 8.09 (s, 1H), 8.06 (s, 1H), 7.55 (d, J = 8.4 Hz, 1H), 7.10 (d, J = 4.4 Hz, 1H), 7.03 (s, 1H), 5.25 -5.17 (m, 1H), 3.66-3.49 (m, 4H), 2.36-2.21 (m, 2H). LCMS (ESI/APCI) m/z: 450.7 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| A114 | 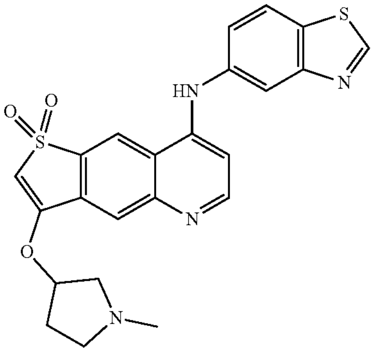 [SMILES: CN1CCC(OC2=CS(=O)(=O)c3cc4c(Nc5ccc6scnc6c5)ccnc4cc32)C1] | AA, AH, BB, BD | $^1$H NMR (400 MHz, DMSO-d6) δ 9.68 (s, 1H), 9.45 (s, 1H), 9.06 (s, 1H), 8.58 (d, J = 4.0 Hz, 1H), 8.22 (d, J = 8.0 Hz, 1H), 8.07 (s, 1H), 8.03 (s, 1H), 7.56 (d, J = 8.0 Hz, 1H), 7.10 (d, J = 3.6 Hz, 1H), 6.97 (s, 1H), 5.18-5.04 (m, 1H), 3.53-3.40 (m, 4H), 2.60 (s, 3H), 2.26-1.86 (m, 2H). LCMS (ESI/APCI) m/z: 464.7 $[M + H]^+$. |
| A115 | 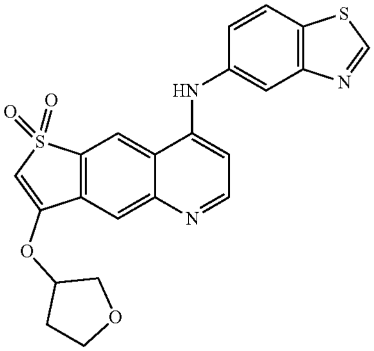 [SMILES: O=S1(=O)C=C(OC2CCOC2)c2cc3nccc(Nc4ccc5scnc5c4)c3cc21] | AA, AH, BB, BD | $^1$H NMR (400 MHz, DMSO-d6) δ 9.64 (s, 1H), 9.45 (s, 1H), 9.05 (s, 1H), 8.58 (d, J = 4.8 Hz, 1H), 8.22 (d, J = 8.4 Hz, 1H), 8.07 (s, 1H), 7.93 (s, 1H), 7.56 (d, J = 8.4 Hz, 1H), 7.10 (d, J =4.8 Hz, 1H), 6.96 (s, 1H), 5.22-5.08 (m, 1H), 4.07-3.89 (m, 3H), 3.85-3.73 (m, 1H), 2.41-2.27 (m, 1H), 2.22-2.09 (m, 1H). LCMS (ESEAPCI) m/z: 451.6 $[M + H]^+$. |
| A116 | 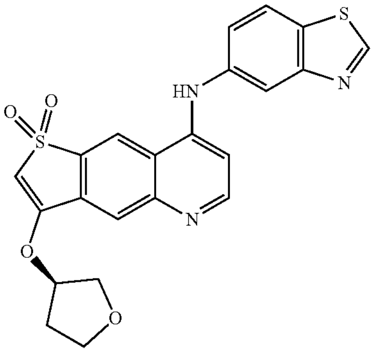 [SMILES: O=S1(=O)C=C(O[C@@H]2CCOC2)c2cc3nccc(Nc4ccc5scnc5c4)c3cc21] | AA, AH, BB, BD | $^1$H NMR (400 MHz, DMSO-d6) δ 9.56 (s, 1H), 9.45 (s, 1H), 9.02 (s, 1H), 8.58 (d, J = 52 Hz, 1H), 8.23 (d, J = 8.4 Hz, 1H), 8.07 (s, 1H), 7.94 (s, 1H), 7.55 (d, J = 8.4 Hz, 1H), 7.10 (d, J = 5.6 Hz, 1H), 6.96 (s, 1H), 5.19-5.07 (m, 1H), 4.07-3.88 (m, 3H), 3.88-3.73 (m, 1H), 2.41-2.28 (m, 1H), 2.21-2.11 (m, 1H). LCMS (ESEAPCI) m/z: 451.7 $[M + H]^+$. |
| A117 | 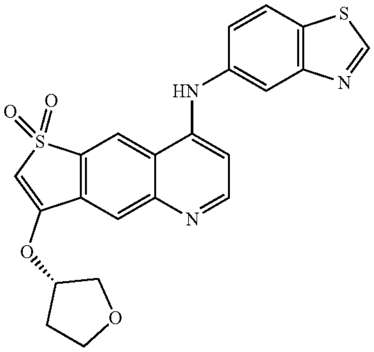 [SMILES: O=S1(=O)C=C(O[C@H]2CCOC2)c2cc3nccc(Nc4ccc5scnc5c4)c3cc21] | AA, AH, BB, BD | $^1$H NMR (400 MHz, DMSO-d6) δ 9.55 (s, 1H), 9.45 (s, 1H), 9.01 (s, 1H), 8.58 (d, J = 52 Hz, 1H), 8.23 (d, J = 8.8 Hz, 1H), 8.06 (s, 1H), 7.94 (s, 1H), 7.55 (d, J = 8.0 Hz, 1H), 7.10 (d, J = 52 Hz, 1H), 6.95 (s, 1H), 5.22-5.07 (m, 1H), 4.07-3.88 (m, 3H), 3.85-3.72 (m, 1H), 2.42-2.28 (m, 1H), 2.24-2.10 (m, 1H). LCMS (ESEAPCI) m/z: 451.6 $[M + H]^+$. |

TABLE 1-continued

Selected compounds synthesized (A1-A118, B1-B29)

| No. | Structure | Method | $^1$H NMR & LC-MS |
| --- | --- | --- | --- |
| A118 | 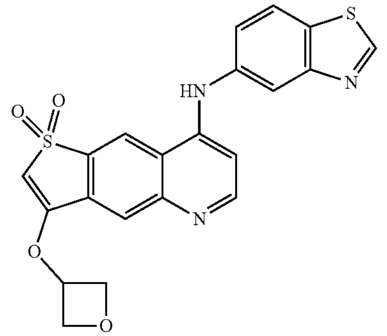 [SMILES: O=S1(=O)C=C(OC2COC2)c2cc3nccc(Nc4ccc5scnc5c4)c3cc21] | AA, AH, BB, BD | $^1$H NMR (400 MHz, DMSO-d6) δ 9.56 (s, 1H), 9.45 (s, 1H), 9.03 (s, 1H), 8.60 (d, J = 52 Hz, 1H), 8.23 (d, J = 8.4 Hz, 1H), 8.06 (s, 1H), 8.04 (s, 1H), 7.55 (d, J = 9.6 Hz, 1H), 7.12 (d, J = 52 Hz, 1H), 6.79 (s, 1H), 5.49-5.39 (m, 1H), 5.03-4.92 (m, 2H), 4.80-4.68 (m, 2H). LCMS (ESEAPCI) m/z: 437.7 $[M + H]^+$. |
| B1 | 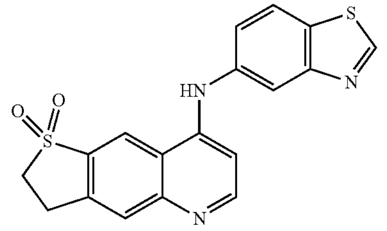 [SMILES: O=S1(=O)CCc2cc3nccc(Nc4ccc5scnc5c4)c3cc21] | AA, BB, BJ | $^1$H NMR (400 MHz, DMSO-$d_6$) δ 9.57 (s, 1H), 9.45 (s, 1H), 9.00 (s, 1H), 8.57 (d, J = 5.6 Hz, 1H), 8.22 (d, J = 8.8 Hz, 1H), 8.06 (s, 1H), 7.98 (s, 1H), 7.56 (d, J = 8.4 Hz, 1H), 7.05 (d, J = 5.2 Hz, 1H), 3.72 (t, J = 6.8 Hz, 2H), 3.54 (t, J = 6.4 Hz, 2H). |
| B2 | 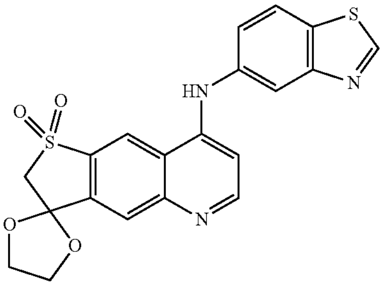 [SMILES: O=S1(=O)CC2(OCCO2)c2cc3nccc(Nc4ccc5scnc5c4)c3cc21] | AA, AH, BB, BC | $^1$H NMR (400 MHz, DMSO-$d_6$) δ 15.02 (s, 1H),11.48 (s, 1H), 9.55 (s, 1H), 9.46 (s, 1H), 8.63 (d, J = 6.8 Hz, 1H), 8.43-8.36 (m, 2H), 8.25 (s, 1H), 7.63 (d, J = 8.4 Hz, 1H), 6.99 (d, J = 6.4 Hz, 1H), 4.33 (s, 2H), 4.25 (s, 2H), 4.14 (s, 2H). LCMS (ESI/APCI) m/z: 425.6 $[M + H]^+$. |
| B3 | 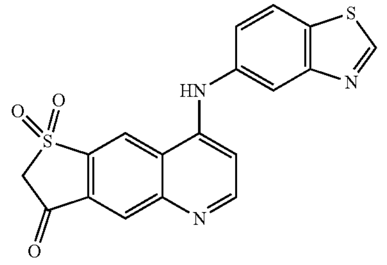 [SMILES: O=C1CS(=O)(=O)c2cc3c(Nc4ccc5scnc5c4)ccnc3cc21] | AA, AH, BB, BK | $^1$H NMR (400 MHz, DMSO-$d_6$) δ 14.97 (s, 1H), 11.64 (s, 0.67H), 11.30 (s, 0.33H), 9.70 (s, 0.67H), 9.55 (s, 1H), 9.30 (s, 0.33H), 8.72 (d, J = 6.4 Hz, 0.67H), 8.63 (s, 0.67H), 8.59 (d, J = 4.8 Hz, 0.33H), 8.43 (d, J = 8.8 Hz, 1H), 8.28 (s, 0.67H), 8.24 (s, 0.33H), 8.20 (s, 0.33H), 7.70-7.58 (m, 1H), 7.07 (d, J = 6.4 Hz, 0.67H), 7.00 (d, J = 4.4 Hz, 0.33H), 6.58 (s, 0.33H), 4.85 (s, 1.33H). LCMS (ESI/APCI) m/z: 381.7 $[M + H]^+$. |
| B4 | 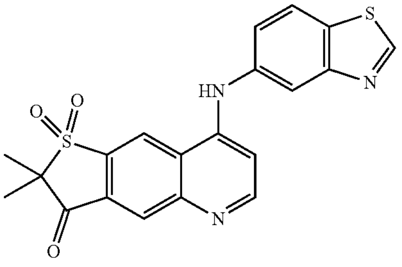 [SMILES: CC1(C)C(=O)c2cc3nccc(Nc4ccc5scnc5c4)c3cc2S1(=O)=O] | AM, BL | $^1$H NMR (400 MHz, $CDCl_3$) δ 9.10 (s, 1H), 8.87 (s, 1H), 8.75 (d, J = 52 Hz, 1H), 8.69 (s, 1H), 8.14 (s, 1H), 8.06 (d, J = 8.4 Hz, 1H), 7.50-7.39 (m, 2H), 7.14 (d, J = 52 Hz, 1H), 1.66 (s, 6H). LC-MS (m/z): 409.7 $[M + H]^+$. |

TABLE 1-continued

Selected compounds synthesized (A1-A118, B1-B29)

| No. | Structure | Method | $^1$H NMR & LC-MS |
| --- | --- | --- | --- |
| B5 | 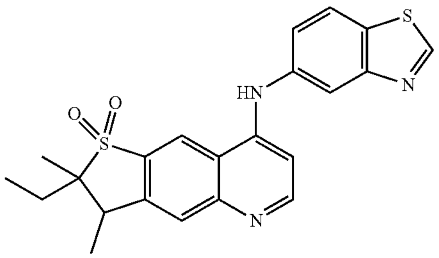 [SMILES: CCC1(C)C(C)c2cc3nccc(Nc4ccc5scnc5c4)c3cc2S1(=O)=O] | AM, BL | $^1$H NMR (400 MHz, DMSO-$d_6$) δ 11.46 (s, 1H), 9.72 (s, 1H), 9.55 (s, 1H), 8.72 (s, 1H), 8.66 (s, 1H), 8.41 (d, J = 8.4 Hz, 1H), 8.25 (s, 1H), 7.64 (d, J = 8.0Hz, 1H), 7.09 (d, J = 6.4 Hz, 1H), 2.20-1.99 (m, 2H), 1.59 (s, 3H), 1.02 (t, J = 7.6 Hz, 3H). LCMS (ESEAPCI) m/z: 423.7 $[M + H]^+$. |
| B6 | 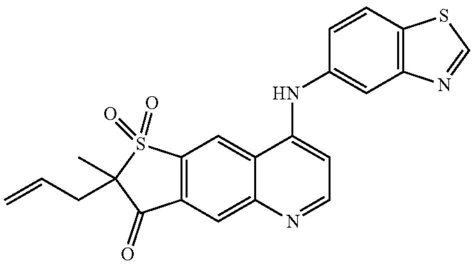 [SMILES: C=CCC1(C)C(=O)c2cc3nccc(Nc4ccc5scnc5c4)c3cc2S1(=O)=O] | AM, BL | $^1$H NMR (400 MHz, DMSO-$d_6$) δ 11.57 (s, 1H), 9.76 (s, 1H), 9.56 (s, 1H), 8.72 (d, J = 6.8 Hz, 1H), 8.67 (s, 1H), 8.42 (d, J = 8.8 Hz, 1H), 8.26 (s, 1H), 7.65 (d, J = 8.4 Hz, 1H), 7.09 (d, J = 7.2 Hz, 1H), 5.86-5.75 (m, 1H), 5.31-5.18 (m, 2H), 2.88-2.76 (m, 2H), 1.58 (s, 3H). LCMS (ESI/APCI) m/z: 435.7 $[M + H]^+$. |
| B7 | 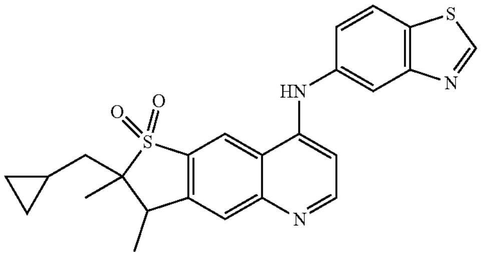 [SMILES: CC1c2cc3nccc(Nc4ccc5scnc5c4)c3cc2S(=O)(=O)C1(C)CC1CC1] | AM, BL | $^1$H NMR (400 MHz, DMSO-$d_6$) δ 11.33 (s, 1H), 9.69 (s, 1H), 9.55 (s, 1H), 8.72 (d, J = 6.8 Hz, 1H), 8.59 (s, 1H), 8.41 (d, J = 8.4 Hz, 1H), 8.24 (s, 1H), 7.63 (d, J = 8.4 Hz, 1H), 7.11 (d, J = 6.4 Hz, 1H), 2.15-2.07 (m, 1H), 1.96-1.85 (m, 1H), 1.66 (s, 3H), 0.82-0.70 (m, 1H), 0.50-0.40 (m, 1H), 0.34-0.26 (m, 1H), 0.20-0.05 (m, 2H). LCMS (ESEAPCI) m/z: 449.6 $[M + H]^+$. |
| B8 | 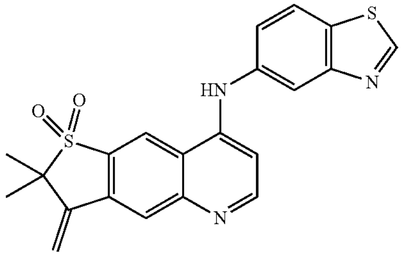 [SMILES: C=C1c2cc3nccc(Nc4ccc5scnc5c4)c3cc2S(=O)(=O)C1(C)C] | AM, BL, BM | $^1$H NMR (400 MHz, DMSO-$d_6$) δ9.63 (s, 1H), 9.45 (s, 1H), 9.13 (s, 1H), 8.60 (d, J = 5.2 Hz, 1H), 8.42 (s, 1H), 8.23 (d, J = 8.4 Hz, 1H), 8.07 (s, 1H), 7.56 (d, J = 7.6 Hz, 1H), 7.06 (d, J = 5.2 Hz, 1H), 6.36 (s, 1H), 5.68 (s, 1H), 1.55 (s, 6H). (ESI/APCI) m/z: 407.7 $[M + H]^+$. |
| B9 | 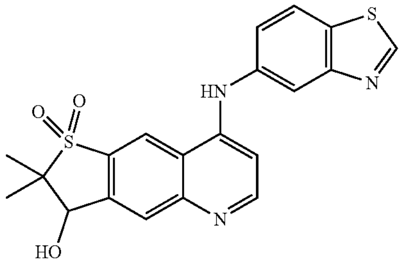 [SMILES: CC1(C)C(O)c2cc3nccc(Nc4ccc5scnc5c4)c3cc2S1(=O)=O] | AM, BL, BN | $^1$H NMR (400 MHz, DMSO-$d_6$) δ9.61 (s, 1H), 9.45 (s, 1H), 9.04 (s, 1H), 8.58 (s, 1H), 8.23 (d, J = 8.4 Hz, 1H), 8.07 (s, 1H), 8.02 (s, 1H), 7.56 (d, J = 8.0 Hz, 1H), 7.07 (s, 1H), 6.66 (d, J = 6.0 Hz, 1H), 5.12 (d, J = 5.6 Hz, 1H), L50 (s, 3H), 1.17 (s, 3H). LCMS (ESI/APCI) m/z: 411.7 $[M + H]^+$. |

TABLE 1-continued

| Selected compounds synthesized (A1-A118, B1-B29) | | | |
|---|---|---|---|
| No. | Structure | Method | $^{1}$H NMR & LC-MS |
| B10 | 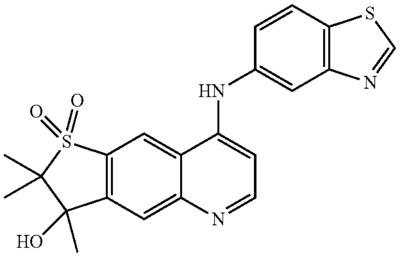 [SMILES: CC1(O)c2cc3nccc(Nc4ccc5scnc5c4)c3cc2S(=O)(=O)C1(C)C] | AM, BL, BM | $^{1}$H NMR (400 MHz, DMSO-$d_6$) δ9.57 (s, 1H), 9.45 (s, 1H), 9.02 (s, 1H), 8.59 (d, J = 5.6 Hz, 1H), 8.22 (d, J = 8.8 Hz, 1H), 8.09 (s, 1H), 8.06 (s, 1H), 7.55 (d, J = 8.4 Hz, 1H), 7.06 (d, J = 5.2 Hz, 1H), 6.19 (s, 1H), 1.60(s, 3H), 1.40(s, 3H), 1.27 (s, 3H). LCMS (ESEAPCI) m/z: 425.7 [M + H]$^+$. |
| B11 | 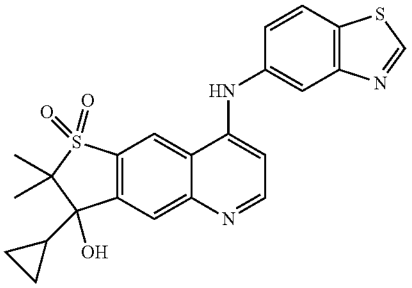 [SMILES: CC1(C)C(O)(C2CC2)c2cc3nccc(Nc4ccc5scnc5c4)c3cc2S1(=O)=O] | AM, BL, BM | $^{1}$H NMR (400 MHz, DMSO-$d_6$) δ9.73 (s, 1H), 9.46 (s, 1H), 9.08 (s, 1H), 8.58 (s, 1H), 8.23 (d, J = 8.8 Hz, 1H), 8.07 (s, 2H), 7.56 (d, J = 8.0 Hz, 1H), 7.06 (s, 1H), 5.79 (s, 1H), 1.50 (s, 3H), 1.28 (s, 3H), 0.83 (s, 1H), 0.65 (s, 1H), 0.55 (s, 1H), 0.41 (s, 1H), 0.31 (s, 1H). LCMS (ESEAPCI) m/z: 451.7 [M + H]$^+$. |
| B12 | 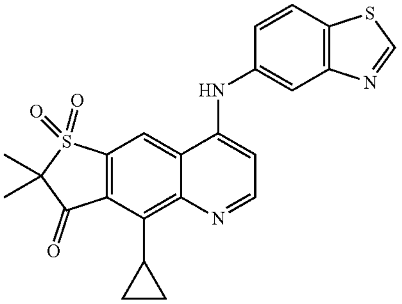 [SMILES: CC1(C)C(=O)c2c(cc3c(Nc4ccc5scnc5c4)ccnc3c2C2CC2)S1(=O)=O] | AM, BL, BO | $^{1}$H NMR (400 MHz, $CDCl_3$) δ 9.10 (s, 1H), 8.69-8.59 (m, 2H), 8.10 (s, 1H), 8.03 (d, J = 8.4 Hz, 1H), 7.42 (d, J = 8.4 Hz, 1H), 7.11 (d, J = 5.2 Hz, 1H), 3.38-3.23 (m, 1H), 1.78-1.70 (m, 2H), 1.63 (s, 6H), 1.34-1.28 (m, 2H). LCMS (ESEAPCI) m/z: 449.6 [M + H]$^+$. |
| B13 | 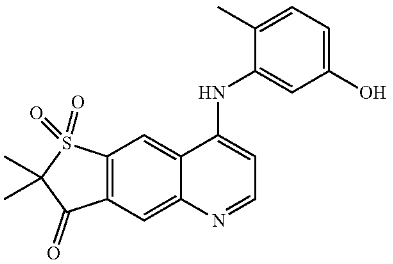 [SMILES: Cc1ccc(O)cc1Nc1ccnc2cc3c(cc12)S(=O)(=O)C(C)(C)C3=O] | AM, BL | $^{1}$H NMR (400 MHz, DMSO-$d_6$) δ9.49 (s, 1H), 9.41 (s, 1H), 9.33 (s, 1H), 8.60 (d, J = 4.4 Hz, 1H), 8.40 (s, 1H), 7.19 (d, J = 8.0 Hz, 1H), 6.77-6.66 (m, 2H), 6.34 (d, J = 4.0 Hz, 1H), 2.05 (s, 3H), 1.57 (s, 6H). LCMS (ESEAPCI) m/z: 382.8 [M + H]$^+$. |
| B14 | 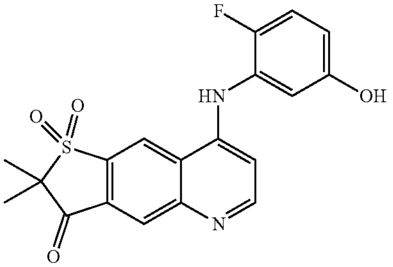 [SMILES: CC1(C)C(=O)c2cc3nccc(Nc4cc(O)ccc4F)c3cc2S1(=O)=O] | AM, BL | $^{1}$H NMR (400 MHz, DMSO-$d_6$) δ 11.13 (s, 1H), 9.98 (s, 1H), 9.67 (s, 1H), 8.79 (d, J = 6.4 Hz, 1H), 8.64 (s, 1H), 7.33 (t, J = 9.6 Hz, 1H), 7.00-6.85 (m, 2H), 6.78 (d, J = 4.0 Hz, 1H), 1.60 (s, 6H). LCMS (ESEAPCI) m/z: 386.7 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| B15 | 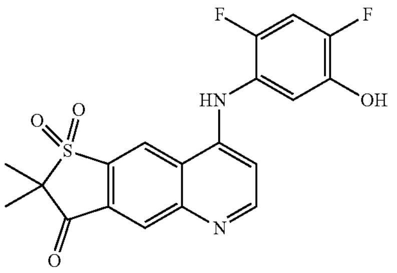 [SMILES: CC1(C)C(=O)c2cc3nccc(Nc4cc(O)c(F)cc4F)c3cc2S1(=O)=O] | AM, BL | $^1$H NMR (400 MHz, DMSO-$d_6$) δ 10.16 (s, 1H), 9.47 (s, 1H), 9.35 (s, 1H), 8.69 (s, 1H), 8.44 (s, 1H), 7.45 (t, J = 10.4 Hz, 1H), 7.03 (t, J = 8.0 Hz, 1H), 6.61 (s, 1H), 1.57 (s, 6H).LCMS (ESEAPCI) m/z: 404.7 $[M + H]^+$. |
| B16 | 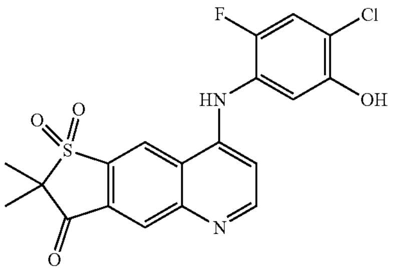 [SMILES: CC1(C)C(=O)c2cc3nccc(Nc4cc(O)c(Cl)cc4F)c3cc2S1(=O)=O] | AM, BL | $^1$H NMR (400 MHz, DMSO-$d_6$) δ 10.51 (s, 1H), 9.81 (s, 1H), 9.39 (s, 1H), 8.72 (s, 1H), 8.47 (s, 1H), 7.57 (d, J = 10.4 Hz, 1H), 7.06 (d, J = 6.4 Hz, 1H), 6.72 (s, 1H), 1.58 (s, 6H). LCMS (ESI/APCI) m/z: 420.7 $[M + H]^+$. |
| B17 | 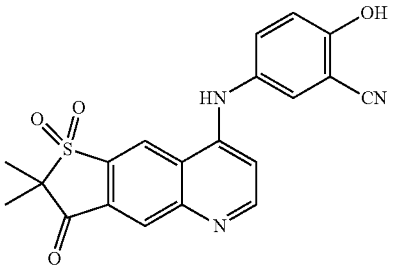 [SMILES: CC1(C)C(=O)c2cc3nccc(Nc4ccc(O)c(C#N)c4)c3cc2S1(=O)=O] | AM, BL | $^1$H NMR (400 MHz, DMSO-$d_6$) δ 11.62 (s, 1H), 11.06 (s, 1H), 9.59 (s, 1H), 8.71 (d, J = 6.4 Hz, 1H), 8.58 (s, 1H), 7.80 (s, 1H), 7.62 (d, J = 8.4 Hz, 1H), 7.24 (d, J = 8.8 Hz, 1H), 6.95 (d, J = 6.4 Hz, 1H), 1.59 (s, 6H). LCMS (ESI/APCI) m/z: 393.7 $[M + H]^+$. |
| B18 | 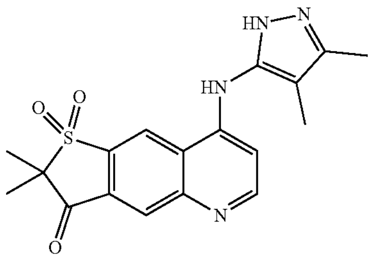 | AM, BL | $^1$H NMR (400 MHz, DMSO-$d_6$) δ 12.34 (s, 1H), 9.47 (s, 1H), 9.32 (s, 1H), 8.65 (d, J = 5.2 Hz, 1H), 8.40 (s, 1H), 6.92 (s, 1H), 2.21 (s, 3H), 1.84 (s, 3H), 1.57 (s, 6H). LCMS (ESEAPCI) m/z: 370.8 $[M + H]^+$. |
| B19 | 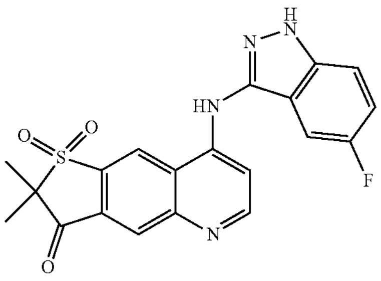 [SMILES: CC1(C)C(=O)c2cc3nccc(Nc4n[nH]c5ccc(F)cc45)c3cc2S1(=O)=O] | AM, BL | $^1$H NMR (400 MHz, DMSO-$d_6$) δ 12.99 (s, 1H), 9.86 (s, 1H), 9.65 (s, 1H), 8.81 (d, J = 5.2 Hz, 1H), 8.48 (s, 1H), 7.82 (d, J = 52 Hz, 1H), 7.77 (d, J = 8.8 Hz, 1H), 7.60 (dd, J = 4.0Hz, 8.8 Hz, 1H),7.34 (t, J = 8.4 Hz, 1H), 1.59 (s, 6H). LCMS (ESI/APCI) m/z: 410.7 $[M + H]^+$. |

TABLE 1-continued

| Selected compounds synthesized (A1-A118, B1-B29) | | | |
|---|---|---|---|
| No. | Structure | Method | $^1$H NMR & LC-MS |
| B20 | 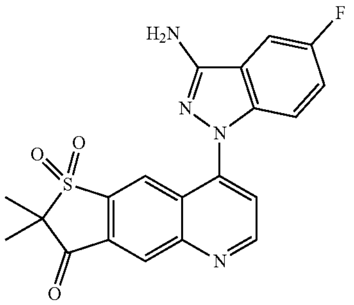 [SMILES: CC1(C)C(=O)c2cc3nccc(-n4nc(N)c5cc(F)ccc54)c3cc2S1(=O)=O] | AM, BL | $^1$H NMR (400 MHz, DMSO-$d_6$) δ 9.45 (s, 1H), 9.17 (d, J = 4.8 Hz, 1H), 8.67 (s, 1H), 7.95 (d, J = 4.8 Hz, 1H), 7.86-7.74 (m, 2H), 7.50-7.38 (m, 1H), 6.51 (s, 2H), 1.57 (s, 6H). LCMS (ESEAPCI) m/z: 410.7 [M + H]$^+$. |
| B21 | 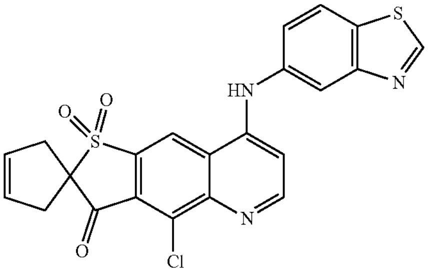 [SMILES: O=C1c2c(cc3c(Nc4ccc5scnc5c4)ccnc3c2Cl)S(=O)(=O)C12CC=CC2] | AN, BL | $^1$H NMR (400 MHz, DMSO-$d_6$) δ 9.91 (s, 1H), 9.47 (s, 1H), 9.38 (s, 1H), 8.75 (d, J = 5.6 Hz, 1H), 8.27 (d, J = 8.4 Hz, 1H), 8.10 (s, 1H), 7.57 (d, J = 8.4 Hz, 1H), 7.23 (d, J = 5.2 Hz, 1H), 5.80 (s, 2H), 3.28 (d, J = 17.6 Hz, 2H), 2.99 (d, J = 17.2 Hz, 2H). LCMS (ESEAPCI) m/z: 467.6 [M + H]$^+$. |
| B22 | 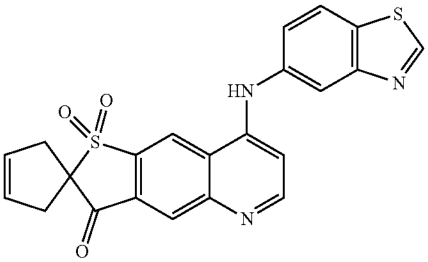 [SMILES: O=C1c2cc3nccc(Nc4ccc5scnc5c4)c3cc2S(=O)(=O)C12CC=CC2] | AN, BL | $^1$H NMR (400 MHz, $CDCl_3$) δ 9.11 (s, 1H), 8.87 (s, 1H), 8.75 (d, J = 5.2 Hz, 1H), 8.69 (s, 1H), 8.13 (s, 1H), 8.06 (d, J = 8.8 Hz, 1H), 7.45 (d, J = 8.4 Hz, 1H) , 7.40 (s, 1H), 7.13 (d, J = 5.6 Hz, 1H), 5.72 (s, 2H), 3.45 (d, J = 17.2 Hz, 2H), 3.03 (d, J = 17.2 Hz, 2H). LCMS (ESEAPCI) m/z: 433.7 [M + H]$^+$. |
| B23 | 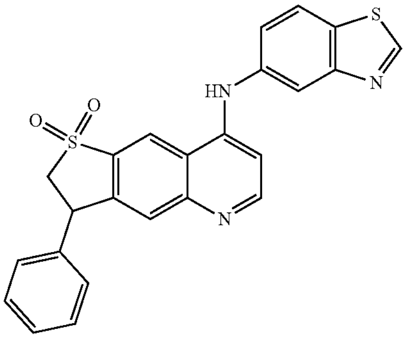 [SMILES: O=S1(=O)CC(c2ccccc2)c2cc3nccc(Nc4ccc5scnc5c4)c3cc21] | AA, AH, BB, BE, BJ | $^1$H NMR (400 MHz, DMSO-$d_6$) δ 9.64 (s, 1H), 9.45 (s, 1H), 9.09(s, 1H), 8.52 (s, 1H), 8.23 (d, J = 8.4 Hz, 1H), 8.07 (s, 1H), 7.59-7.53 (m, 1H), 7.65-7.39 (m, 5H), 7.39-7.33 (m, 1H), 7.06-7.01 (m, 1H), 5.17-5.11 (m, 1H), 4.30-4.15 (m, 1H), 3.94-3.74 (m, 1H). LCMS (ESEAPCI) m/z: 443.7 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| B24 | 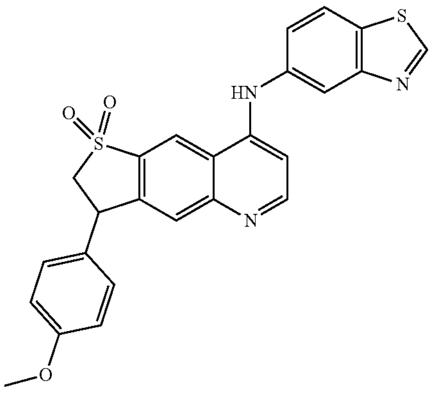 [SMILES: COc1ccc(C2CS(=O)(=O)c3cc4c(Nc5ccc6scnc6c5)ccnc4cc32)cc1] | AA, AH, BB, BE, BJ | $^1$H NMR (400 MHz, DMSO-$d_6$) δ 9.60 (s, 1H), 9.45 (s, 1H), 9.07 (s, 1H), 8.52 (d, J = 4.8 Hz, 1H), 8.23 (d, J = 8.8 Hz, 1H), 8.07 (s, 1H), 7.56 (d, J = 8.8 Hz, 1H), 7.45 (s, 1H), 7.37 (d, J = 8.0 Hz, 2H), 7.04 (d, J = 52 Hz, 1H), 6.98 (d, J = 8.0 Hz, 2H), 5.07 (t, J = 7.6 Hz, 1H), 4.19 (dd, J = 13.2, 7.6 Hz, 1H), 3.81-3.72 (s, 4H). LCMS (ESEAPCI) m/z: 473.6 [M + H]$^+$. |
| B25 | 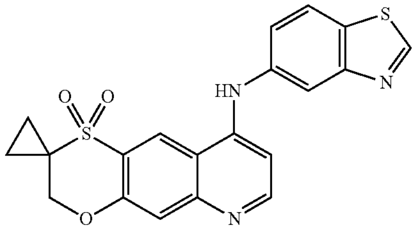 [SMILES: O=S1(=O)c2cc3c(Nc4ccc5scnc5c4)ccnc3cc2OCC12CC2] | AO, BL | $^1$H NMR (400 MHz, $CDCl_3$) δ 9.07 (s, 1H), 8.63-8.51 (m, 2H), 8.10 (s, 1H), 8.01 (d, J = 8.8 Hz, 1H), 7.60 (s, 1H), 7.42(d, J = 8.4 Hz, 1H), 7.08 (s, 1H), 6.91 (d, J = 52 Hz, 1H), 4.75 (s, 2H),1.76 (t, J = 6.8 Hz, 2H), 1.31 (t, J = 6.8 Hz, 2H). LCMS (ESEAPCI) m/z: 409.7 [M + H]$^+$. |
| B26 | 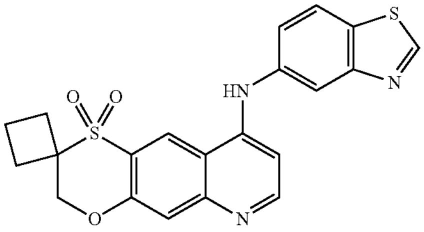 [SMILES: O=S1(=O)c2cc3c(Nc4ccc5scnc5c4)ccnc3cc2OCC12CCC2] | AO, BL | $^1$H NMR (400 MHz, $CDCl_3$) δ 9.07 (s, 1H), 8.68 (s, 1H), 8.53 (d, J = 4.4 Hz, 1H), 8.10 (s, 1H), 8.01 (d, J = 8.4 Hz, 1H), 7.57 (s, 1H), 7.43 (d, J = 8.4 Hz, 1H), 6.89 (d, J = 4.8 Hz, 1H), 4.85 (s, 2H), 2.90-2.75 (m, 2H), 2.30-2.10 (m, 4H). LCMS (ESEAPCI) m/z: 423.7 [M + H]$^+$. |
| B27 | 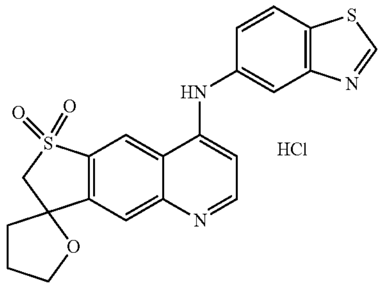 [SMILES: O=S1(=O)CC2(CCCO2)c2cc3nccc(Nc4ccc5scnc5c4)c3cc21 ; Cl] HCl | AP, BB | $^1$H NMR (400 MHz, DMSO-$d_6$) δ 14.67 (s, 1H), 11.41 (s, 1H), 9.55 (s, 1H), 9.36 (s, 1H), 8.61 (d, J = 6.4 Hz, 1H), 8.40 (d, J = 8.4 Hz, 1H), 8.25 (s, 2H), 7.62 (d, J = 8.0 Hz, 1H), 6.97 (d, J = 6.8 Hz, 1H), 4.21-4.03 (m, 3H), 3.79 (d, J = 13.2 Hz, 1H), 2.49-2.43 (m, 1H), 2.29-2.17 (m, 3H). LCMS (ESEAPCI) m/z: 423.7 [M + H]$^+$. |
| B28 | 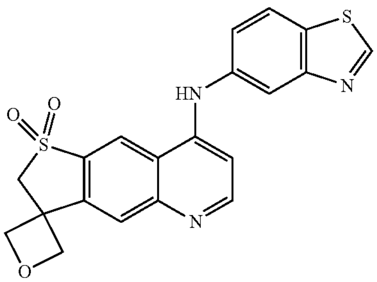 [SMILES: O=S1(=O)CC2(COC2)c2cc3nccc(Nc4ccc5scnc5c4)c3cc21] | BP | $^1$H NMR (400 MHz, DMSO-$d_6$) δ 9.59 (s, 1H), 9.45 (s, 1H), 8.99 (s, 1H), 8.63 (d, J = 5.6 Hz, 1H), 8.47 (s, 1H), 8.23 (d, J = 8.8 Hz, 1H), 8.07 (d, J = 1.6 Hz, 1H), 7.57 (dd, J = 8.8, 1.6 Hz, 1H), 7.09 (d, J = 5.6 Hz, 1H), 4.97 (d, J = 6.4 Hz, 2H), 4.94 (d, J = 6.4 Hz, 2H), 4.23 (s, 2H). LCMS (ESEAPCI) m/z: 409.7 [M + H]$^+$. |

TABLE 1-continued

| Selected compounds synthesized (A1-A118, B1-B29) | | | |
|---|---|---|---|
| No. | Structure | Method | $^1$H NMR & LC-MS |
| B29 | 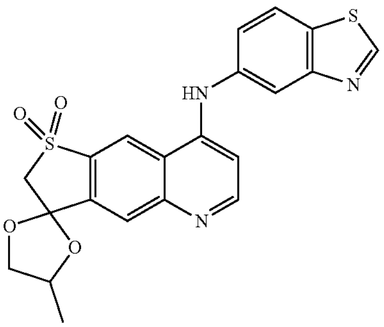 | AA, AH, BB, BC | $^1$H NMR (400 MHz, DMSO-$d_6$) δ 14.67 (s, 1H), 11.41 (s, 1H), 9.55 (s, 1H), 9.36 (s, 1H), 8.61 (d, J = 6.4 Hz, 1H), 8.40 (d, J = 8.4 Hz, 1H), 8.25 (s, 2H), 7.62 (d, J = 8.0 Hz, 1H), 6.97 (d, J = 6.8 Hz, 1H), 4.21-4.03 (m, 3H), 3.79 (d, J = 13.2 Hz, 1H), 2.49-2.43 (m, 1H), 2.29-2.17 (m, 3H). LCMS (ESEAPCI) m/z: 423.7 [M + H]$^+$. |

Biological Activities

The efficacies of some of the compounds disclosed herein were tested for their inhibition activities in necroptosis assays as follows:

Example 32: in Vitro HT-29 Cell Viability Assay

Human colon cancer HT-29 cells were used in a necroptosis assay. For this assay, HT-29 cells were added to 96-well plates. The compounds at different concentrations (0.3, 1.0, 3.0, 10.0, 20.0 μM) were then preprocessed for two hours. TNF-α (40 ng/mL), Smac mimetic (100 nM) and z-VAD (20 μM) were added, and the mixture was incubated for 40 h. Quantitative analysis of cell viability was conducted. DMSO pretreatment group was used as a negative control. Concentration for 50% of maximal effect was calculated according to the curve of the survival rate measured at different concentrations. FIG. 1 depicts the $EC_{50}$ curves of compound A16.

TABLE 2

Results of the compounds of the present invention tested by HT-29 cell viability assay

| NO. | HT-29(20 μM) Survival | HT29 $EC_{50}$ (μM) | NO. | HT-29(20 μM) Survival | HT-29 $EC_{50}$ (μM) |
|---|---|---|---|---|---|
| A1 | 4.5 | | A2 | | 1.02 |
| A3 | | 0.62 | A4 | | 0.98 |
| A5 | | 0.76 | A6 | | 0.54 |
| A7 | | 0.38 | A8 | | 0.53 |
| A9 | | 0.085 | A10 | | 1.38 |
| A11 | 34.5 | | A12 | | 1.03 |
| A13 | | 0.43 | A14 | | 0.28 |
| A15 | | 0.50 | A16 | | 1.29 |
| A17 | | 0.26 | A18 | | 0.31 |
| A19 | | 0.20 | A20 | | 0.28 |
| A21 | | 0.31 | A22 | | 0.45 |
| A23 | | 1.04 | A24 | | 0.50 |
| A25 | | 0.30 | A26 | | 0.57 |
| A27 | | 0.49 | A28 | | 1.01 |
| A29 | 1.1 | | A30 | | 0.097 |
| A31 | | 1.03 | A32 | | 1.20 |
| A33 | | 0.35 | A34 | 15.5 | |
| A35 | 33.0 | | A36 | | 5.79 |
| | | | A38 | 37.6 | |
| A39 | 63.5 | | A40 | 5.8 | |
| A41 | 9.8 | | A42 | 23.1 | |
| A43 | 48.8 | | A44 | 20.1 | |

TABLE 2-continued

Results of the compounds of the present invention tested by HT-29 cell viability assay

| NO. | HT-29(20 μM) Survival | HT29 $EC_{50}$ (μM) | NO. | HT-29(20 μM) Survival | HT-29 $EC_{50}$ (μM) |
|---|---|---|---|---|---|
| A45 | 27.6 | | A46 | 13.1 | |
| A47 | 17.5 | | A48 | 7.8 | |
| A49 | 60.3 | | A50 | 17.9 | |
| A51 | 16.1 | | A52 | | 0.26 |
| A53 | | | A54 | 31.9 | |
| A55 | 25.6 | | A56 | 23.2 | |
| A57 | 15.3 | | A58 | | 3.95 |
| A59 | 27.9 | | A60 | 13.9 | |
| A61 | 29.2 | | A62 | 22.3 | |
| A63 | 48.8 | | A64 | 20.2 | |
| A65 | 19.5 | | A66 | 48.6 | |
| A67 | | 5.71 | A68 | 11.9 | |
| A69 | 10.5 | | A70 | 16.5 | |
| A71 | 23.4 | | A72 | 40.7 | |
| A73 | 40.7 | | | | |
| A75 | 32.3 | | A76 | 33.82 | |
| A77 | 12.9 | | A78 | 10.5 | |
| A79 | 39.4 | | A80 | 14.4 | |
| A81 | 28.8 | | A82 | 11.0 | |
| A83 | | 1.0 | A84 | 18.1 | |
| | | | A86 | 20.5 | |
| A87 | 15.5 | | A88 | 41.3 | |
| A89 | | 0.22 | A90 | 36.0 | |
| A91 | | 0.16 | A92 | | 0.42 |
| A93 | 11.1 | | A94 | 28.9 | |
| A95 | | 0.30 | A96 | | 0.59 |
| A97 | 22.5 | | A98 | 14.8 | |
| A99 | 72.7 | | A100 | | 0.95 |
| A101 | | 0.40 | A102 | | 9.0 |
| A103 | 46.1 | | A104 | | 12.0 |
| A105 | | | A106 | | |
| A107 | | 1.06 | A108 | | 0.63 |
| A109 | 25.0 | | A110 | | 2.08 |
| A111 | 42.0 | | A112 | 37.2 | |
| A113 | | 1.99 | A114 | | 0.31 |
| A115 | | 0.28 | A116 | | 0.26 |
| A117 | | 0.39 | A118 | | 0.29 |
| B1 | | 1.74 | B2 | | 0.30 |
| B3 | | 3.24 | B4 | | 2.08 |
| B5 | 39.2 | | B6 | 42.5 | |
| B7 | 19.1 | | B8 | | 0.93 |
| B9 | | 0.62 | B10 | 36.4 | |
| B11 | 26.2 | | B12 | 10.3 | |
| B13 | | 0.52 | B14 | | 0.32 |
| B15 | | 0.72 | B16 | | 1.26 |
| B17 | 22.8 | | B18 | 22.7 | |
| B19 | 7.2 | | | | |
| B21 | 4.9 | | B22 | 23.5 | |

TABLE 2-continued

Results of the compounds of the present invention tested by HT-29 cell viability assay

| NO. | HT-29(20 μM) Survival | HT29 $EC_{50}$ (μM) | NO. | HT-29(20 μM) Survival | HT-29 $EC_{50}$ (μM) |
|---|---|---|---|---|---|
| B23 | 12.7 | | B24 | 16.5 | |
| B25 | 70.7 | | B26 | 72.6 | |
| B27 | | 2.2 | B28 | 15.0 | |
| B29 | | 0.67 | | | |

Example 33: in Vitro MEF Cell Assay

Figure 2:
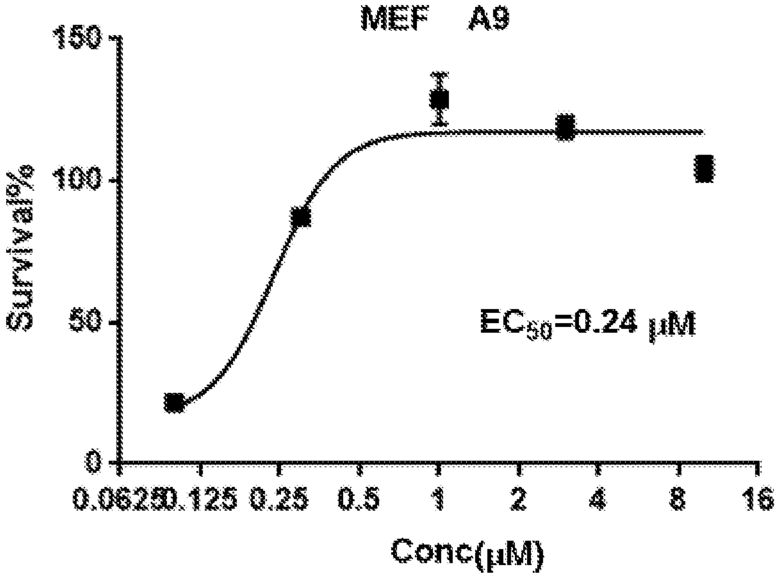
FIG. 2 depicts the inhibition of TNF-α induced-necrosis in MEF cells by compound A9.

MEF cells were added to 96-well plate. The compounds at different concentrations (0.3, 1.0, 3.0, 10.0, 20.0 μM) were then preprocessed for two hours. TNF-α (40 ng/mL), Smac mimetic (100 nM) and z-VAD (20 μM) were added, and the mixture was incubated for 12 h. Quantitative analysis of cell survival was conducted. DMSO pretreatment group was used as a negative control. Concentration for 50% of maximal effect was calculated according to the curve of the survival rate measured at different concentrations. FIG. 2 depicts the $EC_{50}$ curves of compound A9.

TABLE 3

Results of the compounds of the present invention tested by MEF cell viability assay

| NO. | $EC_{50}$ (μM) | NO. | $EC_{50}$ (μM) | NO. | $EC_{50}$ (μM) |
|---|---|---|---|---|---|
| A9 | 0.24 | A13 | 0.20 | A14 | 0.29 |
| A17 | 0.30 | A20 | 0.31 | A21 | 0.44 |
| A22 | 0.83 | A33 | 0.38 | B2 | 0.435 |
| B4 | 9.33 | B8 | 1.77 | | |

Example 34: in Vitro L929 Cell Viability Assay

Figure 3:
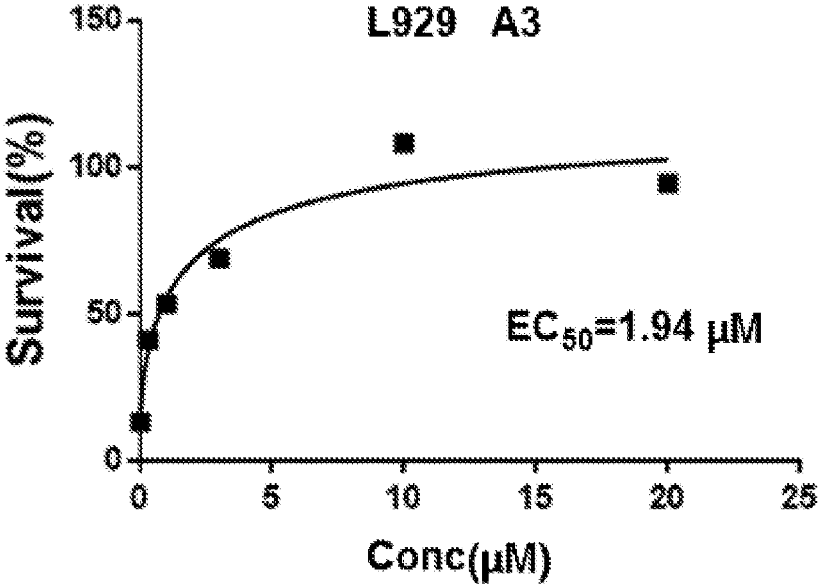
FIG. 3 depicts the inhibition of TNF-α induced-necrosis in L929 cells by compound A3.
Figure 4:
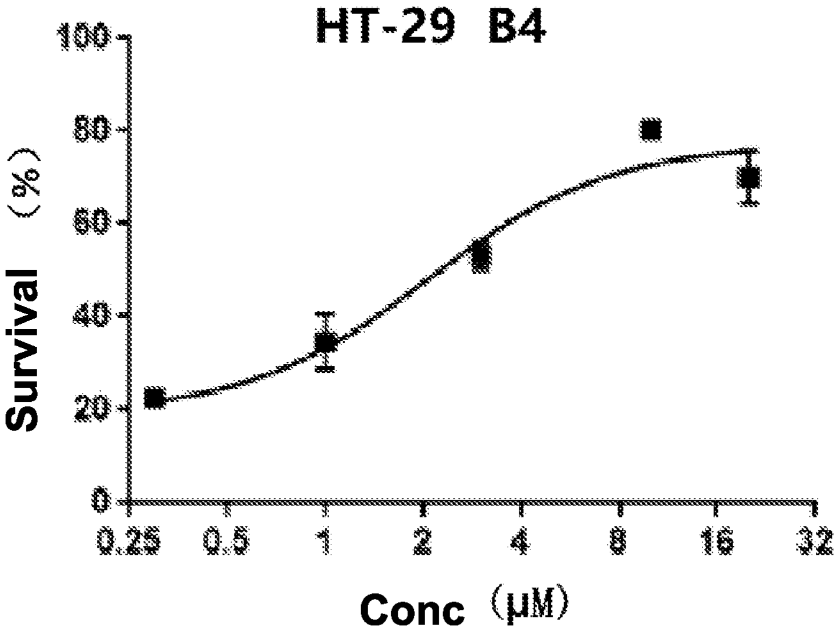
FIG. 4 depicts the inhibition of TNF-α induced-necrosis in HT-29 cells by compound B4.
Figure 5:
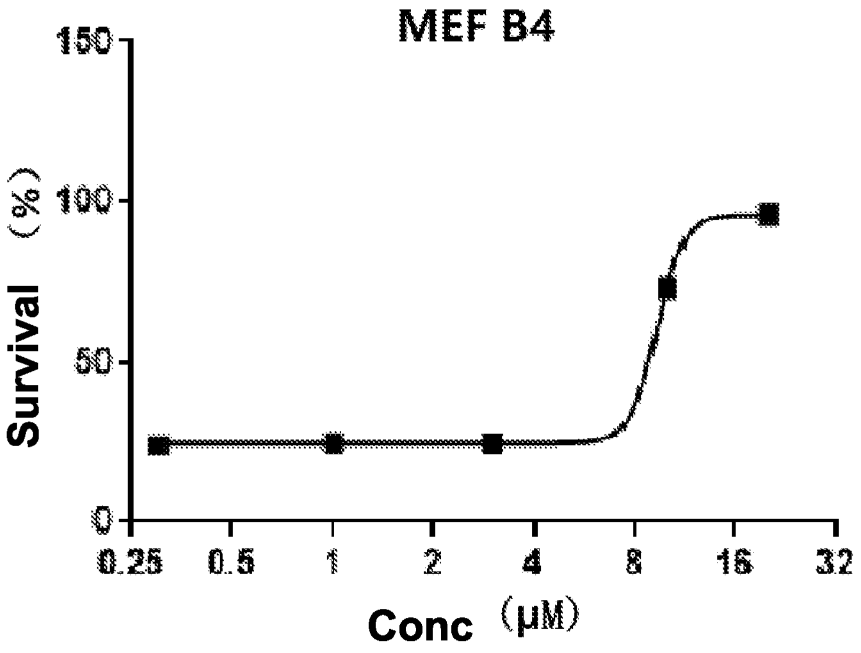
FIG. 5 depicts the inhibition of TNF-α induced-necrosis in MEF cells by compound B4.

L929 cells were added to 96-well plate. The compounds at different concentrations (0.3, 1.0, 3.0, 10.0, 20.0 μM) were then preprocessed for two hours. TNF-α (40 ng/mL), and z-VAD (20 μM) were added, and the mixture was incubated for 16 h. Quantitative analysis of cell survival was conducted. DMSO pretreatment was used as a negative control. Concentration for 50% of maximal effect was calculated according to the curve of the survival rate measured at different concentrations. FIG. 3 depicts the $EC_{50}$ curves of compound A3.

TABLE 4

Results of the compounds of the present invention tested by L929 cell viability assay

| NO. | $EC_{50}$ (μμM) | NO. | $EC_{50}$ (μM) | NO. | $EC_{50}$ (μM) |
|---|---|---|---|---|---|
| A3 | 1.94 | A7 | 0.24 | A9 | 0.21 |
| A13 | 0.78 | A20 | 0.42 | A21 | 8.73 |
| B1 | 64 | B2 | 0.43 | | |

As shown in FIGS. 1-3 and Tables 2-4, the heteroaryl compounds of the present disclosure can be effective inhibitors for RIP3, and can be used in treating or preventing diseases caused by or associate with activated necrotic pathways.

What is claimed is:

1. A compound of Formula I:

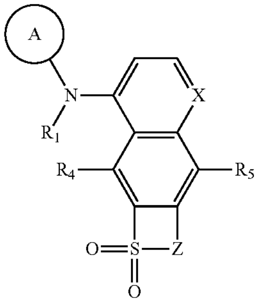

I or a pharmaceutically acceptable salt, ester, solvate, isotope-labeled derivative, stereoisomer or tautomer thereof, wherein X is N or $CR_6$;

Z is

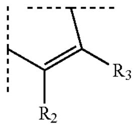

or

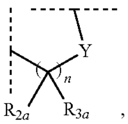

, wherein the sulfonyl group in Formula I is connected to the carbon bearing $R_2$ or $R_{2a}$;

wherein when Z is

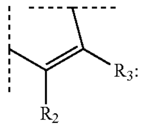

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_7$ groups;

$R_1$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium;

$R_2$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and deuterium;

$R_3$ is independently H, deuterium, halide, amino, —OH, —$CO_2H$, —$CO_2(C_{1-6}$ alkyl), —CN, $C_{1-6}$ alkyl, $C_{3-6}$ cycloalkyl, 3-6 membered heterocycle, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, $C_{1-3}$ alkoxy, —NH($C_{1-3}$ alkyl), —N($C_{1-3}$ alkyl)$_2$, cyclopropyl, halide and deuterium;

or $R_3$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_8$ groups;

or $R_3$ is L-BB, wherein L is —O—, —S—, —NH— or —$CH_2$—, BB is $C_{3-8}$ cycloalkyl or 3-8 membered heterocycle, wherein 3-8 membered heteroaryl comprises 1 to 3 heteroatoms independently selected from N, O and S, wherein $C_{3-8}$ cycloalkyl and 3-8 membered heterocycle are unsubstituted or substituted with 1 to 3 $R_9$ groups;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_7$ is independently H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl, —C(═O)$NH_2$ or —$CO_2(C_{1-6}$ alkyl), wherein amino, $C_{1-6}$ alkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium, or two adjacent $R_7$ groups being connected to form a ring together with the atoms they are attached to; and each of $R_8$ and $R_9$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2(C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium;

wherein when Z is

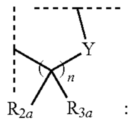
:

n is 1 or 2;

Y is O, $NR_{7a}$ or $CR_{7a}R_{8a}$;

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_{9a}$ groups;

$R_1$ is independently H, deuterium, $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium;

each of $R_{2a}$ and $R_{3a}$ is independently H, deuterium, halide, amino, —OH, —$CO_2H$, —$CO_2(C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl, or $R_{2a}$ and $R_{3a}$ forming ring B together with atoms connected to $R_{2a}$ or $R_{3a}$;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_{7a}$ is H, deuterium, halide, amino, —OH, —$CO_2H$, —$CO_2(C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl;

$R_{8a}$ is H, deuterium, halide, amino, —OH, —$CO_2H$, —$CO_2(C_{1-6}$ alkyl), —CN, —$SOR_{20}$, —$SO_2R_{20}$, $C_{1-6}$ alkyl, $C_{3-6}$ cycloalkyl, 3-6 membered heterocycle comprising 1-3 heteroatoms independently selected from N, O and S, $C_{1-6}$ alkoxy, —NH($C_{1-6}$ alkyl), —N($C_{1-6}$ alkyl)$_2$, $C_{2-6}$ alkenyl, $C_{2-6}$ alkynyl, —C(═O)$NH_2$ or —$CO_2(C_{1-6}$ alkyl), wherein amino, $C_{1-6}$ alkyl, $C_{1-6}$ alkoxy, $C_{3-6}$ cycloalkyl, $C_{2-6}$ alkenyl and $C_{2-6}$ alkynyl are unsubstituted or substituted with 1 to 3 groups independently selected from —OH, $C_{1-3}$ alkoxy, cyclopropyl, halide and deuterium, or $R_{8a}$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 R10$a$ groups;

or $R_{7a}$ and Rea together with the carbon they attached to are C═O or C═$CH_2$;

or $R_{7a}$ and Rea form ring C together with atoms attached to $R_{7a}$ and $R_{8a}$;

each of ring B and ring C is independently selected from the group consisting of $C_{3-8}$ cycloalkyl, 3-8 membered heterocycle, $C_{4-8}$ cycloalkenyl and $C_{4-8}$ heterocycloalkenyl, wherein $C_{3-8}$ cycloalkyl, 3-8 membered heterocycle, $C_{4-8}$ cycloalkenyl and $C_{4-8}$ heterocycloalkenyl are unsubstituted or substituted with 1 to 3 $R_{11a}$ groups, wherein 3-8 membered heterocycle and $C_{4-8}$ heterocycloalkenyl comprises 1 to 3 groups independently selected from the group consisting of heteroatom(s) of N, O and S, and hetero group(s) of —C(═O)N($R_{11a}$)—, —C(═O)O—, —C(═O)—, —C(═S)—, —S(═O)—, —S(═O)$_2$— and —NHC(═O)NH—;

each of $R_{9a}$ and $R_{10a}$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium;

$R_{11a}$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium; and $R_{20}$ is $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium.

2. The compound of claim 1 having Formula II:

II

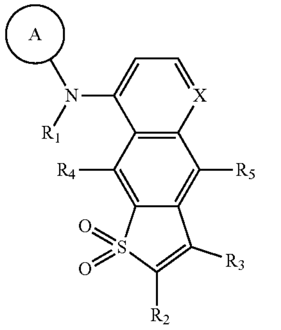

or a pharmaceutically acceptable salt, ester, solvate, isotope-labeled derivative, stereoisomer or tautomer thereof, wherein X is N or $CR_6$;

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_7$ groups;

$R_1$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium;

$R_2$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and deuterium;

$R_3$ is independently H, deuterium, halide, amino, —OH, —$CO_2$H, —$CO_2$($C_{1-6}$ alkyl), —CN, $C_{1-6}$ alkyl, $C_{3-6}$ cycloalkyl, 3-6 membered heterocycle, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, $C_{1-3}$ alkoxy, —NH($C_{1-3}$ alkyl), —N($C_{1-3}$ alkyl)$_2$, cyclopropyl, halide and deuterium;

or $R_3$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_8$ groups;

or $R_3$ is L-BB, wherein L is —O—, —S—, —NH— or —$CH_2$—, BB is $C_{3-8}$ cycloalkyl or 3-8 membered heterocycle, wherein 3-8 membered heteroaryl comprises 1 to 3 heteroatoms independently selected from N, O and S, wherein $C_{3-8}$ cycloalkyl and 3-8 membered heterocycle are unsubstituted or substituted with 1 to 3 $R_9$ groups;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_7$ is independently H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium, or two adjacent $R_7$ groups being connected to form a ring together with the atoms they are attached to; and each of $R_8$ and $R_9$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium.

3. The compound of claim 1 having Formula III:

III

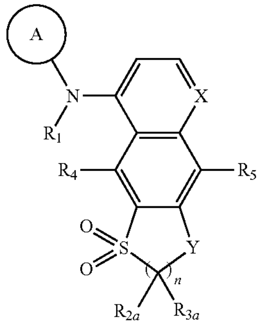

or a pharmaceutically acceptable salt, ester, solvate, isotope-labeled derivative, stereoisomer or tautomer thereof, wherein n is 1 or 2;

X is N or $CR_6$;

Y is O, $NR_{7a}$ or $CR_{7a}R_{8a}$;

ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_{9a}$ groups;

$R_1$ is independently H, deuterium, $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium;

each of $R_{2a}$ and $R_{3a}$ is independently H, deuterium, halide, amino, —OH, —$CO_2H$, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl, or $R_{2a}$ and $R_{3a}$ forming ring B together with atoms connected to $R_{2a}$ or $R_{3a}$;

each of $R_4$, $R_5$ and $R_6$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-6}$ alkoxy, $C_{2-6}$ alkenyl and $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from halide and —OH;

$R_{7a}$ is H, deuterium, halide, amino, —OH, —$CO_2H$, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl;

$R_{8a}$ is H, deuterium, halide, amino, —OH, —$CO_2H$, —$CO_2$($C_{1-6}$ alkyl), —CN, —$SOR_{20}$, —$SO_2R_{20}$, $C_{1-6}$ alkyl, $C_{3-6}$ cycloalkyl, 3-6 membered heterocycle comprising 1-3 heteroatoms independently selected from N, O and S, $C_{1-6}$ alkoxy, —NH($C_{1-6}$ alkyl), —N($C_{1-6}$ alkyl)$_2$, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-6}$ alkoxy, $C_{3-6}$ cycloalkyl, $C_{2-6}$ alkenyl and $C_{2-6}$ alkynyl are unsubstituted or substituted with 1 to 3 groups independently selected from —OH, $C_{1-3}$ alkoxy, cyclopropyl, halide and deuterium, or $R_{8a}$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_{10a}$ groups;

or $R_{7a}$ and $R_{8a}$ together with the carbon they attached to is C═O or C═$CH_2$;

or $R_{7a}$ and $R_{8a}$ form ring C together with atoms attached to $R_{7a}$ and $R_{8a}$;

each of ring B and ring C is independently selected from the group consisting of $C_{3-8}$ cycloalkyl, 3-8 membered heterocycle, $C_{4-8}$ cycloalkenyl and $C_{4-8}$ heterocycloalkenyl, wherein $C_{3-8}$ cycloalkyl, 3-8 membered heterocycle, $C_{4-8}$ cycloalkenyl and $C_{4-8}$ heterocycloalkenyl are unsubstituted or substituted with 1 to 3 $R_{11a}$ groups, wherein 3-8 membered heterocycle and $C_{4-8}$ heterocycloalkenyl comprises 1 to 3 groups independently selected from the group consisting of heteroatom(s) of N, O and S, and hetero group(s) of —C(═O)N($R_{11a}$)—, —C(═O)O—, —C(═O)—, —C(═S)—, —S(═O)—, —S(═O)$_2$— and —NHC(═O)NH—;

each of $R_{9a}$ and $R_{10a}$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl and —$CO_2$($C_{1-6}$ alkyl), wherein amino, $C_{1-6}$ alkyl, $C_{3-6}$ cycloalkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium;

$R_{11a}$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from halide and deuterium; and $R_{20}$ is $C_{1-6}$ alkyl or $C_{3-6}$ cycloalkyl, wherein $C_{1-6}$ alkyl and $C_{3-6}$ cycloalkyl are unsubstituted or substituted with 1 to 3 groups independently selected from halide and deuterium.

4. The compound of claim 2, or a pharmaceutically acceptable salt, ester, solvate, isotope-labeled derivative, stereoisomer or tautomer thereof, wherein ring A is $C_{6-10}$ aryl or 5-10 membered heteroaryl, wherein heteroaryl comprises 1 to 4 heteroatoms independently selected from N, O and S, wherein $C_{6-10}$ aryl and 5-10 membered heteroaryl are unsubstituted or substituted with 1 to 4 $R_7$ groups; and $R_7$ is independently H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl, $C_{1-8}$ alkoxy, $C_{2-6}$ alkenyl, $C_{2-6}$ alkynyl, —C(═O) $NH_2$ or —$CO_2$($C_{1-6}$ alkyl), wherein amino, $C_{1-6}$ alkyl, $C_{1-8}$ alkoxy, $C_{2-6}$ alkenyl and $C_{2-6}$ alkynyl are unsubstituted or substituted with 1 to 3 groups independently selected from halide, —OH, amino, acetyl and deuterium, or two adjacent $R_7$ groups being connected to form a 4-8 membered ring together with the atoms they are attached to.

5. The compound of claim 2, or a pharmaceutically acceptable salt, ester, solvate, isotope-labeled derivative, stereoisomer or tautomer thereof, wherein $R_3$ is independently H, deuterium, halide, amino, —OH, —$CO_2H$, —$CO_2$($C_{1-6}$ alkyl), —CN, $C_{1-6}$ alkyl, $C_{3-6}$ cycloalkyl, 3-6 membered heterocycle, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, $C_{1-3}$ alkoxy, —NH($C_{1-3}$ alkyl), —N($C_{1-3}$ alkyl)$_2$, cyclopropyl, halide and deuterium;

or $R_3$ is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_8$ groups;

or $R_3$ is L-BB, wherein L is —O—, —S—, —NH— or —$CH_2$—, BB is $C_{3-8}$ cycloalkyl or 4-7 membered heterocycle, wherein 4-7 membered heteroaryl comprises 1 to 3 heteroatoms independently selected from N, O and S, wherein $C_{3-8}$ cycloalkyl and 3-8 membered heterocycle are unsubstituted or substituted with 1 to 3 $R_9$ groups; and each of $R_8$ and $R_9$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, $C_{3-6}$ cycloalkyl or $C_{1-8}$ alkoxy, wherein amino, $C_{1-6}$ alkyl, $C_{3-6}$ cycloalkyl and $C_{1-8}$ alkoxy are unsubstituted or substituted with 1 to 3 groups independently selected from halide, —OH, amino, acetyl and deuterium.

6. The compound of claim 2, or a pharmaceutically acceptable salt, ester, solvate, isotope-labeled derivative, stereoisomer or tautomer thereof, wherein ring A is selected from the group consisting of:

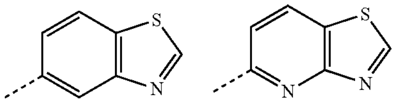
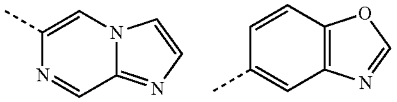
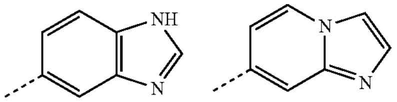
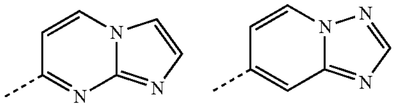
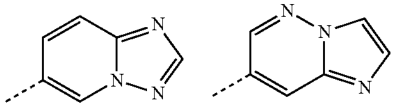
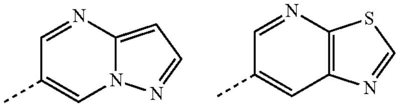
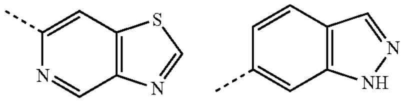
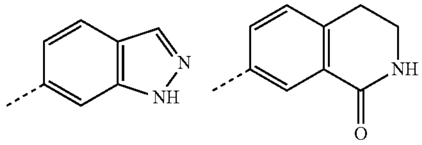
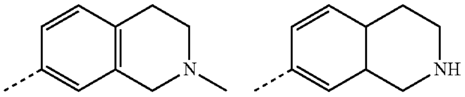
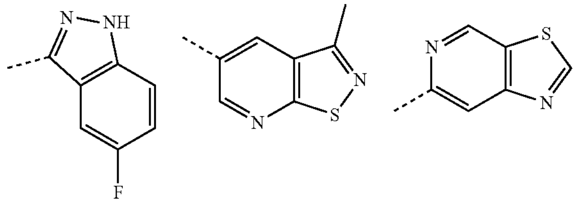
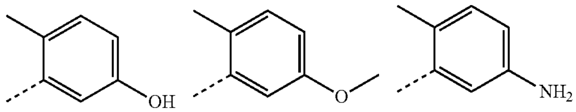
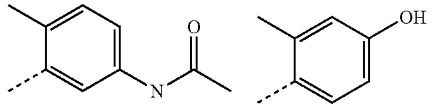
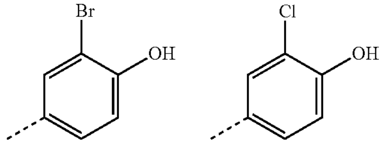
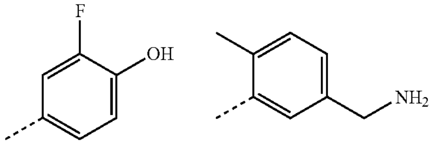

-continued

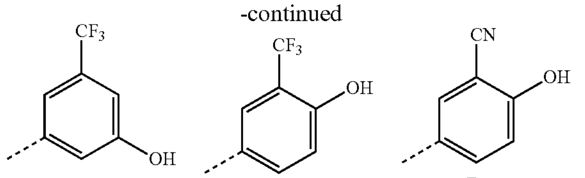
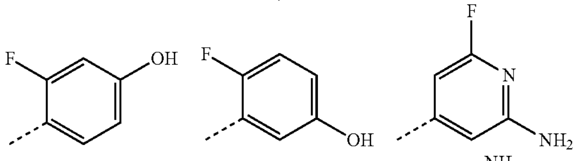
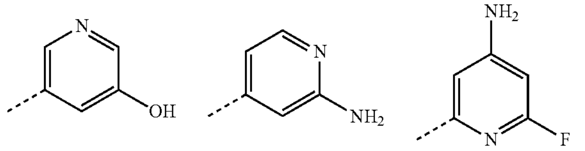
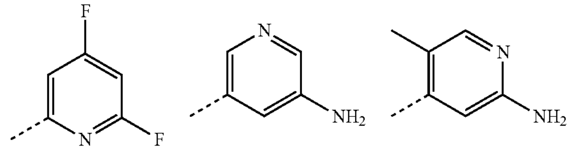
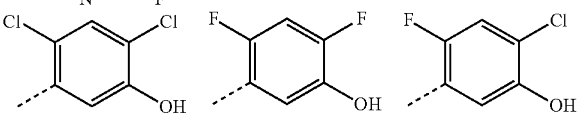
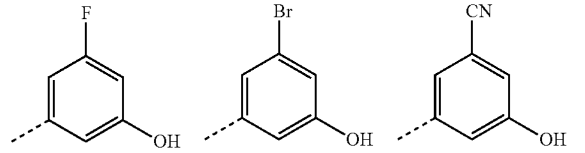
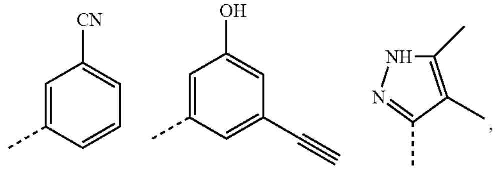
, ring A is unsubstituted or substituted with 1 to 3 groups independently selected from deuterium, halide, —OH, $C_{1-3}$ alkyl and $C_{1-3}$ alkoxy.

7. The compound of claim 2, or a pharmaceutically acceptable salt, ester, solvate, isotope-labeled derivative, stereoisomer or tautomer thereof, wherein $R_3$ is selected from the group consisting of:

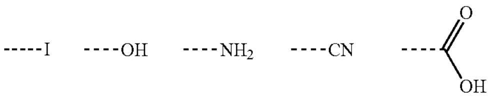
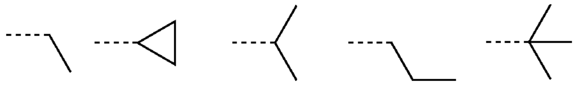
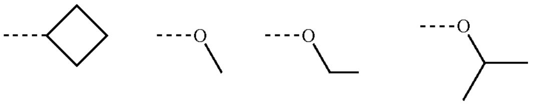
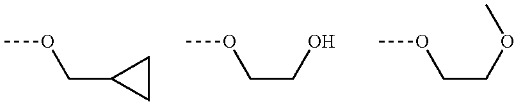

-continued
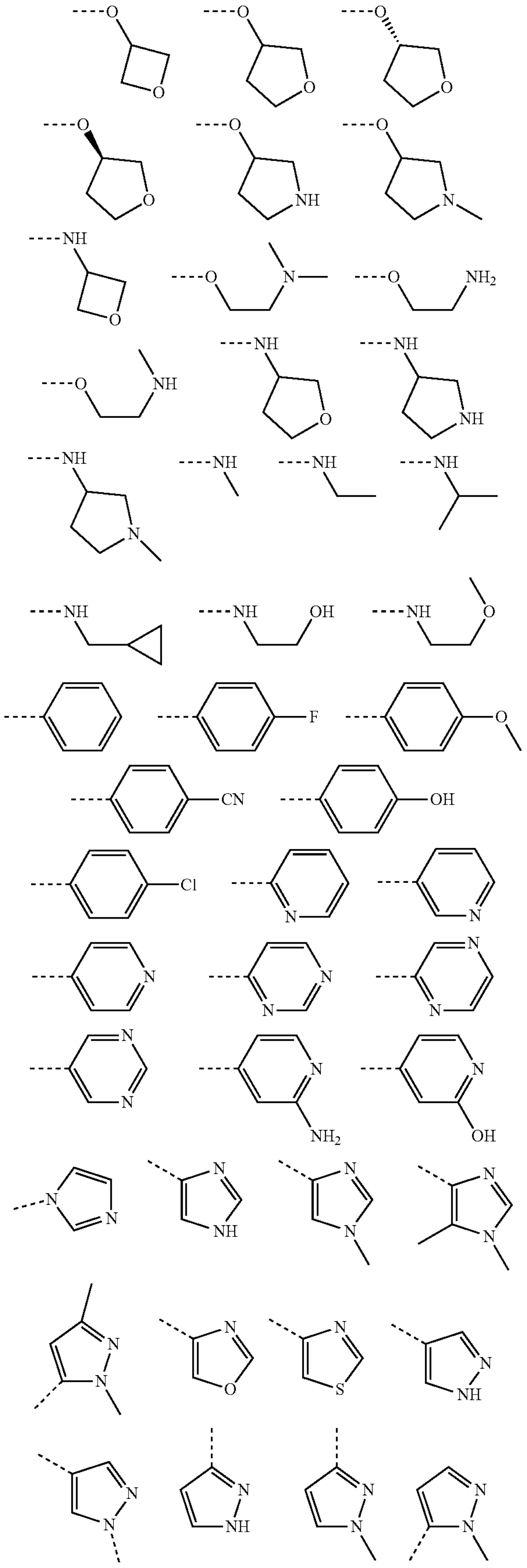
-continued
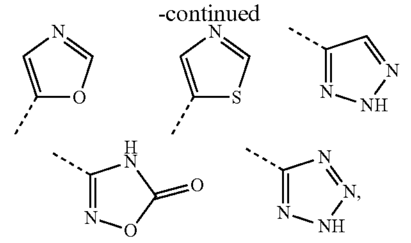
unsubstituted or substituted with 1 to 3 groups of —OH, $C_{1-3}$ alkoxy, —NH($C_{1-3}$ alkyl), —N($C_{1-3}$ alkyl)$_2$, cyclopropyl, halide, deuterium, $R_8$ or $R_9$.
8. The compound of claim 2 selected from the group consisting of:
A1
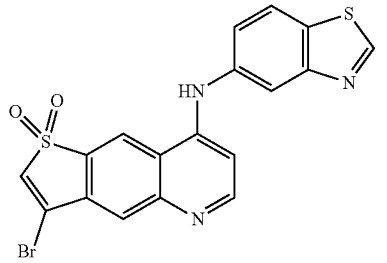
A2
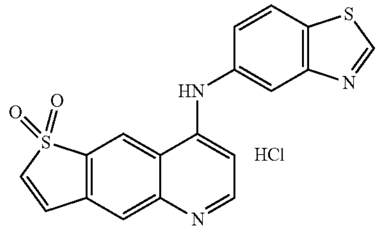
A3
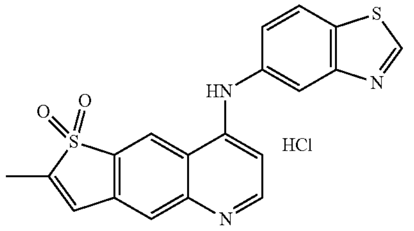
A4
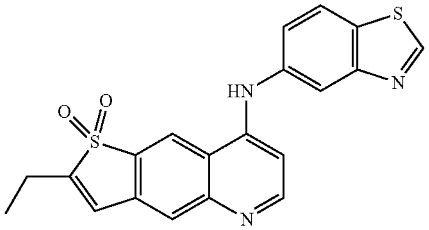
A5
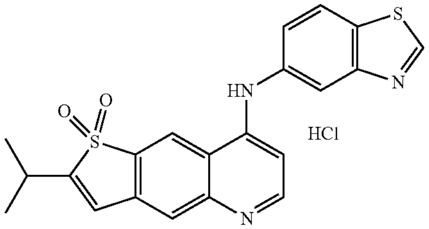

-continued
A6
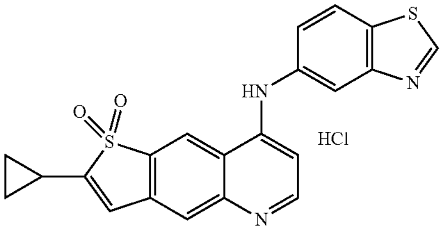
A7
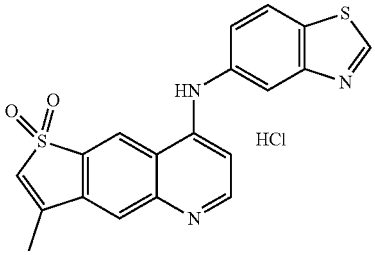
A8
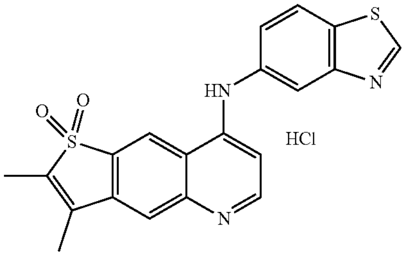
A9
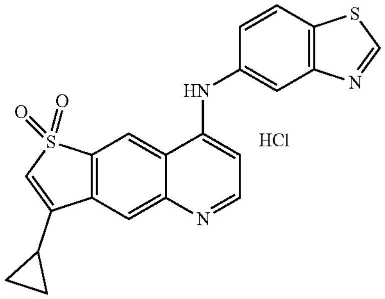
A10
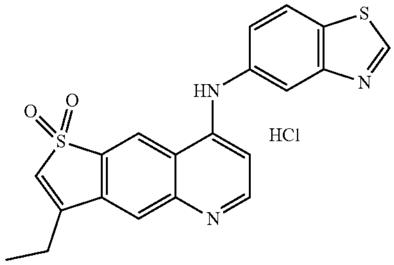
A11
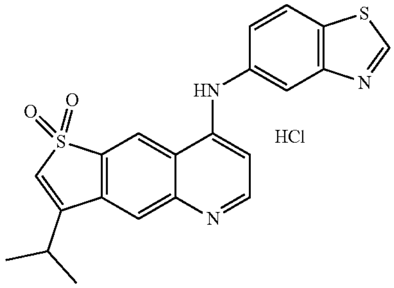
-continued
A12
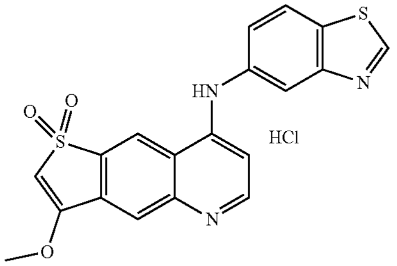
A13
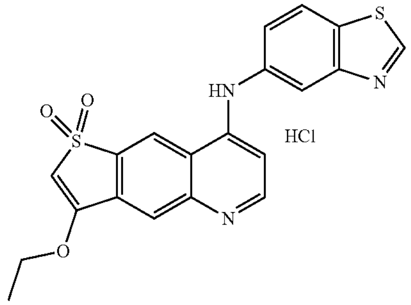
A14
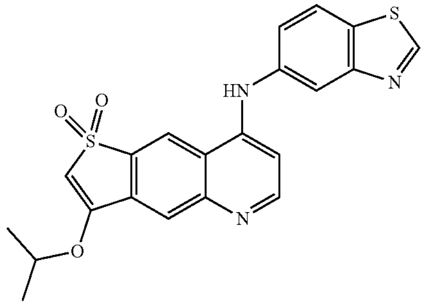
A15
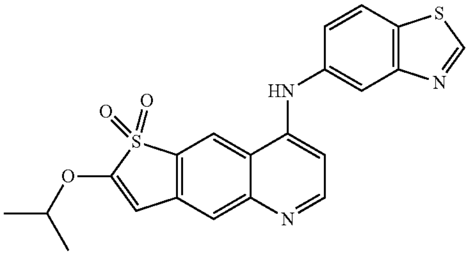
A16
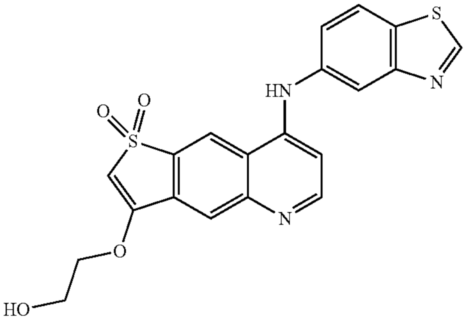

-continued
A17
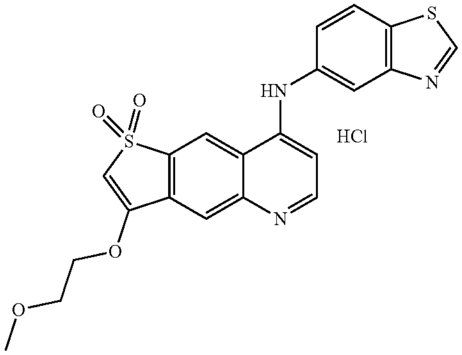
A18
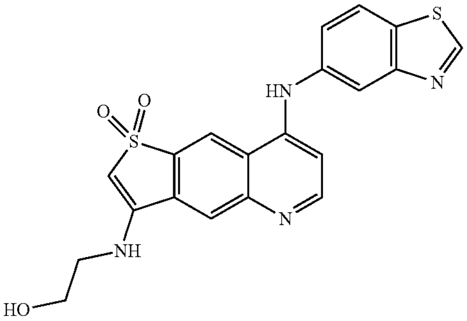
A19
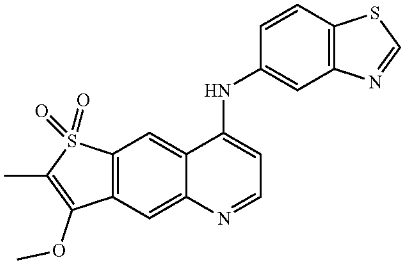
A20
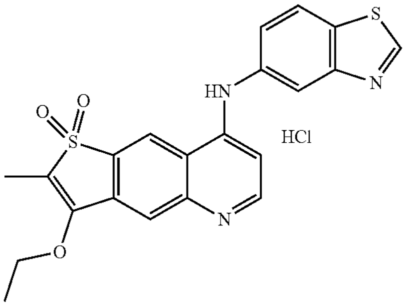
A21
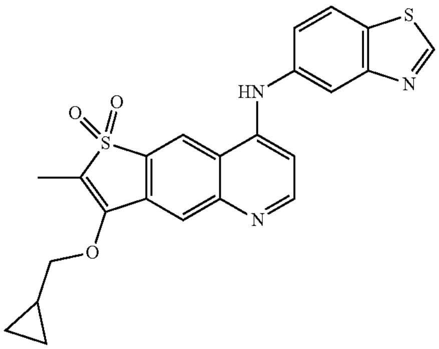
-continued
A22
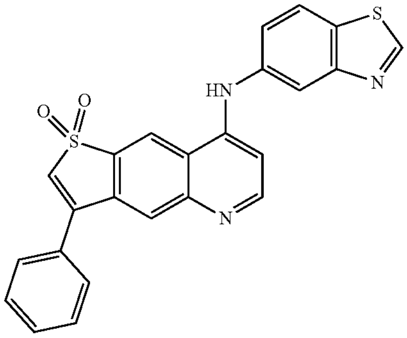
A23
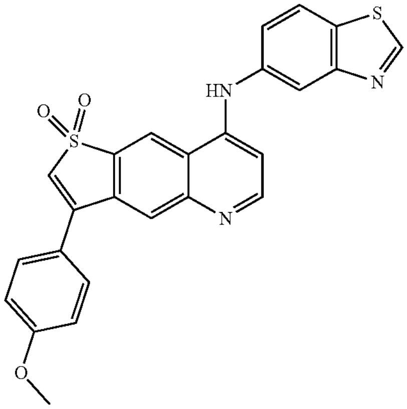
A24
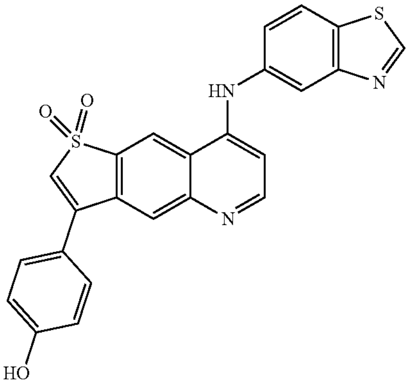
A25
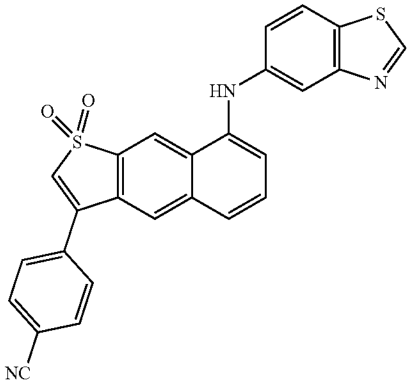

-continued
A26
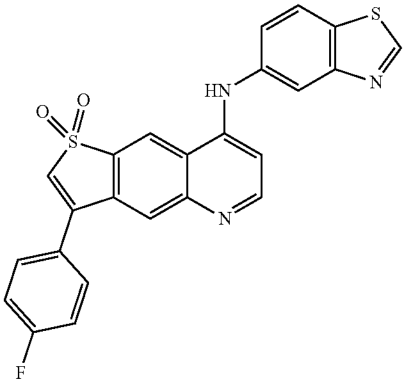
A27
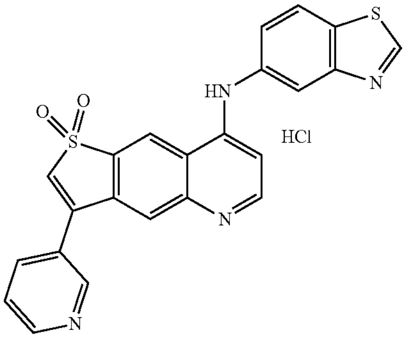
A28
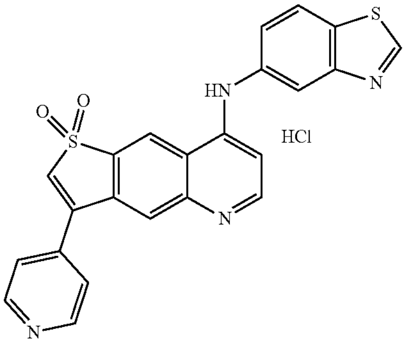
A29
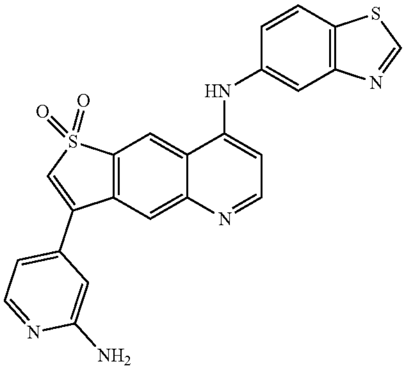
-continued
A30
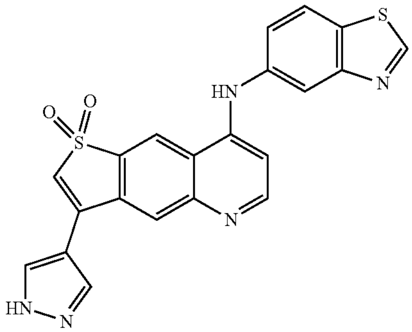
A31
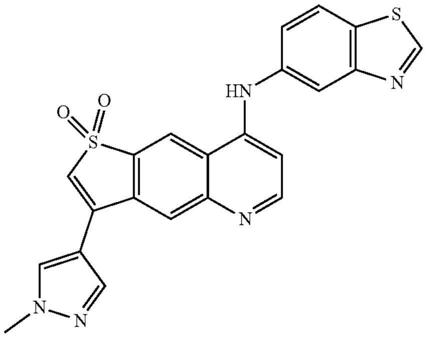
A32
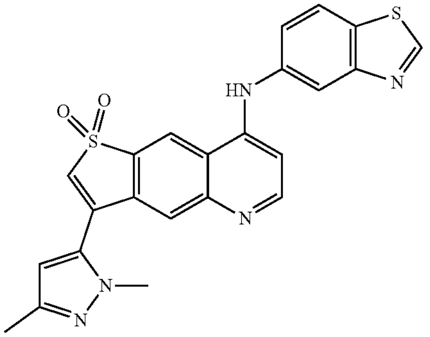
A33
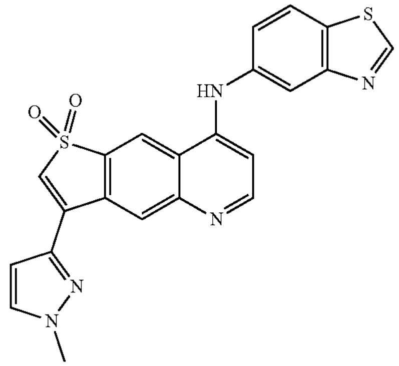

-continued
A34
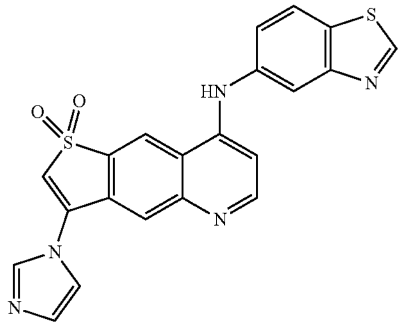
A35
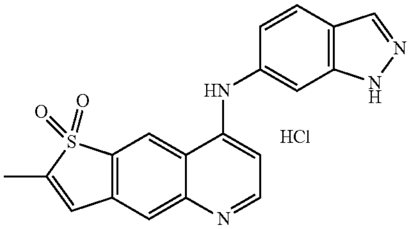
A36
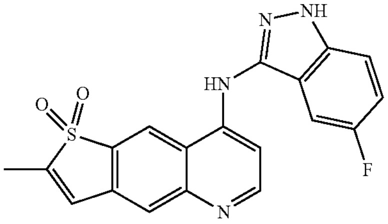
A38
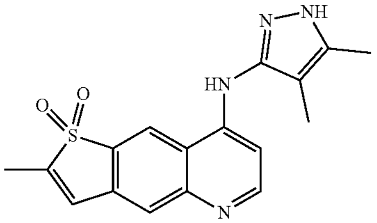
A39
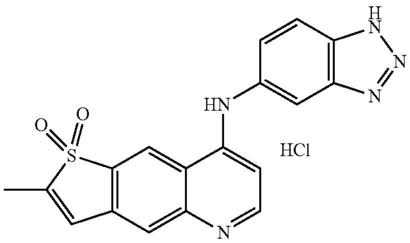
A40
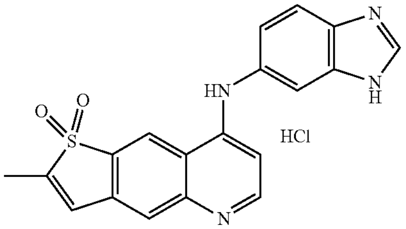
-continued
A41
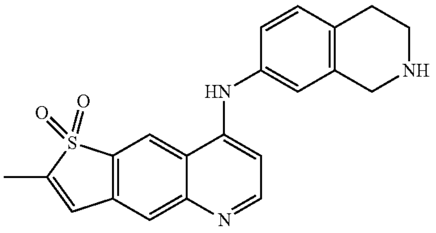
A42
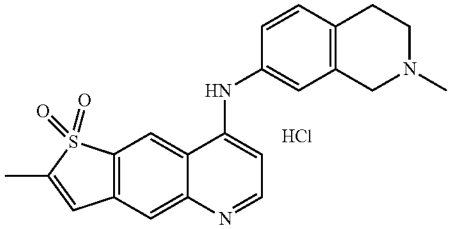
A43
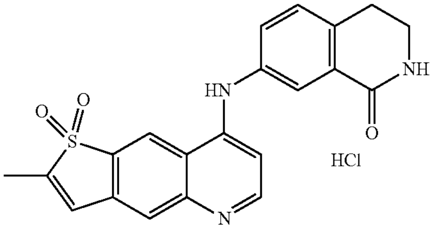
A44
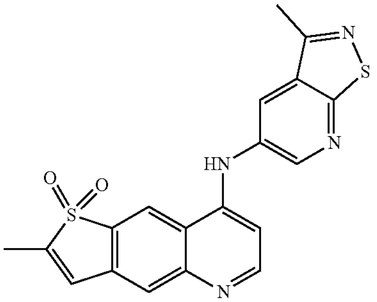
A45
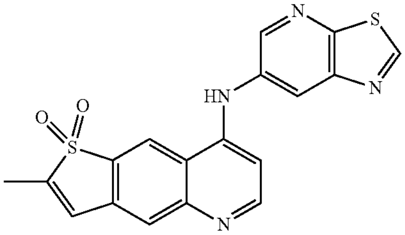
A46
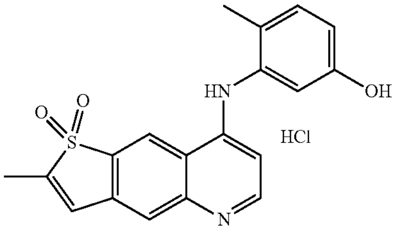

-continued
A47
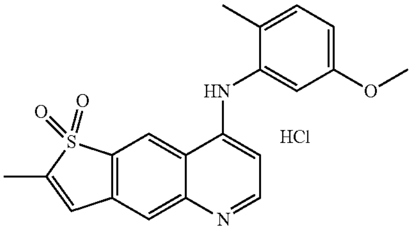
A48
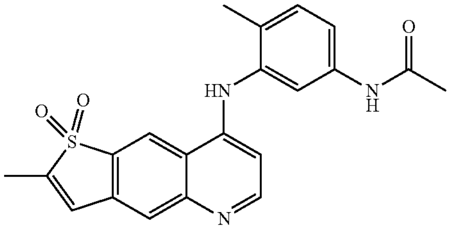
A49
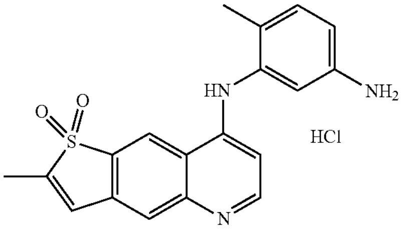
A50
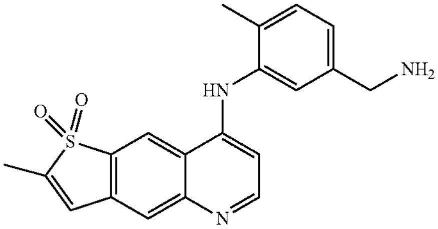
A51
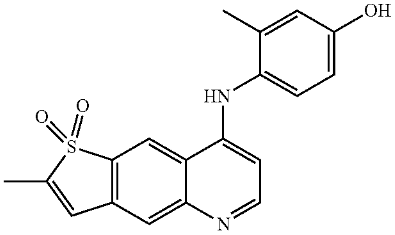
A52
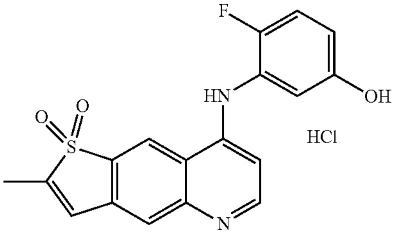
-continued
A53
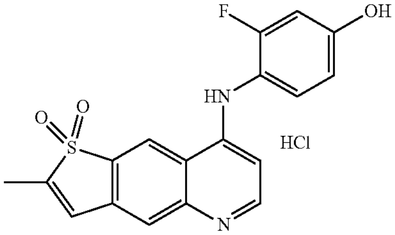
A54
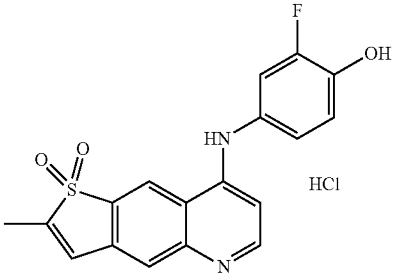
A55
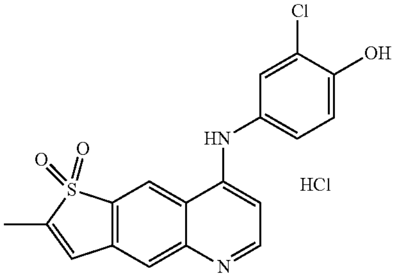
A56
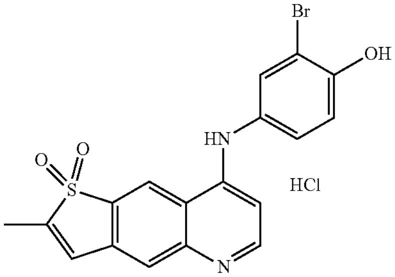
A57
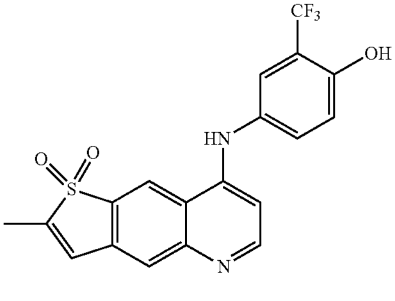

-continued
A58
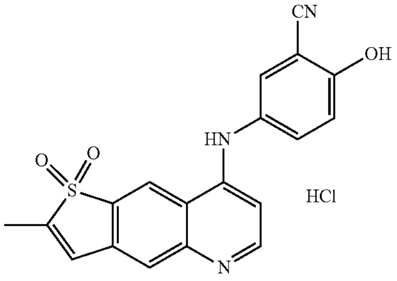
A59
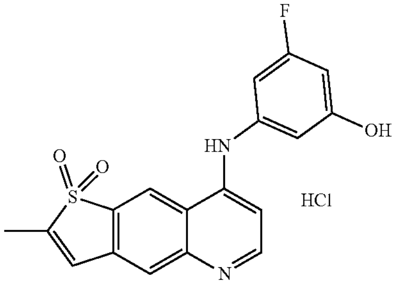
A60
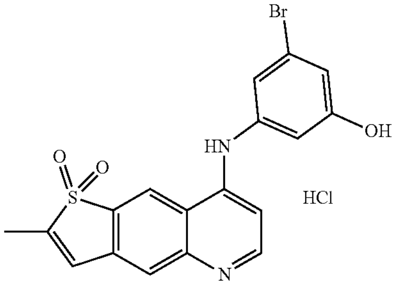
A61
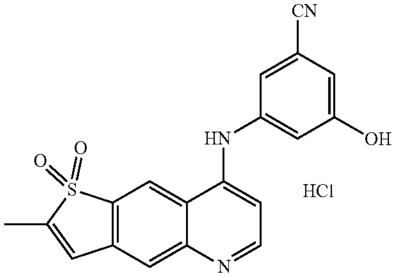
A62
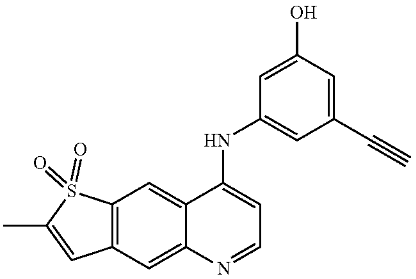
-continued
A63
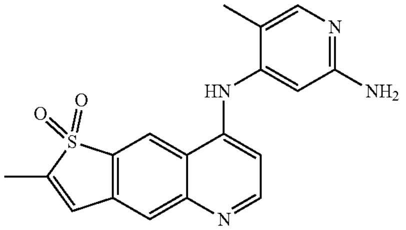
A64
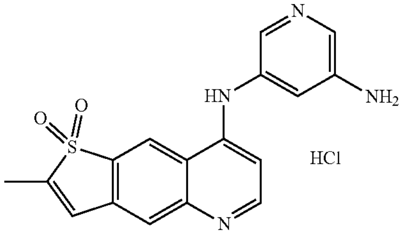
A65
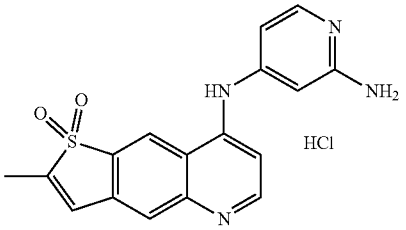
A66
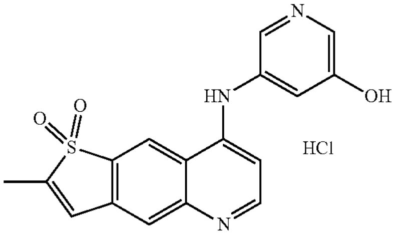
A67
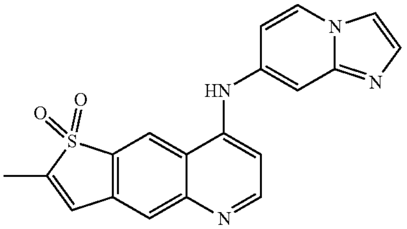
A68
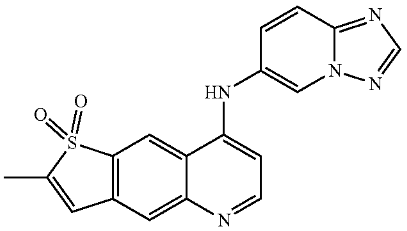

-continued
A69
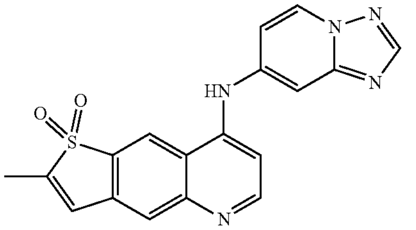
A70
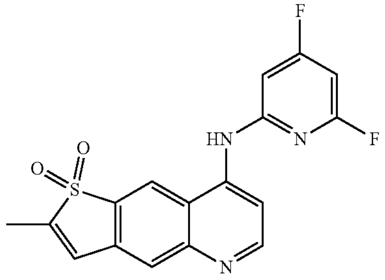
A71
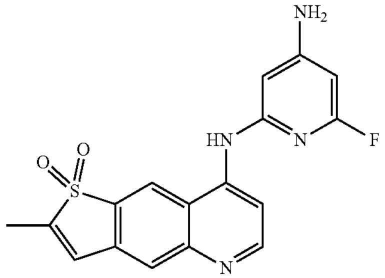
A72
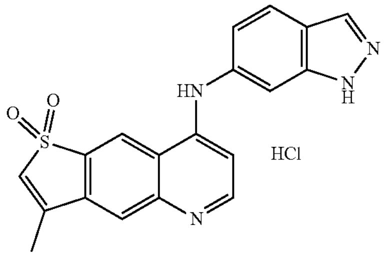
HCl
A73
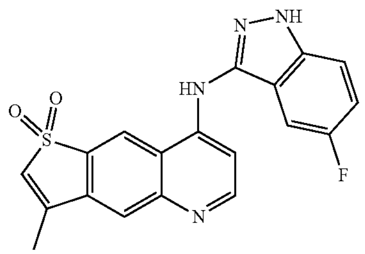
A75
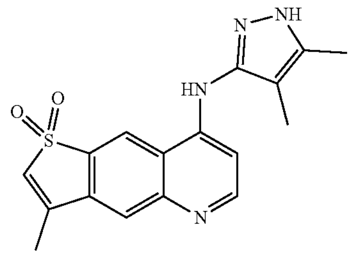
-continued
A76
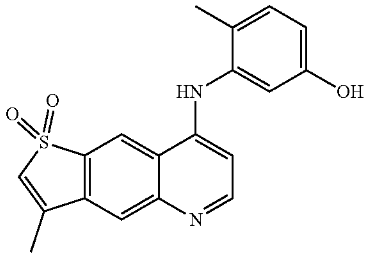
A77
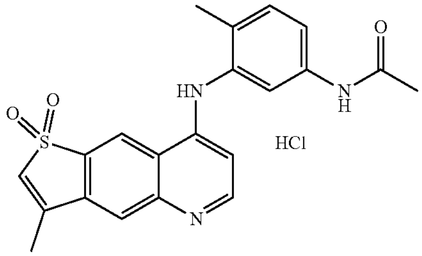
HCl
A78
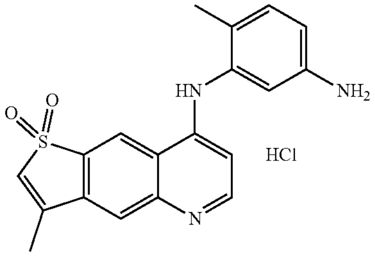
HCl
A79
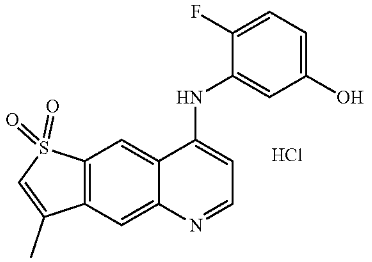
HCl
A80
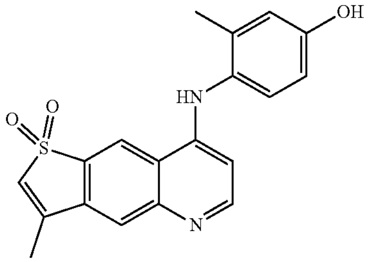
A81
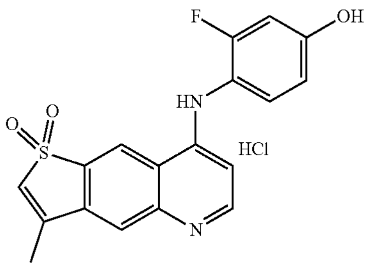
HCl -continued
A82
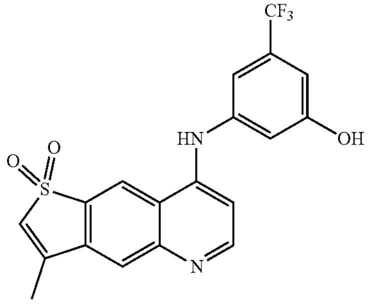
A83
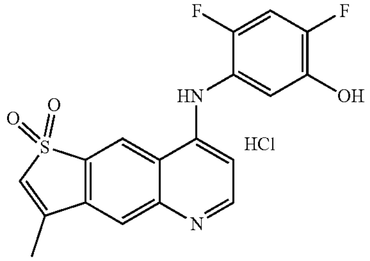
A84
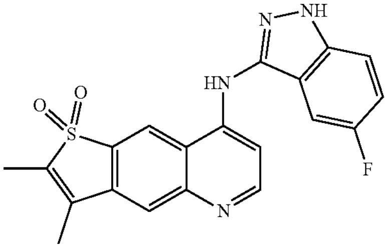
A86
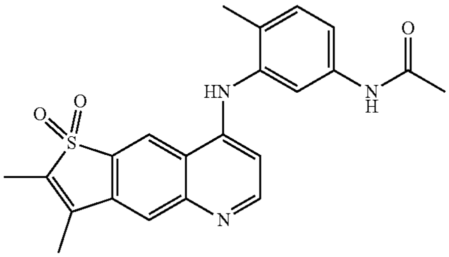
A87
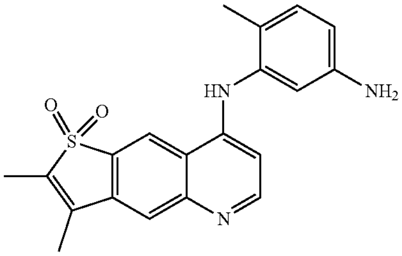
A88
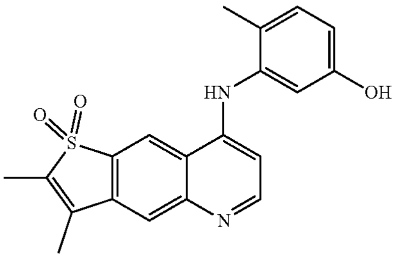
-continued
A89
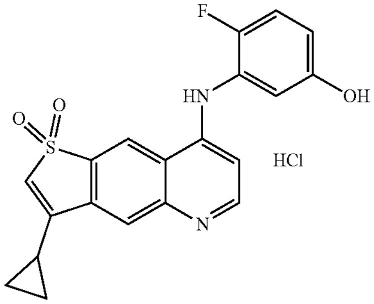
A90
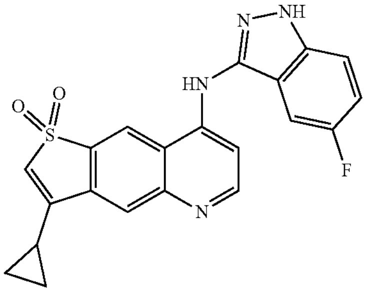
A91
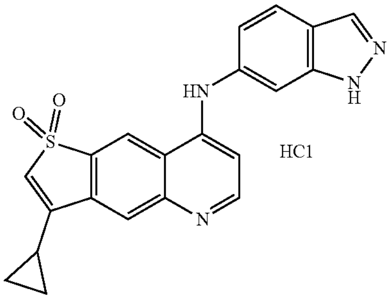
A92
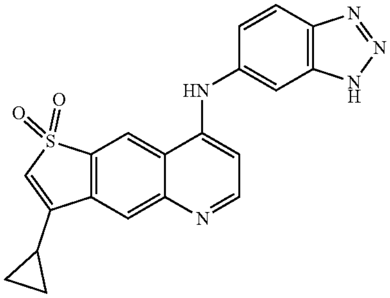
A93
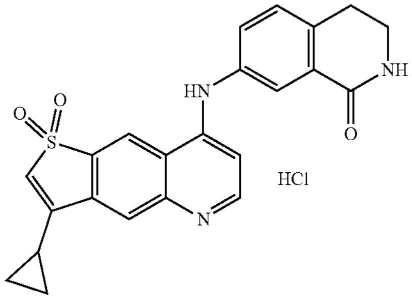

-continued
A94
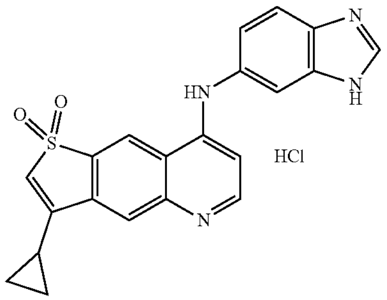
A95
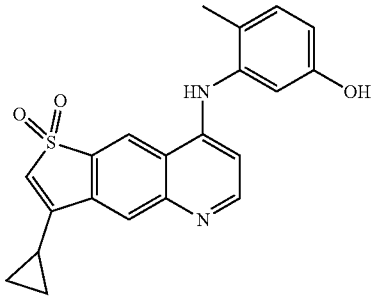
A96
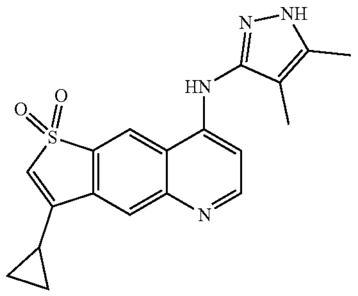
A97
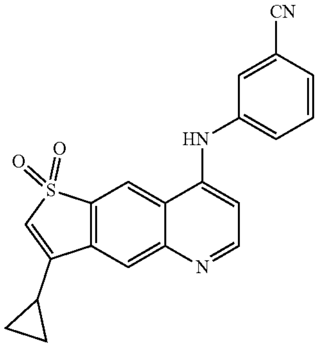
A98
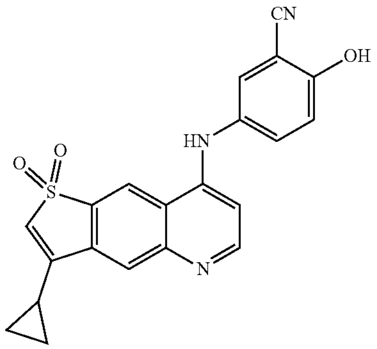
-continued
A99
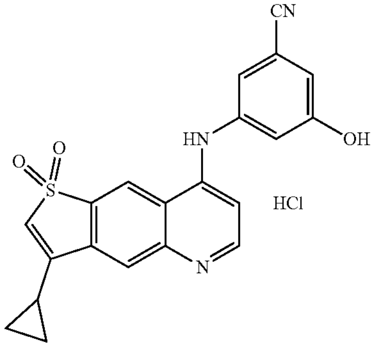
A100
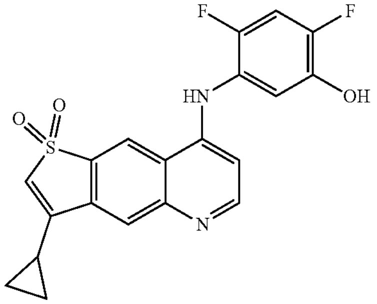
A101
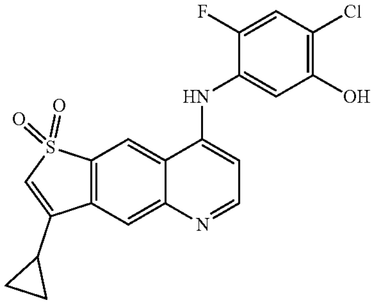
A102
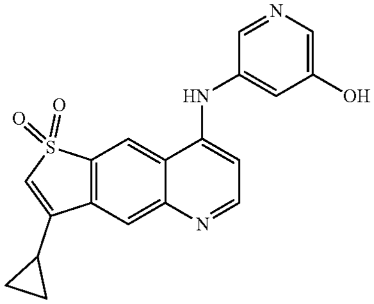
A103
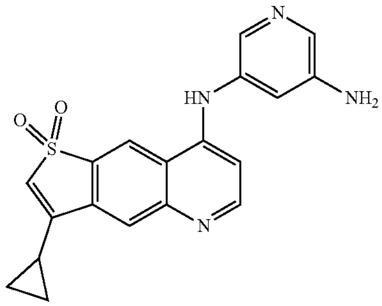

A104
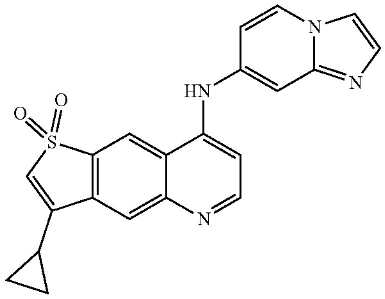
A105
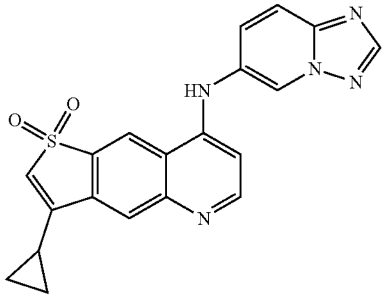
A106
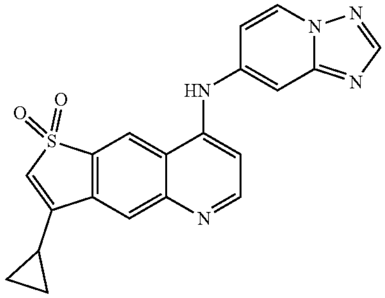
A107
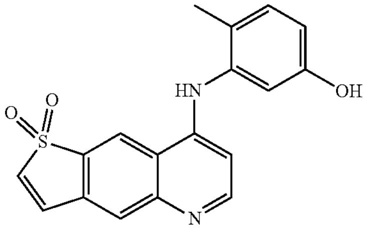
A108
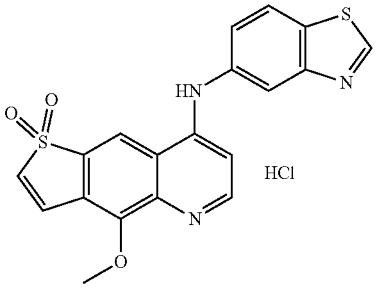
HCl
A109
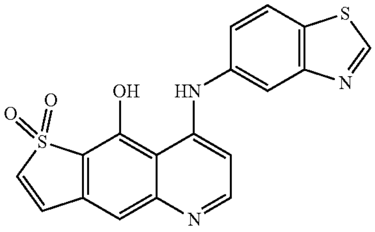
A110
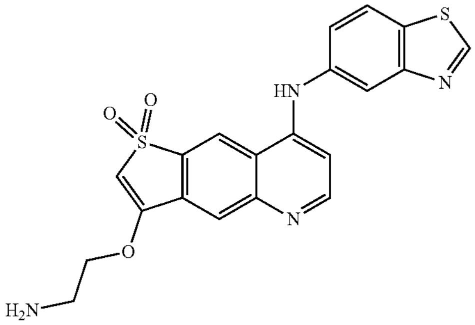
A111
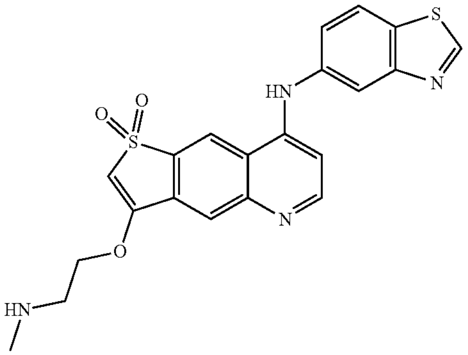
A112
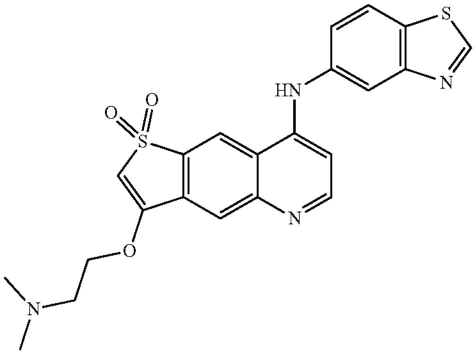

-continued

A113

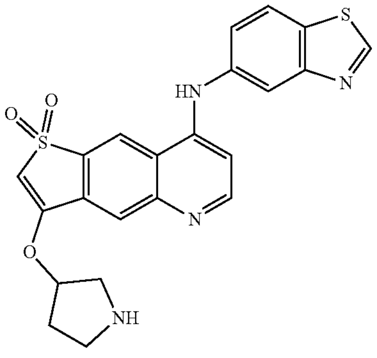

A114

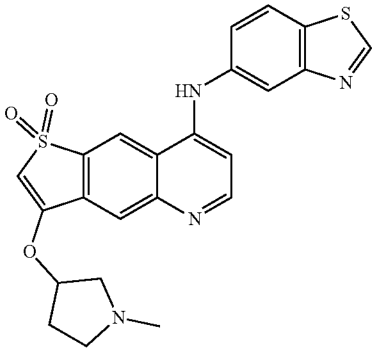

A115

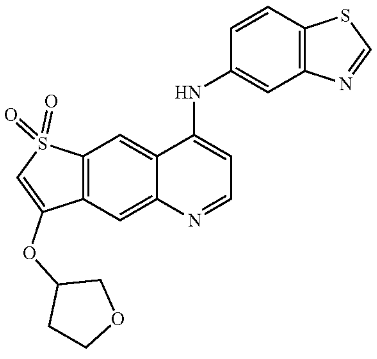

A116

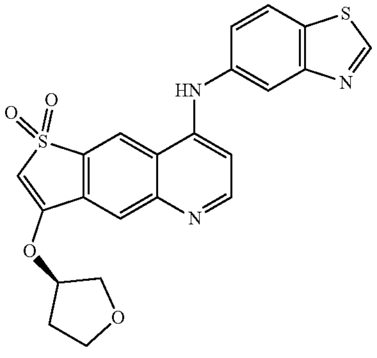

-continued

A117

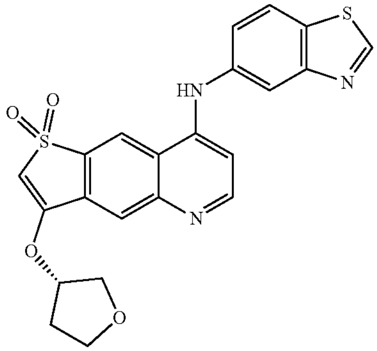

A118

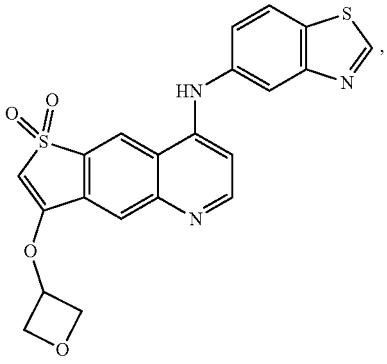

or a pharmaceutically acceptable salt, ester, solvate, isotope-labeled derivative, stereoisomer or tautomer thereof.

9. The compound of claim 3, or a pharmaceutically acceptable salt, ester, solvate, isotope-labeled derivative, stereoisomer or tautomer thereof, wherein when $R_{7a}$ and $R_{8a}$ together with the carbon they attached to are C═O or C═CH or when $R_{7a}$ and $R_{8a}$ form ring C together with atoms attached to $R_{7a}$ and $R_{8a}$, each of $R_{2a}$ and $R_{3a}$ is independently H, deuterium, halide, amino, —OH, —$CO_2H$, —$CO_2$($C_{1-6}$ alkyl), —CN, $C_{1-6}$ alkyl, $C_{3-6}$ cycloalkyl, $C_{1-6}$ alkoxy, —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{1-6}$ alkoxy, $C_{2-6}$ alkenyl and $C_{2-6}$ alkynyl are unsubstituted or substituted with 1 to 3 groups independently selected from —OH, halide and cyclopropyl, or $R_{2a}$ and $R_{3a}$ forming ring B together with atoms connected to $R_{2a}$ or $R_{3a}$;

or when $R_{2a}$ and $R_{3a}$ form ring B together with atoms connected to $R_{2a}$ or $R_{3a}$, $R_{8a}$ is H, deuterium, halide, amino, —OH, —$CO_2H$, —$CO_2$($C_{1-6}$ alkyl), —CN, $C_{1-6}$ alkyl, $C_{3-6}$ cycloalkyl, 3-6 membered heterocycle comprising 1-3 heteroatoms independently selected from N, O and S, $C_{1-6}$ alkoxy, —NH($C_{1-6}$ alkyl), —N($C_{1-6}$ alkyl)$_2$, $C_{2-6}$ alkenyl, $C_{2-6}$ alkynyl, —C(═O)$NH_2$ or —$CO_2$($C_{1-6}$ alkyl), wherein amino, $C_{1-6}$ alkyl, $C_{1-6}$ alkoxy, $C_{3-6}$ cycloalkyl, $C_{2-6}$ alkenyl and $C_{2-6}$ alkynyl are unsubstituted or substituted with 1 to 3 groups independently selected from —OH, $C_{1-3}$ alkoxy, cyclopropyl, halide and deuterium, or Rea is $C_{6-10}$ aryl or 5-10 membered heteroaryl, wherein heteroaryl comprises 1 to 3 heteroatoms independently selected from N, O and S, wherein $C_{6-10}$ aryl and 5-10 membered heteroaryl are unsubstituted or substituted with 1 to 3 $R_{10a}$ groups.

10. The compound of claim 3, or a pharmaceutically acceptable salt, ester, solvate, isotope-labeled derivative, stereoisomer or tautomer thereof, wherein ring A is selected from the group consisting of:

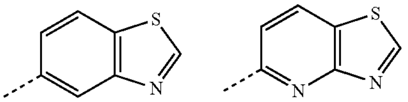
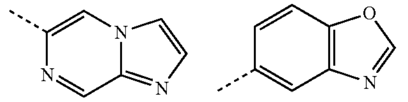
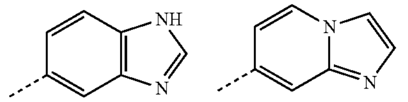
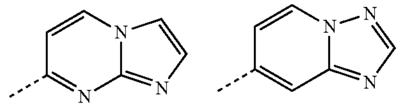
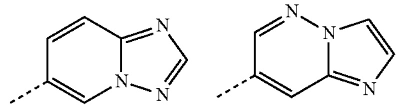
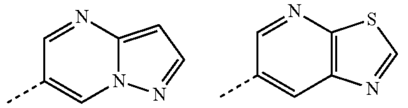
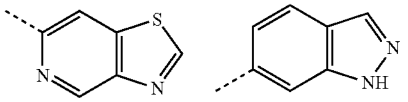
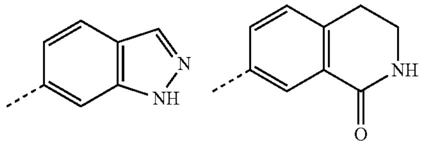
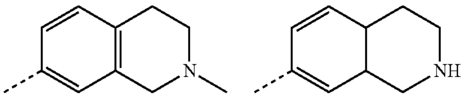
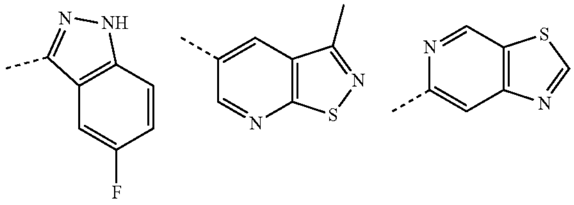
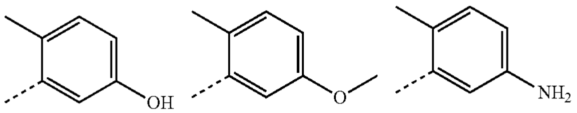
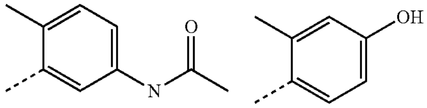
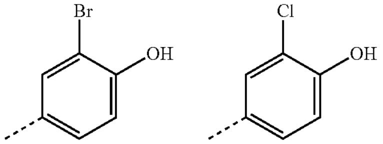

-continued

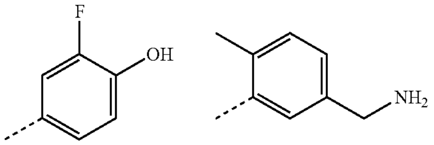
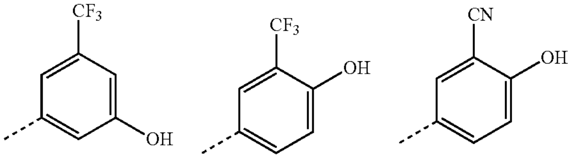
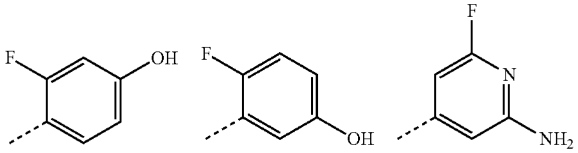
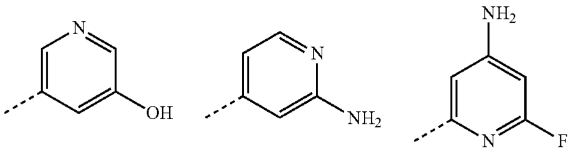
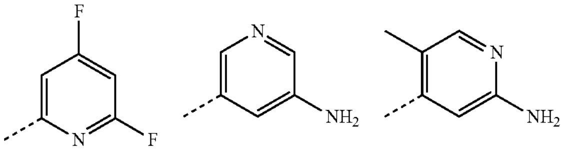
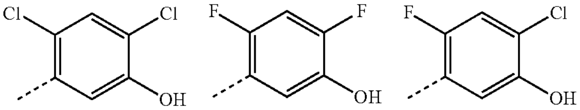
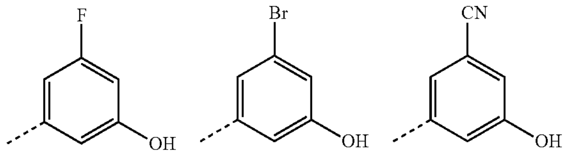
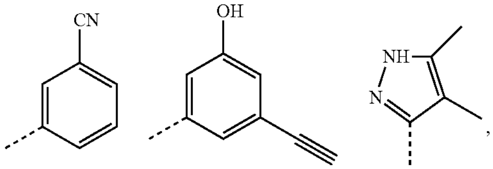
, ring A is unsubstituted or substituted with 1 to 3 groups independently selected from deuterium, halide, —OH, $C_{1-3}$ alkyl and $C_{1-3}$ alkoxy.

11. The compound of claim 3 selected from the group consisting of:

B1

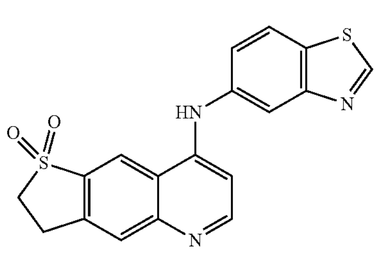

-continued
B2
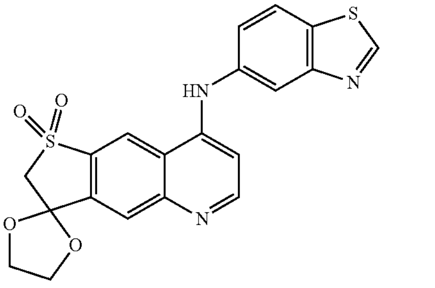
B3
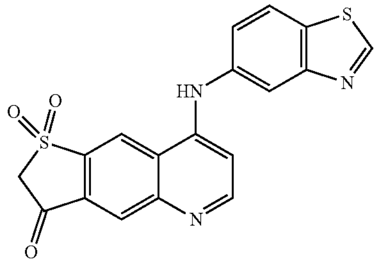
B4
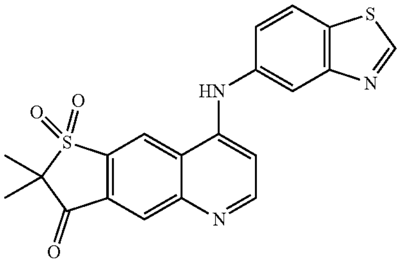
B5
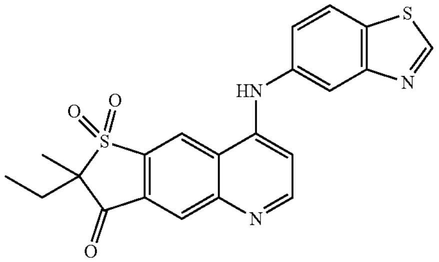
B6
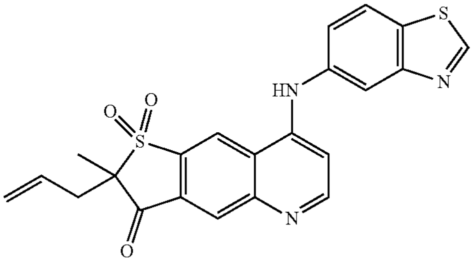
B7
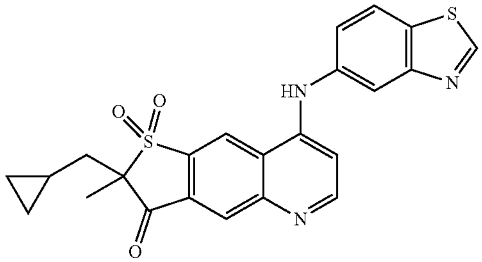
-continued
B7
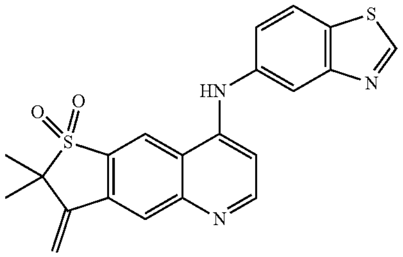
B9
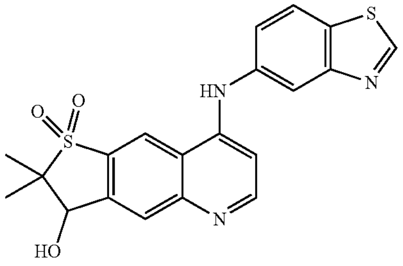
B10
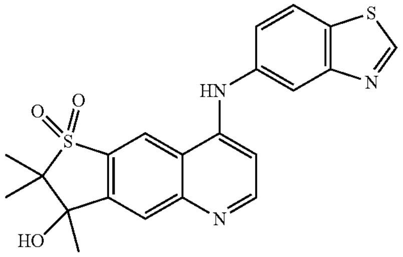
B11
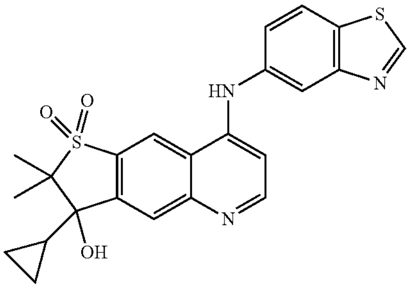
B12
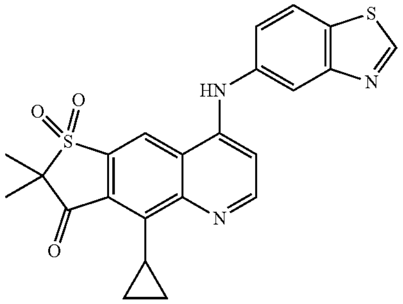

-continued
B13
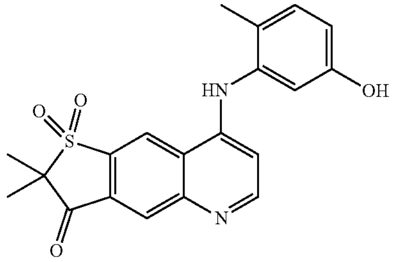
B14
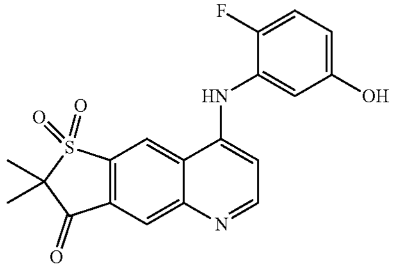
B15
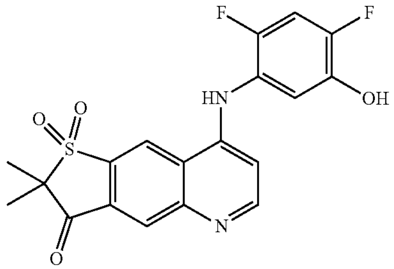
B16
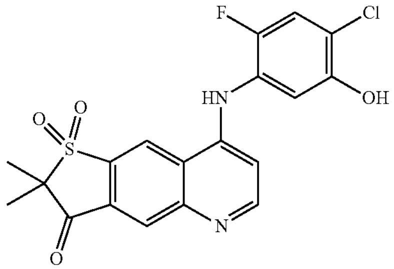
B17
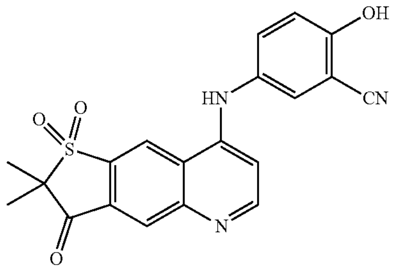
B18
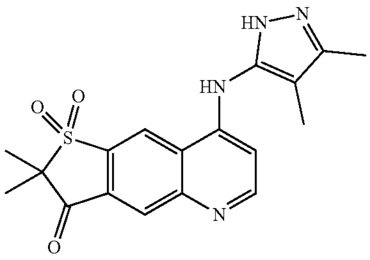
-continued
B19
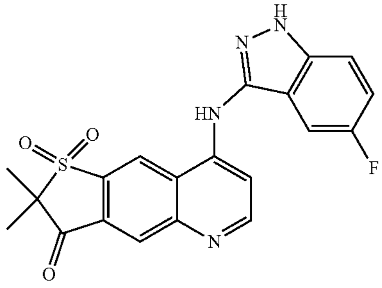
B21
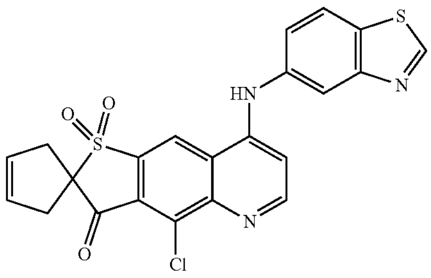
B22
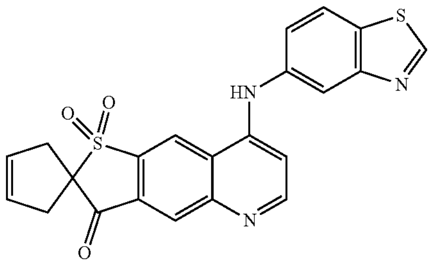
B23
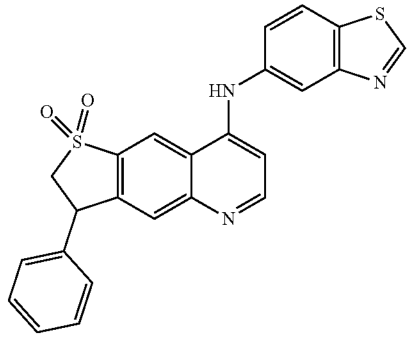
B24
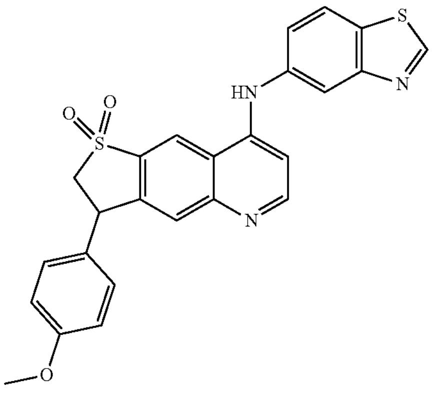

-continued

B25

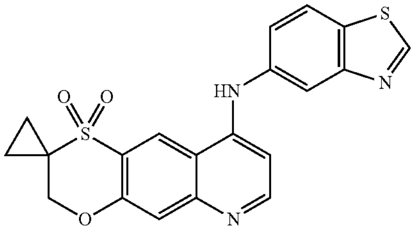

B26

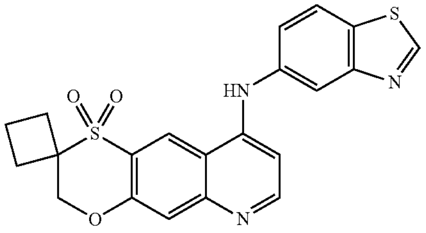

B27

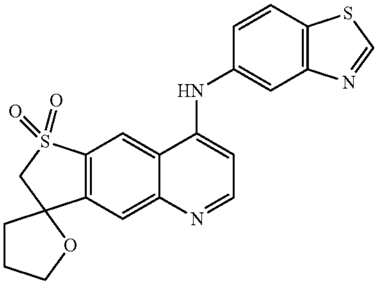

B28

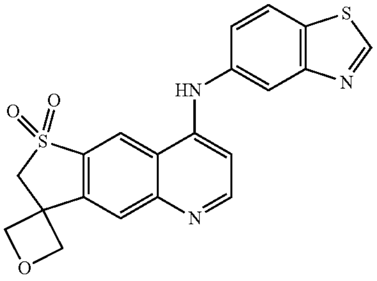

-continued

B29

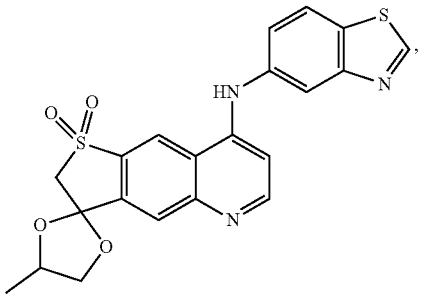

or a pharmaceutically acceptable salt, ester, solvate, isotope-labeled derivative, stereoisomer or tautomer thereof.

12. The compound of claim 1, or a pharmaceutically acceptable salt, ester, solvate, isotope-labeled derivative, stereoisomer or tautomer thereof, wherein X is N.

13. A pharmaceutical composition comprising a therapeutically effective amount of a compound of claim 1 or a pharmaceutically acceptable salt, ester, solvate, isotope-labeled derivative, stereoisomer or tautomer thereof, and a pharmaceutically acceptable carrier.

14. A composition comprising:

(i) a compound of claim 1 or a pharmaceutically acceptable salt, ester, solvate, isotope-labeled derivative, stereoisomer or tautomer thereof; and (ii) at least one additional therapeutic agent selected from the group consisting of anti-tumor agent, agent treating autoimmune disease, anti-neurodegenerative agent, agent treating metabolic disease, and anti-aging agent.

15. A composition comprising:

(i) a pharmaceutical composition comprising a therapeutically effective amount of a compound of claim 1 or a pharmaceutically acceptable salt, ester, solvate, isotope-labeled derivative, stereoisomer or tautomer thereof, and a pharmaceutically acceptable carrier; and (ii) at least one additional therapeutic agent selected from the group consisting of anti-tumor agent, agent treating autoimmune disease, anti-neurodegenerative agent, agent treating metabolic disease, and anti-aging agent.

16. A method for treating a disease or disorder associated with programmed necrosis pathway in a mammal suffering therefrom, comprising administering to the mammal a therapeutically effective amount of at a compound of claim 1 or a pharmaceutically acceptable salt, ester, solvate, isotope-labeled derivative, stereoisomer or tautomer thereof, or a pharmaceutical composition thereof, wherein the disease or disorder associated with programmed necrosis pathway is arthritis, ulcerative colitis, Crohn's disease, early-onset inflammatory bowel disease, extraintestinal inflammatory bowel disease, ischemia reperfusion injury in solid organ transplant, myocardial infarction, rheumatoid arthritis, or psoriasis.

* * * * *